(12) United States Patent
Benz et al.

(10) Patent No.: US 11,420,961 B2
(45) Date of Patent: Aug. 23, 2022

(54) HETEROCYCLIC COMPOUNDS

(71) Applicant: Hoffmann-La Roche Inc., Little Falls, NJ (US)

(72) Inventors: Joerg Benz, Basel (CH); Uwe Grether, Basel (CH); Benoit Hornsperger, Basel (CH); Buelent Kocer, Basel (CH); Bernd Kuhn, Basel (CH); Hans Richter, Basel (CH); Satoshi Tsuchiya, Tokyo (JP); Charles Bell, Basel (CH); Xiang Wu, Hubei (CN); Xiaofei Yan, Hubei (CN); Luca Gobbi, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/884,562

(22) Filed: May 27, 2020

(65) Prior Publication Data
US 2020/0392125 A1  Dec. 17, 2020

Related U.S. Application Data

(63) Continuation of application No. PCT/EP2018/082659, filed on Nov. 27, 2018.

(30) Foreign Application Priority Data

Nov. 28, 2017  (EP) .................................... 17204120
Oct. 25, 2018  (WO) ................ PCT/CN2018/111860

(51) Int. Cl.
*C07D 413/06*  (2006.01)
*A61K 31/536*  (2006.01)

(52) U.S. Cl.
CPC .......... *C07D 413/06* (2013.01); *A61K 31/536* (2013.01)

(58) Field of Classification Search
CPC .. C07D 413/02; C07D 413/10; C07D 413/12; C07D 413/06; C07D 413/14; C07D 401/06; C07D 417/12; C07D 265/36; A61P 25/24; A61P 25/04; A61P 25/16; A61P 25/22; A61P 25/28; A61P 35/00; A61P 25/06; A61P 25/08; A61K 31/536
See application file for complete search history.

(56) References Cited

U.S. PATENT DOCUMENTS

| 4,454,130 | A | * | 6/1984 | Tominaga | ............. C07C 205/57 514/235.2 |
|---|---|---|---|---|---|
| 10,106,556 | B2 | | 10/2018 | Ikeda et al. | |
| 10,610,520 | B2 | | 4/2020 | Ikeda et al. | |
| 2020/0255439 | A1 | | 8/2020 | Kamata et al. | |
| 2020/0299277 | A1 | | 9/2020 | Benz et al. | |
| 2020/0308158 | A1 | | 10/2020 | Bell et al. | |
| 2020/0308190 | A1 | | 10/2020 | Bell et al. | |
| 2020/0392125 | A1 | | 12/2020 | Benz et al. | |
| 2021/0024546 | A1 | | 1/2021 | Petersen et al. | |
| 2021/0094943 | A1 | | 4/2021 | Benz et al. | |
| 2021/0094971 | A1 | | 4/2021 | Grether et al. | |
| 2021/0094972 | A1 | | 4/2021 | Benz et al. | |
| 2021/0094973 | A1 | | 4/2021 | Gobbi et al. | |
| 2021/0107920 | A1 | | 4/2021 | Bell et al. | |
| 2021/0107921 | A1 | | 4/2021 | Benz et al. | |
| 2021/0277020 | A1 | | 9/2021 | Anselm et al. | |
| 2021/0038999 | A1 | | 12/2021 | Kuhn et al. | |

FOREIGN PATENT DOCUMENTS

| WO | 2010/111626 A2 | 9/2010 |
|---|---|---|
| WO | 2010/124122 A1 | 10/2010 |
| WO | 2011/151808 A1 | 12/2011 |
| WO | 2016/158956 A1 | 10/2016 |
| WO | 2017/171100 A1 | 10/2017 |
| WO | 2019/065791 A1 | 4/2019 |
| WO | 2019/072785 A1 | 4/2019 |
| WO | 2019/105915 A1 | 6/2019 |
| WO | 2019/115660 A1 | 6/2019 |
| WO | 2019/134985 A1 | 7/2019 |
| WO | 2019/180185 A1 | 9/2019 |
| WO | 2020/035424 A1 | 2/2020 |
| WO | 2020/035425 A1 | 2/2020 |
| WO | 2020/104494 A1 | 5/2020 |

OTHER PUBLICATIONS

Regsitry-1 (Registry No. 1907579-56-9 (Entered STN: May 10, 2016)).*
Registry-2 (Registry No. 931085-56-2, Entered STN: Apr. 20, 2007).*
Alpar et al., "Endocannabinoids modulate cortical development by configuring Slit2/Robo1 signaling" Nat Commun 5(4421):1-13 (Jul. 17, 2014).
Barany and Merrifield, "A Nucleophilic Acetaldehyde Equivalent. Preparation and Synthetic Applications of cis-2-Ethoxyvinyl-lithium" J. Am. Chem. Soc 99:7363-7365 ( 1997).
Bernal-Chico et al., "Blockade of Monoacylglycerol Lipase Inhibits Oligodendrocyte Excitotoxicity and Prevents Demyelination In Vivo" Glia 63:163-176 ( 2015).
CAS Registry Database, RN-924119-47-1, Mar. 1, 2007.
Chanda et al., "Monoacylglycerol Lipase Activity Is a Critical Modulator of the Tone and Integrity of the Endocannabinoid System" Mol Pharmacol 78(6):996-1003 ( 2010).

(Continued)

*Primary Examiner* — Robert H Havlin
(74) *Attorney, Agent, or Firm* — Katherine J. Mackenzie

(57) ABSTRACT

The invention provides new heterocyclic compounds having the general formula (IA)

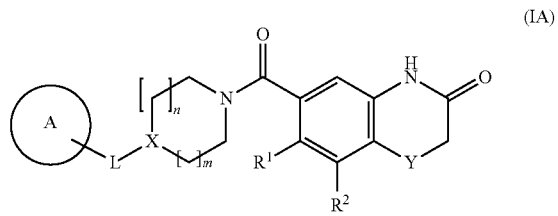

(IA)

wherein A, L, X, Y, m, n, $R^1$ and $R^2$ are as described herein, compositions including the compounds, processes of manufacturing the compounds and methods of using the compounds.

19 Claims, No Drawings

(56) References Cited

OTHER PUBLICATIONS

Drummen et al., "Fluorescent Probes and Fluorescence (Microscopy) Techniques—Illuminating Biological and Biomedical Research" Molecules 17:14067-14090 (2012).
Feliu et al., "2-Arachidonoylglycerol Reduces Proteoglycans and Enhances Remyelination in a Progressive Model of Demyelination" J Neurosci 37(35):8385-8398 (Aug. 30, 2017).
Iannotti et al., "Endocannabinoids and endocannabinoid-related mediators: Targets, metabolism and role in neurological disorders" Prog Lipid Res 62:107-128 (2016).
Ignatowska-Jankowska et al., "Selective Monoacylglycerol Lipase Inhibitors: Antinociceptive versus Cannabimimetic Effects in Mice" J Pharmacol Exp Ther 353:424-432 (2015).
International Preliminary Report on Patentability for PCT/EP2018/082659 dated Jun. 2, 2020.
International Search Report and Written Opinion for PCT/EP2018/082659 dated Jan. 23, 2019.
Lleo et al., "Molecular targets of non-steroidal anti-inflammatory drugs in neurodegenerative diseases" Cell Mol Life Sci 64:1403-1418 (2007).
Long et al., "Selective blockade of 2-arachidonoylglycerol hydrolysis produces cannabinoid behavioral effects" Nat Chem Biol 5:37-44 (2009).
Muccioli et al., "CAY10499, a Novel Monoglyceride Lipase Inhibitor Evidenced by an Expeditious MGL Assay" Chem Bio Chem 9:2704-2710 (2008).
Nomura et al., "Endocannabinoid Hydrolysis Generates Brain Prostaglandins That Promote Neuroinflammation" Science 334(6057):809-813 (2011).
Nomura et al., "Monoacylglycerol Lipase Exerts Dual Control over Endocannabinoid and Fatty Acid Pathways to Support Prostate Cancer" Chem Biol 18(7):846-856 (2011).
Nomura et al., "Monoacylglycerol Lipase Regulates a Fatty Acid Network that Promotes Cancer Pathogenesis" Cell 140:49-61 (2010).
Qin et al., "The role of monoacylglycerol lipase (MAGL) in the cancer progress" Cell Biochem Biophys 70:33-36 (2014).
U.S. Appl. No. 16/827,211.
U.S. Appl. No. 16/844,262.
U.S. Appl. No. 16/899,928.
U.S. Appl. No. 16/922,427.
Viader et al., "Reports Article Metabolic Interplay between Astrocytes and Neurons Regulates Endocannabinoid Action" Cell Rep 12(5):798-808 (2015).
Waldmann et al., "Protecting Group Strategies in Organic Synthesis" Angew. Chem. Int. Ed. Engl. 35:2056-2083 (1996).
Zhong et al., "Monoacylglycerol Lipase Inhibition Blocks Chronic Stress-Induced Depressive-Like Behaviors via Activation of mTOR Signaling" Neuropsychopharmacology 39:1763-1776 (2014).
CAS Registry Database, RN-1090729-35-3, pp. 1 Dec. 28, 2008.
CAS Registry Database, RN-1427582-77-1, pp. 1 Apr. 9, 2013.
CAS Registry Database, RN-1901859-22-0, pp. 1 May 2, 2015.
CAS Registry Database, RN-1955365-84-0, pp. 1 Jul. 19, 2016.
CAS Registry Database, RN-1955469-88-1, pp. 1 Jul. 19, 2016.
CAS Registry Database, RN-1956945-68-8, pp. 1 Jul. 21, 2016.
CAS Registry Database, RN-2129025-04-1, pp. 1 Sep. 21, 2017
International Preliminary Report on Patentability for PCT/EP2018/084653 dated Jun. 16, 2020.
International Search Report for PCT/EP2018/084653 dated Feb. 5, 2019.
U.S. Appl. No. 17/325,934, filed May 20, 2021.
U.S. Appl. No. 17/174,000, filed Feb. 11, 2021.
Mulvihill, M., et al., "Therapeutic Potential of Monoacylglycerol Lipase Inhibitors" Life Sci 92(8-9):492-497 (Nov. 8, 2013).
"U.S. Appl. No. 17/497,633, filed Oct. 8, 2021".
"U.S. Appl. No. 17/552,792, filed Dec. 16, 2021".
"U.S. Appl. No. 17/569,749, filed Jan. 6, 2022".
"U.S. Appl. No. 17/465,536, filed Sep. 2, 2021".
U.S. Appl. No. 17/692,632, filed Mar. 11, 2022.
U.S. Appl. No. 17/700,987, filed Mar. 22, 2022.

\* cited by examiner

HETEROCYCLIC COMPOUNDS

CROSS REFERENCE TO RELATED APPLICATIONS

This application is a continuation of International Application No. PCT/EP2018/082659, filed Nov. 27, 2018, which claims priority to International Application No. PCT/CN2018/111860, filed Oct. 25, 2018, and EP Application No. 17204120.4, filed Nov. 28, 2017, the disclosure of each of which is incorporated herein by reference in its entirety.

FIELD OF THE INVENTION

The present invention relates to organic compounds useful for therapy or prophylaxis in a mammal, and in particular to monoacylglycerol lipase (MAGE) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine and/or depression in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28.). In the brain, the main endocannabinoid, 2-arachidonoylglycerol (2-AG), is produced by diacyglycerol lipases (DAGL) and hydrolyzed by the monoacylglycerol lipase, MAGE. MAGE hydrolyses 85% of 2-AG; the remaining 15% being hydrolysed by ABHD6 and ABDH12 (Nomura, D. K., et al., *Science* 2011, 334, 809.). MAGE is expressed throughout the brain and in most brain cell types, including neurons, astrocytes, oligodendrocytes and microglia cells (Chanda, P. K., et al., *Molecular pharmacology* 2010, 78, 996; Viader, A., et al., *Cell reports* 2015, 72, 798.), 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclooxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoy-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (EPS) produces a robust, time-dependent increase in brain eicosanoids that is markedly blunted in Mgll−/− mice. EPS treatment also induces a widespread elevation in pro-inflammatory cytokines including interleukin-1-a (IL-1-a), IL-1b, IL-6, and tumor necrosis factor-a (TNF-a) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo A., *Cell Mol Life Sci.* 2007, 64, 1403.). Importantly, genetic and/or pharmacological disruption of MAGL activity also blocks EPS-induced activation of microglial cells in the brain (Nomura, D. K., et al., *Science* 2011, 334, 809.).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37.). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809.), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J. Pharmacol. Exp. Ther.* 2015, 353, 424.) and on mental disorders, such as depression in chronic stress models (Zhong P. et al., *Neuropsychopharmacology* 2014, 39, 1763.).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bemal-Chico, A., et al., *Glia* 2015, 63, 163.). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421.). Inhibition of MAGL was also shown to promote remyelination and functional recovery in a mouse model of progressive multiple sclerosis (Feliu A. et al., *Journal of Neuroscience* 2017, 37 (35), 8385.).

Finally, in recent years, metabolism is talked highly important in cancer research, especially the lipid metabolism. Researchers believe that the de novo fatty acid synthesis plays an important role in tumor development, while many studies illustrated that endocannabinoids have anti-tumorigenic actions, including anti-proliferation, apoptosis induction, and anti-metastatic effects, MAGL as an important decomposing enzyme of both lipid metabolism and endocannabinoids system, additionally as a part of a gene expression signature contributes to different aspects of tumourigenesis (Qin, H., et al., *Cell Biochem. Biophys.* 2014, 70, 33; Nomura D K et al., *Cell* 2009, 140(1), 49-61; Nomura D K et al, Chem. Biol. 2011, 75(7), 846-856).

In conclusion, suppressing the action and/or the activation of MAGL is a promising new therapeutic strategy for the treatment or prevention of neuroinflammation, neurodegenerative diseases, pain, cancer and mental disorders. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides compounds of formula (IA)

(IA)

wherein
X is CH or N and L is —C($R^3R^4$)— or a covalent bond; or
X is C($sp^2$) and together with L forms a group (E,Z)

wherein the asterisk indicates the point of attachment to ring A;
Y is $CH_2$ or O;
n and m are independently 0, 1 or 2;
A is selected from the group consisting of
  (i) aryl substituted with $R^5$, $R^6$ and $R^7$; and
  (ii) heteroaryl substituted with $R^8$, $R^9$ and $R^{10}$;
$R^1$ and $R^2$ are each independently selected from the group consisting of hydrogen, halogen, alkoxy and haloalkoxy;
$R^3$ is selected from the group consisting of
  (i) aryl substituted with $R^{11}$ and $R^{12}$,
  (ii) heteroaryl substituted with $R^{13}$ and $R^{14}$,
  (iii) cycloalkyl substituted with $R^{15}$ and $R^{16}$; and
  (iv) heterocyclyl substituted with $R^{17}$ and $R^{18}$;
$R^4$ is hydrogen or hydroxy; or
$R^3$ and $R^4$ together with the carbon atom to which they are attached form a heterocycle or a carbocycle; and
$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are each independently selected from the group consisting of hydrogen, halogen, alkyl, haloalkyl, hydroxy alkyl, alkoxy, haloalkoxy, haloalkoxyalkoxy, aryl, cycloalkyl, haloaryl, haloarylalkyl, alkylsulfonyl, oxo and a fluorescent label;
or a pharmaceutically acceptable salt thereof.

In a further aspect, the present invention provides a process of manufacturing the compounds of formula (IA) as described herein, comprising the steps of:
a) reacting an amine 1, wherein A, L, m and n are as described herein,

1 with an acid 2a or 2b, wherein $R^1$ and $R^2$ are as described herein

2a

2b b) reacting an amine 1, wherein A, L, m and n are as described herein,

1 with an acid chloride 2c or 2d, wherein $R^1$ and $R^2$ are as described herein

2c

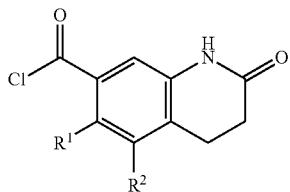

to form said compound of formula (IA). formula (IA)

In a further aspect, the present invention provides a compound of formula (IA) as described herein, when manufactured according to the processes described herein.

In a further aspect, the present invention provides a compound of formula (IA) as described herein, for use as therapeutically active substance.

In a further aspect, the present invention provides a pharmaceutical composition comprising a compound of formula (IA) as described herein and a therapeutically inert carrier.

In a further aspect, the present invention provides the use of a compound of formula (IA) as described herein for inhibiting monoacylglycerol lipase (MAGL) in a mammal.

In a further aspect, the present invention provides the use of a compound of formula (IA) as described herein for the treatment or prophylaxis of neuroinflammation, neurodegenerative diseases, pain, cancer and/or mental disorders in a mammal.

In a further aspect, the present invention provides the use of a compound of formula (IA) as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides a compound of formula (IA) as described herein for use in a method of inhibiting monoacylglycerol lipase in a mammal.

In a further aspect, the present invention provides a compound of formula (IA) as described herein for use in the treatment or prophylaxis of neuroinflammation, neurodegenerative diseases, pain, cancer and/or mental disorders in a mammal.

In a further aspect, the present invention provides a compound of formula (IA) as described herein, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (IA) as described herein for the preparation of a medicament for inhibiting monoacylglycerol lipase in a mammal.

In a further aspect, the present invention provides the use of a compound of formula (IA) as described herein for the preparation of a medicament for the treatment or prophylaxis of neuroinflammation, neurodegenerative diseases, pain, cancer and/or mental disorders in a mammal.

In a further aspect, the present invention provides the use of a compound of formula (IA) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides a method for inhibiting monoacylglycerol lipase in a mammal, which method comprises administering an effective amount of a compound of formula (IA) as described herein to the mammal.

In a further aspect, the present invention provides a method for the treatment or prophylaxis of neuroinflammation, neurodegenerative diseases, pain, cancer and/or mental disorders in a mammal, which method comprises administering an effective amount of a compound of formula (IA) as described herein to the mammal.

In a further aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal, which method comprises administering an effective amount of a compound of formula (IA) as described herein to the mammal.

In a further aspect, the present invention provides a compound of formula (IA) comprising one or more imaging isotopes and/or one or more fluorescent labels as described herein, for use in medical diagnosis.

In a further aspect, the present invention provides a method for diagnosing neuroinflammation, neurodegenerative diseases, pain, cancer and/or mental disorders in a mammal, comprising administering a compound of formula (IA) comprising one or more imaging isotopes and/or one or more fluorescent labels as described herein to the mammal.

In a further aspect, the present invention provides a method for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal, comprising administering a compound of formula (IA) comprising one or more imaging isotopes and/or one or more fluorescent labels as described herein, to the mammal.

In a further aspect, the present invention provides a compound of formula (IA) comprising one or more imaging isotopes and/or one or more fluorescent labels as described herein, for use in a method for diagnosing neuroinflammation, neurodegenerative diseases, pain, cancer and/or mental disorders in a mammal.

In a further aspect, the present invention provides a compound of formula (IA) comprising one or more imaging isotopes and/or one or more fluorescent labels as described herein, for use in a method for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (IA) comprising one or more imaging isotopes and/or one or more fluorescent labels as described herein, for the preparation of a composition for diagnosing neuroinflammation, neurodegenerative diseases, pain, cancer and/or mental disorders in a mammal.

In a further aspect, the present invention provides the use of a compound of formula (IA) comprising one or more imaging isotopes and/or one or more fluorescent labels as described herein, for the preparation of a composition for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (IA) comprising one or more imaging isotopes and/or one or more fluorescent labels as described herein, for diagnosing neuroinflammation, neurodegenerative diseases, pain, cancer and/or mental disorders in a mammal.

In a further aspect, the present invention provides the use of a compound of formula (IA) comprising one or more imaging isotopes and/or one or more fluorescent labels as described herein, for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (IA) comprising one or more imaging isotopes and/or one or more fluorescent labels as described herein, for diagnosing neuroinflammation, neurodegenerative diseases, pain, cancer and/or mental disorders in vitro.

In a further aspect, the present invention provides the use of a compound of formula (IA) comprising one or more imaging isotopes and/or one or more fluorescent labels as described herein, for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in vitro.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 12 carbon atoms. In some preferred embodiments, the alkyl group contains 1 to 6 carbon atoms, e.g., 1, 2, 3, 4, 5, or 6 carbon atoms. In other embodiments, the alkyl group contains 1 to 3 carbon atoms, e.g., 1, 2 or 3 carbon atoms. Examples of such groups include, but are not limited to, methyl, ethyl, propyl, 2-propyl (isopropyl), n-butyl, iso-butyl, sec-butyl, tert-butyl, and 2,2-dimethylpropyl. In a particularly preferred embodiment, alkyl is methyl.

The term "alkoxy" refers to an alkyl group, as previously defined, attached to the parent molecular moiety via an oxygen atom. Unless otherwise specified, the alkoxy group contains 1 to 12 carbon atoms. In some embodiments, the alkoxy group contains 1 to 6 carbon atoms. In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. In a preferred embodiment, alkoxy is methoxy, ethoxy and isopropoxy. In a particularly preferred embodiment, alkoxy is methoxy.

The term "halogen" or "halo" refers to fluoro (F), chloro (Cl), bromo (Br), or iodo (I). In a preferred embodiment, the term "halogen" or "halo" refers to fluoro (F), chloro (Cl) or bromo (Br). In a particularly preferred embodiment, "halogen" or "halo" is fluoro (F).

The term "haloalkyl" or "haloalkoxy", respectively, refers to an alkyl or alkoxy group, as the case may be, substituted with one or more halogen atoms, wherein each of the alkyl or alkoxy is defined as described herein. In a preferred embodiment, the haloalkyl or haloalkoxy group, respectively, contains 1, 2 or 3 halogen atoms, most preferably 1, 2 or 3 F atoms. Examples of such groups include, but are not limited to, fluoromethyl, difluoromethyl, trifluoromethyl ($CF_3$), 2,2,2-trifluoroethyl, trifluoromethoxy, 2,2,2-trifluoroethoxy, 2,2,3,3-tetrafluoropropoxy, and the like. A particularly preferred haloalkoxy group is 2-fluoroethoxy.

The term "haloalkoxyalkoxy" refers to an alkoxy group, wherein at least one of the hydrogen atoms of the alkoxy group has been replaced by a haloalkoxy group. In one embodiment, "haloalkoxyalkoxy" refers to an alkoxy group wherein 1, 2 or 3 hydrogen atoms, preferably 1 or 2 hydrogen atoms of the alkoxy group have been replaced by a haloalkoxy group. A particularly preferred haloalkoxyalkoxy group is 2-(2-fluoroethoxy)ethoxy.

The term "hydroxyalkyl" refers to an alkyl group substituted with one or more hydroxy (—OH) groups, wherein the alkyl is defined as described herein. In a preferred embodiment, the hydroxy alkyl group contains 1 hydroxy group. In a particularly preferred embodiment, "hydroxy alkyl" refers to hydroxy ethyl.

The term "$C(sp^2)$" refers to an $sp^2$ hybridized carbon atom, such as a carbon atom in a C—C double bond.

The terms "cycloalkyl" and "carbocycle" are used herein synonymously and refer to a saturated or partly unsaturated monocyclic or bicyclic hydrocarbon group of 3 to 10 ring carbon atoms. In some embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two atoms, and to spirocyclic moieties, i.e., the two rings are connected via one common ring atom. In a preferred embodiment, the cycloalkyl group is a saturated monocyclic hydrocarbon group of 3 to 6 ring carbon atoms, e.g., of 3, 4, 5 or 6 carbon atoms. Examples for monocyclic cycloalkyl groups include, but are not limited to, cyclopropyl, cyclobutyl, cyclopentyl, cyclohexyl or cycloheptyl. Examples for bicyclic cycloalkyl groups include, but are not limited to, bicyclo[2.2.1]heptanyl or bicyclo[2.2.2]octanyl. In a particularly preferred embodiment, the cycloalkyl group is a cyclopropyl group.

The terms "heterocyclyl" and "heterocycle" are used herein synonymously and refer to a saturated or partly unsaturated mono- or bicyclic ring system of 3 to 10 ring atoms, wherein 1, 2, or 3 of said ring atoms are heteroatoms selected from the group consisting of N, O and S, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Examples for monocyclic cycloalkyl groups include, but are not limited to, oxolan-2-yl, oxolan-3-yl, 1,3-dioxolan-2-yl and 1,3-dioxolan-4-yl.

The term "aryl" refers to a monocyclic, bicyclic, or tricyclic carbocyclic ring system having a total of 6 to 14 ring members, preferably, 6 to 12 ring members, and more preferably 6 to 10 ring members, and wherein at least one ring in the system is aromatic. Examples of aryl rings may include phenyl, naphthyl, indanyl and anthracenyl. In a particularly preferred embodiment, "aryl" refers to phenyl.

The term "heteroaryl" refers to a mono- or multivalent, monocyclic, bicyclic or tricyclic ring system having a total of 5 to 12 ring members, preferably, 5 to 10 ring members, and more preferably 5 to 6 ring members, wherein at least one ring in the system is aromatic, and at least one ring in the system contains one or more heteroatoms. In one embodiment, a 5-10 membered heteroaryl comprises 1, 2, 3 or 4 heteroatoms independently selected from the group consisting of O, S and N. Some non-limiting examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, pyri mi din-2-yl, pyrimidin-4-yl, pyrimidin-5-yl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,3,4-oxadiazol-2-yl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles, but are not limited to: benzimidazolyl (e.g., benzimidazol-1-yl), benzofuryl, benzothiophenyl (e.g., benzothiophen-2-yl), indolyl (e.g., 1H-indol-5-yl), indazolyl (e.g., indazol-1-yl), benzoxazolyl (e.g., 1,2-benzoxazol-3-yl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, 2,3-dihydro-1H-pyrrolo[2,3-b]pyridyl or 2,3-dihydropyrrolo[2,3-b]pyrid-1-yl, 1H-pyrrolo[2,3-b]pyridin-2-yl, 1H-pyrrolo[2,3-b]pyridin-3-yl, 1H-pyrrolo[2,3-b]pyridin-4-yl, 1H-pyrrolo[2,3-b]pyridin-5-yl, 1H-pyrrolo[2,3-b]pyridin-6-yl, pyrrolo[2,3-b]pyridin-1-yl and the like. In a preferred embodiment, the term "heteroaryl" refers to a heteroaryl residue selected from the group consisting of indazol-1-yl, 1H-indazol-3-yl, 1H-indazol-4-yl, 1H-indazol-5-yl, 1H-indazol-6-yl, 1H-indazol-7-yl, benzothiophen-2-yl, benzothiophen-3-yl, benzothiophen-4-yl, benzothiophen-5-yl, benzothiophen-6-yl, benzothiophen-7-yl, pyrazol-1-yl, 1H-pyrazol-3-yl, 1H-pyrazol-4-yl, 1H-pyrazol-5-yl, 1H-pyrrolo[2,3-b]pyridin-2-yl, 1H-pyrrolo[2,3-b]pyridin-3-yl, 1H-pyrrolo[2,3-b]pyridin-4-yl, 1H-pyrrolo[2,3-b]pyridin-5-yl, 1H-pyrrolo[2,3-b]pyridin-6-yl, pyrrolo[2,3-b]pyridin-1-yl, 1,3,4-oxadiazol-2-yl, benzimidazol-1-yl, 1H-benzimidazol-2-yl, 1H-benzimidazol-4-yl, 1H-benzimidazol-5-yl, 3H-benzimidazol-4-yl, 3H-benzimidazol-5-yl, 1,2-benzoxazol-3-yl, 1,2-benzoxazol-4-yl, 1,2-benzoxazol-5-yl, 1,2-benzoxazol-6-yl, 1,2-benzoxazol-7-yl, pyrimidin-2-yl, pyrimidin-4-yl and pyrimidin-5-yl.

The term "haloaryl" refers to an aryl group, wherein at least one of the hydrogen atoms of the aryl group has been replaced by a halogen atom. In one embodiment, "haloaryl" refers to an aryl group wherein 1, 2 or 3 hydrogen atoms, preferably 1 or 2 hydrogen atoms of the aryl group have been replaced by a halogen atom. In a preferred embodiment, haloaryl refers to chlorophenyl e.g., 4-chlorophenyl.

The term "haloarylalkyl" refers to an alkyl group, wherein at least one of the hydrogen atoms of the alkyl group has been replaced by a haloaryl group. In a preferred embodiment, "haloarylalkyl" refers to an alkyl group wherein 1 hydrogen atom of the alkyl group has been replaced by a haloaryl group. In a particularly preferred embodiment, "haloarylalkyl" is 3-chlorobenzyl (synonymous to (3-chlorophenyl)methyl).

The term "hydroxy" refers to an —OH group.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanol amine, lysine, arginine, N-ethylpiperidine, piperidine, polyimine resins and the like. Particular pharmaceutically acceptable salts of compounds of formula (IA) are the hydrochloride salts, methanesulfonic acid salts and citric acid salts.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxy carbonyl (Fmoc). More particular protecting group is the tert-butoxycarbonyl (Boc). Exemplary protecting groups and their application in organic synthesis are described, for example, in "Protective Groups in Organic Chemistry" by T. W. Greene and P. G. M. Wutts, 5th Ed., 2014, John Wiley & Sons, N.Y.

The compounds of formula (IA) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The abbreviation "MAGE" refers to the enzyme monoacylglycerol lipase. The terms "MAGE" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human, that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain, phantom pain and psychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "mammal" as used herein includes both humans and non-humans and includes but is not limited to humans, non-human primates, canines, felines, murines, bovines, equines, and porcines. In a particularly preferred embodiment, the term "mammal" refers to humans.

The term "diagnosing" as used herein refers to any kind of procedure aiming to obtain information instrumental in the assessment whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient with regard to a certain treatment. In other words, the term "diagnosing" comprises not only diagnosing, but also prognosticating and/or monitoring the course of a disease or disorder.

Imaging Isotopes and Imaging

Diagnostic techniques in nuclear medicine use radioactive tracers which emit gamma rays from within the body. These tracers are generally short-lived isotopes linked to chemical compounds which permit specific physiological processes to be scrutinized. They can be given by injection, inhalation or orally. The first type is where single photons are detected by a gamma camera which can view organs from many different angles. The camera builds up an image from the points from which radiation is emitted; this image is enhanced by a computer and viewed by a physician on a monitor for indications of abnormal conditions.

Positron Emission Tomography (PET) is a precise and sophisticated technique using isotopes produced in a cyclotron. A positron-emitting radionuclide is introduced, usually by injection, and accumulates in the target tissue. As it decays it emits a positron, which promptly combines with a nearby electron resulting in the simultaneous emission of two identifiable gamma rays in opposite directions. These are detected by a PET camera and give a very precise indication of their origin. PET's most important clinical role is in oncology, with fluorine-18 fluorodeoxyglucose ($[^{18}F]$ FDG) as the tracer, since it has proven to be the most accurate non-invasive method of detecting and evaluating most cancers. It is also well used in cardiac and brain imaging.

A number of medical diagnostic procedures, including PET and SPECT, utilize radiolabeled compounds and are well known in the art. PET and SPECT are very sensitive techniques and require small quantities of radiolabeled compounds, called tracers. The labeled compounds are transported, accumulated and converted in vivo in a similar manner as the corresponding non-radioactively labeled compound. Tracers, or probes, can be radiolabeled with a radionuclide useful for PET imaging, such as $^{11}C$, $^{13}N$, $^{15}O$, $^{18}F$, $^{64}Cu$, and $^{124}I$, or with a radionuclide useful for SPECT imaging, such as $^{99}Tc$, $^{77}Br$, $^{61}Cu$, $^{153}Gd$, $^{123}I$, $^{125}I$, $^{131}I$ and $^{32}P$. These are non-limiting examples of "imaging isotopes," as that term is used herein.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

Regarding radiohalogens, $^{125}$I isotopes are useful for laboratory testing but they will generally not be useful for diagnostic purposes because of the relatively long half-life (60 days) and low gamma-emission (30-65 keV) of $^{125}$I. The isotope $^{123}$I has a half-life of thirteen hours and gamma energy of 159 keV, and it is therefore typical that labeling of ligands to be used for diagnostic purposes would be with this isotope or with $^{18}$F (half-life of 2 hours). Other imaging isotopes which may be used include $^{131}$I, $^{77}$Br and $^{76}$Br.

In another embodiment, compounds of the present invention contain a radioactive isotope of carbon as the radiolabel. This refers to a compound that comprises one or more radioactive carbon atoms, preferably $^{11}$C, with a specific activity above that of the background level for that atom. It is well known that naturally occurring elements are present in the form of varying isotopes, some of which are radioactive. The radioactivity of the naturally occurring elements is a result of the natural distribution or abundance of these isotopes, and is commonly referred to as a background level. The carbon labeled compounds of the present invention have a specific activity that is higher than the natural abundance, and therefore above the background level. The carbon labeled compositions of the present invention can be used for tracing, imaging, radiotherapy, and the like.

Those skilled in the art are familiar with the various ways to detect labeled compounds for imaging purposes. For example, positron emission tomography (PET) or single photon emission computed tomography (SPECT) can be used to detect radiolabeled compounds. The label that is introduced into the compound can depend on the detection method desired. Those skilled in the art are familiar with PET detection of a positron-emitting atom, such as $^{18}$F. The present invention is also directed to specific compounds described herein where the $^{18}$F atom is replaced with a non-radiolabeled fluorine atom. Those skilled in the art are familiar with SPECT detection of a photon-emitting atom, such as $^{123}$I or $^{99}$Tc.

The radioactive diagnostic or detection agent should have sufficient radioactivity and radioactivity concentration which can assure reliable diagnosis and detection. The desired level of radioactivity can be attained by the methods provided herein for preparing compounds.

Typically, a prerequisite for an in vivo imaging agent of the brain is the ability to cross the intact blood-brain barrier. In a first step of a method of imaging, a labeled compound is introduced into a tissue or a patient in a detectable quantity. The compound is typically part of a pharmaceutical composition and is administered to the tissue or the patient by methods well known to those skilled in the art. Typically, administration is intravenously.

In other embodiments of the invention, the labeled compound is introduced into a patient in a detectable quantity and after sufficient time has passed for the compound to become associated with MAGL, the labeled compound is detected noninvasively. In another embodiment of the invention, a labeled compound is introduced into a patient, sufficient time is allowed for the compound to become associated with MAGL, and then a sample of tissue from the patient is removed and the labeled compound in the tissue is detected apart from the patient. In another embodiment of the invention, a tissue sample is removed from a patient and a labeled compound is introduced into the tissue sample. After a sufficient amount of time for the compound to become bound to MAGL, the compound is detected.

A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The amount of time necessary can easily be determined by introducing a detectable amount of a labeled compound into a patient and then detecting the labeled compound at various times after administration.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate MAGL protein levels in the brain in order to diagnose or track the progress of e.g., neuroinflammation in a patient.

One or more imaging isotopes can be incorporated into a compound of formula (IA) by replacing one or more atoms (e.g., hydrogen or carbon atoms) in the compound of formula (IA) with an imaging isotope. The incorporation of an imaging isotope can be carried out using known techniques. For example, techniques may be based on nucleophilic or electrophilic $^{18}$F-fluorination of suitable precursors as reviewed, for example, in Medicinal Chemistry Approaches to Personalized Medicine (Lackey, Roth Eds), Chapter 12 (Wiley-VCH, ISBN 978-3-527-33394-3). See also U.S. Patent Application No. 2011/0182812, incorporated herein by reference in its entirety.

Fluorescent Labeling

The term "fluorescent label", as used herein, refers to a fluorophore that can be covalently attached to another molecule, such as a compound of formula (IA), which attachment is generally accomplished by using a reactive derivative of the fluorophore that selectively binds to a functional group contained in the target molecule. Fluorescent labels include, but are not limited to, NBD, MR121, DY-480XL, allophycocyanin (APC), fluoresceins (FITC), rhodamines (e.g., FAM, R6G, TET, TAMRA, JOE, HEX, CAL Red, VIC, and ROX), Texas red, BODIPY, coumarins, cyanine dyes (e.g., indocyan green [ICG], thiazole orange [TO], oxazole yellow [YO], TOTO, YOYO; Cy3, Cy5), ALEXA FLUOR® dyes (e.g., Alexas 405, 488, 546, 633 and 647), DYLIGHT® dyes, Green Fluorescent Protein (GFP), and phycoerythrin (PE).

Methods of using compounds comprising fluorescent labels in medical research and diagnosis, such as fluorescence microscopy, in particular epifluorescence microscopy, are well known in the art (see e.g., G. P. C. Drummen, Molecules 2012, 77, 14067-14090).

Compounds of the Invention

In a first aspect, the present invention provides compounds of formula (IA)

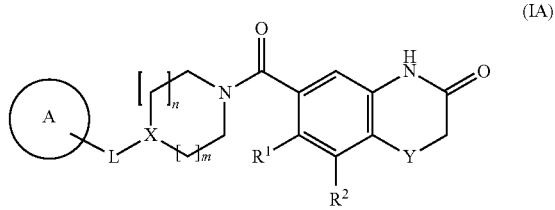

(IA)

wherein
X is CH or N and L is —C(R³R⁴)— or a covalent bond; or
X is C(sp²) and together with L forms a group

(E,Z)

wherein the asterisk indicates the point of attachment to ring A;
Y is CH$_2$ or O;
n and m are independently 0, 1 or 2;
A is selected from the group consisting of
(i) aryl substituted with R⁵, R⁶ and R⁷; and
(ii) heteroaryl substituted with R⁸, R⁹ and R¹⁰;
R¹ and R² are each independently selected from the group consisting of hydrogen, halogen, alkoxy and haloalkoxy;
R³ is selected from the group consisting of
(i) aryl substituted with R¹¹ and R¹²,
(ii) heteroaryl substituted with R¹³ and R¹⁴,
(iii) cycloalkyl substituted with R¹⁵ and R¹⁶; and
(iv) heterocyclyl substituted with R¹⁷ and R¹⁸;
R⁴ is hydrogen or hydroxy; or
R³ and R⁴ together with the carbon atom to which they are attached form a heterocycle or a carbocycle; and
R⁵, R⁶, R⁷, R⁸, R⁹, R¹⁰, R¹¹, R¹², R¹³, R¹⁴, R¹⁵, R¹⁶, R¹⁷ and R¹⁸ are each independently selected from the group consisting of hydrogen, halogen, alkyl, haloalkyl, hydroxy alkyl, alkoxy, haloalkoxy, haloalkoxy alkoxy, aryl, cycloalkyl, haloaryl, haloarylalkyl, alkylsulfonyl, oxo and a fluorescent label;
or a pharmaceutically acceptable salt thereof.

In a preferred embodiment, the compound of formula (IA) is a compound of formula (I)

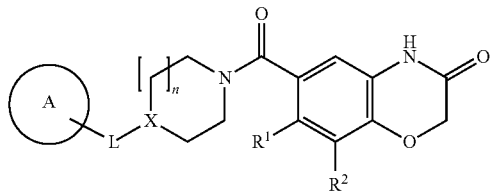

(I)

wherein
X is CH or N;
L is —C(R³R⁴)— or a covalent bond;
n is 0, 1 or 2;
A is selected from the group consisting of
(i) aryl substituted with R⁵, R⁶ and R⁷; and
(ii) heteroaryl substituted with R⁸, R⁹ and R¹⁰;
R¹ and R² are each independently selected from the group consisting of hydrogen, halogen, alkoxy and haloalkoxy;
R³ is selected from the group consisting of
(i) aryl substituted with R¹¹ and R¹²,
(i) heteroaryl substituted with R¹³ and R¹⁴,
(ii) cycloalkyl substituted with R¹⁵ and R¹⁶; and
(iii) heterocyclyl substituted with R¹⁷ and R¹⁸;
R⁴ is hydrogen or hydroxy; or
R³ and R⁴ together with the carbon atom to which they are attached form a heterocycle or a carbocycle; and
R⁵, R⁶, R⁷, R⁸, R⁹, R¹⁰, R¹¹, R¹², R¹³, R¹⁴, R¹⁵, R¹⁶, R¹⁷ and R¹⁸ are each independently selected from the group consisting of hydrogen, halogen, alkyl, haloalkyl, hydroxy alkyl, alkoxy, aryl, cycloalkyl, haloaryl, haloarylalkyl, alkylsulfonyl, oxo and a fluorescent label;
or a pharmaceutically acceptable salt thereof.

In one embodiment, there is provided a compound of formula (IA), in particular of formula (I), as described herein, or a pharmaceutically acceptable salt thereof, wherein L is —C(R³R⁴)— and A is aryl substituted with R⁵, R⁶ and R⁷.

In one embodiment, there is provided a compound of formula (IA), in particular of formula (I), as described herein, or a pharmaceutically acceptable salt thereof, wherein L is a covalent bond and A is heteroaryl substituted with R⁸, R⁹ and R¹⁰.

In one embodiment, the compound of formula (IA) is a compound of formula (IB), or a pharmaceutically acceptable salt thereof, wherein A, n, R¹, R² and R³ are as defined herein.

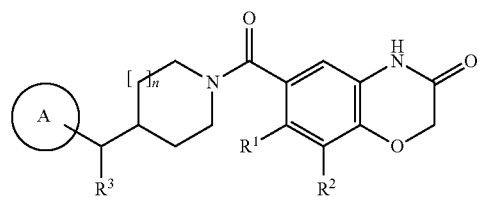

IB

In one embodiment, the compound of formula (I) is a compound of formula (IB), or a pharmaceutically acceptable salt thereof, wherein A, n, R¹, R² and R³ are as defined herein.

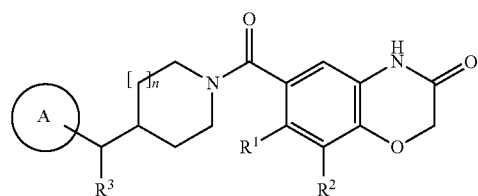

IB

In one embodiment, the compound of formula (IA) is a compound of formula (IC), or a pharmaceutically acceptable salt thereof, wherein A, n, R¹ and R² are as defined herein.

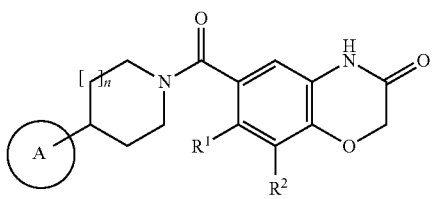

IC

In one embodiment, the compound of formula (I) is a compound of formula (IC), or a pharmaceutically acceptable salt thereof, wherein A, n, $R^1$ and $R^2$ are as defined herein.

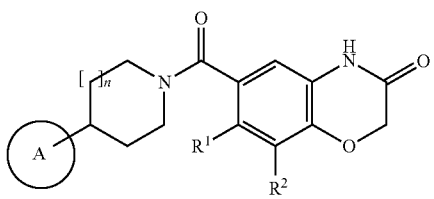

IC

In one embodiment, the compound of formula (IA) is a compound of formula (ID), or a pharmaceutically acceptable salt thereof, wherein A is heteroaryl comprising at least one nitrogen atom and $R^1$, $R^2$, $R^8$, $R^9$, $R^{10}$ and n are as defined herein.

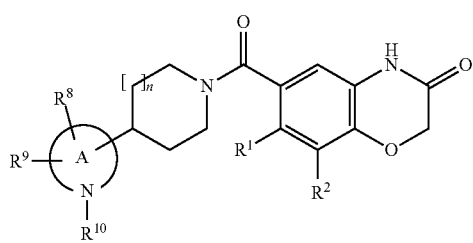

ID

In one embodiment, the compound of formula (I) is a compound of formula (ID), or a pharmaceutically acceptable salt thereof, wherein A is heteroaryl comprising at least one nitrogen atom and $R^1$, $R^2$, $R^8$, $R^9$, $R^{10}$ and n are as defined herein.

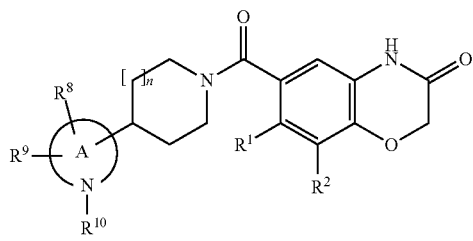

ID

In one embodiment, the compound of formula (IA) is a compound of formula (IE), or a pharmaceutically acceptable salt thereof, wherein $R^1$, $R^2$, $R^8$, $R^9$, $R^{10}$ and n are as defined herein.

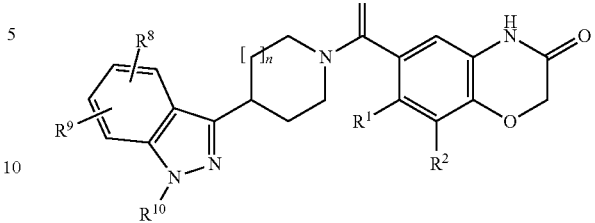

IE

In one embodiment, the compound of formula (I) is a compound of formula (IE), or a pharmaceutically acceptable salt thereof, wherein $R^1$, $R^2$, $R^8$, $R^9$, $R^{10}$ and n are as defined herein.

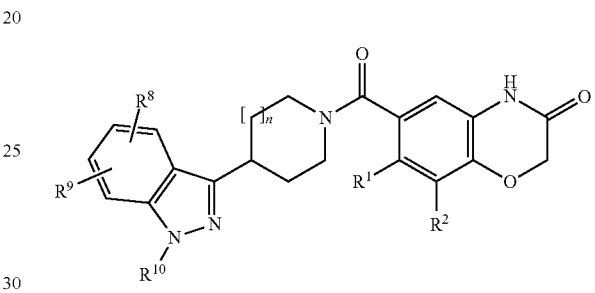

IE

In one embodiment, there is provided a compound of formula (IA), in particular of formula (I) as described herein, or a pharmaceutically acceptable salt thereof, wherein n is 0 or 1.

In a preferred embodiment, there is provided a compound of formula (IA), in particular of formula (I) as described herein, or a pharmaceutically acceptable salt thereof, wherein n is 1.

In one embodiment, there is provided a compound of formula (IA), as described herein, wherein m is 0 or 1.

In a preferred embodiment, there is provided a compound of formula (IA) as described herein, wherein m is 1.

In a preferred embodiment, there is provided a compound of formula (IA) as described herein, wherein m and n are both 1.

In a preferred embodiment, there is provided a compound of formula (IA) as described herein, wherein Y is O.

In one embodiment, there is provided a compound of formula (IA) as described herein, wherein Y is $CH_2$.

In one embodiment, there is provided a compound of formula (IA), in particular of formula (I) as described herein, or a pharmaceutically acceptable salt thereof, wherein A is selected from the group consisting of
 (i) monocyclic aryl substituted with $R^5$, $R^6$ and $R^7$; and
 (ii) heteroaryl substituted with $R^8$, $R^9$ and $R^{10}$, wherein said heteroaryl comprises 1 or 2 heteroatoms selected from the group consisting of O and N.

In one embodiment, there is provided a compound of formula (IA), in particular of formula (I) as described herein, or a pharmaceutically acceptable salt thereof, wherein A is selected from the group consisting of
 (i) monocyclic aryl substituted with $R^5$, $R^6$ and $R^7$; and
 (ii) bicyclic heteroaryl substituted with $R^8$, $R^{10}$ and $R^{11}$, wherein said bicyclic heteroaryl comprises 1 or 2 heteroatoms selected from the group consisting of O and N.

In a preferred embodiment, there is provided a compound of formula (IA), in particular of formula (I) as described herein, or a pharmaceutically acceptable salt thereof, wherein A is selected from the group consisting of
(i) phenyl substituted with $R^5$, $R^6$ and $R^7$; and
(ii) heteroaryl substituted with $R^8$, $R^9$ and $R^{10}$, wherein said heteroaryl is selected from the group consisting of indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl and 1,2-benzoxazol-7-yl.

In one embodiment, there is provided a compound of formula (IA), in particular of formula (I) as described herein, or a pharmaceutically acceptable salt thereof, wherein $R^1$ is hydrogen, haloalkoxy or halogen.

In one embodiment, there is provided a compound of formula (IA), in particular of formula (I) as described herein, or a pharmaceutically acceptable salt thereof, wherein $R^1$ is hydrogen or halogen.

In a preferred embodiment, there is provided a compound of formula (IA), in particular of formula (I) as described herein, or a pharmaceutically acceptable salt thereof, wherein $R^1$ is hydrogen or F.

In a preferred embodiment, there is provided a compound of formula (IA), in particular of formula (I) as described herein, or a pharmaceutically acceptable salt thereof, wherein $R^2$ is hydrogen or alkoxy.

In a preferred embodiment, there is provided a compound of formula (IA), in particular of formula (I) as described herein, or a pharmaceutically acceptable salt thereof, wherein $R^2$ is hydrogen.

In one embodiment, there is provided a compound of formula (IA), in particular of formula (I) as described herein, or a pharmaceutically acceptable salt thereof, wherein
(i) $R^3$ is aryl substituted with $R^{11}$ and $R^{12}$; and $R^4$ is hydrogen or hydroxy; or
(ii) $R^3$ is heteroaryl substituted with $R^{13}$ and $R^{14}$, and $R^4$ is hydrogen; or
(iii) $R^3$ is heterocyclyl substituted with $R^{17}$ and $R^{18}$; and $R^4$ is hydrogen; or
(iv) $R^3$ and $R^4$ together with the carbon atom to which they are attached form a heterocycle or a carbocycle.

In one embodiment, there is provided a compound of formula (IA), in particular of formula (I) as described herein, or a pharmaceutically acceptable salt thereof, wherein
$R^3$ is aryl substituted with $R^{11}$ and $R^{12}$; and
$R^4$ is hydrogen or hydroxy; or
$R^3$ and $R^4$ together with the carbon atom to which they are attached form a heterocycle or a carbocycle.

In a preferred embodiment, there is provided a compound of formula (IA), in particular of formula (I) as described herein, or a pharmaceutically acceptable salt thereof, wherein
$R^3$ is aryl substituted with $R^{11}$ and $R^{12}$; and
$R^4$ is hydrogen; or
$R^3$ and $R^4$ together with the carbon atom to which they are attached form a monocyclic heterocycle comprising 1 oxygen atom or a monocyclic carbocycle.

In a particularly preferred embodiment, there is provided a compound of formula (IA), in particular of formula (I) as described herein, or a pharmaceutically acceptable salt thereof, wherein
$R^3$ is phenyl substituted with $R^{11}$ and $R^{12}$; and
$R^4$ is hydrogen; or
$R^3$ and $R^4$ together with the carbon atom to which they are attached form an oxolane or a cyclopropyl.

In one embodiment, there is provided a compound of formula (IA) in particular of formula (I) as described herein, or a pharmaceutically acceptable salt thereof, wherein
$R^5$ is selected from the group consisting of hydrogen, alkoxy, haloalkyl and halogen;
$R^6$ is selected from the group consisting of hydrogen, alkoxy and halogen; and
$R^7$ is selected from the group consisting of hydrogen and alkoxy.

In a preferred embodiment, there is provided a compound of formula (IA), in particular of formula (I) as described herein, or a pharmaceutically acceptable salt thereof, wherein $R^5$, $R^6$ and $R^7$ are hydrogen.

In a preferred embodiment, there is provided a compound of formula (IA), in particular of formula (I) as described herein, or a pharmaceutically acceptable salt thereof, wherein A is selected from the group consisting of
(i) monocyclic aryl substituted with $R^5$, $R^6$ and $R^7$; wherein
$R^5$ is selected from the group consisting of hydrogen, haloalkyl and halogen; and
$R^6$ is selected from the group consisting of hydrogen and halogen; and
$R^7$ is hydrogen; and
(ii) bicyclic heteroaryl substituted with $R^8$, $R^9$ and $R^{10}$, wherein said bicyclic heteroaryl comprises 1 or 2 heteroatoms selected from the group consisting of O and N, wherein
$R^8$ is selected from the group consisting of halogen and alkyl; and
$R^9$ and $R^{10}$ are each independently selected from the group consisting of hydrogen and halogen.

In a particularly preferred embodiment, there is provided a compound of formula (IA) in particular of formula (I) as described herein, or a pharmaceutically acceptable salt thereof, wherein A is selected from the group consisting of
(i) phenyl; and
(ii) heteroaryl substituted with $R^8$, $R^9$ and $R^{10}$, wherein said heteroaryl is selected from the group consisting of indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl and 1,2-benzoxazol-7-yl;
$R^8$ is selected from the group consisting of F, Cl and methyl; and
$R^9$ and $R^{10}$ are each independently selected from the group consisting of hydrogen, F and Cl.

In one embodiment, there is provided a compound of formula (IA), in particular of formula (I) as described herein, or a pharmaceutically acceptable salt thereof, wherein
$R^8$ is selected from the group consisting of hydrogen, halogen, alkyl, hydroxy alkyl, alkoxy, aryl, cycloalkyl, haloalkyl, haloaryl and haloarylalkyl; and
$R^9$ and $R^{10}$ are each independently selected from the group consisting of hydrogen and halogen.

In one embodiment, there is provided a compound of formula (IA), in particular of formula (I) as described herein, or a pharmaceutically acceptable salt thereof, wherein
$R^8$ is selected from the group consisting of halogen and alkyl; and
$R^9$ and $R^{10}$ are each independently selected from the group consisting of hydrogen and halogen.

In a preferred embodiment, there is provided a compound of formula (IA), in particular of formula (I) as described herein, or a pharmaceutically acceptable salt thereof, wherein $R^8$ is selected from the group consisting of F, Cl and methyl; and $R^9$ and $R^{10}$ are each independently selected from the group consisting of hydrogen, F and Cl.

In one embodiment, there is provided a compound of formula (IA), in particular of formula (I) as described herein, or a pharmaceutically acceptable salt thereof, wherein $R^{11}$ is selected from the group consisting of hydrogen, halogen, alkoxy, haloalkoxy, haloalkoxyalkoxy, alkylsulfonyl and alkyl; and $R^{12}$ is hydrogen or alkoxy.

In one embodiment, there is provided a compound of formula (IA), in particular of formula (I) as described herein, or a pharmaceutically acceptable salt thereof, wherein $R^{11}$ is selected from the group consisting of hydrogen, halogen, alkoxy, haloalkoxy and alkyl; and $R^{12}$ is hydrogen or alkoxy.

In a preferred embodiment, there is provided a compound of formula (IA), in particular of formula (I) as described herein, or a pharmaceutically acceptable salt thereof, wherein $R^{11}$ is halogen or alkoxy; and $R^{12}$ is hydrogen.

In a particularly preferred embodiment, there is provided a compound of formula (IA), in particular of formula (I) as described herein, or a pharmaceutically acceptable salt thereof wherein $R^{11}$ is F or methoxy; and $R^{12}$ is hydrogen.

In one embodiment, there is provided a compound of formula (IA), in particular of formula (I) as described herein, or a pharmaceutically acceptable salt thereof, wherein $R^{13}$ is hydrogen, halogen, alkoxy or alkyl; and $R^{14}$ is hydrogen.

In one embodiment, there is provided a compound of formula (IA), in particular of formula (I) as described herein, or a pharmaceutically acceptable salt thereof, wherein X is N.

In one embodiment, there is provided a compound of formula (IA), in particular of formula (I) as described herein, or a pharmaceutically acceptable salt thereof, wherein X is CH.

In one embodiment, there is provided a compound of formula (IA) as described herein, or a pharmaceutically acceptable salt thereof, wherein X is $C(sp^2)$ and together with L forms a group

(E,Z)

(wherein the asterisk indicates the point of attachment to ring A.

In one embodiment, there is provided a compound of formula (I) as described herein, or a pharmaceutically acceptable salt thereof, wherein X is CH or N;

L is —C($R^3R^4$)— or a covalent bond;

n is 0 or 1;

A is selected from the group consisting of
(i) aryl substituted with $R^5$, $R^6$ and $R^7$; and
(ii) heteroaryl substituted with $R^8$, $R^9$ and $R^{10}$;

$R^1$ is hydrogen, haloalkoxy or halogen;

$R^2$ is hydrogen or alkoxy;

(i) $R^3$ is aryl substituted with $R^{11}$ and $R^{12}$; and
$R^4$ is hydrogen or hydroxy; or
(ii) $R^3$ is heteroaryl substituted with $R^{13}$ and $R^{14}$, and
$R^4$ is hydrogen; or
(iii) $R^3$ is heterocyclyl substituted with $R^{17}$ and $R^{18}$; and
$R^4$ is hydrogen; or
(iv) $R^3$ and $R^4$ together with the carbon atom to which they are attached form a heterocycle or a carbocycle;

$R^5$ is selected from the group consisting of hydrogen, alkoxy, haloalkyl and halogen;

$R^6$ is selected from the group consisting of hydrogen, alkoxy and halogen;

$R^7$ is selected from the group consisting of hydrogen and alkoxy;

$R^8$ is selected from the group consisting of hydrogen, halogen, alkyl, hydroxy alkyl, alkoxy, aryl, cycloalkyl, haloalkyl, haloaryl and haloarylalkyl;

$R^9$ and $R^{10}$ are each independently selected from the group consisting of hydrogen and halogen;

$R^{11}$ is selected from the group consisting of hydrogen, halogen, alkoxy, haloalkoxy, haloalkoxy alkoxy, alkylsulfonyl and alkyl;

$R^{12}$ is hydrogen or alkoxy;

$R^{13}$ is selected from the group consisting of hydrogen, halogen, alkoxy and alkyl;

$R^{14}$ is hydrogen;

$R^{17}$ is oxo; and $R^{18}$ is alkyl;

or a pharmaceutically acceptable salt thereof.

In one embodiment, there is provided a compound of formula (I) as described herein, or a pharmaceutically acceptable salt thereof, wherein X is CH or N;

L is —C($R^3R^4$)— or a covalent bond;

n is 0 or 1;

A is selected from the group consisting of
(i) aryl substituted with $R^5$, $R^6$ and $R^7$; and
(ii) heteroaryl substituted with $R^8$, $R^9$ and $R^{10}$;

$R^1$ is hydrogen or halogen;

$R^2$ is hydrogen;

$R^3$ is aryl substituted with $R^{11}$ and $R^{12}$;

$R^4$ is hydrogen or hydroxy; or $R^3$ and $R^4$ together with the carbon atom to which they are attached form a heterocycle or a carbocycle;

$R^5$ is selected from the group consisting of hydrogen, alkoxy, haloalkyl and halogen;

$R^6$ is selected from the group consisting of hydrogen, alkoxy and halogen;

$R^7$ is hydrogen or alkoxy;

$R^8$ is selected from the group consisting of hydrogen, halogen, alkyl, hydroxy alkyl, alkoxy, aryl, cycloalkyl, haloalkyl, haloaryl and haloarylalkyl;

$R^9$ and $R^{10}$ are each independently selected from the group consisting of hydrogen and halogen;

$R^{11}$ is selected from the group consisting of hydrogen, halogen, alkoxy, haloalkoxy and alkyl; and $R^{12}$ is hydrogen or alkoxy.

In a preferred embodiment, there is provided a compound of formula (I) as described herein, or a pharmaceutically acceptable salt thereof, wherein X is CH;

L is —C($R^3R^4$)— or a covalent bond;

n is 1;

A is selected from the group consisting of
(i) monocyclic aryl substituted with $R^5$, $R^6$ and $R^7$; and
(ii) bicyclic heteroaryl substituted with $R^8$, $R^9$ and $R^{10}$, wherein said bicyclic heteroaryl comprises 1 or 2 heteroatoms selected from the group consisting of O and N;
$R^1$ is hydrogen or halogen;
$R^2$ is hydrogen;
$R^3$ is aryl substituted with $R^{11}$ and $R^{12}$;
$R^4$ is hydrogen; or
$R^3$ and $R^4$ together with the carbon atom to which they are attached form a monocyclic heterocycle comprising 1 oxygen atom or a monocyclic carbocycle;
$R^5$, $R^6$ and $R^7$ are hydrogen;
$R^8$ is selected from the group consisting of halogen and alkyl;
$R^9$ and $R^{10}$ are each independently selected from the group consisting of hydrogen and halogen;
$R^{11}$ is halogen or alkoxy; and
$R^{12}$ is hydrogen.

In a particularly preferred embodiment, there is provided a compound of formula (I) as described herein, or a pharmaceutically acceptable salt thereof, wherein
X is CH;
L is —C($R^3R^4$)— or a covalent bond;
n is 1;
A is selected from the group consisting of
  (i) phenyl; and
  (ii) heteroaryl substituted with $R^8$, $R^9$ and $R^{10}$, wherein said heteroaryl is selected from the group consisting of indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl and 1,2-benzoxazol-7-yl;
$R^1$ is hydrogen or F;
$R^2$ is hydrogen;
$R^3$ is phenyl substituted with $R^{11}$ and $R^{12}$; and
$R^4$ is hydrogen; or
$R^3$ and $R^4$ together with the carbon atom to which they are attached form an oxolane or a cyclopropyl;
$R^8$ is selected from the group consisting of F, Cl and methyl; and
$R^9$ and $R^{10}$ are each independently selected from the group consisting of hydrogen, F and Cl;
$R^{11}$ is F or methoxy; and
$R^{12}$ is hydrogen.

In one embodiment, there is provided a compound of formula (IA) as described herein, wherein said compound of formula (IA) is selected from the group consisting of:
6-(4-Benzhydrylpiperidine-1-carbonyl)-7-fluoro-4H-1,4-benzoxazin-3-one,
6-(4-Benzhydrylpiperidine-1-carbonyl)-4H-1,4-benzoxazin-3-one,
6-[4-[Bis(4-fluorophenyl)methyl]piperidine-1-carbonyl]-4H-1,4-benzoxazin-3-one,
6-[4-[(3,4-Dichlorophenyl)-phenylmethyl]piperidine-1-carbonyl]-4H-1,4-benzoxazin-3-one,
6-[4-[Hydroxy(diphenyl)methyl]piperidine-1-carbonyl]-4H-1,4-benzoxazin-3-one,
6-[4-[(R)-(4-fluorophenyl)-phenylmethyl]piperidine-1-carbonyl]-4H-1,4-benzoxazin-3-one,
6-[4-[(S)-(4-fluorophenyl)-phenylmethyl]piperidine-1-carbonyl]-4H-1,4-benzoxazin-3-one,
6-[4-[(R)-(3,4-dimethoxyphenyl)-phenylmethyl]piperidine-1-carbonyl]-4H-1,4-benzoxazin-3-one,
6-[4-[(S)-(3,4-dimethoxy phenyl)-phenylmethyl]piperidine-1-carbonyl]-4H-1,4-benzoxazin-3-one,
6-[4-[(R)-(4-methoxyphenyl)-phenylmethyl]piperidine-1-carbonyl]-4H-1,4-benzoxazin-3-one,
6-[4-[(S)-(4-methoxyphenyl)-phenylmethyl]piperidine-1-carbonyl]-4H-1,4-benzoxazin-3-one,
6-[4-[(R)-(3-methoxyphenyl)-phenylmethyl]piperidine-1-carbonyl]-4H-1,4-benzoxazin-3-one,
6-[4-[(S)-(3-methoxyphenyl)-phenylmethyl]piperidine-1-carbonyl]-4H-1,4-benzoxazin-3-one,
6-[4-[(R)-(4-methylphenyl)-phenylmethyl]piperidine-1-carbonyl]-4H-1,4-benzoxazin-3-one,
6-[4-[(S)-(4-methylphenyl)-phenylmethyl]piperidine-1-carbonyl]-4H-1,4-benzoxazin-3-one,
6-[4-[(R)-(3-methylphenyl)-phenylmethyl]piperidine-1-carbonyl]-4H-1,4-benzoxazin-3-one,
6-[4-[(S)-(3-methylphenyl)-phenylmethyl]piperidine-1-carbonyl]-4H-1,4-benzoxazin-3-one,
6-[4-(1H-indol-3-yl)piperidine-1-carbonyl]-4H-1,4-benzoxazin-3-one,
6-[4-(5-chloro-6-fluoro-1H-indol-3-yl)piperidine-1-carbonyl]-4H-1,4-benzoxazin-3-one,
6-[4-(5-chloro-1H-indol-3-yl)piperidine-1-carbonyl]-4H-1,4-benzoxazin-3-one,
6-[4-(6-chloro-1H-indol-3-yl)piperidine-1-carbonyl]-4H-1,4-benzoxazin-3-one,
6-[4-(5-fluoro-1H-indol-3-yl)piperidine-1-carbonyl]-4H-1,4-benzoxazin-3-one,
6-[4-(6-fluoro-1H-indol-3-yl)piperidine-1-carbonyl]-4H-1,4-benzoxazin-3-one,
6-[4-(5-methoxy-1H-indol-3-yl)piperidine-1-carbonyl]-4H-1,4-benzoxazin-3-one,
6-[4-[6-(trifluoromethyl)-1H-indol-3-yl]piperidine-1-carbonyl]-4H-1,4-benzoxazin-3-one,
6-[4-(5-chloro-6-fluoro-1-methylindol-3-yl)piperidine-1-carbonyl]-7-fluoro-4H-1,4-benzoxazin-3-one,
6-[4-(5-chloro-6-fluoro-1-methylindol-3-yl)piperidine-1-carbonyl]-4H-1,4-benzoxazin-3-one,
6-[4-(5-chloro-1-methylindol-3-yl)piperidine-1-carbonyl]-7-fluoro-4H-1,4-benzoxazin-3-one,
6-[4-(6-chloro-1-methylindol-3-yl)piperidine-1-carbonyl]-7-fluoro-4H-1,4-benzoxazin-3-one,
6-[4-(6-chloro-1-methylindol-3-yl)piperidine-1-carbonyl]-4H-1,4-benzoxazin-3-one,
6-[4-(1-methylindol-3-yl)piperidine-1-carbonyl]-4H-1,4-benzoxazin-3-one,
6-[4-(5-fluoro-1-methylindol-3-yl)piperidine-1-carbonyl]-4H-1,4-benzoxazin-3-one,
6-[4-(6-fluoro-1-methylindol-3-yl)piperidine-1-carbonyl]-4H-1,4-benzoxazin-3-one,
6-[4-(6-chloro-1-cyclopropylindol-3-yl)piperidine-1-carbonyl]-4H-1,4-benzoxazin-3-one,
6-[4-[1-[(3-chlorophenyl)methyl]indol-3-yl]piperidine-1-carbonyl]-4H-1,4-benzoxazin-3-one,
6-[4-(1H-indazol-3-yl)piperidine-1-carbonyl]-4H-1,4-benzoxazin-3-one,
6-[4-[6-fluoro-1-(2-hydroxyethyl)indazol-3-yl]piperidine-1-carbonyl]-4H-1,4-benzoxazin-3-one,
6-[4-(6-fluoro-1-propan-2-ylindazol-3-yl)piperidine-1-carbonyl]-4H-1,4-benzoxazin-3-one,
6-[4-(6-chloro-1-methylindazol-3-yl)piperidine-1-carbonyl]-4H-1,4-benzoxazin-3-one,
6-[4-(1H-indol-2-yl)piperidine-1-carbonyl]-4H-1,4-benzoxazin-3-one,
6-[4-(5-methoxy-2-methyl-1H-indol-3-yl)piperidine-1-carbonyl]-4H-1,4-benzoxazin-3-one,
6-[4-(1-benzothiophen-3-yl)piperidine-1-carbonyl]-4H-1,4-benzoxazin-3-one,
6-[4-(6-fluoro-1H-indazol-3-yl)piperidine-1-carbonyl]-4H-1,4-benzoxazin-3-one, 6-[4-[5-(4-chlorophenyl)-1H-pyrazol-3-yl]piperidine-1-carbonyl]-4H-1,4-benzoxazin-3-one,
6-[4-(1H-pyrrolo[2,3-b]pyridin-3-yl)piperidine-1-carbonyl]-4H-1,4-benzoxazin-3-one,
6-[4-(6-chloro-1H-indol-2-yl)piperidine-1-carbonyl]-4H-1,4-benzoxazin-3-one,
6-[4-(5-chloro-2-methyl-1H-indol-3-yl)piperidine-1-carbonyl]-4H-1,4-benzoxazin-3-one,
6-[4-(5-phenyl-1,3,4-oxadiazol-2-yl)piperidine-1-carbonyl]-4H-1,4-benzoxazin-3-one,
6-[4-(benzimidazol-1-yl)piperidine-1-carbonyl]-4H-1,4-benzoxazin-3-one,
6-[4-[6-(trifluoromethyl)-1,2-benzoxazol-3-yl]piperidine-1-carbonyl]-4H-1,4-benzoxazin-3-one,
6-[4-(6-fluoro-1,2-benzoxazol-3-yl)piperidine-1-carbonyl]-4H-1,4-benzoxazin-3-one,
6-[4-(5-fluoro-1,2-benzoxazol-3-yl)piperidine-1-carbonyl]-4H-1,4-benzoxazin-3-one,
6-[4-[2-(4-chlorophenyl)oxolan-2-yl]piperidine-1-carbonyl]-4H-1,4-benzoxazin-3-one,
6-[4-[2-(4-bromophenyl)-1,3-dioxolan-2-yl]piperidine-1-carbonyl]-4H-1,4-benzoxazin-3-one,
6-[4-(1-phenylcyclopropyl)piperidine-1-carbonyl]-4H-1,4-benzoxazin-3-one,
6-[3-(3-chlorophenyl)pyrrolidine-1-carbonyl]-4H-1,4-benzoxazin-3-one,
6-[3-[4-(trifluoromethyl)pyrimidin-2-yl]pyrrolidine-1-carbonyl]-4H-1,4-benzoxazin-3-one,
6-[4-[(4-methoxyphenyl)-phenyl-methyl]piperidine-1-carbonyl]-4H-1,4-benzoxazin-3-one,
6-[4-[m-tolyl(phenyl)methyl]piperidine-1-carbonyl]-4H-1,4-benzoxazin-3-one,
6-[4-[indol-1-yl(phenyl)methyl]piperidine-1-carbonyl]-4H-1,4-benzoxazin-3-one,
6-[4-[[4-(2-fluoroethoxy)phenyl]-(4-fluorophenyl)methyl]piperidine-1-carbonyl]-4H-1,4-benzoxazin-3-one,
6-[4-[(R)-(2-fluoro-4-pyridyl)-phenyl-methyl]piperidine-1-carbonyl]-4H-1,4-benzoxazin-3-one,
6-[4-[(S)-(2-fluoro-4-pyridyl)-phenyl-methyl]piperidine-1-carbonyl]-4H-1,4-benzoxazin-3-one,
6-[4-[(S)-[4-(2-fluoroethoxy)phenyl]-(4-fluorophenyl)methyl]piperidine-1-carbonyl]-4H-1,4-benzoxazin-3-one,
6-[4-[(R)-[4-(2-fluoroethoxy)phenyl]-(4-fluorophenyl)methyl]piperidine-1-carbonyl]-4H-1,4-benzoxazin-3-one,
6-[4-[(R)-3-[2-(2-fluoroethoxy)ethoxy]phenyl]-phenyl-methyl]piperidine-1-carbonyl]-4H-1,4-benzoxazin-3-one,
6-[4-[(S)-3-[2-(2-fluoroethoxy)ethoxy]phenyl]-phenyl-methyl]piperidine-1-carbonyl]-4H-1,4-benzoxazin-3-one,
6-[4-(6-methoxy-1-methyl-indol-3-yl)piperidine-1-carbonyl]-4H-1,4-benzoxazin-3-one,
6-[4-[(4-fluorophenyl)-(4-methoxyphenyl)methyl]piperidine-1-carbonyl]-4H-1,4-benzoxazin-3-one,
6-[4-[(S)-(4-fluorophenyl)-(4-methoxyphenyl)methyl]piperidine-1-carbonyl]-4H-1,4-benzoxazin-3-one,
6-[4-[(R)-(4-fluorophenyl)-(4-methoxyphenyl)methyl]piperidine-1-carbonyl]-4H-1,4-benzoxazin-3-one,
6-[4-[[3-(2-fluoroethoxy)phenyl]-phenyl-methyl]piperidine-1-carbonyl]-4H-1,4-benzoxazin-3-one,
6-[4-[[4-(2-fluoroethoxy)phenyl]-phenyl-methyl]piperidine-1-carbonyl]-4H-1,4-benzoxazin-3-one,
6-[4-[(S)-(3-fluorophenyl)-phenyl-methyl]piperidine-1-carbonyl]-4H-1,4-benzoxazin-3-one,
6-[4-[(R)-(3-fluorophenyl)-phenyl-methyl]piperidine-1-carbonyl]-4H-1,4-benzoxazin-3-one,
6-[4-[(R)-[3-(2-fluoroethoxy)phenyl]-(4-fluorophenyl)methyl]piperidine-1-carbonyl]-4H-1,4-benzoxazin-3-one,
6-[4-[(S)-[3-(2-fluoroethoxy)phenyl]-(4-fluorophenyl)methyl]piperidine-1-carbonyl]-4H-1,4-benzoxazin-3-one,
6-[4-[(2-fluoro-3-pyridyl)-phenyl-methyl]piperidine-1-carbonyl]-4H-1,4-benzoxazin-3-one,
6-[4-[(R)-[4-(2-fluoroethoxy)phenyl]-phenyl-methyl]piperidine-1-carbonyl]-4H-1,4-benzoxazin-3-one,
6-[4-[(S)-[4-(2-fluoroethoxy)phenyl]-phenyl-methyl]piperidine-1-carbonyl]-4H-1,4-benzoxazin-3-one,
6-[4-[(S)-[3-(2-fluoroethoxy)phenyl]-phenyl-methyl]piperidine-1-carbonyl]-4H-1,4-benzoxazin-3-one,
6-[4-[(3-fluorophenyl)-phenyl-methyl]piperidine-1-carbonyl]-4H-1,4-benzoxazin-3-one,
6-(4-benzhydrylpiperazine-1-carbonyl)-4H-1,4-benzoxazin-3-one,
6-[4-[bis(4-fluorophenyl)methyl]piperazine-1-carbonyl]-4H-1,4-benzoxazin-3-one,
6-[4-[4-chloro-3-(trifluoromethyl)phenyl]piperazine-1-carbonyl]-4H-1,4-benzoxazin-3-one,
6-[4-(3,4-dichlorophenyl)piperazine-1-carbonyl]-4H-1,4-benzoxazin-3-one,
6-[4-(3,5-dichlorophenyl)piperazine-1-carbonyl]-4H-1,4-benzoxazin-3-one,
6-[4-[4-(trifluoromethyl)-2-pyridyl]piperazine-1-carbonyl]-4H-1,4-benzoxazin-3-one,
6-[4-(3,5-dimethoxyphenyl)piperazine-1-carbonyl]-4H-1,4-benzoxazin-3-one,
6-[4-[5-(trifluoromethyl)-2-pyridyl]piperazine-1-carbonyl]-4H-1,4-benzoxazin-3-one,
6-[4-(1,2-benzothiazol-3-yl)piperazine-1-carbonyl]-4H-1,4-benzoxazin-3-one,
6-[4-(3,4,5-trimethoxyphenyl)piperazine-1-carbonyl]-4H-1,4-benzoxazin-3-one;
6-[4-[[4-(2-fluoroethoxy)phenyl]-(4-fluorophenyl)methylene]piperidine-1-carbonyl]-4H-1,4-benzoxazin-3-one;
6-[4-[(S)-3-[2-(2-fluoroethoxy)ethoxy]phenyl]-(4-fluorophenyl)methyl]piperidine-1-carbonyl]-4H-1,4-benzoxazin-3-one;
6-[4-[(R)-3-[2-(2-fluoroethoxy)ethoxy]phenyl]-(4-fluorophenyl)methyl]piperidine-1-carbonyl]-4H-1,4-benzoxazin-3-one;
6-[4-[(S)-4-[2-(2-fluoroethoxy)ethoxy]phenyl]-phenyl-methyl]piperidine-1-carbonyl]-4H-1,4-benzoxazin-3-one;
6-[4-[(R)-4-[2-(2-fluoroethoxy)ethoxy]phenyl]-phenyl-methyl]piperidine-1-carbonyl]-4H-1,4-benzoxazin-3-one;
6-[4-[(S)-(6-fluoro-2-pyridyl)-phenyl-methyl]piperidine-1-carbonyl]-4H-1,4-benzoxazin-3-one;
6-[4-[(R)-(6-fluoro-2-pyridyl)-phenyl-methyl]piperidine-1-carbonyl]-4H-1,4-benzoxazin-3-one;
7-[4-[bis(4-fluorophenyl)methyl]piperidine-1-carbonyl]-5-methoxy-3,4-dihydro-1H-quinolin-2-one;
7-(4-benzhydrylpiperidine-1-carbonyl)-5-methoxy-3,4-dihydro-1H-quinolin-2-one;
6-[4-[(S)-(6-fluoro-3-pyridyl)-phenyl-methyl]piperidine-1-carbonyl]-4H-1,4-benzoxazin-3-one;
6-[4-[(R)-(6-fluoro-3-pyridyl)-phenyl-methyl]piperidine-1-carbonyl]-4H-1,4-benzoxazin-3-one;
6-[4-[(S)-(3,4-dimethoxyphenyl)-(4-fluorophenyl)methyl]piperidine-1-carbonyl]-4H-1,4-benzoxazin-3-one;

6-[4-[(R)-(3,4-dimethoxyphenyl)-(4-fluorophenyl)methyl]
piperidine-1-carbonyl]-4H-1,4-benzoxazin-3-one; 7-[4-
[bis(4-fluorophenyl)methyl]piperidine-1-carbonyl]-5-(2-
fluoroethoxy)-3,4-dihydro-1H-quinolin-2-one;
6-[4-[(R)-[4-[2-(2-fluoroethoxy)ethoxy]phenyl]-(4-fluoro-
phenyl)methyl]piperidine-1-carbonyl]-4H-1,4-benzo-
xazin-3-one;
6-[4-[(S)-[4-[2-(2-fluoroethoxy)ethoxy]phenyl]-(4-fluoro-
phenyl)methyl]piperidine-1-carbonyl]-4H-1,4-benzo-
xazin-3-one;
7-(4-benzhydrylpiperidine-1-carbonyl)-5-(2-fluoroethoxy)-
3,4-dihydro-1H-quinolin-2-one;
6-[4-[(S)-(4-fluorophenyl)-(2-fluoro-4-pyridyl)methyl]pip-
eridine-1-carbonyl]-4H-1,4-benzoxazin-3-one;
6-[4-[(R)-(4-fluorophenyl)-(2-fluoro-4-pyridyl)methyl]pip-
eridine-1-carbonyl]-4H-1,4-benzoxazin-3-one;
6-[4-[(S)-(4-fluorophenyl)-(p-tolyl)methyl]piperidine-1-
carbonyl]-4H-1,4-benzoxazin-3-one;
6-[4-[(R)-(4-fluorophenyl)-(p-tolyl)methyl]piperidine-1-
carbonyl]-4H-1,4-benzoxazin-3-one;
6-[4-[(S)-(4-fluorophenyl)-(6-fluoro-3-pyridyl)methyl]pip-
eridine-1-carbonyl]-4H-1,4-benzoxazin-3-one;
6-[4-[(R)-(4-fluorophenyl)-(6-fluoro-3-pyridyl)methyl]pip-
eridine-1-carbonyl]-4H-1,4-benzoxazin-3-one;
6-[4-[(R)-(3,4-dimethoxyphenyl)-(2-pyridyl)methyl]piperi-
dine-1-carbonyl]-4H-1,4-benzoxazin-3-one;
6-[4-[(S)-(3,4-dimethoxyphenyl)-(2-pyridyl)methyl]piperi-
dine-1-carbonyl]-4H-1,4-benzoxazin-3-one;
6-[4-[(S)-(4-fluorophenyl)-(6-fluoro-2-pyridyl)methyl]pip-
eridine-1-carbonyl]-4H-1,4-benzoxazin-3-one;
6-[4-[(R)-(4-fluorophenyl)-(6-fluoro-2-pyridyl)methyl]pip-
eridine-1-carbonyl]-4H-1,4-benzoxazin-3-one;
6-[4-[(R)-(4-fluorophenyl)-(3-methoxyphenyl)methyl]pip-
eridine-1-carbonyl]-4H-1,4-benzoxazin-3-one;
6-[4-[(S)-(4-fluorophenyl)-(3-methoxyphenyl)methyl]pip-
eridine-1-carbonyl]-4H-1,4-benzoxazin-3-one;
6-[4-[(R)-(3,4-dimethoxyphenyl)-(3-pyridyl)methyl]piperi-
dine-1-carbonyl]-4H-1,4-benzoxazin-3-one;
6-[4-[(S)-(3,4-dimethoxyphenyl)-(3-pyridyl)methyl]piperi-
dine-1-carbonyl]-4H-1,4-benzoxazin-3-one;
6-(3-benzhydrylazetidine-1-carbonyl)-4H-1,4-benzoxazin-
3-one;
6-[4-[(S)-(3,4-dimethoxyphenyl)-(4-pyridyl)methyl]piperi-
dine-1-carbonyl]-4H-1,4-benzoxazin-3-one;
6-[4-[(R)-(3,4-dimethoxyphenyl)-(4-pyridyl)methyl]piperi-
dine-1-carbonyl]-4H-1,4-benzoxazin-3-one;
6-[3-[(3,4-dimethoxyphenyl)-phenyl-methyl]azetidine-1-
carbonyl]-4H-1,4-benzoxazin-3-one;
6-[4-[(S)-(3-methylsulfonylphenyl)-phenyl-methyl]piperi-
dine-1-carbonyl]-4H-1,4-benzoxazin-3-one;
6-[4-[(R)-(3-methylsulfonylphenyl)-phenyl-methyl]piperi-
dine-1-carbonyl]-4H-1,4-benzoxazin-3-one;
6-[3-[phenyl-[4-(trifluoromethyl)phenyl]methyl]azetidine-
1-carbonyl]-4H-1,4-benzoxazin-3-one;
6-[3-[(3-methoxyphenyl)-phenyl-methyl]azetidine-1-carbo-
nyl]-4H-1,4-benzoxazin-3-one;
6-[4-[(S)-(4-methylsulfonylphenyl)-phenyl-methyl]piperi-
dine-1-carbonyl]-4H-1,4-benzoxazin-3-one;
6-[4-[(R)-(4-methylsulfonylphenyl)-phenyl-methyl]piperi-
dine-1-carbonyl]-4H-1,4-benzoxazin-3-one;
6-[4-[(S)-[3-(2-fluoroethoxy)-4-methoxy-phenyl]-phenyl-
methyl]piperidine-1-carbonyl]-4H-1,4-benzoxazin-3-
one;
6-[4-[(R)-[3-(2-fluoroethoxy)-4-methoxy-phenyl]-phenyl-
methyl]piperidine-1-carbonyl]-4H-1,4-benzoxazin-3-
one;

6-[4-[(S)-(2-methoxy-4-pyridyl)-phenyl-methyl]piperidine-
1-carbonyl]-4H-1,4-benzoxazin-3-one;
6-[4-[(R)-(2-methoxy-4-pyridyl)-phenyl-methyl]piperidine-
1-carbonyl]-4H-1,4-benzoxazin-3-one;
6-[4-[(S)-[4-(2-fluoroethoxy)-3-methoxy-phenyl]-phenyl-
methyl]piperidine-1-carbonyl]-4H-1,4-benzoxazin-3-
one;
6-[4-[(R)-[4-(2-fluoroethoxy)-3-methoxy-phenyl]-phenyl-
methyl]piperidine-1-carbonyl]-4H-1,4-benzoxazin-3-
one;
6-[4-[(S)-(1-methylpyrazol-4-yl)-phenyl-methyl]piperidine-
1-carbonyl]-4H-1,4-benzoxazin-3-one;
6-[4-[(R)-(1-methylpyrazol-4-yl)-phenyl-methyl]piperi-
dine-1-carbonyl]-4H-1,4-benzoxazin-3-one;
6-[4-[(S)-(1-methyl-2-oxo-4-pyridyl)-phenyl-methyl]pip-
eridine-1-carbonyl]-4H-1,4-benzoxazin-3-one; or
6-[4-[(R)-(1-methyl-2-oxo-4-pyridyl)-phenyl-methyl]pip-
eridine-1-carbonyl]-4H-1,4-benzoxazin-3-one;
or a pharmaceutically acceptable salt thereof.

In a preferred embodiment, there is provided a compound of formula (IA) as described herein, wherein said compound of formula (IA) is: selected from the group consisting of
6-(4-Benzhydrylpiperidine-1-carbonyl)-7-fluoro-4H-1,4-
benzoxazin-3-one,
6-(4-Benzhydrylpiperidine-1-carbonyl)-4H-1,4-benzo-
xazin-3-one,
6-[4-[Bis(4-fluorophenyl)methyl]piperidine-1-carbonyl]-
4H-1,4-benzoxazin-3-one,
6-[4-[(R)-(4-fluorophenyl)-phenylmethyl]piperidine-1-car-
bonyl]-4H-1,4-benzoxazin-3-one,
6-[4-[(S)-(4-fluorophenyl)-phenylmethyl]piperidine-1-car-
bonyl]-4H-1,4-benzoxazin-3-one,
6-[4-[(R)-(4-methoxyphenyl)-phenylmethyl]piperidine-1-
carbonyl]-4H-1,4-benzoxazin-3-one,
6-[4-[(S)-(4-methoxyphenyl)-phenylmethyl]piperidine-1-
carbonyl]-4H-1,4-benzoxazin-3-one,
6-[4-[(R)-(3-methoxyphenyl)-phenylmethyl]piperidine-1-
carbonyl]-4H-1,4-benzoxazin-3-one,
6-[4-[(S)-(3-methoxyphenyl)-phenylmethyl]piperidine-1-
carbonyl]-4H-1,4-benzoxazin-3-one,
6-[4-(5-chloro-6-fluoro-1H-indol-3-yl)piperidine-1-carbo-
nyl]-4H-1,4-benzoxazin-3-one,
6-[4-(5-chloro-1H-indol-3-yl)piperidine-1-carbonyl]-4H-1,
4-benzoxazin-3-one,
6-[4-(5-chloro-6-fluoro-1-methylindol-3-yl)piperidine-1-
carbonyl]-7-fluoro-4H-1,4-benzoxazin-3-one,
6-[4-(5-chloro-6-fluoro-1-methylindol-3-yl)piperidine-1-
carbonyl]-4H-1,4-benzoxazin-3-one,
6-[4-(5-chloro-1-methylindol-3-yl)piperidine-1-carbonyl]-
7-fluoro-4H-1,4-benzoxazin-3-one,
6-[4-(6-chloro-1-methylindol-3-yl)piperidine-1-carbonyl]-
7-fluoro-4H-1,4-benzoxazin-3-one,
6-[4-(5-fluoro-1-methylindol-3-yl)piperidine-1-carbonyl]-
4H-1,4-benzoxazin-3-one,
6-[4-(5-fluoro-1,2-benzoxazol-3-yl)piperidine-1-carbonyl]-
4H-1,4-benzoxazin-3-one,
6-[4-[2-(4-chlorophenyl)oxolan-2-yl]piperidine-1-carbo-
nyl]-4H-1,4-benzoxazin-3-one, or
6-[4-(1-phenylcyclopropyl)piperidine-1-carbonyl]-4H-1,4-
benzoxazin-3-one; or a pharmaceutically acceptable salt
thereof.

In one embodiment, there is provided a compound of formula (IA), in particular of formula (I) as described herein, or a pharmaceutically acceptable salt thereof, wherein said compound comprises one or more imaging isotopes for positron-emission tomography (PET), single-photon emission computed tomography (SPECT) and/or autoradiography.

In one embodiment, there is provided a compound of formula (IA), in particular of formula (I) as described herein, or a pharmaceutically acceptable salt thereof, wherein said compound comprises one or more imaging isotopes independently selected from the group consisting of $^2$H, $^3$H, $^{11}$C, $^{14}$C, $^{13}$N, $^{15}$O, $^{18}$F, $^{64}$Cu, $^{124}$I, $^{99}$Tc, $^{77}$Br, $^{61}$Cu, $^{153}$Gd, $^{123}$I, $^{125}$I, $^{131}$I, $^{32}$P, $^{33}$P and $^{35}$S.

In one embodiment, there is provided a compound of formula (IA), in particular of formula (I) as described herein, or a pharmaceutically acceptable salt thereof, wherein said compound comprises one or more imaging isotopes independently selected from the group consisting of $^2$H, $^3$H, $^{11}$C, $^{14}$C, $^{13}$N, $^{15}$O, $^{18}$F, $^{77}$Br, $^{123}$I, $^{125}$I, $^{131}$I, $^{32}$P, $^{33}$P and $^{35}$S.

In one embodiment, there is provided a compound of formula (IA), in particular of formula (I) as described herein, or a pharmaceutically acceptable salt thereof, wherein said compound comprises one or more imaging isotopes independently selected from the group consisting of $^2$H, $^3$H, $^{11}$C, $^{14}$C, $^{13}$N, $^{15}$O, $^{18}$F, and $^{35}$S.

In one embodiment, there is provided a compound of formula (IA), in particular of formula (I) as described herein, or a pharmaceutically acceptable salt thereof, wherein said compound comprises one or more imaging isotopes independently selected from the group consisting of $^{11}$C and $^{18}$F.

In one embodiment, there is provided a compound of formula (IA), in particular of formula (I) as described herein, or a pharmaceutically acceptable salt thereof, wherein said compound comprises one or more fluorescent labels.

In one embodiment, there is provided a compound of formula (IA), in particular of formula (I) as described herein, or a pharmaceutically acceptable salt thereof, wherein at least one of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ is a fluorescent label.

In one embodiment, there is provided a compound of formula (IA), in particular of formula (I) as described herein, or a pharmaceutically acceptable salt thereof, wherein at least one of $R^{11}$, $R^{12}$, $R^{13}$, $R^{14}$, $R^{15}$, $R^{16}$, $R^{17}$ and $R^{18}$ is a fluorescent label.

In a particular embodiment, the present invention provides pharmaceutically acceptable salts of the compounds of formula (IA) as described herein. In a further particular embodiment, the present invention provides compounds according to formula (IA) as described herein.

Processes of Manufacturing

The preparation of compounds of formula (IA) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (IA) contain one or more functional groups which are not stable or are reactive under the reaction conditions of one or more reaction steps, appropriate protecting groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protecting groups can be removed at a later stage of the synthesis using standard methods described in the literature.

If starting materials or intermediates contain stereogenic centers, compounds of formula (IA) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent.

A person skilled in the art will acknowledge that in the synthesis of compounds of formula (IA)—insofar not desired otherwise—an "orthogonal protection group strategy" will be applied, allowing the cleavage of several protective groups one at a time each without affecting other protecting groups in the molecule. The principle of orthogonal protection is well known in the art and has also been described in literature (e.g. Bar any and R. B. Merrifield, *J. Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (IA) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 2nd Edition*, Richard C. Larock. John Wiley & Sons, New York, N.Y. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

The following abbreviations are used in the present text:
AcOH=acetic acid, aq.=aqueous, Boc=tert-butyloxycarbonyl, BnBr=Benzylbromide, n-BuLi=n-butyllithium, n-BuOH=Butanol, CAS RN=chemical abstracts registration number, CHCb=Chloroform, CyPrI=Cyclopropyl iodide, DCM=dichloromethane, DCE=1,2-dichloroethane, DCC=N,N'-dicyclohexylcarbodiimide. DMA=N,N-di methyl acetamide. DMAP=4-dimethylaminopyridine, DMF=N,N-dimethylformamide, EDCI=A-(3-di methylaminopropyl)-N'-ethylcarbodiimide hydrochloride, EtOAc=ethylacetate, EtOH=ethanol, EtI=Ethyl iodide, HATU=O-(7-azabenzotriazol-1-yl)-1,1,3,3-tetramethyluronium hexafluorophosphate, HCl=hydrogen chloride, HPLC=high performance liquid chromatography, HOBt=1-hydroxybenzotriazole, Huenig's base=iPr$_2$NEt=A-ethyl diisopropylamine, iPrI=isopropyl iodide, K$_2$CO$_3$=potassium carbonate, KH=potassium hydride, EDA=lithium diisopropylamine, LiHMDS=lithium bis(trimethylsilyl)amide, MeOH=methanol, RT=room temperature, MeI=methyl iodide, MS=mass spectrum, NaH=sodium hydride, NaEtCCb=sodium hydrogen carbonate, Na₂CO₃=sodium carbonate, NaHMDS=sodium bis(trimethylsilyl)amide, NaOH=sodium hydroxide, Na₂SO₄=sodium sulfate, NH₄Cl=ammonium chloride, sat.=saturated, Pd/C=palladium on activated carbon, Pd(OH)₂=palladium hydroxyde=Pearlman's catalyst, PtO₂=platinum dioxide, PE=petroleum ether, SEC=Supercritical Fluid Chromatography, TBTU=O-benzotriazol-1-yl-N,N,N',N'-tetramethyluronium tetrafluoroborate, TEA=triethylamine, TEA=trifluoroacetic acid, THF=tetrahydrofuran, T₃P=propylphosphonic anhydride.

Compounds of formula (IA) wherein $R^1$, $R^2$, X, L, A, Y, m and n are as defined herein may be synthesized according to the general procedure outlined in Scheme 1.

Benzoxazin-3(4H)-one carboxylic acid compounds 2a can be prepared by a variety of conditions, which may be exemplified by the general synthetic procedures outlined in Schemes 2 and 3.

Scheme 2

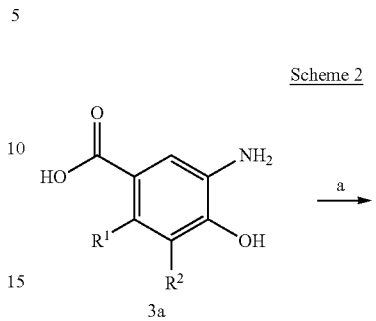

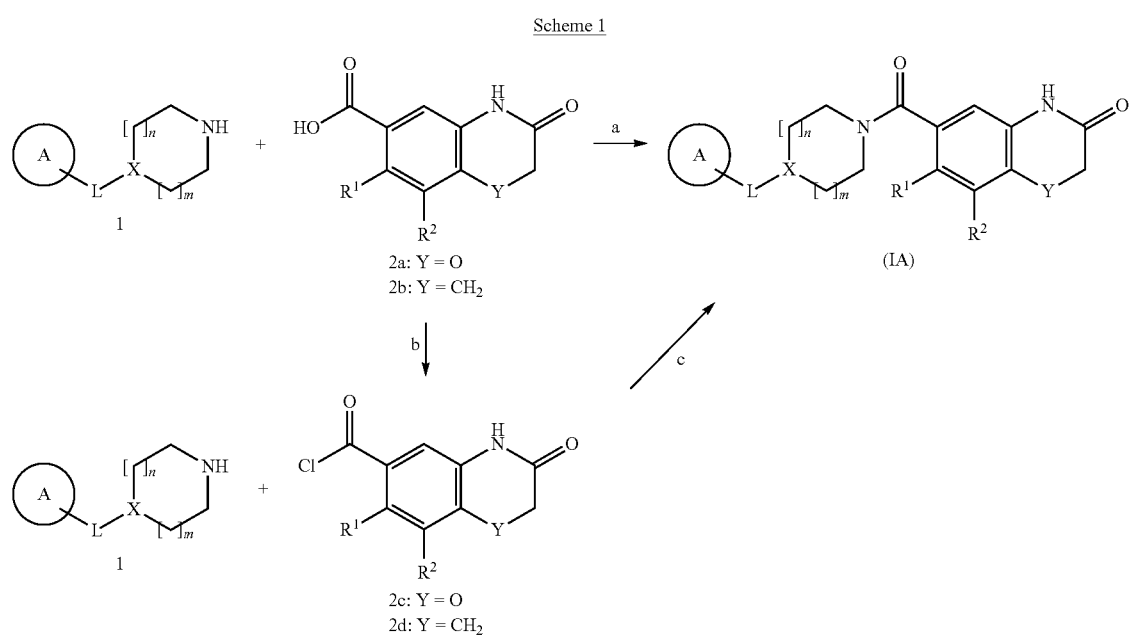

Scheme 1

Reaction of intermediates 1 (either commercially available or prepared by methods described in Schemes 4, 5, 6 and 7 or in literature), wherein A, L, X, m and n are as defined herein, with benzoxazin-3(4H)-one carboxylic acid compounds 2a,b, wherein $R^1$, $R^2$ and Y are as defined herein, gives compounds of formula (IA) (step a). Amide couplings of this type can be accomplished by using one of the well-known coupling reagents such as, DCC, HATU, EDCI, HOBt, TBTU, T3P, etc. and a base like Huenig's base, triethyl amine or DMAP in a suitable solvent like N, A-di methyl formamide. DMA, DCM or dioxane, preferably between 0° C. and room temperature.

Alternatively, the benzoxazin-3(4H)-one carboxylic acid compounds 2a,b can be converted into their acid chlorides 2c,d by treatment with, e.g. thionyl chloride or oxalyl chloride, neat or optionally in a solvent such as DCM (step b). Reaction of the acid chloride 2c,d with intermediates 1 in an appropriate solvent such as DCM or DMF and a base, e.g. NEt₃, Huenig's base, pyridine or DMAP at temperatures ranging from 0° C. to the reflux temperature of the solvent yields compounds of formula (IA) (step c).

-continued

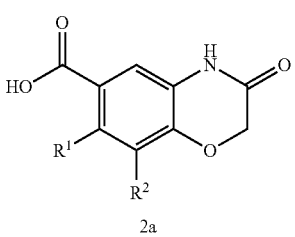

Cyclisation of commercially available 3-amino-4-hydroxy-benzoic acids 3a, wherein $R^1$ and $R^2$ are as defined herein, can be achieved in presence of chloroacetyl chloride in a solvent like CHCl₃, DCM, THF or a mixture thereof, preferably in a mixture of THF and water and in a temperature range preferably between 0° C. and room temperature, to give the corresponding benzoxazin-3(4H)-one carboxylic acid compounds 2a (Scheme 2, step a).

Scheme 3

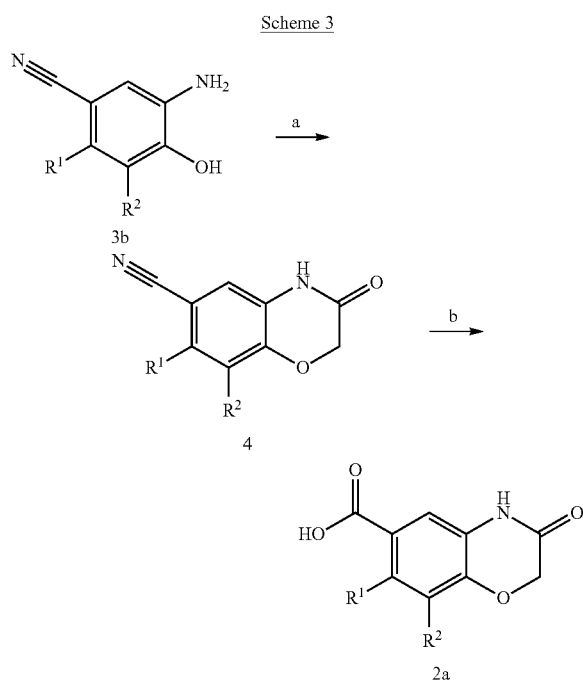

Alternatively, starting from commercially available 3-amino-4-hydroxy-benzonitriles 3b, wherein $R^1$ and $R^2$ are as defined herein, reaction with chloroacetyl chloride in a solvent like DCM or THF, preferably in a mixture of $CHCl_3$ and water, in presence of a base such as $Na_2CO_3$, TEA, $NaHCO_3$, $K_2CO_3$, or a mixture thereof, preferably $Na_2CO_3$ and a phase transfer catalyst such as tetrabutylammonium chloride or bromide, benzyltriethylammonium chloride or a mixture thereof, preferably benzyltriethylammonium chloride and in a temperature range between 0° C. and room temperature gives the corresponding benzoxazin-3 (4H)-one carbonitrile compounds 4, wherein $R^1$ and $R^2$ are as defined herein (Scheme 3, step a). Subsequent nitrile hydrolysis under alkaline conditions using a sodium hydroxide solution or under acidic conditions using a hydrochloric acid solution, preferably an aqueous concentrated hydrochloric acid solution (ca. 37% wt/wt in water) and in a temperature range between 70° C. to 100° C., preferably around boiling point of the reaction mixture, gives the corresponding benzoxazin-3(4H)-one carboxylic acid compounds 2a (Scheme 3, step b).

In one embodiment, intermediate 1 is an intermediate of type B, C, D or E. Intermediates of type B, C, D and E can be prepared e.g., as exemplified by the synthetic procedures outlined in Schemes 4, 5, 6 and 7.

Intermediates of type B can be prepared by a variety of conditions, which may be exemplified by the general synthetic procedure outlined in Scheme 4.

Scheme 4

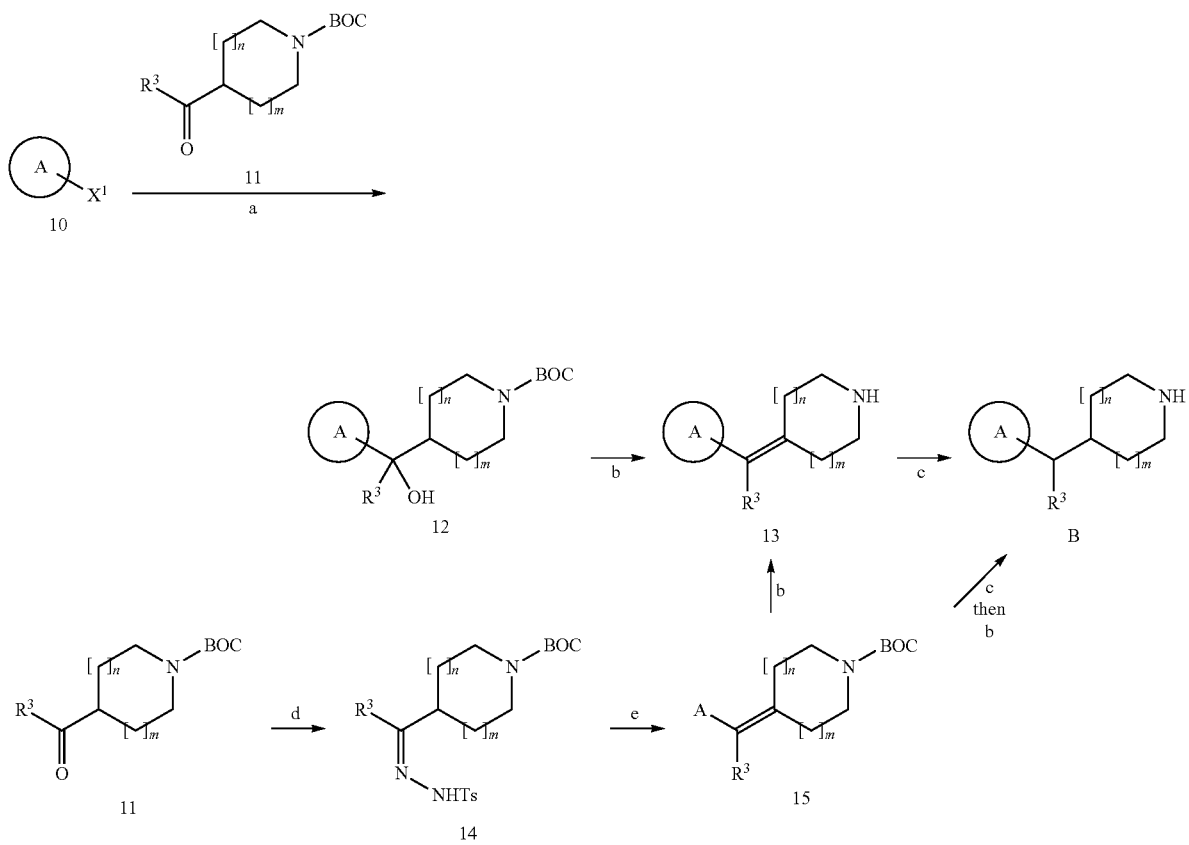

Starting from aryl or heteroaryl halides 10, wherein $X^1$ is selected from the group consisting of Cl, Br and I and A is as defined herein, preferably aryl substituted with $R^5$ and $R^6$, most preferably phenyl substituted with $R^5$ and $R^6$, wherein $R^5$ and $R^6$ are as defined herein, a lithium halogen exchange reaction can be performed using a solution of LiHMDS or n-BuLi, preferably n-BuLi in a solvent like THF, diethylether, pentane, hexane or a mixture thereof, preferably THF and in a temperature range between −20° C. and −78° C., preferably at −78° C. to generate the corresponding lithiated aryl or heteroaryl intermediate. Nucleophilic addition of said lithiated aryl or heteroaryl intermediate to a ketone or aldehyde, respectively, 11, wherein $R^3$ and n are as defined herein, in a solvent such as THF and preferably at a temperature of −78° C. gives the corresponding tertiary alcohol 12 (step a). Subsequent elimination of the tertiary hydroxy group with concomitant removal of the Boc protecting group using acidic conditions such as 4M HCl in dioxane in a solvent like MeOH, or, preferably, TFA in DCM at around room temperature yields the corresponding olefin 13 (step b). Finally, heterogeneous catalytic hydrogenation of the olefin 13 using a catalyst such as $Pd(OH)_2$ or Pd/C, preferably Pd/C in a solvent like THF, MeOH, EtOH, EtOAc or a mixture thereof, preferably in THF at around room temperature and under e.g., atmospheric pressure of hydrogen, affords intermediates of type B (step c).

Alternatively a ketone of formula 11 can be reacted to a N-tosylhydrazone 14, for example using $NH_2NHTs$ in a solvent as 1,4-dioxane preferably by heating to 80° C. In a further step TV-tosylhydrazones of formula 14 are reacted with aryl or heteroaryl bromides in the presence of a catalyst system to give intermediates of structure 15. An appropriate catalytic system for such a transformation consists for instance, but is not limited, of $[Pd(PPPh_3)_2Cl_2]$ in the presence of LiOtBu in a solvent such as 1,4-dioxane at a temperature of 80° C. The BOC group of intermediates 15 is cleaved to give 13 using one of the several conditions described above for the transformation of 12 to 13. Alternatively hydrogenation of 15 is performed first using one of the methods described above, followed in a second step by deprotection to give intermediates B.

Compounds of formula (IA) wherein A and $R^3$ are as defined herein and are different from each other are chiral. The single enantiomers can be obtained by chiral separation of the racemic final compounds, or by separation of chiral intermediates of type B. Chiral separation can be achieved with several methods known to a persons skilled in the art. For instance, SCF separation on a chiral stationary phase can be used.

Intermediates of type C, wherein A and n are as defined herein, can be prepared by a variety of conditions, which may be exemplified by the general synthetic procedures outlined in Scheme 5.

Scheme 5

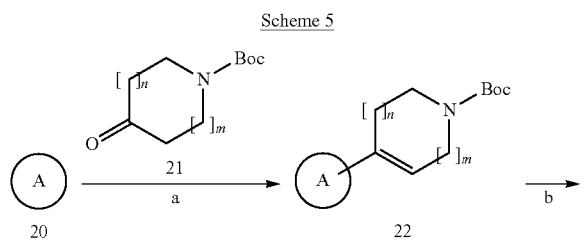

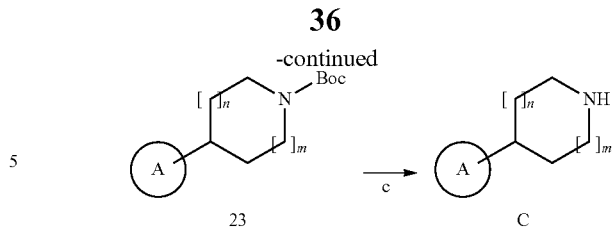

Treatment of a mixture of aryl or heteroaryl compounds 20, wherein A is as defined herein, preferably wherein A is heteroaryl substituted with $R^7$ and $R^8$ as defined herein, most preferably indolyl substituted with $R^7$ and $R^8$ as defined herein, and ketone 21, wherein n is as defined herein, with a base such as NaOH or KOH in a solvent like EtOH or MeOH and in a temperature range between room temperature and 80° C., preferably around the reflux temperature of the mixture, gives olefines 22 (step a). Subsequent heterogeneous catalytic hydrogenation using a transition metal catalyst, such as $PtO_2$ in a polar solvent like MeOH, EtOH, AcOEt, AcOH or a mixture thereof, preferably a mixture of EtOH/AcOH at around room temperature and under 5 bar pressure of hydrogen gas, yields intermediates 23 (step b). Finally, removal of the Boc protecting group using acidic conditions such as treatment with TEA in DCM or preferably with 4M HCl in dioxane in a solvent like MeOH at around room temperature gives the corresponding intermediates of type C (step c).

In some embodiments, intermediate 23 is an intermediate of formula 23a, wherein ring A is heteroaryl comprising a secondary amino group (i.e., "—NH—", such as in indolyl), and wherein $R^7$, $R^8$ and n are as defined herein. As outlined in Scheme 6, intermediates 23a may be transformed to intermediates of type D, wherein A is heteroaryl comprising at least one nitrogen atom and $R^7$, $R^8$, $R^9$ and n are as defined herein.

Scheme 6

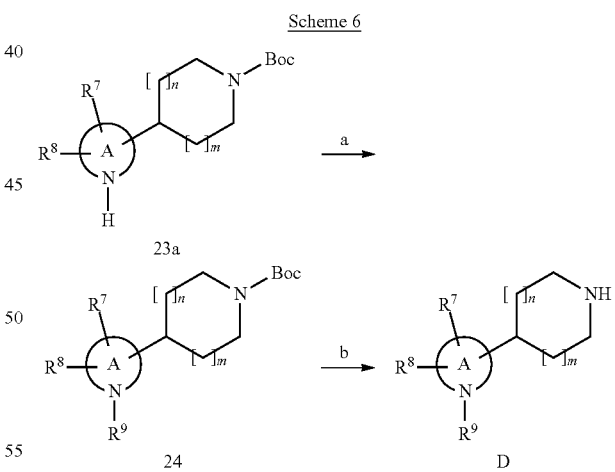

Thus, intermediate 23a can be TV-functionalized by treatment with an appropriate base, such as NaH, KH, NaHMDS, LiHMDS, EDA, or a mixture thereof, preferably with NaH in a solvent like DMF, THF, dioxane, or a mixture thereof, preferably DMF and in a temperature range between −78° C. and room temperature, preferably at 0° C., followed by addition of e.g., alkyl-, cycloalkyl- or benzyl halides, such as MeI, EtI, iPrI, CyPrI or BnBr to give the corresponding TV-functionalized compounds 24, wherein $R^9$ is alkyl, cycloalkyl or benzyl, preferably methyl, ethyl, iso-propyl, cyclohexyl or benzyl (step a). Deprotection of compounds 24 using the same conditions as described above for compounds 23 (see Scheme 5, step c) affords intermediates of type D (step b).

In one embodiment, intermediate D is a 3-(4-piperidyl)-indazole of type E, wherein $R^7$, $R^8$, $R^9$ and n are as defined herein. In addition to the procedure outlined in Scheme 6, intermediates of type E can be prepared by a variety of conditions, in particular by the general synthetic procedure outlined in Scheme 7.

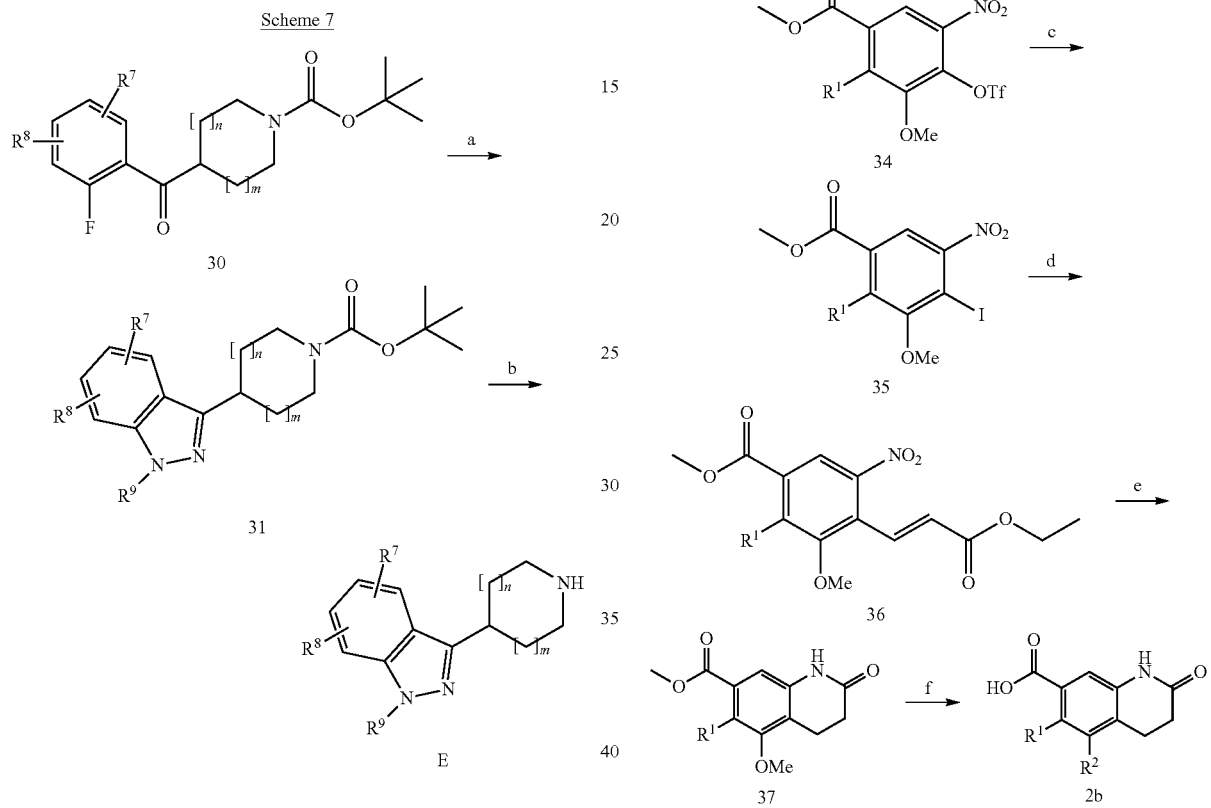

Condensation of tert-butyl 4-(2-fluorobenzoyl)piperidine-1-carboxylate compound 30 with an $R^9$-substituted hydrazine, such as methylhydrazine, isopropylhydrazine or 2-hydroxyethyl)hydrazine in a solvent like n-BuOH, DMA, DMF, DMSO, or a mixture thereof, preferably in n-BuOH, in a sealed reaction vessel at elevated temperature, e.g. 120° C., yields indazole compound 31 (step a). Subsequent, removal of the Boc protecting group using acidic conditions, such as treatment with HCl in dioxane or TFA in DCM, preferably with 4M HCl in dioxane in a solvent like MeOH, preferably at around room temperature affords intermediates of type E (step b).

Scheme 8

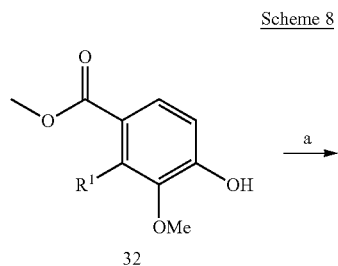

3,4-Dihydro-1H-quinolin-2-ones 2b can be prepared from methyl vanillate 32. In a first step regioselective nitration is achieved with a reagent such as for example nitric acid in acetic acid. The resulting intermediate 33 can be further elaborated, for instance in a two step procedure comprising the reaction with a reagent such as Tf$_2$O in the presence of a base such as Py in a solvent such as DCM, and subsequent reaction of triflate 34 with NaI in a solvent such as DMSO under heating. The so obtained aryl iodode 35 can be used as starting material for a vast array of Pd catalized cross-coupling reactions. For instance, reaction with ethyl acrylate under appropriate Heck-coupling reaction conditions leads to 36. Concomitant reduction of the nitro group of 36 and the alkene moiety and cyclization can be achieved for example using a catalyst such as Pd/C, a reducing reagent such as H$_2$ in a solvent as 1,4-dioxane and heating the reaction mixture. This leads to a 3,4-dihydro-1H-quinolin-2-one of formula 37. Variation at the alkoxy group at position R$^2$ can optionally be achieved by demethylation to 38 with a reagent as BBr$_3$ in a solvent as DCM followed by alkylation, as for instance with a reagent as 1-bromo-2-floromethane in the presence of a bases as K$_2$CO$_3$ and an appropriate solvent, as for instance DMF, to give compounds like compound 39. Methyl esters 37 and 39 can be saponified to the desired intermediates of formula 2b by a vast array of conditions, as for instance using NaOH in a solvent mixture consisting of water and MeOH.

In one aspect, the present invention provides a process of manufacturing the compounds of formula (IA) as described herein, comprising the steps of:

a) reacting an amine 1, wherein A, L, m and n are as described herein,

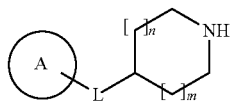

1 with an acid 2a or 2b, wherein R$^1$ and R$^2$ are as described herein

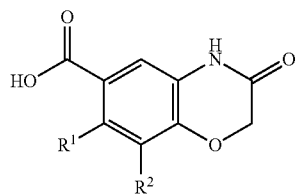

2a

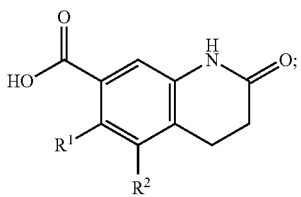

2b b) reacting an amine 1, wherein A, L, m and n are as described herein,

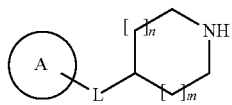

1 with an acid chloride 2c or 2d, wherein R$^1$ and R$^2$ are as described herein

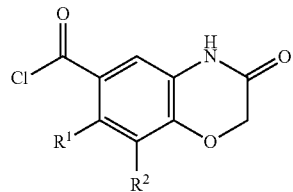

2c

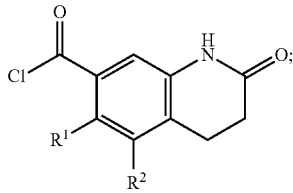

2d to form said compound of formula (IA).

In a further aspect, the present invention provides a compound according to formula (IA) as described herein, when manufactured according to any one of the processes described herein.

In one embodiment, there is provided a process of manufacturing compounds of formula (IA) as described herein, comprising reacting an amine 1, wherein A, L, m and n are as described herein,

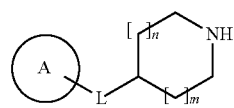

1 with an acid 2a, wherein R$^1$ and R$^2$ are as described herein,

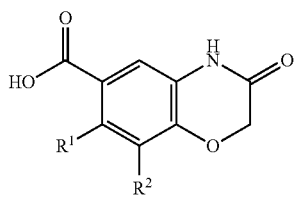

2a to form said compound of formula (IA).

In one embodiment, said amine 1 is reacted with said acid 2a or 2b in the presence of a coupling reagent, preferably in the presence of a coupling reagent selected from the group consisting of DCC, HATU, EDCI, HOBt, TBTU and T3P.

In one embodiment, said amine 1 is reacted with said acid 2a or 2b in a solvent, preferably in a solvent selected from the group consisting of DMF, DMA, DCM and dioxane.

In one embodiment, said amine 1 is reacted with said acid 2a or 2b in the presence of a base, preferably in the presence of a base selected from the group consisting of NEt$_3$, DIPEA (Huenig's base) and DMAP.

In a preferred embodiment, said amine 1 is reacted with said acid 2a or 2b in a solvent and in the presence of a coupling reagent and a base, preferably in a solvent selected from the group consisting of DMF, DMA, DCM and dioxane, in the presence of a coupling reagent selected from the group consisting of DCC, HATU, EDCI, HOBt, TBTU and T3P and in the presence of a base selected from the group consisting of NEt$_3$, DIPEA (Huenig's base) and DMAP.

In one embodiment, there is provided a process of manufacturing compounds of formula (IA) as described herein, comprising reacting an amine 1, wherein A, L and n are as described herein,

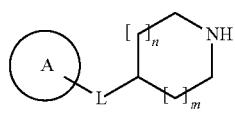

with an acid chloride 2c or 2d, wherein R$^1$ and R$^2$ are as described herein,

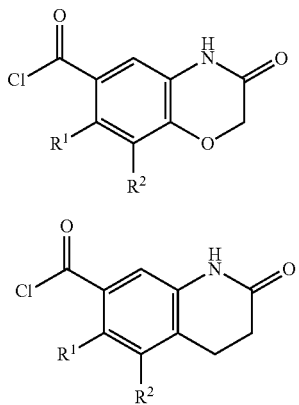

to form said compound of formula (IA).

In one embodiment, there is provided a process as described above, wherein said acid chloride 2c,d is obtained by reacting a carboxylic acid 2a,b, wherein R$^1$ and R$^2$ are as described herein, with thionyl chloride or oxalyl chloride.

In one embodiment, said amine 1 is reacted with said acid chloride 2c,d in a solvent, preferably in a solvent selected from the group consisting of DCM and DMF, or a mixture thereof.

In one embodiment, said amine 1 is reacted with said acid chloride 2c,d in the presence of a base, preferably in the presence of a base selected from the group consisting of NEt$_3$, Huenig's base, pyridine and DMAP.

In a preferred embodiment, said amine 1 is reacted with said acid chloride 2c,d in a solvent and in the presence of a base, preferably in a solvent selected from the group consisting of DCM and DMF, or a mixture thereof, and in the presence of a base selected from the group consisting of NEt$_3$, Huenig's base, pyridine and DMAP.

MAGL Inhibitory Activity

Compounds of the present invention are MAGL inhibitors. Thus, in one aspect, the present invention provides the use of compounds of formula (IA) as described herein for inhibiting MAGL in a mammal.

In a further aspect, the present invention provides compounds of formula (IA) as described herein for use in a method of inhibiting MAGL in a mammal.

In a further aspect, the present invention provides the use of compounds of formula (IA) as described herein for the preparation of a medicament for inhibiting MAGL in a mammal.

In a further aspect, the present invention provides a method for inhibiting MAGL in a mammal, which method comprises administering an effective amount of a compound of formula (IA) as described herein to the mammal.

Compounds were profiled for MAGL inhibitory activity by measuring the enzymatic activity of MAGL by following the hydrolysis of 4-nitorphenylacetate resulting in 4-nitrophenol, which absorbs at 405-412 nm (G. G. Muccioli, G. Labar, D M. Lambert, *Chem. Bio. Chem.* 2008, 9, 2704-2710). This assay is hereinafter abbreviated "4-NPA assay".

The 4-NPA assay was carried out in 384 well assay plates (black with clear bottom, non-binding surface treated, Corning Ref. 3655) in a total volume of 40 µL. Compound dilutions were made in 100% DMSO (VWR Chemicals 23500.297) in a polypropylene plate in 3-fold dilution steps to give a final concentration range in the assay from 25 µM to 1.7 nM. 1 µL compound dilutions (100% DMSO) were added to 19 µL MAGL (recombinant wild-type) in assay buffer (50 mM TRIS (GIBCO, 15567-027), 1 mM EDTA (Fluka, 03690-100 ml)). The plate was shaked for 1 min at 2000 rpm (Variomag Teleshake) and then incubated for 15 min at RT. To start the reaction, 20 µL 4-Nitrophenlyacetate (Sigma N-8130) in assay buffer with 6% EtOH was added. The final concentrations in the assay were 1 nM MAGL and 300 µM 4-Nitrophenylacetate. After shaking (1 min, 2000 rpm) and 5 min incubation at RT, the absorbance at 405 nm was measured for a first time (Molecular Devices, SpectraMax Paradigm). A second measurement was then done after incubation for 80 min at RT. From the two measurements, the slope was calculated by substracting the first from the second measurement.

Alternatively, compounds were profiled for MAGL inhibitory activity by determining the enzymatic activity by following the hydrolysis of the natural substrate, 2-arachidonoylglycerol, resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 µL. Compound dilutions were made in 100% DMSO (VWR Chemicals 23500.297) in a polypropylene plate in 3-fold dilution steps to give a final concentration range in the assay from 12.5 µM to 0.8 µM. 0.25 µL compound dilutions (100% DMSO) were added to 9 µL MAGL in assay buffer (50 mM TRIS (GIBCO, 15567-027), 1 mM EDTA (Fluka, 03690-100 ml), 0.01% (v/v) Tween. After shaking, the plate was incubated for 15 min at RT. To start the reaction, 10 µL 2-arachidonoylglycerol in assay buffer was added. The final concentrations in the assay was 50 µM MAGL and 8 µM 2-arachidonoylglyerol. After shaking and 30 min incubation at RT, the reaction was quenched by the addition of 40 µL of acetonitrile containing 4 µM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an acetonitrile/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

| Example | IC$_{50}$MAGL [µM] |
|---|---|
| 1 | 0.00095 |
| 2 | 0.00050 |

-continued

| Example | IC$_{50}$MAGL [μM] |
|---|---|
| 3 | 0.00203 |
| 4 | 0.00069 |
| 5 | 0.01500 |
| 6 | 0.00090 |
| 7 | 0.00090 |
| 8 | 0.00400 |
| 9 | 0.00030 |
| 10 | 0.00190 |
| 11 | 0.00060 |
| 12 | 0.00040 |
| 13 | 0.00050 |
| 14 | 0.00050 |
| 15 | 0.00110 |
| 16 | 0.00050 |
| 17 | 0.00020 |
| 18 | 0.03300 |
| 20 | 0.00355 |
| 21 | 0.01400 |
| 22 | 0.00827 |
| 23 | 0.01063 |
| 24 | 0.02000 |
| 25 | 0.02900 |
| 26 | 0.00180 |
| 27 | 0.00280 |
| 28 | 0.00100 |
| 29 | 0.00170 |
| 30 | 0.02290 |
| 31 | 0.02891 |
| 34 | 0.03600 |
| 35 | 0.03700 |
| 36 | 0.15808 |
| 37 | 0.35000 |
| 38 | 0.08600 |
| 39 | 0.08400 |
| 40 | 0.55000 |
| 41 | 0.44000 |
| 42 | 0.09700 |
| 43 | 0.18000 |
| 44 | 0.39000 |
| 45 | 0.22000 |
| 46 | 1.11000 |
| 47 | 0.05900 |
| 48 | 0.54880 |
| 49 | 5.54000 |
| 50 | 0.15000 |
| 51 | 0.37000 |
| 52 | 0.14000 |
| 53 | 0.00630 |
| 54 | 0.00730 |
| 55 | 0.068 |
| 56 | 1.40000 |
| 57 | 3.02000 |
| 58 | 0.00080 |
| 59 | 0.00050 |
| 60 | 0.00062 |
| 66 | 0.00024 |
| 67 | 0.00065 |
| 72 | 0.00055 |
| 73 | 0.00073 |
| 74 | 0.00056 |
| 75 | 0.00043 |
| 76 | 0.00053 |
| 77 | 0.00166 |
| 78 | 0.00184 |
| 79 | 0.00600 |
| 80 | 0.00030 |
| 81 | 0.00110 |
| 82 | 0.00069 |
| 83 | 0.00309 |
| 84 | 0.00583 |
| 85 | 0.49670 |
| 86 | 0.61220 |
| 87 | 1.31770 |
| 88 | 1.47510 |
| 89 | 1.90236 |
| 90 | 2.22440 |

-continued

| Example | IC$_{50}$MAGL [μM] |
|---|---|
| 91 | 2.40270 |
| 92 | 2.74100 |
| 93 | 0.00350 |
| 94 | 0.00040 |
| 95 | 0.00140 |
| 96 | 0.00020 |
| 97 | 0.00740 |
| 98 | 0.00180 |
| 99 | 0.00260 |
| 100 | 0.00640 |
| 101 | 0.00270 |
| 102 | 0.00350 |
| 103 | 0.00220 |
| 104 | 0.00030 |
| 105 | 0.00080 |
| 106 | 0.00790 |
| 107 | 0.00020 |
| 108 | 0.00960 |
| 109 | 0.00620 |
| 110 | 0.00620 |
| 111 | 0.00150 |
| 112 | 0.00030 |
| 113 | 0.00040 |
| 114 | 0.00400 |
| 115 | 0.00140 |
| 116 | 0.05540 |
| 117 | 0.00730 |
| 118 | 0.00480 |
| 119 | 0.00910 |
| 120 | 0.00060 |
| 121 | 0.00040 |
| 122 | 0.00360 |
| 123 | 0.00870 |
| 124 | 0.25825[a] |
| 125 | 0.00770 |
| 126 | 0.00850 |
| 127 | 0.80230 |
| 128 | 0.00060 |
| 129 | 0.01220 |
| 130 | 0.08533[a] |
| 131 | 0.18218[a] |
| 132 | 0.00027[a] |
| 133 | 0.02513[a] |
| 134 | 0.00011[a] |
| 135 | 0.00416[a] |
| 137 | 0.00024[a] |
| 138 | 0.00941[a] |
| 139 | 0.00017[a] |
| 140 | 0.00062[a] |
| 141 | 0.00668[a] |
| 142 | 0.00066[a] |
| 143 | 0.07931[a] |

[a]measured using the 2-AG assay; if nothing else is indicated, the value was measured using the 4-NPA assay.

In one aspect, the present invention provides compounds of formula (IA) and their a pharmaceutically acceptable salt as described herein, wherein said compounds of formula (IA) and their a pharmaceutically acceptable salt have IC$_{50}$'s for MAGE inhibition below 25 μM, preferably below 10 μM, more preferably below 5 μM as measured in the MAGE assay described herein.

In one embodiment, compounds of formula (IA) and their a pharmaceutically acceptable salt as described herein have IC$_{50}$ (MAGE inhibition) values between 0.000001 μM and 25 μM, particular compounds have IC$_{50}$ values between 0.000005 μM and 10 μM, further particular compounds have IC$_{50}$ values between 0.00005 μM and 5 μM, as measured in the MAGL assay described herein.

In one embodiment, the present invention provides compounds of formula (IA) and their a pharmaceutically acceptable salt as described herein, wherein said compounds of formula (IA) and their a pharmaceutically acceptable salt have an IC$_{50}$ for MAGL below 25 µM, preferably below 10 µM, more preferably below 5 µM as measured in an assay comprising the steps of:
- a) providing a solution of a compound formula (IA), or a pharmaceutically acceptable salt thereof, in DMSO;
- b) providing a solution of MAGL (recombinant wild-type) in assay buffer (50 mM tris(hydroxymethyl) aminomethane; 1 mM ethylenediaminetetraacetic acid);
- c) adding 1 µL of compound solution from step a) to 19 µL of MAGL solution from step b);
- d) shaking the mixture for 1 min at 2000 rpm;
- e) incubating for 15 min at RT;
- f) adding 20 µL of a solution of 4-nitrophenlyacetate in assay buffer (50 mM tris(hydroxymethyl)aminomethane; 1 mM ethylenediaminetetraacetic acid, 6% EtOH);
- g) shaking the mixture for 1 min at 2000 rpm;
- h) incubating for 5 min at RT;
- i) measuring the absorbance of the mixture at 405 nm a first time;
- j) incubating a further 80 min at RT;
- k) measuring the absorbance of the mixture at 405 nm a second time;
- l) substracting the absorbance measured under i) from the absorbance measured under k) and calculating the slope of absorbance;

wherein:
- i) the concentration of the compound of formula (IA), or the pharmaceutically acceptable salt thereof in the assay after step f) is in the range of 25 µM to 1.7 nM;
- ii) the concentration of MAGL in the assay after step f) is 1 nM;
- iii) the concentration of 4-nitrophenylacetate in the assay after step f) is 300 µM; and
- iv) steps a) to 1) are repeated for at least 3 times, each time with a different concentration of the compound of formula (IA), or the pharmaceutically acceptable salt thereof.

Using the Compounds of the Invention

In one aspect, the present invention provides compounds of formula (IA) as described herein for use as therapeutically active substance.

In a further aspect, the present invention provides the use of compounds of formula (IA) as described herein for the treatment or prophylaxis of neuroinflammation, neurodegenerative diseases, pain, cancer and/or mental disorders in a mammal.

In one embodiment, the present invention provides the use of compounds of formula (IA) as described herein for the treatment or prophylaxis of neuroinflammation and/or neurodegenerative diseases in a mammal.

In one embodiment, the present invention provides the use of compounds of formula (IA) as described herein for the treatment or prophylaxis of neurodegenerative diseases in a mammal.

In one embodiment, the present invention provides the use of compounds of formula (IA) as described herein for the treatment or prophylaxis of cancer in a mammal.

In one aspect, the present invention provides the use of compounds of formula (IA) as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a preferred embodiment, the present invention provides the use of compounds of formula (IA) as described herein for the treatment or prophylaxis of multiple sclerosis, Alzheimer's disease and/or Parkinson's disease in a mammal.

In a particularly preferred embodiment, the present invention provides the use of compounds of formula (IA) as described herein for the treatment or prophylaxis of multiple sclerosis in a mammal.

In one aspect, the present invention provides compounds of formula (IA) as described herein for use in the treatment or prophylaxis of neuroinflammation, neurodegenerative diseases, pain, cancer and/or mental disorders in a mammal.

In one embodiment, the present invention provides compounds of formula (IA) as described herein for use in the treatment or prophylaxis of neuroinflammation and/or neurodegenerative diseases in a mammal.

In one embodiment, the present invention provides compounds of formula (IA) as described herein for use in the treatment or prophylaxis of cancer in a mammal.

In one embodiment, the present invention provides compounds of formula (IA) as described herein for use in the treatment or prophylaxis of neurodegenerative diseases in a mammal.

In one aspect, the present invention provides compounds of formula (IA) as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a preferred embodiment, the present invention provides compounds of formula (IA) as described herein for use in the treatment or prophylaxis of multiple sclerosis, Alzheimer's disease and/or Parkinson's disease in a mammal.

In a particularly preferred embodiment, the present invention provides compounds of formula (IA) as described herein for use in the treatment or prophylaxis of multiple sclerosis in a mammal.

In one aspect, the present invention provides the use of compounds of formula (IA) as described herein for the preparation of a medicament for the treatment or prophylaxis of neuroinflammation, neurodegenerative diseases, pain, cancer and/or mental disorders in a mammal.

In one embodiment, the present invention provides the use of compounds of formula (IA) as described herein for the preparation of a medicament for the treatment or prophylaxis of neuroinflammation and/or neurodegenerative diseases in a mammal.

In one embodiment, the present invention provides the use of compounds of formula (IA) as described herein for the preparation of a medicament for the treatment or prophylaxis of neurodegenerative diseases in a mammal.

In one embodiment, the present invention provides the use of compounds of formula (IA) as described herein for the preparation of a medicament for the treatment or prophylaxis of cancer in a mammal.

In a further aspect, the present invention provides the use of compounds of formula (IA) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a preferred embodiment, the present invention provides the use of compounds of formula (IA) as described herein for the preparation of a medicament for the treatment or prophylaxis of multiple sclerosis, Alzheimer's disease and/or Parkinson's disease in a mammal.

In a particularly preferred embodiment, the present invention provides the use of compounds of formula (IA) as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer and/or mental disorders in a mammal, which method comprises administering an effective amount of a compound of formula (IA) as described herein to the mammal.

In one embodiment, the present invention provides a method for the treatment or prophylaxis of neuroinflammation and/or neurodegenerative diseases in a mammal, which method comprises administering an effective amount of a compound of formula (IA) as described herein to the mammal.

In one embodiment, the present invention provides a method for the treatment or prophylaxis of neurodegenerative diseases in a mammal, which method comprises administering an effective amount of a compound of formula (IA) as described herein to the mammal.

In one aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression and/or pain in a mammal, which method comprises administering an effective amount of a compound of formula (IA) as described herein to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (IA) as described herein to the mammal.

In a particularly preferred embodiment, the present invention provides a method for the treatment or prophylaxis of multiple sclerosis in a mammal, which method comprises administering an effective amount of a compound of formula (IA) as described herein to the mammal.

In a further aspect, the present invention provides a compound of formula (IA) comprising one or more imaging isotopes and/or one or more fluorescent labels as described herein, for use in medical diagnosis.

In a further aspect, the present invention provides a method for diagnosing neuroinflammation, neurodegenerative diseases, pain, cancer and/or mental disorders in a mammal, comprising administering a compound of formula (IA) comprising one or more imaging isotopes and/or one or more fluorescent labels as described herein to the mammal.

In a further aspect, the present invention provides a method for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal, comprising administering a compound of formula (IA) comprising one or more imaging isotopes and/or one or more fluorescent labels as described herein, to the mammal.

In one embodiment, the diagnostic methods described herein comprising administering a compound of formula (IA) comprising one or more imaging isotopes and/or one or more fluorescent labels as described herein, to a mammal, further comprise measuring a radioactive signal and/or fluorescence signal.

In a further aspect, the present invention provides a compound of formula (IA) comprising one or more imaging isotopes and/or one or more fluorescent labels as described herein, for use in a method for diagnosing neuroinflammation, neurodegenerative diseases, pain, cancer and/or mental disorders in a mammal.

In a further aspect, the present invention provides a compound of formula (IA) comprising one or more imaging isotopes and/or one or more fluorescent labels as described herein, for use in a method for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (IA) comprising one or more imaging isotopes and/or one or more fluorescent labels as described herein, for the preparation of a composition for diagnosing neuroinflammation, neurodegenerative diseases, pain, cancer and/or mental disorders in a mammal.

In a further aspect, the present invention provides the use of a compound of formula (IA) comprising one or more imaging isotopes and/or one or more fluorescent labels as described herein, for the preparation of a composition for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (IA) comprising one or more imaging isotopes and/or one or more fluorescent labels as described herein, for diagnosing neuroinflammation, neurodegenerative diseases, pain, cancer and/or mental disorders in a mammal.

In a further aspect, the present invention provides the use of a compound of formula (IA) comprising one or more imaging isotopes and/or one or more fluorescent labels as described herein, for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (IA) comprising one or more imaging isotopes and/or one or more fluorescent labels as described herein, for diagnosing neuroinflammation, neurodegenerative diseases, pain, cancer and/or mental disorders in vitro.

In a further aspect, the present invention provides the use of a compound of formula (IA) comprising one or more imaging isotopes and/or one or more fluorescent labels as described herein, for diagnosing multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in vitro.

In one embodiment, "diagnosing" as used herein comprises gamma imaging.

In one embodiment, "diagnosing" as used herein comprises fluorescent microscopy.

Pharmaceutical Compositions and Administration

In one aspect, the present invention provides a pharmaceutical composition comprising a compound of formula (IA) as described herein and a therapeutically inert carrier.

The compounds of formula (IA) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (IA) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (IA) or their pharmaceutically acceptable salts and esters can be used for the treatment or prophylaxis of type 2 diabetes related microvascular complications (such as, but not limited to diabetic retinopathy, diabetic neuropathy and diabetic nephropathy), coronary artery disease, obesity and underlying inflammatory diseases, chronic inflammatory and autoimmune/inflammatory diseases.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Intermediate A-1

3-Oxo-4H-1,4-benzoxazine-6-carboxylic acid

To a solution of 3-amino-4-hydroxybenzoic acid (10.0 g, 65.3 mmol) and potassium carbonate (10.83 g, 78.36 mmol) in THF (15 mL) and water (30 mL) cooled at 0° C. was added chloroacetyl chloride (8.85 g, 78.36 mmol) and the reaction mixture was then stirred at 25° C. overnight. The reaction was quenched using concentrated hydrochloric acid until pH of 2. The solid precipitate was filtered off, washed with water (50 mL) and MeOH (5 mL) to give the crude title compound (8.6 g, 65%) as light yellow solid. MS: 194.1 (M+H$^+$).

Intermediate A-2

7-Fluoro-3-oxo-4H-1,4-benzoxazine-6-carboxylic acid

Step [A]
7-Fluoro-3-oxo-4H-1,4-benzoxazine-6-carbonitrile

A mixture of 5-amino-2-fluoro-4-hydroxybenzonitrile (0.2 g, 1.31 mmol), benzyltriethylammonium chloride (0.299 g, 1.31 mmol) and sodium bicarbonate (0.442 g, 5.26 mmol) in chloroform (4 mL) and water (2 mL) at 0° C. was treated with chloroacetyl chloride (0.125 mL, 1.58 mmol) and then stirred at room temperature over night. The mixture was concentrated in vacuo, then partitioned between water and EtOAc. The combined organic layers were washed with brine, dried over Na$_2$SO$_4$, filtered and evaporated to dryness. The residue was purified by preparative HPLC (Gemini NX column) to give the title compound (0.157 g, 62%) as light brown solid. MS: 191.2 (M−H$^-$).

Step [B]
7-fluoro-3-oxo-4H-1,4-benzoxazine-6-carboxylic acid

A solution of 7-fluoro-3-oxo-4H-1,4-benzoxazine-6-carbonitrile (0.05 g, 0.260 mmol) in concentrated hydrochloric acid (1.5 mL, 12.2 mmoL) was heated to 90° C. for 18 hours. The reaction was cooled and concentrated in vacuo, then partitioned between water and EtOAc. The combined organic layers were washed with brine, dried over Na$_2$SO$_4$, filtered and evaporated to dryness to give the crude title compound (0.23 g, 42%) as light brown solid. MS: 210.2 (M−H$^-$).

Intermediate B-1

4-Benzhydrylpiperidine

To a mixture of 4-benzhydrylpyridine (5.0 g, 20.38 mmol) in glacial acetic acid (50.0 mL, 20.38 mmol) was added PtO$_2$ (0.462 g, 2.04 mmol) under N$_2$. The mixture was degassed under vacuum and purged with H$_2$ several times. The reaction mixture was then stirred under H$_2$ (45 psi) at 85° C. for 12 hours. The mixture was filtered and concentrated. The residue was treated with petroleum ether/EtOAc 10:1 (30 mL), filtered and further dried under high vacuum to give the title compound as a off white solid (4.8 g, 93%); MS: 252.3 (M+H$^+$).

Intermediate B-2

4-[(4-Fluorophenyl)-phenyl-methyl]piperidine

Step [A] tert-Butyl 4-[(4-fluorophenyl)-hydroxy-phenyl-methyl]piperidine-1-carboxylate To a solution of 4-bromofluorobenzene (2 g, 11.4 mmol) in THE (20 mL) cooled to −78° C., was added/1-butyllithium dropwise (5.81 mL, 14.51 mmol) and the reaction mixture was stirred for 30 min. Then, a solution of tert-butyl 4-benzoylpiperidine-1-carboxylate (3 g, 10.37 mmol) in THF (15 mL) was added to the mixture which was stirred at −78° C. for 2 hours. The mixture was allowed to warm up to room temperature, poured into a solution of sat. NH$_4$Cl aqueous solution (50 mL) and extracted with EtOAc. The combined organic layers were dried over Na$_2$SO$_4$, filtered and concentrated in vacuo. The residue was purified preparative HPLC (Gemini NX column) to give the title compound (1.18 g, 29%) as colorless solid; MS: 312.1 (M-tBu-H$_2$O)$^+$.

Step [B] 4-[(4-Fluorophenyl)-phenyl-methylene] piperidine

To a solution of tert-butyl 4-[(4-fluorophenyl)-hydroxyphenyl-methyl]piperidine-1-carboxylate (0.7 g, 1.82 mmol) in DCM (10 mL) was added trifluoroacetic acid (1.4 mL, 18.16 mmol) and the reaction was stirred at room temperature for 8 hours. The mixture was concentrated in vacuo to give the crude title compound (0.3 g, 62%) as a light yellow solid; MS: 268.0 (M+H$^+$).

Step [C] 4-[(4-Fluorophenyl)-phenyl-methyl]piperidine

A mixture of 4-[(4-fluorophenyl)-phenyl-methylene]piperidine (0.300 g, 1.12 mmol) and Pd/C (0.119 g, 0.110 mmol) in THF (3 mL) was stirred at room temperature for 16 hours under H$_2$ (760 mmHg). The suspension was filtered and the filtrate concentrated in vacuo to give the crude title compound (0.260 g, 86%) as a colorless oil; MS: 270.1 (M+H$^+$).

Intermediate B-3

4-[bis(4-fluorophenyl)methyl]piperidine

The title compound was prepared in analogy to intermediate B-2, but using in step [A] tert-butyl 4-(4-fluorobenzoyl)piperidine-1-carboxylate to give the title compound as a white solid.

Intermediate B-4

4-[(3,4-Dichlorophenyl)-phenyl-methyl]piperidine

The title compound was prepared in analogy to intermediate B-2, but using in step [A] 4-bromo-1,2-dichlorobenzene to give the title compound as a colorless solid; MS: 320.2 (M+H$^+$).

Intermediate B-5

4-[(3,4-Dimethoxyphenyl)-phenyl-methyl]piperidine

The title compound was prepared in analogy to intermediate B-2, but using in step [A] 4-bromo-1,2-dimethoxybenzene to give the title compound as a colorless oil; MS: 312.1 (M+H$^+$).

Intermediate B-6

4-[(4-methoxyphenyl)-phenyl-methyl]piperidine

The title compound was prepared in analogy to intermediate B-2, but using in step [A] 1-bromo-4-methoxy-benzene to give the title compound as a light yellow oil; MS: 282.1 (M+H$^+$).

Intermediate B-7

4-[(3-Methoxyphenyl)-phenyl-methyl]piperidine

The title compound was prepared in analogy to intermediate B-2, but using in step [A] 1-bromo-3-methoxy-benzene to give the title compound as a colorless oil; MS: 282.1 (M+H$^+$).

Intermediate B-8

4-[phenyl(p-tolyl)methyl]piperidine

The title compound was prepared in analogy to intermediate B-2, but using in step [A] 1-bromo-4-methyl-benzene to give the title compound as a light yellow oil; MS: 266.1 (M+H$^+$).

Intermediate B-9

4-[m-tolyl(phenyl)methyl]piperidine

The title compound was prepared in analogy to intermediate B-2, but using in step [A] 1-bromo-3-methyl-benzene to give the title compound as a white solid; MS: 266.1 (M+H$^+$).

Intermediate B-10

1-[phenyl(4-piperidyl)methyl]indole

The title compound is prepared in analogy to the synthesis described in *Organic Process Research & Development*, 2006, 10, 776-783 using indoline (CAS RN 496-15-1) and tert-butyl 4-[chloro(phenyl)methyl]piperidine-1-carboxylate and the resulting indoline intermediate is then oxidized with 2,3-dichloro-5,6-dicyano-1,4-benzoquinone (DDQ) in THF at room temperature overnight, to give the title compound as a white solid. The starting material tert-butyl 4-[chloro(phenyl)methyl]piperidine-1-carboxylate is obtained by treatment of tert-butyl 4-[hydroxy(phenyl)methyl]piperidine-1-carboxylate (CAS RN 269740-46-7) with thionyl chloride in DCM at room temperature overnight.

Intermediate C-1

5-Chloro-6-fluoro-3-(4-piperidyl)-1H-indole

Step [A] tert-Butyl 4-(5-chloro-6-fluoro-1H-indol-3-yl)-3,6-dihydro-2H-pyridine-1-carboxylate A mixture of 5-chloro-6-fluoro-1H-indole (0.2 g, 1.18 mmol), tert-butyl 4-oxopiperidine-1-carboxylate (0.258 g, 1.3 mmol) and potassium hydroxide (0.146 g, 2.59 mmol) in MeOH (3 mL) was heated to 70° C. overnight. The solvent was evaporated in vacuo and the residue was treated with H$_2$O and EtOAc. The combined organics were washed with brine, dried over Na$_2$SO$_4$, filtered and concentrated in vacuo. The residue was purified by flash chromatography, eluting with a 0 to 80% EtOAc-heptane gradient to give the title compound (0.372 g, 90%) as a brown solid; MS: 295.3 (M-tBu+H$^+$).

Step [B] tert-Butyl 4-(5-chloro-6-fluoro-1H-indol-3-yl)piperidine-1-carboxylate

A solution of tert-butyl 4-(5-chloro-6-fluoro-1H-indol-3-yl)-3,6-dihydro-2H-pyridine-1-carboxylate (0.300 g, 0.855 mmol) in EtOH (3 mL) and AcOH (1.5 mL), was purged with Argon and platinum (iv) oxide (194 mg, 0.085 mmol) was added. The suspension was then purged with hydrogen and stirred at room temperature for 20 hours under 5 bar pressure of hydrogen. The reaction mixture was diluted with EtOH and filtered over decalite. The resulting solution was concentrated in vacuo and the residue purified by silica gel flash chromatography, eluting with a 0 to 40% EtOAc-heptane gradient to give the title compound (0.070 g, 23%) as a white solid; MS: 351.4 (M–H$^-$).

Step [C] 5-chloro-6-fluoro-3-(4-piperidyl)-1H-indole

4M HCl in dioxane (0.042 mL, 0.170 mmol) was added to a solution of tert-butyl 4-(5-chloro-6-fluoro-1H-indol-3-yl)piperidine-1-carboxylate (0.012 g, 0.034 mmol) in MeOH (0.5 mL) and the reaction mixture was stirred at room temperature for 2 hours. The mixture was evaporated to dryness and the residue was triturated with diisopropylether. The solid precipitate was filtered off and further dried under the high vacuum to give the title compound (0.095 g, 97%) as a light pink solid as hydrochloride; MS: 253.2 (M+H$^+$).

Intermediate C-2

5-Chloro-3-(4-piperidyl)-1H-indole

The title compound was prepared in analogy to intermediate C-1, but using in step [A] 5-chloro-1H-indole to give the title compound as an off-white solid as hydrochloride; MS: 235.2 (M+H$^+$).

Intermediate C-3

6-Chloro-3-(4-piperidyl)-1H-indole

The title compound was prepared in analogy to intermediate C-1, but using in step [A] 6-chloro-1H-indole to give the title compound as a yellow solid as hydrochloride; MS: 235.2 (M+H$^+$).

Intermediate C-4

5-Fluoro-3-(4-piperidyl)-1H-indole

The title compound was prepared in analogy to intermediate C-1, but using in step [A] 5-fluoro-1H-indole, to give the title compound as a off-white solid; MS: 219.2 (M+H$^+$).

Intermediate C-5

6-Fluoro-3-(4-piperidyl)-1H-indole

The title compound was prepared in analogy to intermediate C-1, but using in step [A] 6-fluoro-1H-indole, to give the title compound as a light yellow solid; MS: 219.0 (M+H$^+$).

Intermediate C-6

3-(4-Piperidyl)-6-(trifluoromethyl)-1H-indole

The title compound was prepared in analogy to intermediate C-1, but using in step [A] 6-(trifluoromethyl)-1H-indole, to give the title compound as a light yellow solid; MS: 269.2 (M+H$^+$).

Intermediate D-1

5-Chloro-6-fluoro-1-methyl-3-(4-piperidyl)indole

Step [A] tert-Butyl 4-(5-chloro-6-fluoro-1-methyl-indol-3-yl)piperidine-1-carboxylate To a solution of tert-butyl 4-(5-chloro-6-fluoro-1H-indol-3-yl)piperidine-1-carboxylate (Intermediate C-1[B], 0.070 g, 0.198 mmol) in DMF (1 mL) cooled to 0° C. was added sodium hydride 65% dispersion in mineral oil (0.095 g, 0.238 mmol) and the reaction mixture was stirred at this temperature for 15 minutes. Then, iodomethane (0.015 mL, 0.238 mmol) was added and the mixture stirred at room temperature for 1 h. The mixture was diluted with EtOAc and poured into a sat. NH$_4$Cl aqueous solution. The combined organic layers were washed with brine, dried over Na$_2$SO$_4$, filtered and evaporated to dryness. The residue was purified by silica gel flash chromatography, eluting with a 0 to 20% EtOAc-heptane gradient to give the title compound (0.040 g, 55%) as an off white solid; MS: 267.3 (M-Boc+H$^+$)

Step [B] 5-chloro-6-fluoro-1-methyl-3-(4-piperidyl)indole

4M HCl in dioxane (0.204 mL, 0.818 mmol) was added to a solution of tert-butyl 4-(5-chloro-6-fluoro-1-methyl-indol-3-yl)piperidine-1-carboxylate (0.050 g, 0.136 mmol) in MeOH (1 mL) and the reaction mixture was stirred at room temperature for 2 hours. The mixture was evaporated to dryness and the residue was triturated with diisopropylether. The solid precipitate was filtered off and further dried under the high vacuum to give the title compound (0.040 g, 97%) as an off-white solid as hydrochloride; MS: 267.2 (M+H$^+$).

Intermediate D-2

5-Chloro-1-methyl-3-(4-piperidyl)indole

The title compound was prepared in analogy to intermediate D-1, but using in step [A] tert-butyl 4-(5-chloro-1H-indol-3-yl)piperidine-1-carboxylate (Intermediate C-2[B]), to give the title compound as a pink solid as hydrochloride; MS: 249.2 (M+H$^+$).

Intermediate D-3

6-Chloro-1-methyl-3-(4-piperidyl)indole

The title compound was prepared in analogy to intermediate D-1, but using in step [A] tert-butyl 4-(6-chloro-1H-indol-3-yl)piperidine-1-carboxylate (Intermediate C-3, step [B]), to give the title compound as an colorless solid as hydrochloride; MS: 249.2 (M+H$^+$).

Intermediate D-4

1-Methyl-3-(4-piperidyl)indole

The title compound was prepared in analogy to intermediate D-1, but using in step [A] tert-butyl 4-(1H-indol-3-yl)

piperidine-1-carboxylate (CAS RN 155302-28-6), to give the title compound as an colorless solid as hydrochloride; MS: 215.3 (M+H$^+$).

Intermediate D-5

5-Fluoro-1-methyl-3-(4-piperidyl)indole

The title compound was prepared in analogy to intermediate D-1, but using in step [A] tert-butyl 4-(5-fluoro-1H-indol-3-yl)piperidine-1-carboxylate (Intermediate C-4, step [B]), to give the title compound as a colorless solid as hydrochloride; MS: 233.1 (M+H$^+$)

Intermediate D-6

6-Fluoro-1-methyl-3-(4-piperidyl)indole

The title compound was prepared in analogy to intermediate D-1, but using in step [A] tert-butyl 4-(5-fluoro-1H-indol-3-yl)piperidine-1-carboxylate (Intermediate C-5, step [B]), to give the title compound as a colorless solid as hydrochloride; MS: 233.1 (M+H$^+$).

Intermediate D-6

6-Chloro-1-cyclopropyl-3-(4-piperidyl)indole

Step [A] tert-butyl 4-(6-chloro-1-cyclopropyl-indol-3-yl)piperidine-1-carboxylate A mixture of tert-butyl 4-(6-chloro-1H-indol-3-yl)piperidine-1-carboxylate (Intermediate C-3[B], 0.05 g, 0.149 mmol), Na$_2$CO$_3$ (0.063 g, 0.597 mmol), cyclopropylboronic acid (0.051 g, 0.597 mmol), copper (II) acetate (0.054 g, 299 μmol) and 2,2'-bipyridine (0.047 g, 0.299 mmol) in DCE (0.5 mL) was heated to 60° C. for 6 hours. The reaction mixture was cooled to room temperature, quenched with a sat.NH$_4$Cl aqueous solution and extracted with dichloromethane. The combined organic layers were dried over Na$_2$SO$_4$, filtered and concentrated in vacuo. The residue was purified by silica gel flash chromatography, eluting with a 0 to 50% EtOAc-heptane gradient to give the title compound (0.034 g, 61%) as a colorless oil; MS: 319.3 (M–tBu+H$^+$).

Step [B] 6-Chloro-1-cyclopropyl-3-(4-piperidyl)indole

4M HCl in dioxane (0.181 mL, 0.726 mmol) was added to a solution of tert-butyl 4-(6-chloro-1-cyclopropyl-indol-3-yl)piperidine-1-carboxylate (0.034 g, 0.091 mmol) in MeOH (0.5 mL) and the reaction mixture was stirred at room temperature for 5 hours. The mixture was evaporated to dryness and the residue was triturated with diisopropyl-ether. The solid precipitate was filtered off and further dried under the high vacuum to give the title compound (0.024 g, 98%) as a yellow solid as hydrochloride; MS: 275.3 (M+H$^+$).

Intermediate D-7

1-[(3-Chlorophenyl)methyl]-3-(4-piperidyl)indole

The title compound was prepared in analogy to intermediate D-1, but using in step [A] tert-butyl 4-(1H-indol-3-yl) piperidine-1-carboxylate and 3-chlorobenzyl bromide, to give the title compound as an off white solid as hydrochloride; MS: 325.2 (M+H$^+$).

Intermediate E-1

2-[6-Fluoro-3-(4-piperidyl)indazol-1-yl]ethanol

Step [A] tert-Butyl 4-[6-fluoro-1-(2-hydroxyethyl)indazol-3-yl]piperidine-1-carboxylate In a sealed tube, a mixture of tert-butyl 4-(2,4-difluorobenzoyl)piperidine-1-carboxylate (0.050 g, 0.154 mmol) and (2-hydroxyethyl)hydrazine (0.021 mL, 0.307 mmol) in n-BuOH (0.8 mL) was heated to 120° C. overnight. On cooling, the reaction mixture was concentrated in vacuo, treated with a sat. aqueous NaHCO$_3$ solution and extracted with dichloromethane. The combined organic layers were washed with brine, dried over Na$_2$SO$_4$, filtered and concentrated in vacuo. The residue was purified by silica gel flash column chromatography, eluting with a 0 to 90% EtOAc-heptane gradient to give the title compound (0.048 g, 86%) as an off-white solid; MS: 308.3 (M-tBu+H$^+$).

Step [B] 2-[6-Fluoro-3-(4-piperidyl)indazol-1-yl]ethanol

4M HCl in dioxane (0.330 mL, 1.32 mmol) was added to a solution of tert-butyl 4-[6-fluoro-1-(2-hydroxyethyl)indazol-3-yl]piperidine-1-carboxylate (0.048 g, 0.132 mmol) in MeOH (0.6 mL) and the reaction mixture was stirred at room temperature for 5 hours. The mixture was concentrated in vacuo and the residue was triturated with diisopropyl-ether. The solid precipitate was filtered off and further dried under the high vacuum to give the title compound (0.030 g, 85%) as an orange solid as hydrochloride; MS: 264.3 (M+H$^+$).

Intermediate E-2

6-Fluoro-1-isopropyl-3-(4-piperidyl)indazole

The title compound was prepared in analogy to intermediate E-1, but using in step [A] isopropylhydrazine, to give the title compound as an light yellow solid as hydrochloride; MS: 262.0 (M+H$^+$).

Intermediate E-3

6-Chloro-1-methyl-3-(4-piperidyl)indazole

The title compound was prepared in analogy to intermediate E-1, but using in step [A] tert-butyl 4-(4-chloro-2-fluorobenzoyl)piperidine-1-carboxylate and methylhydrazine, to give the title compound as an off-white solid as hydrochloride; MS: 250.2 (M+H$^+$).

Example 1

6-(4-Benzhydrylpiperidine-1-carbonyl)-7-fluoro-4H-1,4-benzoxazin-3-one

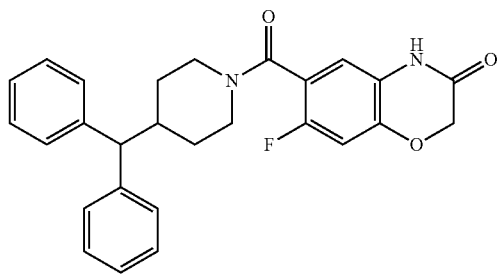 [SMILES: O=C1COc2cc(F)c(C(=O)N3CCC(C(c4ccccc4)c4ccccc4)CC3)cc2N1]

In a flask, 4-benzhydrylpiperidine (Intermediate B-1, 0.02 g, 0.080 mmol), 7-fluoro-3-oxo-3,4-dihydro-2H-benzo[b][1,4]oxazine-6-carboxylic acid (Intermediate A-2, 0.02 g, 0.095 mmol) and HATU (0.036 g, 0.095 mmol) were mixed in DMF (0.5 mL). Then, Hünig's base (0.035 mL, 0.199 mmol) was added and the reaction mixture was stirred at room temperature overnight. The reaction was diluted with EtOAc, poured into water and the aqueous layer was extracted with EtOAc. The combined organic layers were washed with brine, dried over $Na_2SO_4$, filtered and concentrated in vacuo. The residue was purified by silica gel flash chromatography eluting with a 0 to 100% EtOAc-heptane gradient to give the title compound (0.026 g, 74%) as an off-white solid; MS: 445.3 (M+H⁺).

The following examples listed in Table 1 were prepared in analogy to the procedures described for the preparation of example 1 by using the indicated intermediates and/or commercial compounds and using the mentioned purification method such as preparative HPLC (Gemini NX column), silica gel flash chromatography or SEC.

TABLE 1

| Ex. | Name / Structure / Aspect / Purification method | Intermediates | MS, m/z [M + H]⁺ or [M − H]⁻ |
|---|---|---|---|
| 2 | 6-(4-Benzhydrylpiperidine-1-carbonyl)-4H-1,4-benzoxazin-3-one<br><br>Colorless solid<br>Preparative HPLC | Intermediate A-1 and Intermediate B-1 | 427.3 |
| 3 | 6-[4-[Bis(4-fluorophenyl)methyl]piperidine-1-carbonyl]-4H-1,4-benzoxain-3-one<br><br>Colorless solid<br>Preparative HPLC | Intermediate A-1 and Intermediate B-3 | 463.2 |

TABLE 1-continued

| Ex. | Name / Structure / Aspect / Purification method | Intermediates | MS, m/z [M + H]⁺ or [M − H]⁻ |
|---|---|---|---|
| 4 | 6-[4-[(3,4-Dichlorophenyl)-phenylmethyl]piperidine-1-carbonyl]-4H-1,4-benzoxazin-3-one<br>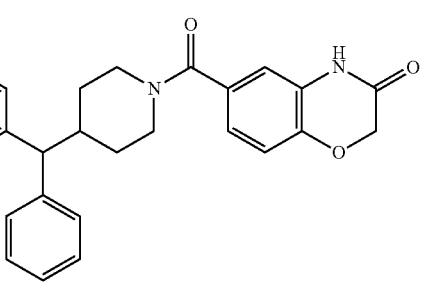<br>Colorless solid<br>Preparative HPLC | Intermediate A-1 and Intermediate B-4 | 495.2 |
| 5 | 6-[4-[Hydroxy(diphenyl)methyl]piperidine-1-carbonyl]-4H-1,4-benzoxazin-3-one<br>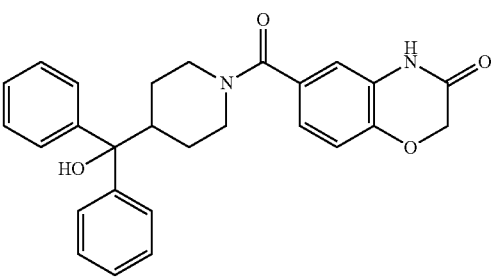<br>Colorless solid<br>Flash chromatography | Intermediate A-1 and Diphenyl(4-piperidyl)methanol, hydrochloride (CAS RN 1798-50-1) | 443.5 |
| 6 | 6-[4-[(R or S)-(4-Fluorophenyl)-phenyl-methyl]piperidine-1-carbonyl]-4H-1,4-benzoxazin-3-one<br>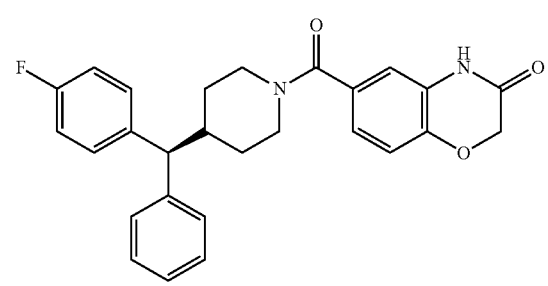<br>Colorless solid<br>SFC | Intermediate A-1 and Intermediate B-2 | 445.1 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 7 | 6-[4-[(S or R)-(4-Fluorophenyl)-phenyl-methyl]piperidine-1-carbonyl]-4H-1,4-benzoxazin-3-one<br>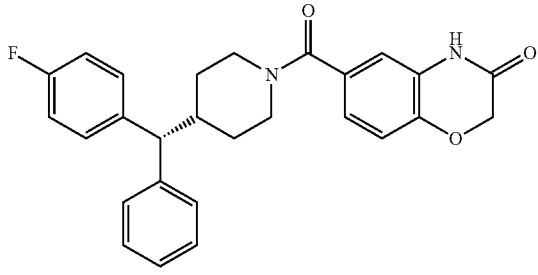<br>yellow solid<br>SFC | Intermediate A-1 and Intermediate B-2 | 445.0 |
| 8 | 6-[4-[(R or S)-(3,4-Dimethoxyphenyl)-phenyl-methyl]piperidine-1-carbonyl]-4H-1,4-benzoxazin-3-one<br>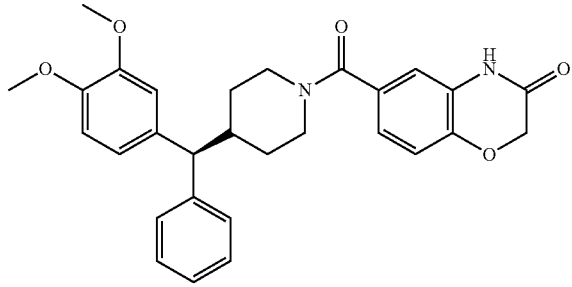<br>Colorless solid<br>SFC | Intermediate A-1 and Intermediate B-5 | 487.1 |
| 9 | 6-[4-[(S or R)-(3,4-Dimethoxyphenyl)-phenyl-methyl]piperidine-1-carbonyl]-4H-1,4-benzoxazin-3-one<br>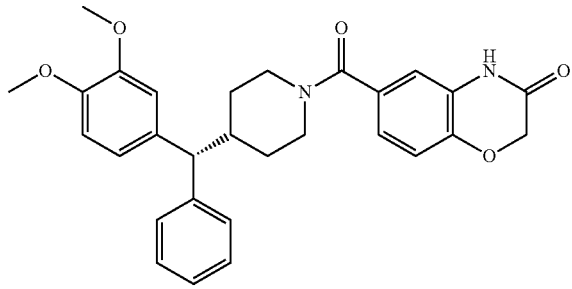<br>Colorless solid<br>SFC | Intermediate A-1 and Intermediate B-5 | 487.1 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 10 | 6-[4-[(R or S)-(4-Methoxyphenyl)-phenyl-methyl]piperidine-1-carbonyl]-4H-1,4-benzoxazin-3-one<br>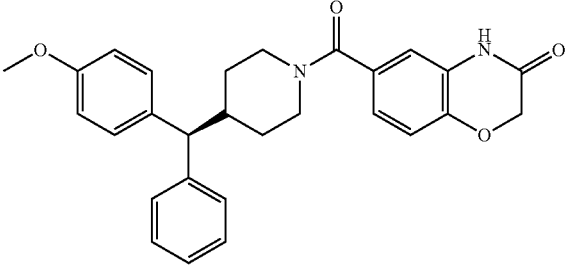<br>Colorless solid<br>SFC | Intermediate A-1 and Intermediate B-6 | 457.3 |
| 11 | 6-[4-[(S or R)-(4-Methoxyphenyl)-phenyl-methyl]piperidine-1-carbonyl]-4H-1,4-benzoxazin-3-one<br>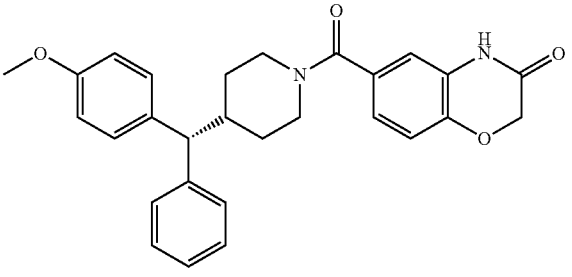<br>Colorless solid<br>SFC | Intermediate A-1 and Intermediate B-6 | 457.3 |
| 12 | 6-[4-[(R or S)-(3-Methoxyphenyl)-phenyl-methyl]piperidine-1-carbonyl]-4H-1,4-benzoxazin-3-one<br>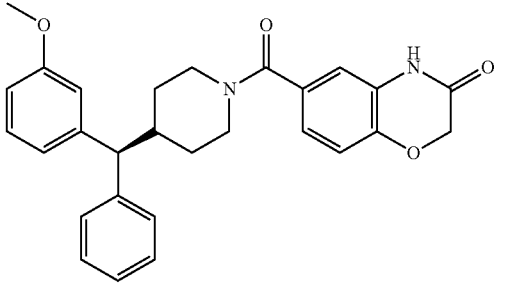<br>Colorless solid<br>SFC | Intermediate A-1 and Intermediate B-7 | |

TABLE 1-continued

| Ex. | Name<br>Structure<br>Aspect<br>Purification method | Intermediates | MS, m/z<br>[M + H]+<br>or<br>[M − H]− |
|---|---|---|---|
| 13 | 6-[4-[(S or R)-(3-Methoxyphenyl)-phenyl-methyl]piperidine-1-carbonyl]-4H-1,4-benzoxazin-3-one<br>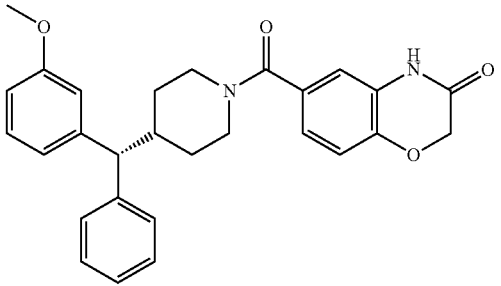<br>Colorless solid<br>SFC | Intermediate A-1 and Intermediate B-7 | 457.1 |
| 14 | 6-[4-[(R or S)-Phenyl(p-tolyl)methyl]piperidine-1-carbonyl]-4H-1,4-benzoxazin-3-one<br>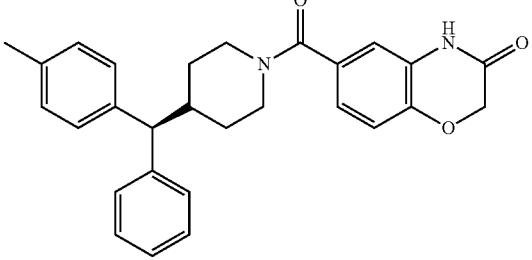<br>Colorless solid<br>SFC | Intermediate A-1 and Intermediate B-8 | 441.2 |
| 15 | 6-[4-[(S or R)-Phenyl(p-tolyl)methyl]piperidine-1-carbonyl]-4H-1,4-benzoxazin-3-one<br>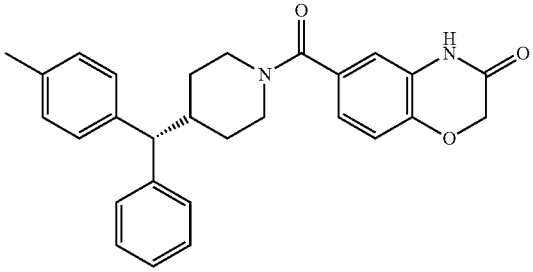<br>Colorless solid<br>SFC | Intermediate A-1 and Intermediate B-8 | 441.2 |

TABLE 1-continued

| Ex. | Name / Structure / Aspect / Purification method | Intermediates | MS, m/z [M + H]⁺ or [M − H]⁻ |
|---|---|---|---|
| 16 | 6-[4-[(R or S)-m-Tolyl(phenyl)methyl]piperidine-1-carbonyl]-4H-1,4-benzoxazin-3-one<br><br>Colorless solid<br>SFC | Intermediate A-1 and Intermediate B-9 | 441.3 |
| 17 | 6-[4-[(S or R)-m-Tolyl(phenyl)methyl]piperidine-1-carbonyl]-4H-1,4-benzoxazin-3-one<br><br>Colorless solid<br>SFC | Intermediate A-1 and Intermediate B-9 | 441.3 |
| 18 | 6-[4-(1H-Indol-3-yl)piperidine-1-carbonyl]-4H-1,4-benzoxazin-3-one<br><br>Colorless solid<br>Flash chromatography | Intermediate A-1 and 3-Piperidin-4-yl-1H-indole (CAS RN 17403-09-7) | 376.2 |

TABLE 1-continued

| Ex. | Name / Structure / Aspect / Purification method | Intermediates | MS, m/z [M + H]+ or [M − H]− |
|---|---|---|---|
| 19 | 6-[4-(5-Chloro-6-fluoro-1H-indol-3-yl)piperidine-1-carbonyl]-4H-1,4-benzoxazin-3-one<br><br>Off-white solid<br>Flash chromatography | Intermediate A-1 and Intermediate C-1 | 428.2 |
| 20 | 6-[4-(5-Chloro-1H-indol-3-yl)piperidine-1-carbonyl]-4H-1,4-benzoxazin-3-one<br><br>Off-white solid<br>Flash chromatography | Intermediate A-1 and Intermediate C-2 | 410.2 |
| 21 | 6-[4-(6-chloro-1H-indol-3-yl)piperidine-1-carbonyl]-4H-1,4-benzoxazin-3-one<br><br>Colorless solid<br>Flash chromatography | Intermediate A-1 and Intermediate C-3 | 410.2 |
| 22 | 6-[4-(5-Fluoro-1H-indol-3-yl)piperidine-1-carbonyl]-4H-1,4-benzoxazin-3-one<br><br>Colorless solid<br>Preparative HPLC | Intermediate A-1 and Intermediate C-4 | 394.8 | ns

TABLE 1-continued

| Ex. | Name / Structure / Aspect / Purification method | Intermediates | MS, m/z [M + H]+ or [M − H]− |
|---|---|---|---|
| 23 | 6-[4-(6-Fluoro-1H-indol-3-yl)piperidine-1-carbonyl]-4H-1,4-benzoxazin-3-one<br>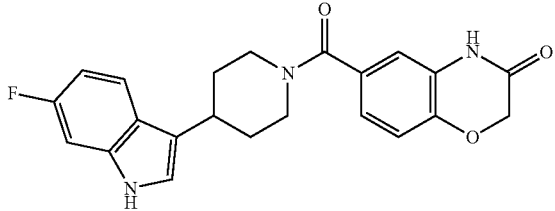<br>Colorless solid<br>Preparative HPLC | Intermediate A-1 and Intermediate C-5 | 394.2 |
| 24 | 6-(4-(5-Methoxy-1H-indol-3-yl)piperidine-1-carbonyl)-2H-benzo[b][1,4]oxazin-3(4H)-one<br>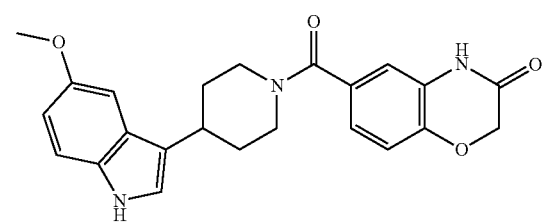<br>Colorless solid<br>Preparative HPLC | Intermediate A-1 and 5-Methoxy-3-(4-piperidinyl)-1H-indol (CAS RN 52157-82-1) | 406.2 |
| 25 | 6-[4-[6-(Trifluoromethyl)-1H-indol-3-yl]piperidine-1-carbonyl]-4H-1,4-benzoxazin-3-one<br>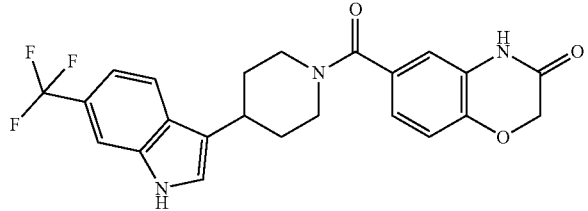<br>Colorless solid<br>Preparative HPLC | Intermediate A-1 and Intermediate C-6 | 444.3 |
| 26 | 6-[4-(5-Chloro-6-fluoro-1-methylindol-3-yl)piperidine-1-carbonyl]-7-fluoro-4H-1,4-benzoxazin-3-one<br>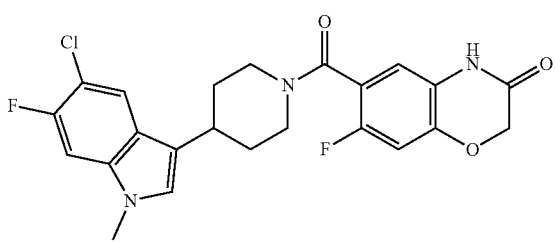<br>Off-white solid<br>Flash chromatography | Intermediate A-2 and Intermediate D-1 | 460.2 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 27 | 6-[4-(5-Chloro-6-fluoro-1-methylindol-3-yl)piperidine-1-carbonyl]-4H-1,4-benzoxazin-3-one<br><br>Off-white solid<br>Flash chromatography | Intermediate A-1<br>and<br>Intermediate D-1 | 442.3 |
| 28 | 6-(4-(5-Chloro-1-methyl-1H-indol-3-yl)piperidine-1-carbonyl)-7-fluoro-2H-benzo[b][1,4]oxazin-3(4H)-one<br><br>Colorless solid<br>Flash chromatography | Intermediate A-2<br>and<br>Intermediate D-2 | 442.3 |
| 29 | 6-[4-(5-Chloro-1-methylindol-3-yl)piperidine-1-carbonyl]-4H-1,4-benzoxazin-3-one<br><br>Colorless solid<br>Preparative HPLC | Intermediate A-1<br>and<br>Intermediate D-2 | 424.1 |
| 30 | 6-[4-(6-Chloro-1-methylindol-3-yl)piperidine-1-carbonyl]-4H-1,4-benzoxazin-3-one<br><br>Colorless solid<br>Flash chromatography | Intermediate A-1<br>and<br>Intermediate D-3 | 424.2 |

TABLE 1-continued

| Ex. | Name / Structure / Aspect / Purification method | Intermediates | MS, m/z [M + H]+ or [M − H]− |
|---|---|---|---|
| 31 | 6-[4-(1-Methylindol-3-yl)piperidine-1-carbonyl]-4H-1,4-benzoxazin-3-one<br>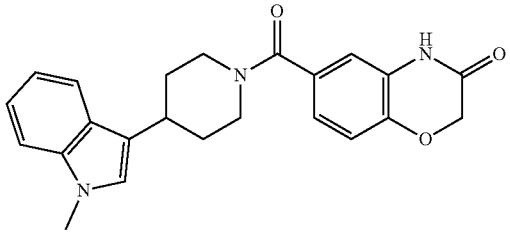<br>Yellow solid<br>Flash chromatography | Intermediate A-1 and Intermediate D-4 | 390.4 |
| 32 | 6-[4-(5-Fluoro-1-methyl-indol-3-yl)piperidine-1-carbonyl]-4H-1,4-benzoxazin-3-one<br>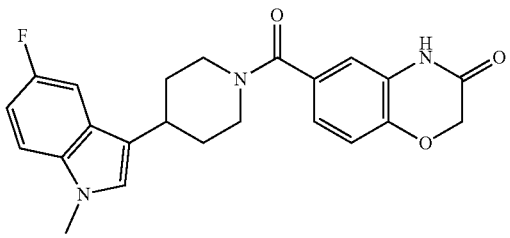<br>Colorless solid<br>Preparative HPLC | Intermediate A-1 and Intermediate D-5 | 408.2 |
| 33 | 6-[4-(6-Fluoro-1-methyl-indol-3-yl)piperidine-1-carbonyl]-4H-1,4-benzoxazin-3-one<br>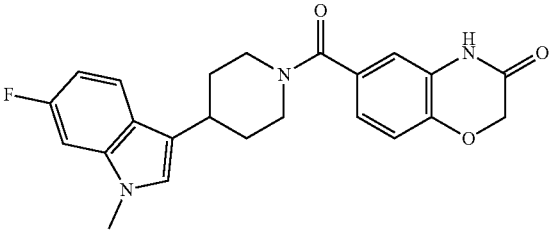<br>Colorless solid<br>Preparative HPLC | Intermediate A-1 and Intermediate D-6 | 408.2 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 34 | 6-[4-(6-Chloro-1-cyclopropylindol-3-yl)piperidine-1-carbonyl]-4H-1,4-benzoxazin-3-one<br>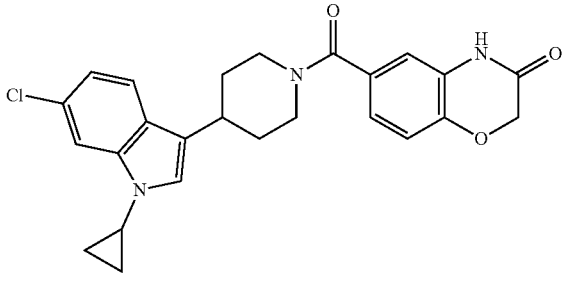<br>Light yellow solid<br>Preparative HPLC | Intermediate A-1 and Intermediate D-7 | 450.4 |
| 35 | 6-[4-[1-[(3-Chlorophenyl)methyl]indol-3-yl]piperidine-1-carbonyl]-4H-1,4-benzoxazin-3-one<br>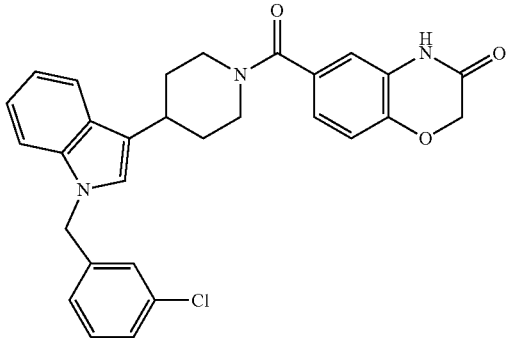<br>White solid<br>Flash chromatography | Intermediate A-1 and Intermediate D-8 | 500.3 |
| 36 | 6-[4-(1H-Indazol-3-yl)piperidine-1-carbonyl]-4H-1,4-benzoxazin-3-one<br>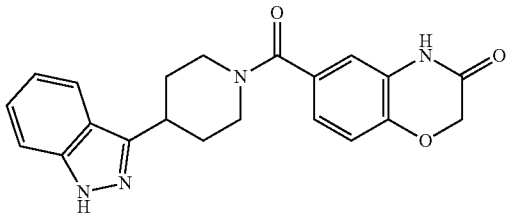<br>Off-white solid<br>Flash chromatography | Intermediate A-1 and 3-(Piperidin-4-yl)-1H-indazol (CAS RN 133455-10-4) | 377.2 |

TABLE 1-continued

| Ex. | Name / Structure / Aspect / Purification method | Intermediates | MS, m/z [M + H]+ or [M − H]− |
|---|---|---|---|
| 37 | 6-[4-[6-Fluoro-1-(2-hydroxyethyl)indazol-3-yl]piperidine-1-carbonyl]-4H-1,4-benzoxazin-3-one<br><br>Off-white solid<br>Flash chromatography | Intermediate A-1 and Intermediate E-1 | 439.4 |
| 38 | 6-[4-(6-Fluoro-1-propan-2-ylindazol-3-yl)piperidine-1-carbonyl]-4H-1,4-benzoxazin-3-one<br><br>Colorless solid<br>Preparative HPLC | Intermediate A-1 and Intermediate E-2 | 437.4 |
| 39 | 6-[4-(6-Chloro-1-methylindazol-3-yl)piperidine-1-carbonyl]-4H-1,4-benzoxazin-3-one<br><br>Colorless solid<br>Preparative HPLC | Intermediate A-1 and Intermediate E-3 | 425.3 |

TABLE 1-continued

| Ex. | Name / Structure / Aspect / Purification method | Intermediates | MS, m/z [M + H]+ or [M − H]− |
|---|---|---|---|
| 40 | 6-[4-(1H-Indol-2-yl)piperidine-1-carbonyl]-4H-1,4-benzoxazin-3-one<br>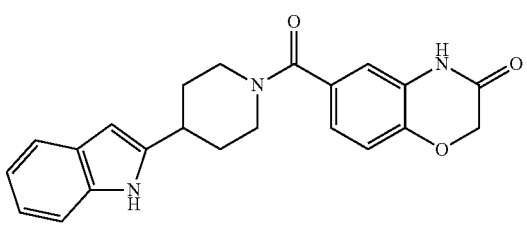<br>Colorless solid<br>Flash chromatography | Intermediate A-1 and 2-(piperidin-4-yl)-1H-indol | 376.2 |
| 41 | 6-[4-(5-Methoxy-2-methyl-1H-indol-3-yl)piperidine-1-carbonyl]-4H-1,4-benzoxazin-3-one<br>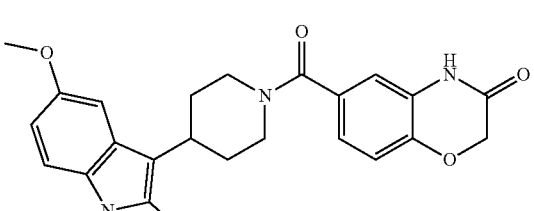<br>Off-white solid<br>Flash chromatography | Intermediate A-1 and 5-Methoxy-2-methyl-3-(piperidin-4-yl)-1H-indole (CAS RN 1260860-11-4) | 420.3 |
| 42 | 6-[4-(1-Benzothiophen-3-yl)piperidine-1-carbonyl]-4H-1,4-benzoxazin-3-one<br>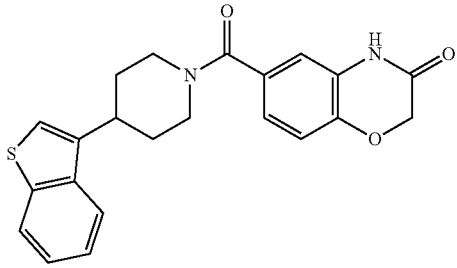<br>Colorless solid<br>Flash chromatography | Intermediate A-1 and 4-(Benzo[b]thiophen-3-yl)piperidine (CAS RN 56839-05-5) | 393.2 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 43 | 6-[4-(6-Fluoro-1H-indazol-3-yl)piperidine-1-carbonyl]-4H-1,4-benzoxazin-3-one<br>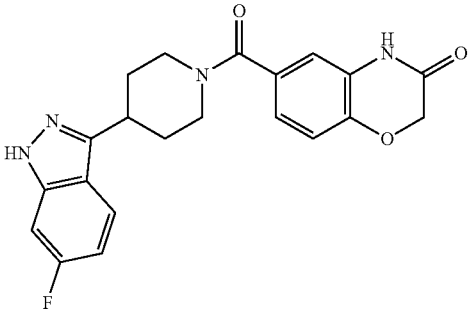<br>Colorless solid<br>Preparative HPLC | Intermediate A-1 and 6-fluoro-3-(4-piperidinyl)-1H-indazole (CAS RN 98294-88-3) | 395.3 |
| 44 | 6-[4-[5-(4-Chlorophenyl)-1H-pyrazol-3-yl]piperidine-1-carbonyl]-4H-1,4-benzoxazin-3-one<br>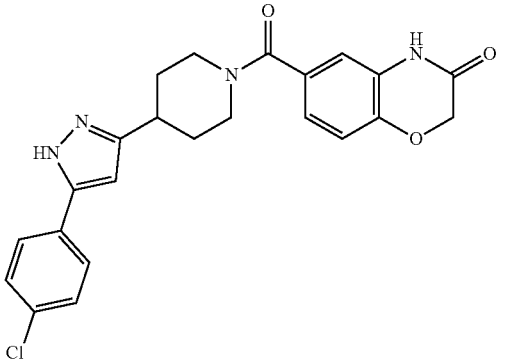<br>Off-white solid<br>Flash chromatography | Intermediate A-1 and 4-[5-(4-Chlorophenyl)-1H-pyrazol-3-yl]piperidine (CAS RN 156336-70-8) | 437.3 |
| 45 | 6-[4-(1H-Pyrrolo[2,3-b]pyridin-3-yl)piperidine-1-carbonyl]-4H-1,4-benzoxazin-3-one<br>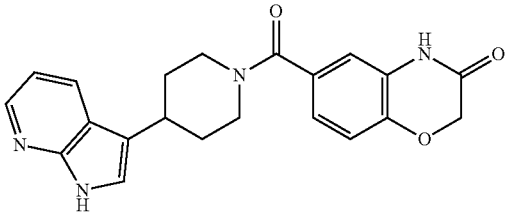<br>Off-white solid<br>Preparative HPLC | Intermediate A-1 and 3-(Piperidin-4-yl)-1H-pyrrolo[2,3-b]pyridine (CAS RN 149692-82-0) | 377.3 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 46 | 6-[4-(6-Chloro-1H-indol-2-yl)piperidine-1-carbonyl]-4H-1,4-benzoxazin-3-one<br>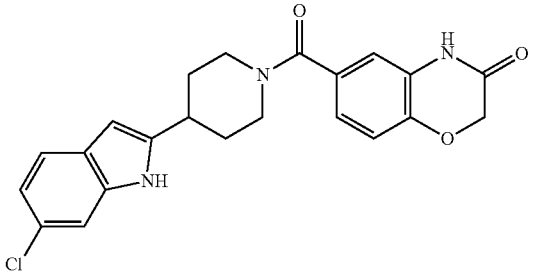<br>Off-white amorphous<br>Preparative HPLC | Intermediate A-1 and 6-Chloro-2-(4-piperidyl)-1H-indole (CAS RN 1541759-83-4) | 410.3 |
| 47 | 6-[4-(5-Chloro-2-methyl-1H-indol-3-yl)piperidine-1-carbonyl]-4H-1,4-benzoxazin-3-one<br>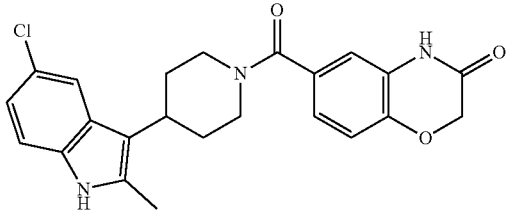<br>Colorless solid<br>Flash chromatography | Intermediate A-1 and 5-Chloro-2-methyl-3-(piperidin-4-yl)-1H-indole (CAS RN 400801-74-3) | 424.3 |
| 48 | 6-[4-(5-Phenyl-1,3,4-oxadiazol-2-yl)piperidine-1-carbonyl]-4H-1,4-benzoxazin-3-one<br>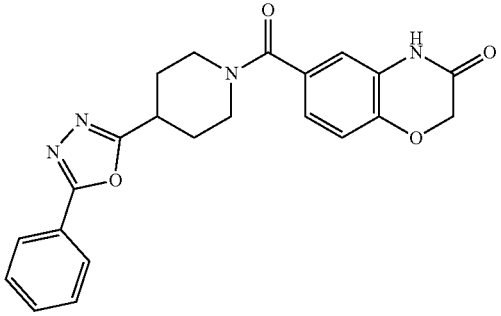<br>Colorless solid<br>Flash chromatography | Intermediate A-1 and 4-(5-Phenyl-1,3,4-oxadiazol-2-yl)piperidine (CAS RN 280110-78-3) | 403.5 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 49 | 6-(4-(1H-Benzo[d]imidazol-1-yl)piperidine-1-carbonyl)-2H-benzo[b][1,4]oxazin-3(4H)-one<br>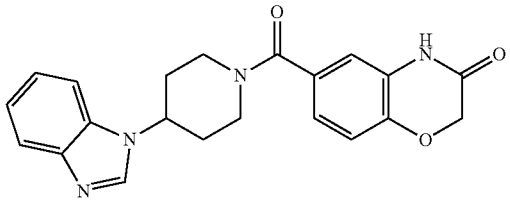<br>Off-white amorphous<br>Preparative HPLC | Intermediate A-1 and 1-(Piperidin-4-yl)-1H-benzo[d]imidazole (CAS RN 83763-11-5) | 377.2 |
| 50 | 6-[4-[6-(Trifluoromethyl)-1,2-benzoxazol-3-yl]piperidine-1-carbonyl]-4H-1,4-benzoxazin-3-one<br>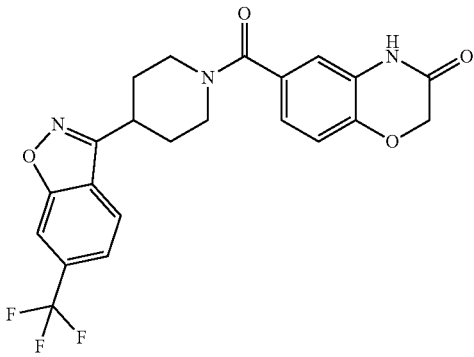<br>Off-white solid<br>Preparative HPLC | Intermediate A-1 and 3-(4-Piperidyl)-6-(trifluoromethyl)-1,2-benzoxazole (CAS RN 733733-84-1) | 446.2 |
| 51 | 6-[4-(6-fluoro-1,2-benzoxazol-3-yl)piperidine-1-carbonyl]-4H-1,4-benzoxazin-3-one<br>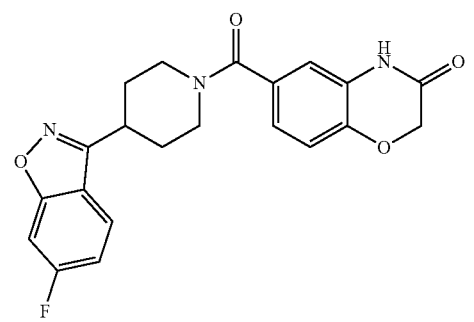<br>Colorless solid<br>Preparative HPLC | Intermediate A-1 and 6-Fluoro-3-(piperidin-4-yl)benzo[d]isoxazole (CAS RN 84163-77-9) | 396.2 |

TABLE 1-continued

| Ex. | Name<br>Structure<br>Aspect<br>Purification method | Intermediates | MS, m/z<br>[M + H]⁺<br>or<br>[M − H]⁻ |
|---|---|---|---|
| 52 | 6-[4-(5-fluoro-1,2-benzoxazol-3-yl)piperidine-1-carbonyl]-4H-1,4-benzoxazin-3-one<br>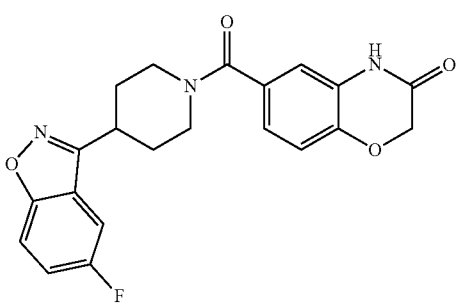<br>Off-white solid<br>Flash chromatography | Intermediate A-1 and 5-Fluoro-3-(piperidin-4-yl)benzo[d]isoxazole (CAS RN 84163-64-4) | 396.4 |
| 53 | 6-[4-[2-(4-chlorophenyl)oxolan-2-yl]piperidine-1-carbonyl]-4H-1,4-benzoxazin-3-one<br>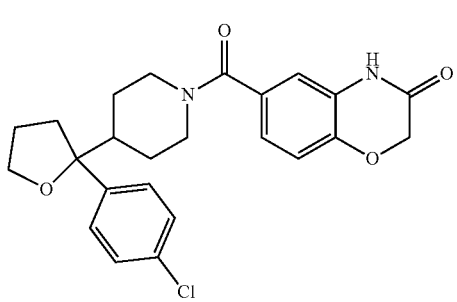<br>Off-white solid<br>Preparative HPLC | Intermediate A-1 and 4-[2-(4-Chlorophenyl)oxolan-2-yl]piperidine (CAS RN 21674-73-7) | 441.3 |
| 54 | 6-[4-[2-(4-Bromophenyl)-1,3-dioxolan-2-yl]piperidine-1-carbonyl]-4H-1,4-benzoxazin-3-one<br>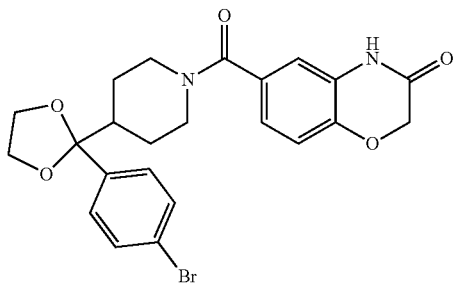<br>Colorless solid<br>Preparative HPLC | Intermediate A-1 and 4-(2-(4-Bromophenyl)-1,3-dioxolan-2-yl)piperidine (CAS RN 203186-02-1) | 488.1 |

TABLE 1-continued

| Ex. | Name<br>Structure<br>Aspect<br>Purification method | Intermediates | MS, m/z<br>[M + H]+<br>or<br>[M − H]− |
|---|---|---|---|
| 55 | 6-[4-(1-Phenylcyclopropyl)piperidine-<br>1-carbonyl]-4H-1,4-benzoxazin-3-one<br>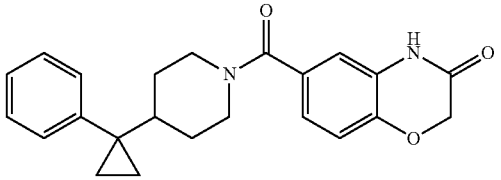<br>Colorless solid<br>Preparative HPLC | Intermediate A-1<br>and<br>4-(1-Phenyl-<br>cyclopropyl)-<br>piperidine<br>(CAS RN<br>1557811-60-5) | 377.2 |
| 56 | 6-[3-(3-chlorophenyl)pyrrolidine-1-<br>carbonyl]-4H-1,4-benzoxazin-3-one<br>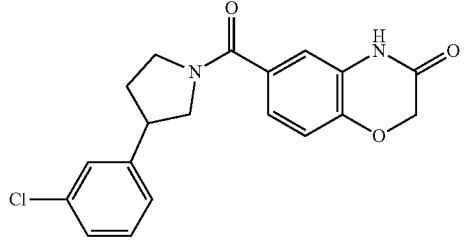<br>Off-white solid<br>Flash chromatography | Intermediate A-1<br>and<br>3-(3-<br>Chlorophenyl)<br>pyrrolidine<br>(CAS RN 914299-59-5) | 357.1 |
| 57 | 6-[3-[4-(trifluoromethyl)pyrimidin-2-<br>yl]pyrrolidine-1-carbonyl]-4H-1,4-<br>benzoxazin-3-one<br>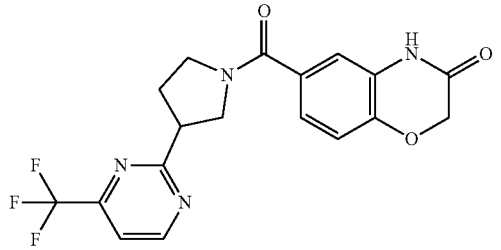<br>Colorless solid<br>Flash chromatography | Intermediate A-1<br>and<br>2-(pyrrolidin-3-yl)-<br>4-<br>(trifluoromethyl)<br>pyrimidine<br>(CAS RN<br>1257522-06-7) | 393.1 |

The following examples listed in Table 2 were also prepared using the procedures described herein, or in analogy to methods described in literature. Purification methods known to the skilled artisan, such as preparative HPLC, silica gel flash chromatography or SFC were used to purify the final products.

TABLE 2

| Ex. | Name and Structure |
|---|---|
| 58 | 6-[4-[(4-methoxyphenyl)-phenyl-methyl]piperidine-1-carbonyl]-4H-1,4-benzoxazin-3-one |
| 59 | 6-[4-[m-tolyl(phenyl)methyl]piperidine-1-carbonyl]-4H-1,4-benzoxazin-3-one |
| 60 | 6-[4-[indol-1-yl(phenyl)methyl]piperidine-1-carbonyl]-4H-1,4-benzoxazin-3-one |
| 61 | 6-[4-[[4-(2-fluoroethoxy)phenyl]-(4-fluorophenyl)methyl]piperidine-1-carbonyl]-4H-1,4-benzoxazin-3-one |

TABLE 2-continued

| Ex. | Name and Structure |
|---|---|
| 62 | 6-[4-[(R)-(2-fluoro-4-pyridyl)-phenyl-methyl]piperidine-1-carbonyl]-4H-1,4-benzoxazin-3-one |
| 63 | 6-[4-[(S)-(2-fluoro-4-pyridyl)-phenyl-methyl]piperidine-1-carbonyl]-4H-1,4-benzoxazin-3-one |
| 64 | 6-[4-[(S)-[4-(2-fluoroethoxy)phenyl]-(4-fluorophenyl)methyl]piperidine-1-carbonyl]-4H-1,4-benzoxazin-3-one |
| 65 | 6-[4-[(R)-[4-(2-fluoroethoxy)phenyl]-(4-fluorophenyl)methyl]piperidine-1-carbonyl]-4H-1,4-benzoxazin-3-one |

TABLE 2-continued

| Ex. | Name and Structure |
|---|---|
| 68 | 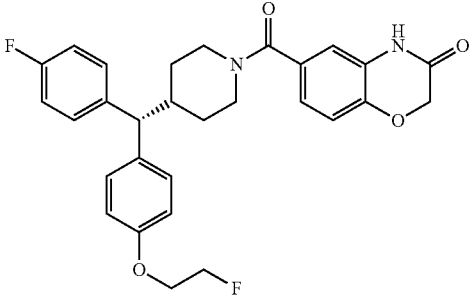 6-[4-(6-methoxy-1-methyl-indol-3-yl)piperidine-1-carbonyl]-4H-1,4-benzoxazin-3-one |
| 69 | 6-[4-[(4-fluorophenyl)-(4-methoxyphenyl)methyl]piperidine-1-carbonyl]-4H-1,4-benzoxazin-3-one |
| 70 | 6-[4-[(S)-(4-fluorophenyl)-(4-methoxyphenyl)methyl]piperidine-1-carbonyl]-4H-1,4-benzoxazin-3-one |
| 71 | 6-[4-[(R)-(4-fluorophenyl)-(4-methoxyphenyl)methyl]piperidine-1-carbonyl]-4H-1,4-benzoxazin-3-one |
| 72 | 6-[4-[[3-(2-fluoroethoxy)phenyl]-phenyl-methyl]piperidine-1-carbonyl]-4H-1,4-benzoxazin-3-one |
| 73 | 6-[4-[[4-(2-fluoroethoxy)phenyl]-penyl-methyl]piperidine-1-carbonyl]-4H-1,4-benzoxazin-3-one |
| 74 | 6-[4-[(S)-(3-fluorophenyl)-phenyl-methyl]piperidine-1-carbonyl]-4H-1,4-benzoxazin-3-one |
| 75 | 6-[4-[(R)-(3-fluorophenyl)-phenyl-methyl]piperidine-1-carbonyl]-4H-1,4-benzoxazin-3-one |

TABLE 2-continued

| Ex. | Name and Structure |
|---|---|
| 76 | 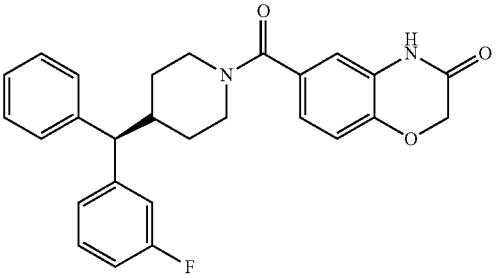 [SMILES: O=C1COc2ccc(C(=O)N3CCC([C@H](c4ccccc4)c4ccnc(F)c4)CC3)cc2N1]<br>6-[4-[(R)-[3-(2-fluoroethoxy)phenyl]-(4-fluorophenyl)methyl]piperidine-1-carbonyl]-4H-1,4-benzoxazin-3-one |
| 77 | 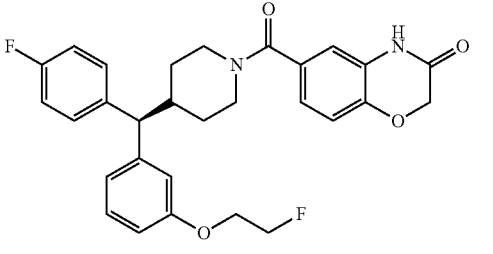 [SMILES: O=C1COc2ccc(C(=O)N3CCC([C@H](c4ccc(F)cc4)c4cccc(OCCF)c4)CC3)cc2N1]<br>6-[4-[(S)-[3-(2-fluoroethoxy)phenyl]-(4-fluorophenyl)methyl]piperidine-1-carbonyl]-4H-1,4-benzoxazin-3-one |
| 78 | 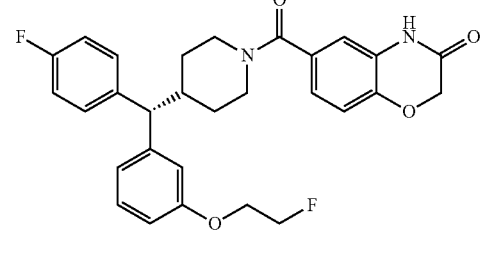<br>6-[4-[(2-fluoro-3-pyridyl)-phenyl-methyl]piperidine-1-carbonyl]-4H-1,4-benzoxazin-3-one |
| 79 | 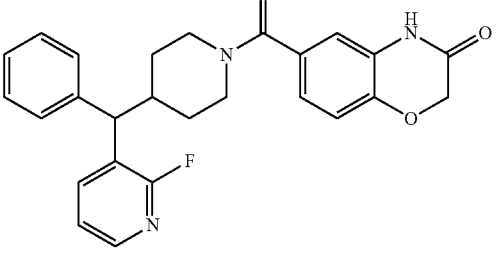<br>6-[4-[(R)-[4-(2-fluoroethoxy)phenyl]-phenyl-methyl]piperidine-1-carbonyl]-4H-1,4-benzoxazin-3-one |
| 80 | 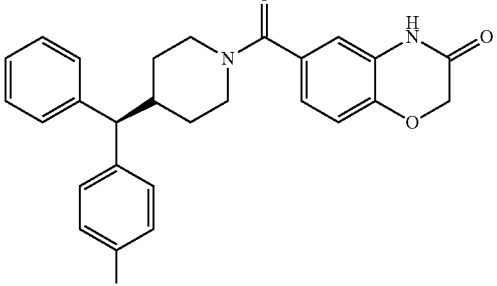<br>6-[4-[(S)-[4-(2-fluoroethoxy)phenyl]-phenyl-methyl]piperidine-1-carbonyl]-4H-1,4-benzoxazin-3-one |
| 81 | 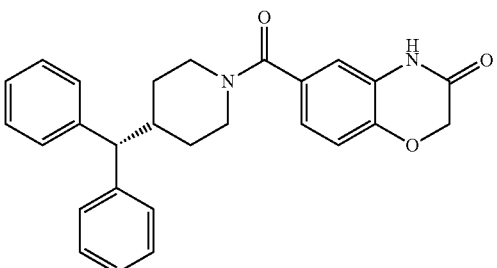<br>6-[4-[(S)-[3-(2-fluoroethoxy)phenyl]-phenyl-methyl]piperidine-1-carbonyl]-4H-1,4-benzoxazin-3-one |
| 82 | 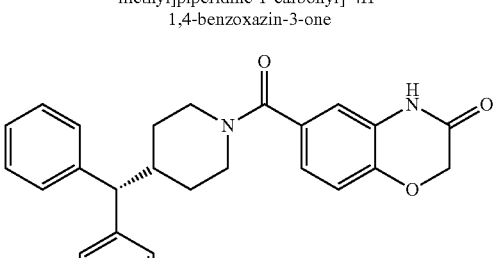<br>6-[4-[(3-fluorophenyl)-phenyl-methyl]piperidine-1-carbonyl]-4H-1,4-benzoxazin-3-one |
| 83 | 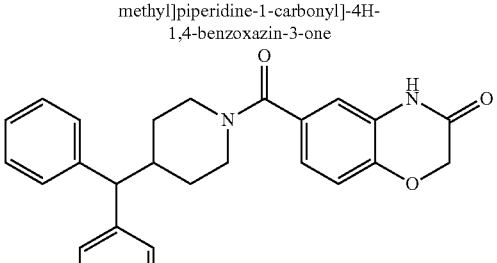<br>6-(4-benzhydrylpiperazine-1-carbonyl)-4H-1,4-benzoxazin-3-one |

TABLE 2-continued

| Ex. | Name and Structure |
|---|---|
| 84 | 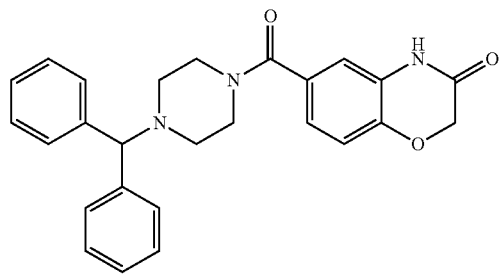 [SMILES: O=C1COc2ccc(C(=O)N3CCN(C(c4ccccc4)c4ccccc4)CC3)cc2N1]
6-[4-[bis(4-fluorophenyl)methyl]piperazine-1-carbonyl]-4H-1,4-benzoxazin-3-one |
| 85 | 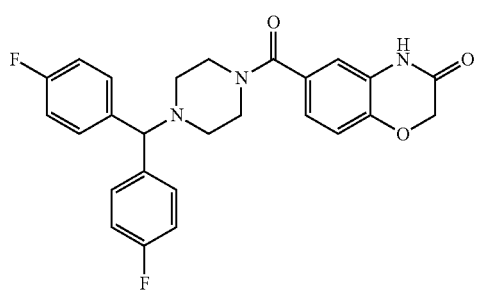 [SMILES: O=C1COc2ccc(C(=O)N3CCN(C(c4ccc(F)cc4)c4ccc(F)cc4)CC3)cc2N1]
6-[4-[4-chloro-3-(trifluoromethyl)phenyl]piperazine-1-carbonyl]-4H-1,4-benzoxazin-3-one |
| 86 | 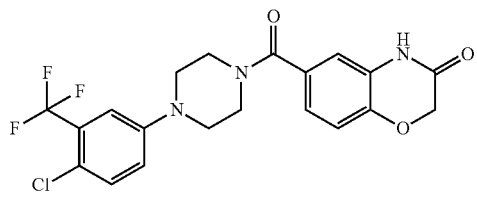 [SMILES: O=C1COc2ccc(C(=O)N3CCN(c4ccc(Cl)c(C(F)(F)F)c4)CC3)cc2N1]
6-[4-(3,4-dichlorophenyl)piperazine-1-carbonyl]-4H-1,4-benzoxazin-3-one |
| 87 | 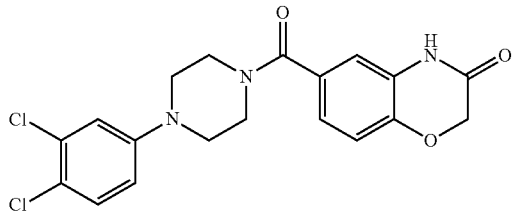 [SMILES: O=C1COc2ccc(C(=O)N3CCN(c4ccc(Cl)c(Cl)c4)CC3)cc2N1]
6-[4-(3,5-dichlorophenyl)piperazine-1-carbonyl]-4H-1,4-benzoxazin-3-one |
| 88 | 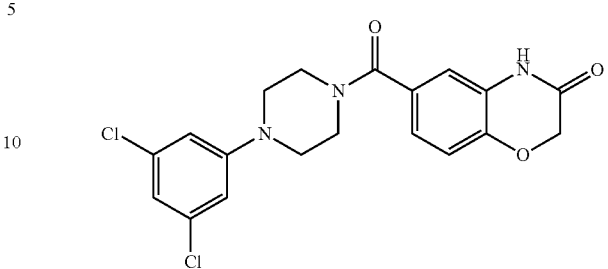
6-[4-[4-(trifluoromethyl)-2-pyridyl]piperazine-1-carbonyl]-4H-1,4-benzoxazin-3-one |
| 89 | 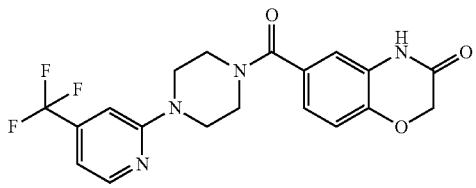 [SMILES: O=C1COc2ccc(C(=O)N3CCN(c4cc(C(F)(F)F)ccn4)CC3)cc2N1]
6-[4-(3,5-dimethoxyphenyl)piperazine-1-carbonyl]-4H-1,4-benzoxazin-3-one |
| 90 | 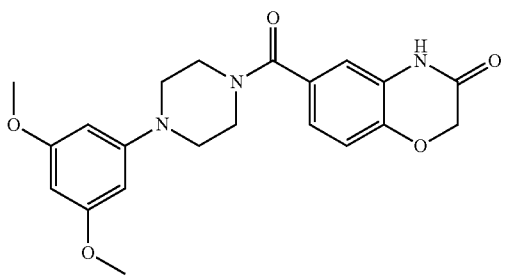 [SMILES: COc1cc(OC)cc(N2CCN(C(=O)c3ccc4c(c3)NC(=O)CO4)CC2)c1]
6-[4-[5-(trifluoromethyl)-2-pyridyl]piperazine-1-carbonyl]-4H-1,4-benzoxazin-3-one |
| 91 | 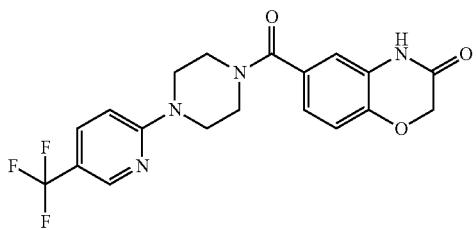 [SMILES: O=C1COc2ccc(C(=O)N3CCN(c4ccc(C(F)(F)F)cn4)CC3)cc2N1]
6-[4-(1,2-benzothiazol-3-yl)piperazine-1-carbonyl]-4H-1,4-benzoxazin-3-one |

TABLE 2-continued

| Ex. | Name and Structure |
|---|---|
| 92 | 6-[4-(3,4,5-trimethoxyphenyl)piperazine-1-carbonyl]-4H-1,4-benzoxazin-3-one 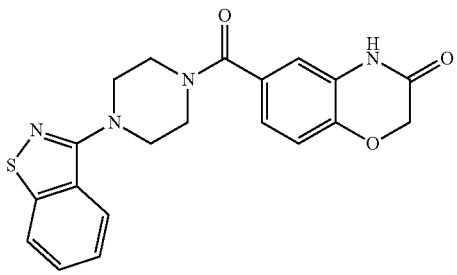 [SMILES: O=C1COc2ccc(C(=O)N3CCN(c4nsc5ccccc45)CC3)cc2N1] |

Examples 66 and 67

Intermediate F-1

2-(2-(3-Bromophenoxy)ethoxy)ethanol

A solution of 2-(2-hydroxyethoxy)ethyl 4-methylbenzenesulfonate (2.50 g, 9.6 mmol), 3-bromophenol (1.99 g, 11.5 mmol), and cesium carbonate (6.26 mg, 19.2 mmol) in MeCN (12 mL) was stirred at 70° C. for 16 h. The reaction mixture was concentrated in vacuo to give a residue, which was purified by silica gel chromatography (petroleum ether: EtOAc 5:1 to 1:1) to afford 2-(2-(3-bromophenoxy)ethoxy)ethanol (1.78 g 63%) as a colorless oil; $^1$H NMR (400 MHz, CDCl$_3$) δ=7.20-7.14 (m, 1H), 7.14-7.07 (m, 2H), 6.94-6.82 (m, 1H), 4.18-4.12 (m, 2H), 3.92-3.86 (m, 2H), 3.88-3.71 (m, 2H), 3.73-3.66 (m, 2H), 2.18 (br s, 1H).

Intermediate F-2

2-(2-(3-Bromophenoxy)ethoxy)ethyl 4-methylbenzenesulfonate

A solution of 2-(2-(3-bromophenoxy)ethoxy)ethanol (1.78 g, 6.8 mmol), p-toluenesulfonyl chloride (1.69 g, 8.8 mmol) and triethylamine (1.9 mL, 13.6 mmol) in DCM (40 mL) was stirred at 25° C. for 16 h. The reaction was concentrated in vacuo to give a residue, which was purified by silica gel chromatography (petroleum ether:EtOAc 5:1 to 1:1) to afford 2-(2-(3-bromophenoxy)ethoxy)ethyl 4-methylbenzenesulfonate (2.01 g, 70%) as colorless oil; LCMS: 414.9 [M+H]$^+$.

Intermediate F-3

1-Bromo-3-(2-(2-fluoroethoxy)ethoxy)benzene

A solution of 2-(2-(3-bromophenoxy)ethoxy)ethyl 4-methylbenzenesulfonate (780 mg, 1.88 mmol) and tetrabutylammonium fluoride (4.91 g, 18.8 mmol) in THF (50 mL) was stirred at 25° C. for 16 h. The reaction solution was poured into brine (30 mL) and extracted with EtOAc (60 mL). The organic layer was washed with brine (5×30 mL), dried over Na$_2$SO$_4$, filtered and concentrated in vacuo to give a residue, which was purified by silica gel chromatography (petroleum ether:ethyl acetate 20:1) to give 1-bromo-3-(2-(2-fluoroethoxy)ethoxy)benzene (350 mg, 70%) as a colorless oil. $^1$H NMR (400 MHz, CDCl$_3$) S=7.19-7.08 (m, 3H), 6.88 (d, J=1.2, 2.3, 8.0 Hz, 1H), 4.71-4.65 (m, 1H), 4.59-4.53 (m, 1H), 4.19-4.11 (m, 2H), 3.95-3.85 (m, 3H), 3.82-3.78 (m, 1H).

Intermediate F-4 tert-Butyl-4-[[3-[2-(2-fluoroethoxy)ethoxy]phenyl]-hydroxy-phenyl-methyl]piperidine-1-carboxylate To a mixture under N$_2$ of 1-bromo-3-(2-(2-fluoroethoxy)ethoxy)benzene (350 mg, 1.33 mmol) in THF (5 mL) was added dropwise a butyllithium solution (0.93 mL, 1.86 mmol) with stirring at −78° C. Stirring was continued at −78° C. for 1 h. Then the solution was added tert-butyl 4-benzoylpiperidine-1-carboxylate (423.44 mg, 1.46 mmol) with and the resulting mixture was stirred at −78° C. for 4 h. The reaction solution was poured into brine (20 mL) and extracted with ethyl acetate (20 mL). The organic layer was concentrated in vacuo to give a residue, which was purified by Prep-HPLC (TEA conditions) to give tert-butyl-4-[[3-[2-(2-fluoroethoxy)ethoxy]phenyl]-hydroxy-phenyl-methyl]piperidine-1-carboxylate (120 mg, 18%) as light yellow solid; LC-MS: 496.1 [M+Na]$^+$.

Intermediate F-5

4-((3-(2-(2-Fluoroethoxy)ethoxy)phenyl)(phenyl)methylene)piperidine

A solution of tert-butyl-4-[[3-[2-(2-fluoroethoxy)ethoxy]phenyl]-hydroxy-phenyl-methyl]piperidine-1-carboxylate (120 mg, 0.250 mmol) and trifluoroacetic acid (0.2 mL, 2.53 mmol) in DCM (2 mL) was stirred at 25° C. for 16 h. The reaction solution was concentrated in vacuo to give 4-((3-(2-(2-fluoroethoxy)ethoxy)phenyl)(phenyl)methylene)piperidine (TFA salt, 90 mg, 99%) as colorless oil; LC-MS: 356.1 [M+H]$^+$.

Intermediate F-6

4-((3-(2-(2-Fluoroethoxy)ethoxy)phenyl)(phenyl)methyl)piperidine

A mixture of 4-((3-(2-(2-fluoroethoxy)ethoxy)phenyl)(phenyl)methylene)piperidine (90 mg, 0.25 mmol) and Pd/C (27 mg, 0.030 mmol) in THF (5 mL) was stirred at 25° C. for 16 h under H$_2$ (760 mmHg). The mixture was filtered and concentrated in vacuo to give 4-((3-(2-(2-fluoroethoxy)ethoxy)phenyl)(phenyl)methyl)piperidine (90 mg, 99%) as a colorless oil; LC-MS: 358.3 [M+H]$^+$.

rac-6-[4-[[3-[2-(2-Fluoroethoxy)ethoxy]phenyl]-phenyl-methyl]piperidine-1-carbonyl]-4H-1,4-benzoxazin-3-one A mixture of 4-((3-(2-(2-fluoroethoxy)ethoxy)phenyl)(phenyl)methyl)piperidine (90 mg, 0.25 mmol), 3-oxo-4H-1,4-benzoxazine-6-carboxylic acid (49 mg, 0.25 mmol), triethylamine (0.04 mL, 0.30 mmol) and <9-(7-azabenzotriazol-1-yl)-N,N,N',N'-tetramethyluroniumhexafluorophosphate (115 mg, 0.300 mmol) in DCM (5 mL) was stirred at 25° C. for 16 h. The reaction mixture was poured into brine (30 mL) and extracted with DCM (2×20 mL). The combined organic layers were concentrated in vacuo to give a residue, which was purified by Prep-HPLC (TFA conditions) to give 6-[4-[[3-[2-(2-Fluoroethoxy)ethoxy]phenyl]-phenyl-methyl]piperidine-1-carbonyl]-4H-1,4-benzoxazin-3-one (70 mg, 52%) as a grey solid; LC-MS: 533.2 [M+H]⁺.

6-(4-((3-(2-(2-Fluoroethoxy)ethoxy)phenyl)(phenyl)methyl)piperidine-1-carbonyl)-2H-benzo[b][1,4]oxazin-3(4H)-one (70 mg, 0.13 mmol) was separated by SFC (Method: Column DAICEL CHIRALPAK AD (250 mm*30 mm. 10 μm). Condition 0.1% NH₃H₂O IPA, Begin B, End B 45, Gradient Time (min) 3.4 min; 70 min, 100% B Hold Time (min) 10 FlowRate (ml/min) 70) to give 6-[4-[(R)-[3-[2-(2-fluoroethoxy)ethoxy]phenyl]-phenyl-methyl]piperidine-1-carbonyl]-4H-1,4-benzoxazin-3-one 66 (16.3 mg, 23% yield; LC-MS: 533.2 [M+H]⁺) and 6-[4-[(S)-[3-[2-(2-fluoroethoxy)ethoxy]phenyl]-phenyl-methyl]piperidine-1-carbonyl]-4H-1,4-benzoxazin-3-one 67 (16.5 mg, 23% yield; LC-MS: 533.1 [M+H]⁺) as a white solids.

Example 93

6-[4-[[4-(2-Fluoroethoxy)phenyl]-(4-fluorophenyl)methylene]piperidine-1-carbonyl]-4H-1,4-benzoxazin-3-one

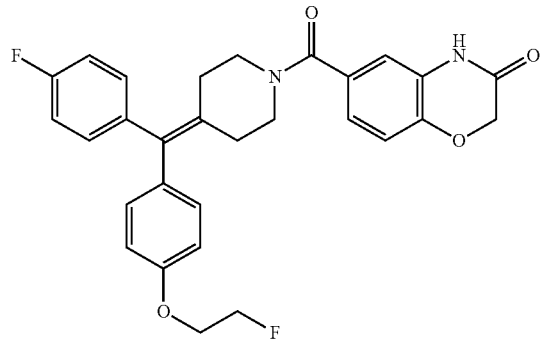 [SMILES: O=C1COc2ccc(C(=O)N3CCC(=C(c4ccc(F)cc4)c4ccc(OCCF)cc4)CC3)cc2N1]

Intermediate G-1

4-[[4-(2-Fluoroethoxy)phenyl]-(4-fluorophenyl)methylene]piperidine

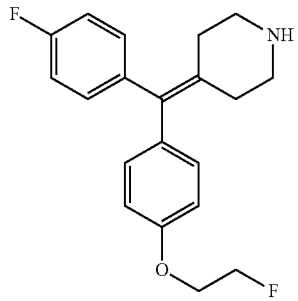 [SMILES: FCCOc1ccc(C(=C2CCNCC2)c2ccc(F)cc2)cc1]

The title compound was prepared in analogy to 4-[[3-[2-(2-fluoroethoxy)ethoxy]phenyl]-(4-fluorophenyl)methylene]piperidine (intermediate H-4) from 1-bromo-4-(2-fluoroethoxy)benzene (CAS Nr. 332-47-8) and tert-butyl 4-(4-fluorobenzoyl)piperidine-1-carboxylate (intermediate H-2). Yield 985 mg (87%), dark red oil; LCMS: 330.1 [M+H]⁺.

6-[4-[[4-(2-Fluoroethoxy)phenyl]-(4-fluorophenyl)methylene]piperidine-1-carbonyl]-4H-1,4-benzoxazin-3-one A solution of 4-[[4-(2-fluoroethoxy)phenyl]-(4-fluorophenyl)methylene]piperidine (485 mg, 1.25 mmol), 3-oxo-4H-1,4-benzoxazine-6-carboxylic acid (242 mg, 1.25 mmol), O-(7-azabenzotriazol-1-yl)-N,N,N',N'-tetramethyluronium hexafluorophosphate (571 mg, 1.5 mmol), and triethylamine (0.21 mL, 1.5 mmol) in DCM (10 mL) was stirred at 25° C. for 16 h. The reaction solution was poured into brine (30 mL) and extracted with DCM (2×20 mL). The combined organic layers were concentrated in vacuo and the resulting residue was purified by prep-HPLC (TFA conditions) to yield 6-[4-[[4-(2-fluoroethoxy)phenyl]-(4-fluorophenyl)methylene]piperidine-1-carbonyl]-4H-1,4-benzoxazin-3-one (344 mg, 52%) as white solid; LC-MS: 505.3 [M+H]⁺.

Examples 94 and 95

6-[4-[(S or R)-[3-[2-(2-Fluoroethoxy)ethoxy]phenyl]-(4-fluorophenyl)methyl]piperidine-1-carbonyl]-4H-1,4-benzoxazin-3-one and 6-[4-[(R or S)-[3-[2-(2-fluoroethoxy)ethoxy]phenyl]-(4-fluorophenyl)methyl]piperidine-1-carbonyl]-4H-1,4-benzoxazin-3-one

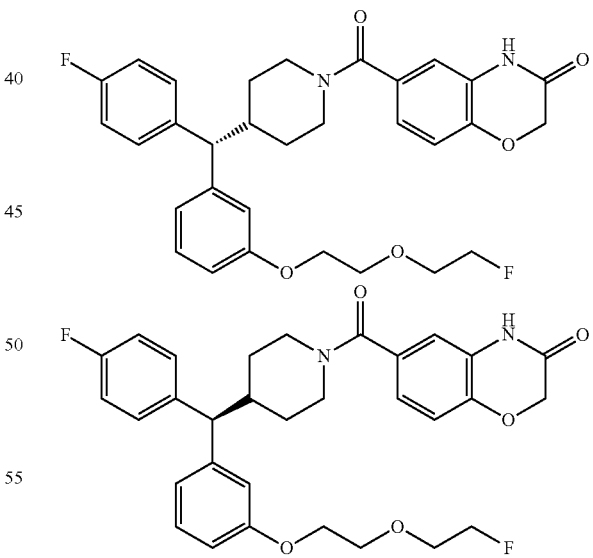

Intermediate H-1 tert-Butyl 4-(methoxy(methyl)carbamoyl)piperidine-1-carboxylate

A mixture of TV-Boc-isonipecotic acid (10.0 g, 43.6 mmol), O,N-dimethylhydroxylamine HCl (6.38 g, 65.4 mmol), triethylamine (12.2 mL, 87.23 mmol) and 1-hydroxybenzotriazole (7.07 g, 52.3 mmol) and EDCl (10.0 g, 52.3 mmol) in DMF (50 mL) was stirred at 25° C. for 16 h. The mixture was concentrated in vacuo to give a residue which was neutralized by HCl (1M) to pH=7 and extracted with ethyl acetate (3×100 mL). The combined organic layers were dried over $Na_2SO_4$, filtered and concentrated in vacuo to give a residue which was purified by flash column (petroleum ether:ethyl acetate 10:1) to give tert-butyl 4-(methoxy(methyl)carbamoyl)piperidine-1-carboxylate (10 g, 84%) as a light yellow solid; LC-MS: 295.1 [M+Na]$^+$.

Intermediate H-2 tert-Butyl 4-(4-fluorobenzoyl)piperidine-1-carboxylate

A mixture of tert-butyl 4-(methoxy(methyl)carbamoyl)piperidine-1-carboxylate (8.2 g, 30 mmol) in THF (20 mL) was added dropwise 4-fluorophenylmagnesium bromide (67.7 mL, 135 mmol) with stirring at 0° C. After addition, the mixture was stirred at 0° C. for 3 h under $N_2$. The mixture was poured into brine (80 mL) and extracted with ethyl acetate (2×50 mL). The combined organic layers were dried over $Na_2SO_4$, filtered and concentrated in vacuo to give a residue which was purified by flash column (petroleum ether:ethyl acetate 10:1) to give tert-butyl 4-(4-fluorobenzoyl)piperidine-1-carboxylate (7.8 g, 62%) as a yellow solid; LC-MS: 330.0 [M+Na]$^+$.

Intermediate H-3 tert-Butyl 4-((3-(2-(2-fluoroethoxy)ethoxy)phenyl)(4-fluorophenyl)(hydroxy)methyl) piperidine-1-carboxylate To a mixture under $N_2$ of 1-bromo-3-[2-(2-fluoroethoxy)ethoxy]benzene (Intermediate F-3) (600 mg, 2.28 mmol) in THF (10 mL) was added dropwise butyllithium (1.6 mL, 3.2 mmol) at −78° C., and the mixture was stirred at −78° C. for 1 h. Then tert-butyl 4-(4-fluorobenzoyl)piperidine-1-carboxylate (771 mg, 2.51 mmol) was added, and the mixture was stirred at −78° C. for additional 5 h. The mixture was poured into brine (20 mL) and extracted with ethyl acetate (20 mL). The organic layer was concentrated in vacuo to give a residue which was purified by Prep-HPLC (TFA conditions) to give tert-butyl 4-((3-(2-(2-fluoroethoxy)ethoxy)phenyl)(4-fluorophenyl)(hydroxy)methyl)piperidine-1-carboxylate (190 mg, 15%) as light yellow oil; LC-MS: 514.1 [M+Na]$^+$.

Intermediate H-4

4-[[3-[2-(2-Fluoroethoxy)ethoxy]phenyl]-(4-fluorophenyl)methylene]piperidine

A solution of tert-butyl 4-((3-(2-(2-fluoroethoxy)ethoxy)phenyl)(4-fluorophenyl) (hydroxy)methyl)piperidine-1-carboxylate (190 mg, 0.390 mmol) and trifluoroacetic acid (0.3 mL, 3.9 mmol) in DCM (2 mL) was stirred at 25° C. for 4 h. The reaction solution was concentrated in vacuo to give 4-((3-(2-(2-fluoroethoxy)ethoxy)phenyl)(4-fluorophenyl)methylene) piperidine (TFA salt, 140 mg, 0.370 mmol, 96%) as a colorless oil; LC-MS: 374.1 [M+H]$^+$.

Intermediate H-5

4-((3-(2-(2-Fluoroethoxy)ethoxy)phenyl)(4-fluorophenyl)methyl)piperidine

A mixture of 4-((3-(2-(2-fluoroethoxy)ethoxy)phenyl)(4-fluorophenyl)methylene)piperidine (140 mg, 0.370 mmol) and Pd/C (40 mg, 0.040 mmol) in THF (5 mL) was stirred at 25° C. for 16 h under $H_2$ (760 mmHg). The mixture was filtered and the filtrate was concentrated in vacuo to give 4-((3-(2-(2-fluoroethoxy)ethoxy)phenyl)(4-fluorophenyl) methyl)piperidine (140 mg, 85%) as a light yellow oil; LC-MS: 376.1 [M+H]$^+$.

rac-6-[4-[[3-[2-(2-Fluoroethoxy)ethoxy]phenyl]-(4-fluorophenyl)methyl]piperidine-1-carbonyl]-4H-1,4-benzoxazin-3-one A mixture of 3-oxo-4H-1,4-benzoxazine-6-carboxylic acid (72 mg, 0.370 mmol), 4-((3-(2-(2-fluoroethoxy)ethoxy)phenyl)(4-fluorophenyl)methyl)piperidine (140 mg, 0.370 mmol), triethylamine (0.06 mL, 0.45 mmol) and O-(7-azabenzotriazol-1-yl)-N,N,N',N'-tetramethyluronium hexafluorophosphate (170 mg, 0.450 mmol) in DCM (5 mL) was stirred at 25° C. for 16 h. The reaction mixture was poured into brine (30 mL) and extracted with DCM (2×20 mL). The combined organic layers were concentrated in vacuo to give a residue which was purified by Prep-HPLC (TFA conditions) to give 6-[4-[[3-[2-(2-fluoroethoxy)ethoxy]phenyl]-(4-fluorophenyl)methyl]piperidine-1-carbonyl]-4H-1,4-benzoxazin-3-one (98 mg, 47%) as a grey solid; LC-MS: 551.4 [M+H]$^+$.

rac-6-[4-[[3-[2-(2-Fluoroethoxy)ethoxy]phenyl]-(4-fluorophenyl)methyl]piperidine-1-carbonyl]-4H-1,4-benzoxazin-3-one (98 mg, 0.18 mmol) was separated by SFC (Method: Column DAICEL CHIRALPAK AD (250 mm*30 mm, 10 μm). Condition 0.1% $NH_3.H_2O$ EtOH, Begin B 50, End B 50, Gradient Time (min) 6.5 min; 70 min, 100% B Hold Time (min) 10 FlowRate (mL/min) 70) to give 6-[4-[(S)-[3-[2-(2-fluoroethoxy)ethoxy]phenyl]-(4-fluorophenyl) methyl]piperidine-1-carbonyl]-4H-1,4-benzoxazin-3-one 64 (23 mg, 23% yield; LC-MS: 551.4 [M+H]$^+$) and 6-[4-[(R)-[3-[2-(2-fluoroethoxy)ethoxy]phenyl]-(4-fluorophenyl) methyl]piperidine-1-carbonyl]-4H-1,4-benzoxazin-3-one 65 (37 mg, 37% yield; LC-MS: 551.4 [M+H]$^+$) as white solids.

Examples 96 and 97

6-[4-[(S or R)-[4-[2-(2-Fluoroethoxy)ethoxy]phenyl]-phenyl-methyl]piperidine-1-carbonyl]-4H-1,4-benzoxazin-3-one and 6-[4-[(R or S)-[4-[2-(2-Fluoroethoxy)ethoxy]phenyl]-phenyl-methyl]piperidine-1-carbonyl]-4H-1,4-benzoxazin-3-one

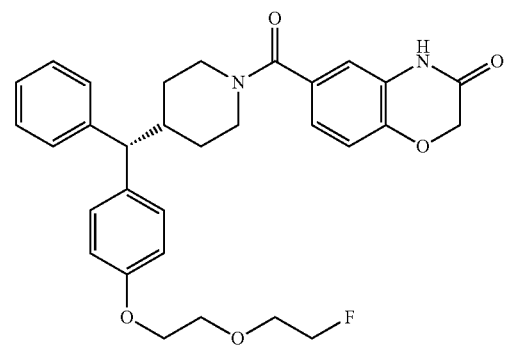

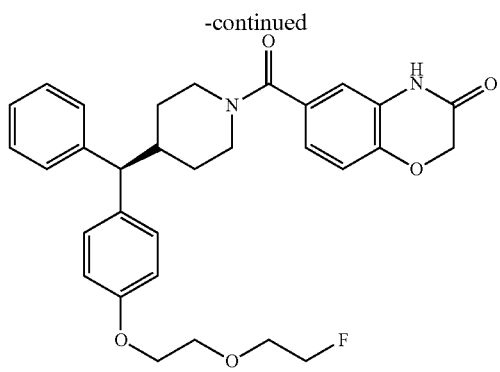

Intermediate I-1

2-(2-hydroxyethoxy)ethyl 4-methylbenzenesulfonate

A solution of diethylene glycol (5.01 g, 47.21 mmol), p-toluenesulfonyl chloride (4.50 mg, 23.6 mmol) and triethylamine (8.55 mL, 61.37 mmol) in DCM (200 mL) was stirred at 25° C. for 16 h. The reaction was added to $H_2O$ (30 mL) and extracted with DCM (2×50 mL). The organic layer was separated, dried with over $Na_2SO_4$ and concentrated under vacuum. The residue was purified by silica gel chromatography (petroleum ether:EtOAc 10:1 to 1:1) to afford 2-(2-hydroxyethoxy)ethyl 4-methylbenzenesulfonate (2.95 g, 40%) as a light yellow oil; LC-MS: 283.0 $[M+Na]^+$.

Intermediate I-2

2-(2-(4-Bromophenoxy)ethoxy)ethanol

A solution of 2-(2-hydroxyethoxy)ethyl 4-methylbenzenesulfonate (2.50 g, 9.6 mmol), 4-bromophenol (1.83 g, 10.6 mmol), and cesium carbonate (6.26 mg, 19.2 mmol) was stirred at 70° C. for 16 h. The reaction solution was concentrated under vacuum. The residue was purified by silica gel chromatography (petroleum ether:EtOAc 5:1 to 1:1) to afford 2-(2-(4-bromophenoxy)ethoxy)ethanol (1.20 g, 43%) as a colorless oil; $^1$H NMR (400 MHz, $CDCl_3$) δ=7.43-7.35 (m, 2H), 6.86-6.78 (m, 2H), 4.14-4.09 (m, 2H), 3.91-3.85 (m, 2H), 3.82-3.75 (m, 2H), 3.72-3.66 (m, 2H).

Intermediate I-3

2-[2-(4-Bromophenoxy)ethoxy]ethyl 4-methylbenzenesulfonate

A solution of 2-(2-(4-bromophenoxy)ethoxy)ethanol (1.20 g, 4.6 mmol), p-toluenesulfonyl chloride (1.14 mg, 5.97 mmol) and triethylamine (1.28 mL, 9.19 mmol) in DCM (40 mL) was stirred at 25° C. for 16 h. The reaction was concentrated under vacuum. The residue was purified by silica gel chromatography (petroleum ether:EtOAc 5:1 to 1:1) to afford 2-(2-(4-bromophenoxy)ethoxy)ethyl-4-methylbenzenesulfonate (1.72 mg, 85%) as white solid; $^1$H NMR (400 MHz, $CDCl_3$) δ=7.81 (d, J=8.3 Hz, 2H), 7.43-7.36 (m, 2H), 7.33 (d, J=8.2 Hz, 2H), 6.83-6.76 (m, 2H), 4.25-4.18 (m, 2H), 4.07-4.01 (m, 2H), 3.83-3.75 (m, 4H), 2.44 (s, 3H).

Intermediate I-4

1-Bromo-4-(2-(2-fluoroethoxy)ethoxy)benzene

A solution of 2-(2-(4-bromophenoxy)ethoxy)ethyl-4-methylbenzenesulfonate (1.72 mg, 4.14 mmol) and TBAF (10.8 g, 41.4 mmol) in THF (30 mL) was stirred at 25° C. for 12 h. EtOAc (200 mL) was added to the reaction and the solution was washed with $H_2O$ (4×50 mL). The organic layer was separated, dried over $Na_2SO_4$, filtered, and concentrated under vacuum. The residue was purified by silica gel chromatography (petroleum ether:EtOAc 20:1 to 5:1) to afford 1-bromo-4-(2-(2-fluoroethoxy)ethoxy)benzene (798 mg, 65%) as a white solid; $^1$H NMR (400 MHz, $CDCl_3$) δ=7.48-7.35 (m, 2H), 6.90-6.78 (m, 2H), 4.74-4.52 (m, 2H), 4.20-4.10 (m, 2H), 3.99-3.78 (m, 4H).

Intermediate I-5 tert-Butyl 4-[[4-[2-(2-fluoroethoxy)ethoxy]phenyl]-hydroxy-phenyl-methyl]piperidine-1-carboxylate To a solution of 1-bromo-4-(2-(2-fluoroethoxy)ethoxy)benzene (300 mg, 1.14 mmol) in THF (7 mL) was added a butyl-lithium solution (0.91 mL, 2.28 mmol) at −78° C. and the resulting mixture was stirred for 1 h. Then the reaction was warmed to 25° C. and tort-butyl 4-benzoylpiperidine-1-carboxylate (330 mg, 1.14 mmol) was added in one portion. Stirring was continued for additional 2 h. The reaction was quenched with $H_2O$ (10 mL) and extracted with EtOAc (60 mL). The organic layer was separated, dried over $Na_2SO_4$, filtered and concentrated under vacuum. The residue was purified by silica gel chromatography (petroleum ether:EtOAc 10:1 to 1:1) to afford the tert-butyl 4-[[4-[2-(2-fluoroethoxy)ethoxy]phenyl]-hydroxy-phenyl-methyl]piperidine-1-carboxylate (105 mg, 19%) as a white solid; LC-MS: 496.3 $[M+Na]^+$.

Intermediate I-6

4-((4-(2-(2-Fluoroethoxy)ethoxy)phenyl)(phenyl)methylene)piperidine

A solution of tert-butyl 4-[[4-[2-(2-fluoroethoxy)ethoxy]phenyl]-hydroxy-phenyl-methyl]piperidine-1-carboxylate (105 mg, 0.220 mmol) and trifluoroacetic acid (0.5 mL, 6.65 mmol) in DCM (0.5 mL) was stirred at 25° C. for 1 h. The reaction was concentrated under vacuum to afford 4-((4-(2-(2-fluoroethoxy)ethoxy)phenyl)(phenyl)methylene)piperidine (TFA salt, 115 mg, 97%) as red oil; LC-MS: 356.2 $[M+H]^+$.

Intermediate I-7

4-((4-(2-(2-Fluoroethoxy)ethoxy)phenyl)(phenyl)methyl)piperidine

A solution of 4-((4-(2-(2-fluoroethoxy)ethoxy)phenyl)(phenyl)methylene)piperidine (115 mg, 0.320 mmol) and Pd/C (20 mg) in THF (5 mL) was stirred at 25° C. for 16 h under $H_2$ (760 mmHg). The reach on was filtered through the Celite. The solution was concentrated under vacuum to afford 4-((4-(2-(2-fluoroethoxy)ethoxy)phenyl)(phenyl)methyl)piperidine (115 mg, 90%) as yellow oil; LCMS: 358.2 $[M+H]^+$.

rac-6-[4-[[4-[2-(2-Fluoroethoxy)ethoxy]phenyl]-phenyl-methyl]piperidine-1-carbonyl]-4H-1,4-benzoxazin-3-one A solution of 3-oxo-4H-1,4-benzoxazine-6-carboxylic acid (74 mg, 0.39 mmol), 4-((4-(2-(2-fluoroethoxy)ethoxy)phenyl)(phenyl)methyl)piperidine (115 mg, 0.320 mmol), O-(7-azabenzotriazol-1-yl)-N,N,N',N'-tetramethyluronium hexafluorophosphate (159 mg, 0.420 mmol) and triethylamine (0.11 mL, 0.770 mmol) in DCM (2 mL) was stirred at 25° C. for 16 h. The reaction was quenched with H₂O (5 mL), and extracted with DCM (5 mL). The organic layer was separated, dried over Na₂SO₄, filtered and concentrated under vacuum. The residue was purified by Prep-HPLC to afford 6-[4-[[4-[2-(2-fluoroethoxy)ethoxy]phenyl]-phenyl-methyl]piperidine-1-carbonyl]-4H-1,4-benzoxazin-3-one (95 mg, 54%) as a white solid; LCMS: 533.3 [M+H]⁺.

6-[4-[[4-[2-(2-fluoroethoxy)ethoxy]phenyl]-phenyl-methyl]piperidine-1-carbonyl]-4H-1,4-benzoxazin-3-one (90 mg, 0.17 mmol) was separated by SFC (Method: Column DAICEL CHIRALPAK AD 250 mm*30 mm, 10 µm. Condition 0.1% NH₃/H₂O IPA, Begin B, End B 45, Gradient Time (min) 3.4 min; 70 min, 100% B Hold Time (min) 10 FlowRate (mL/min) 70) to afford 6-[4-[(S)-[4-[2-(2-fluoroethoxy)ethoxy]phenyl]-phenyl-methyl]piperidine-1-carbonyl]-4H-1,4-benzoxazin-3-one (22 mg, 24% yield; LC-MS: 533.3 [M+H]⁺) and 6-[4-[(R)-[4-[2-(2-fluoroethoxy)ethoxy]phenyl]-phenyl-methyl]piperidine-1-carbonyl]-4H-1,4-benzoxazin-3-one (35 mg, 38% yield; LC-MS: 533.3 [M+H]⁺) as a white solids.

Examples 98 and 99

6-[4-[(S or R)-(6-Fluoro-2-pyridyl)-phenyl-methyl] piperidine-1-carbonyl]-4H-1,4-benzoxazin-3-one and 6-[4-[(R or S)-(6-fluoro-2-pyridyl)-phenyl-methyl] piperidine-1-carbonyl]-4H-1,4-benzoxazin-3-one

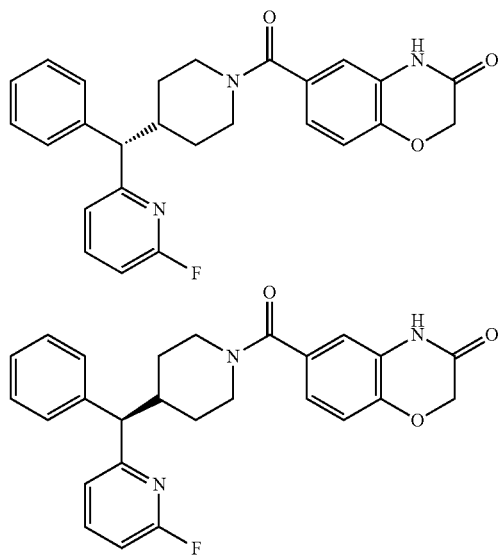

Intermediate J-1 tert-Butyl 4-(phenyl(2-tosylhydrazono)methyl)piperidine-1-carboxylate

A solution of 4-methylbenzenesulfonhydrazide (1.7 g, 9.1 mmol) and tert-butyl 4-benzoylpiperidine-1-carboxylate (2.2 g, 7.6 mmol) in 1,4-dioxane (10 mL) was stirred at 80° C. for 16 h. The reaction solution was concentrated in vacuo to give a residue which was purified by flash column chromatography (petroleum ether:ethyl acetate 5:1) to give tert-butyl 4-(phenyl(2-tosylhydrazono)methyl)piperidine-1-carboxylate (2.0 g, 48%) as a white solid; LC-MS: 480.2 [M+Na]⁺.

Intermediate J-2 tert-Butyl 4-((6-fluoropyridin-2-yl)(phenyl)methylene)piperidine-1-carboxylate

A mixture of 2-bromo-6-fluoropyridine (415 mg, 2.36 mmol), tert-butyl 4-(phenyl(2-tosylhydrazono)methyl)piperidine-1-carboxylate (900 mg, 1.97 mmol), LiOtBu (236 mg, 2.95 mmol) and bis(triphenylphosphine)palladium(II) chloride (138 mg, 0.200 mmol) in 1,4-dioxane (10 mL) was stirred at 80° C. for 16 h under N₂. The reaction mixture was filtered and concentrated in vacuo to give a residue which was purified by flash column (petroleum ether:ethyl acetate 20:1) to give tert-butyl 4-((6-fluoropyridin-2-yl)(phenyl) methylene)piperidine-1-carboxylate (220 mg, 0.600 mmol, 29%) as light yellow solid; LC-MS: 391.3 [M+Na]⁺.

Intermediate J-3

2-Fluoro-6-(phenyl(piperidin-4-ylidene)methyl)pyridine

To a solution of tert-butyl 4-((6-fluoropyridin-2-yl)(phenyl)methylene)piperidine-1-carboxylate (220 mg, 0.600 mmol) in DCM (5 mL) was added trifluoroacetic acid (0.46 mL, 5.97 mmol) and the mixture was stirring at 25° C. for 3 h. The reaction mixture was concentrated in vacuo to give 2-fluoro-6-(phenyl(piperidin-4-ylidene)methyl)pyridine (TFA salt, 155 mg, 96%) as a brown oil; LC-MS: 269.1 [M+H]⁺.

Intermediate J-4

2-Fluoro-6-(phenyl(piperidin-4-yl)methyl)pyridine

A mixture of 2-fluoro-6-(phenyl(piperidin-4-ylidene) methyl)pyridine (155 mg, 0.580 mmol) and Pd/C (615 mg, 0.580 mmol) in THF (3 mL) was stirred at 25° C. for 16 h under H₂ (760 mmHg). The mixture was filtered and concentrated in vacuo to give 2-fluoro-6-(phenyl (piperidin-4-yl)methyl)pyridine (156 mg, 99%) as a colorless oil. LC-MS: 271.3 [M+H]⁺.

rac-6-[4-[(6-Fluoro-2-pyridyl)-phenyl-methyl]piperidine-1-carbonyl]-4H-1,4-benzoxazin-3-one A solution of 3-oxo-4H-1,4-benzoxazine-6-carboxylic acid (111 mg, 0.580 mmol), 2-fluoro-6-(phenyl (piperidin-4-yl)methyl)pyridine (156 mg, 0.580 mmol), triethylamine (0.10 mL, 0.69 mmol) and O-(7-azabenzotriazol-1-yl)-N,N,N',N'-tetramethyluronium hexafluorophosphate (263 mg, 0.690 mmol) in DCM (5 mL) was stirred at 25° C. for 3 h. The reaction solution was poured into brine (30 mL) and extracted with DCM (2×20 mL). The combined organic layers were concentrated in vacuo to give a residue, which was purified by Prep-HPLC (TFA condition) to give 6-[4-[(6-fluoro-2-pyridyl)-phenyl-methyl]piperidine-1-carbonyl]-4H-1,4-benzoxazin-3-one (67 mg, 26%) as a white solid; LC-MS: 446.2 [M+H]⁺.

6-(4-((6-Fluoropyridin-2-yl)(phenyl)methyl)piperidine-1-carbonyl)-2H-benzo[b][1,4]oxazin-3(4H)-one (62 mg, 0.14 mmol) was separated by SFC (Method Column DAICEL CHIRALCEL OJ (250 mm*30 mm, 10 μm), Condition 0.1% NH$_3$*H$_2$O MeOH, Begin B 45 End B 45, Gradient Time (min) 3.4 min; 50 min 100% B Hold Time (min) 0 FlowRate (ml/min) 70 g/min) to give 6-[4-[(S or R)-(6-fluoro-2-pyridyl)-phenyl-methyl]piperidine-1-carbonyl]-4H-1,4-benzoxazin-3-one (17 mg, 28% yield; LC-MS: 446.3 [M+H]$^+$) and 6-[4-[(R or S)-(6-fluoro-2-pyridyl)-phenyl-methyl]piperidine-1-carbonyl]-4H-1,4-benzoxazin-3-one (14 mg, 22% yield; LC-MS: 446.3 [M+H]$^+$) as white solids.

Example 100

7-[4-[Bis(4-fluorophenyl)methyl]piperidine-1-carbonyl]-5-methoxy-3,4-dihydro-1H-quinolin-2-one

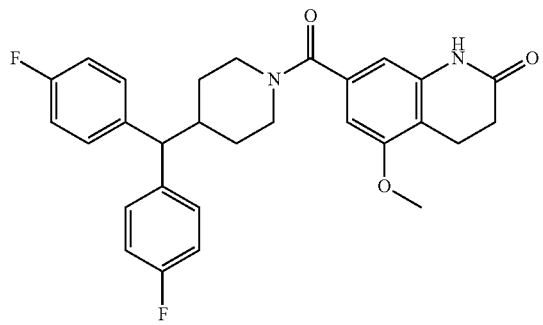 [SMILES: COc1cc(C(=O)N2CCC(C(c3ccc(F)cc3)c3ccc(F)cc3)CC2)cc2c1CCC(=O)N2]

Intermediate K-1

Methyl 4-hydroxy-3-methoxy-5-nitrobenzoate

To a solution of methyl vanillate (8.00 g, 43.9 mmol) in acetic acid (20 mL) was added HNO$_3$ (3.69 g, 52.7 mmol) at 25° C. for 3 h. The resulting solid was filtered and washed with H$_2$O (3×100 mL), then dried under vacuum to afford methyl 4-hydroxy-3-methoxy-5-nitro-benzoate (6.20 g, 59%) as a light yellow solid; $^1$H NMR (400 MHz, CDCl$_3$) S=11.09 (hr, 1H), 8.46 (d, J=1.9 Hz, 1H), 7.78 (d, J=1.9 Hz, 1H), 4.03 (s, 3H), 3.97 (s, 3H).

Intermediate K-2

Methyl 3-methoxy-5-nitro-4-[[(trifluoromethyl)sulfonyl]oxy]benzoate

To a solution of methyl 4-hydroxy-3-methoxy-5-nitrobenzoate (6.20 g, 27.3 mmol) and pyridine (4.37 g, 54.6 mmol) in DCM (100 mL) was added trifluoromethanesulfonic anhydride (8.47 g, 30.0 mmol) at 25° C. and the resulting mixture was stirred for 1 h. The reaction was quenched with H$_2$O (80 mL). The organic layer was separated, dried over Na$_2$SO$_4$, filtered and concentrated under vacuum. The residue was purified by silica gel chromatography (petroleum ether:EtOAc 20:1 to 10:1) to afford methyl 3-methoxy-5-nitro-4-[[(trifluoromethyl)sulfonyl]oxy]benzoate (5.80 g, 53%) as a light yellow solid; $^1$H NMR (400 MHz, CDCl$_3$) S=8.22 (d, J=1.6 Hz, 1H), 7.89 (d, J=1.6 Hz, 1H), 3.99 (s, 3H), 3.93 (s, 3H).

Intermediate K-3

Methyl 4-iodo-3-methoxy-5-nitrobenzoate

A solution of methyl 3-methoxy-5-nitro-4-[[(trifluoromethyl)sulfonyl]oxy]benzoate (3.80 g, 10.6 mmol) and NaI (2.38 g, 15.9 mmol) in DMSO (30 mL) was stirred at 80° C. for 40 h. The reaction was quenched with water (20 mL). The resulting yellow solid was collected by filtration, then dissolved in EtOAc (50 mL), dried over Na$_2$SO$_4$, filtered and concentrated under vacuum. The residue was purified by silica gel chromatography (petroleum ether:EtOAc 10:1) to afford methyl 4-iodo-3-methoxy-5-nitrobenzoate (2.30 g, 58%) as a light yellow solid; $^1$H NMR (400 MHz, CDCl$_3$) S=7.94 (d, J=1.5 Hz, 1H), 7.62 (d, J=1.5 Hz, 1H), 4.04 (s, 3H), 3.99 (s, 3H).

Intermediate K-4

Methyl 4-(3-ethoxy-3-oxoprop-1-en-1-yl)-3-methoxy-5-nitrobenzoate

A solution of methyl 4-iodo-3-methoxy-5-nitrobenzoate (2.00 g, 5.9 mmol), ethyl acrylate (1.19 mg, 119 mmol), palladium acetate (403 mg, 1.8 mmol), tri-o-tolylphosphine (542 mg, 1.78 mmol) and triethylamine (1.7 mL, 12 mmol) in DMF (2 mL) was stirred at 110° C. for 16 h. The reaction was filtered, and the filtrate was concentrated under vacuum. The residue was purified by silica gel chromatography (petroleum ether:EtOAc 2:1) to afford methyl 4-(3-ethoxy-3-oxoprop-1-en-1-yl)-3-methoxy-5-nitrobenzoate (640 mg, 27%) as light yellow solid. This material was used as such in the next step.

Intermediate K-5

Methyl 5-methoxy-2-oxo-1,2,3,4-tetrahydroquinoline-7-carboxylate

A solution of methyl methyl 4-(3-ethoxy-3-oxoprop-1-en-1-yl)-3-methoxy-5-nitrobenzoate (640 mg, 2.1 mmol) and Pd/C (100 mg) in 1,4-dioxane (30 mL) was stirred at 90° C. for 16 h under H$_2$ (2500 mmHg). The mixture was filtered through the Celite, and the filtrate was concentrated in vacuum to afford methyl 5-methoxy-2-oxo-1,2,3,4-tetrahydroquinoline-7-carboxylate (445 mg, 74%) as a light yellow solid; LCMS: 236.0 [M+H]$^+$.

Intermediate K-6

5-Methoxy-2-oxo-1,2,3,4-tetrahydroquinoline-7-carboxylic acid

A solution of methyl 5-methoxy-2-oxo-1,2,3,4-tetrahydroquinoline-7-carboxylate (480 mg, 2.0 mmol) and sodium hydroxide (163.2 mg, 4.1 mmol, 2 eq) in H$_2$O (4 mL) and MeOH (20 mL) was stirred at 50° C. for 1 h. The reaction was concentrated under vacuum. The residue was dissolved in H$_2$O (10 mL) and the solution was acidified with HCl (aq., 1M) to pH=23. The precipitated solid was collected by filtration to afford 5-methoxy-2-oxo-1,2,3,4-tetrahydroquinoline-7-carboxylic acid (298 mg, 63%) as yellow solid; LCMS: 222.0 [M+H]$^+$.

7-[4-[Bis(4-fluorophenyl)methyl]piperidine-1-carbonyl]-5-methoxy-3,4-dihydro-1H-quinolin-2-one A solution of 4-(bis(4-fluorophenyl)methyl)piperidine (intermediate B-3) (100 mg, 0.35 mmol), 5-methoxy-2-oxo-

113

1,2,3,4-tetrahydroquinoline-7-carboxylic acid (77 mg, 0.35 mmol), O-(7-azabenzotriazol-1-yl)-N,N,N',N'-tetramethyluronium hexafluorophosphate (159 mg, 0.4 mmol) and triethylamine (0.1 mL, 0.7 mmol) in DCM (3 mL) was stirred at 25° C. for 16 h. The reaction was quenched with H₂O (5 mL) and extracted with DCM (5 mL). The organic layer was separated, dried over Na₂SO₄, filtered and concentrated under vacuum. The residue was purified Prep-HPLC (TFA as additive), then the resulting solution was lyophilized to afford 7-[4-[bis(4-fluorophenyl)methyl]piperidine-1-carbonyl]-5-methoxy-3,4-dihydro-1H-quinolin-2-one (8.5 mg, 4.9%) as a white solid; LC-MS: 491.1 [M+H]⁺.

Example 101

7-(4-Benzhydrylpiperidine-1-carbonyl)-5-methoxy-3,4-dihydro-1H-quinolin-2-one

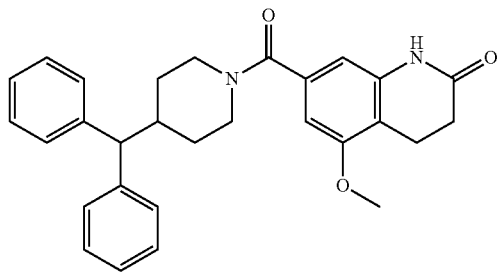 [SMILES: COc1cc(C(=O)N2CCC(C(c3ccccc3)c3ccccc3)CC2)cc2c1CCC(=O)N2]

A mixture of 4-benzhydrylpiperidine (142 mg, 0.56 mmol), 5-methoxy-2-oxo-3,4-dihydro-1H-quinoline-7-carboxylic acid (125 mg, 0.56 mmol), triethylamine (0.1 mL, 0.68 mmol) and O-(7-azabenzotriazol-1-yl)-N,N,N',N'-tetramethyluronium hexafluorophosphate (258 mg, 0.68 mmol) in DCM (5 mL) was stirred at 25° C. for 16 h. The reaction mixture was poured into brine (30 mL) and extracted with DCM (2×20 mL). The combined organic layers were washed with water (2×50 mL), dried over Na₂SO₄, filtered and concentrated in vacuo to give a residue, which was purified by Prep-HPLC (TFA condition) to give 7-(4-benzhydrylpiperidine-1-carbonyl)-5-methoxy-3,4-dihydro-1H-quinolin-2-one (113 mg, 43%) as white solid; LC-MS: 455.1 [M+H]⁺.

Examples 102 and 103

6-[4-[(S or R)-(6-Fluoro-3-pyridyl)-phenyl-methyl]piperidine-1-carbonyl]-4H-1,4-benzoxazin-3-one
and
6-[4-[(R or S)-(6-Fluoro-3-pyridyl)-phenyl-methyl]piperidine-1-carbonyl]-4H-1,4-benzoxazin-3-one

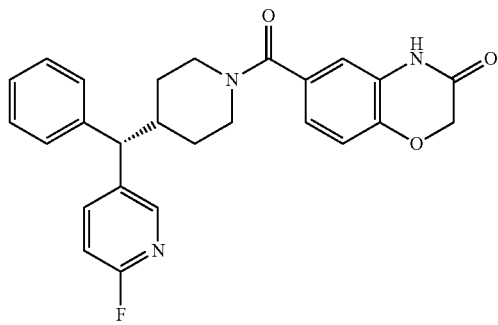

114

-continued

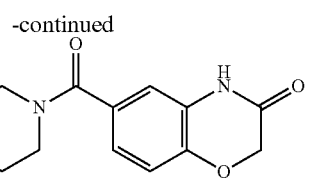

Intermediate L-1 tert-Butyl 4-((6-fluoropyridin-3-yl)(phenyl)methylene)piperidine-1-carboxylate

A mixture of 5-bromo-2-fluoropyridine (577 mg, 3.28 mmol), tert-butyl 4-(phenyl(2-tosylhydrazono)methyl)piperidine-1-carboxylate (intermediate J-1) (1.00 g, 2.19 mmol), LiOtBu (262 mg, 3.28 mmol) and bis(triphenylphosphine)palladium(II) chloride (153 mg, 0.220 mmol) in 1,4-dioxane (10 mL) was stirred at 80° C. for 16 h under N₂. The reaction mixture was filtered and concentrated in vacuo to give a residue which was purified by flash column (petroleum ether:ethyl acetate 20:1) to give tert-butyl 4-((6-fluoropyridin-3-yl)(phenyl)methylene)piperidine-1-carboxylate (180 mg, 22%) as light yellow solid; LC-MS: 313.2 [M−56+H]⁺.

Intermediate L-2

2-Fluoro-5-(phenyl(piperidin-4-ylidene)methyl)pyridine

A solution of tert-butyl 4-((6-fluoropyridin-3-yl)(phenyl)methylene)piperidine-1-carboxylate (180 mg, 0.490 mmol) and trifluoroacetic acid (1.0 mL, 13 mmol) in DCM (20 mL) was stirred at 25° C. for 16 h. The reaction mixture was concentrated in vacuo to give product 2-fluoro-5-(phenyl(piperidin-4-ylidene)methyl)pyridine (TFA salt, 120 mg, 92%) as a colorless oil; LC-MS: 269.3 [M+H]⁺.

Intermediate L-3

2-Fluoro-5-[phenyl(piperidin-4-yl)methyl]pyridine

A mixture of 2-fluoro-5-[phenyl(piperidin-4-ylidene)methyl]pyridine (120 mg, 0.450 mmol) and Pd/C (24 mg, 0.020 mmol) in THF (10 mL) was stirred at 25° C. for 16 h under H₂ (760 mmHg). The mixture was filtered and concentrated in vacuo to give 2-fluoro-5-[phenyl(piperidin-4-yl)methyl]pyridine (122 mg, 70%) as a white solid; LC-MS: 271.1 [M+H]⁺.

Rac-6-[4-[(6-Fluoro-3-pyridyl)-phenyl-methyl]piperidine-1-carbonyl]-4H-1,4-benzoxazin-3-one A solution of 3-oxo-4H-1,4-benzoxazine-6-carboxylic acid (87 mg, 0.450 mmol), 2-fluoro-5-(phenyl(piperidin-4-yl)methyl)pyridine (122 mg, 0.450 mmol), triethylamine (0.08 mL, 0.54 mmol) and <9-(7-azabenzotriazol-1-yl)-N,N,N',N'-tetramethyluronium hexafluorophosphate (206 mg, 0.540 mmol) in DCM (5 mL) was stirred at 25° C. for 3 h. The reaction solution was poured into brine (30 mL) and extracted with DCM (2×20 mL). The combined organic layers were concentrated in vacuo to give a residue, which was purified by Prep-HPLC (TFA condition) to give 6-[4-[(6-fluoro-3-pyridyl)-phenyl-methyl]piperidine-1-carbonyl]-4H-1,4-benzoxazin-3-one (89 mg, 44%) as white solid; LC-MS: 446.1 [M+H]+.

6-[4-[(6-Fluoro-3-pyridyl)-phenyl-methyl]piperidine-1-carbonyl]-4H-1,4-benzoxazin-3-one (89 mg, 0.20 mmol) was separated by SFC (Method: Column DAICEL CHIRALCEL OJ (250 mm*50 mm, 10 μm), Condition 0.1% NH$_3$*H$_2$O MeOH Begin B 30% MeOH, End B 30% MeOH Gradient Time (min) 5.2 min; 140 min, 100% B Hold Time (min) 0, FlowRate (ml/min) 60 g/min) to give 6-[4-[(S or R)-(6-fluoro-3-pyridyl)-phenyl-methyl]piperidine-1-carbonyl]-4H-1,4-benzoxazin-3-one (16 mg, 17% yield; LC-MS: 446.3 [M+H]+) and 6-[4-[(R or S)-(6-fluoro-3-pyridyl)-phenyl-methyl]piperidine-1-carbonyl]-4H-1,4-benzoxazin-3-one (26 mg, 29% yield; LC-MS: 446.3 [M+H]+) as a white solids.

Examples 104 and 105

6-[4-[(S or R)-(3,4-Dimethoxyphenyl)-(4-fluorophenyl)methyl]piperidine-1-carbonyl]-4H-1,4-benzoxazin-3-one and 6-[4-[(R or S)-(3,4-Dimethoxyphenyl)-(4-fluorophenyl)methyl]piperidine-1-carbonyl]-4H-1,4-benzoxazin-3-one

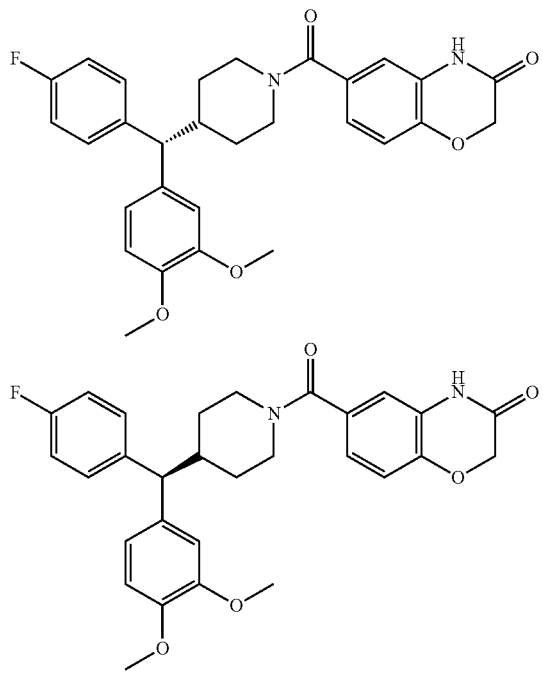

Intermediate M-1 tert-Butyl 4-((3,4-dimethoxyphenyl)(4-fluorophenyl)(hydroxy)methyl)piperidine-1-carboxylate To a solution of 4-bromoveratrole (1.27 g, 5.86 mmol) in THF (30 mL) was added dropwise butyllithium (3.28 mL, 8.2 mmol) with stirring at −78° C. Stirring was continued at −78° C. for 1 h. Then tert-butyl 4-(4-fluorobenzoyl)piperidine-1-carboxylate (1.80 g, 5.86 mmol) was added and the mixture was stirred at −78° C. for 5 h. The mixture was poured into brine (50 mL) and extracted with ethyl acetate (2×30 mL). The combined organic layers were concentrated in vacuo to give tert-butyl 4-((3,4-dimethoxyphenyl)(4-fluorophenyl)(hydroxy)methyl)piperidine-1-carboxylate (2.4 g, 91%) as a colorless oil; LC-MS: 468.4 [M+Na]+.

Intermediate M-2

4-((3,4-Dimethoxyphenyl)(4-fluorophenyl)methylene)piperidine

A mixture of tert-butyl 4-((3,4-dimethoxyphenyl)(4-fluorophenyl)(hydroxy)methyl)piperidine-1-carboxylate (2.4 g, 5.4 mmol) and trifluoroacetic acid (4.15 mL, 53.87 mmol) in DCM (20 mL) was stirred at 25° C. for 4 h. The reaction mixture was concentrated in vacuo to give 4-((3,4-dimethoxyphenyl)(4-fluorophenyl)methylene)piperidine (TFA salt, 1.7 g, 96%) as a brown oil; LC-MS: 328.3 [M+H]+.

Intermediate M-3

4-((3,4-Dimethoxyphenyl)(4-fluorophenyl)methyl)piperidine

A mixture of 4-((3,4-dimethoxyphenyl)(4-fluorophenyl)methylene)piperidine (1.7 g, 5.2 mmol) and Pd/C (276 mg, 0.260 mmol) in THF (10 mL) was stirred at 25° C. for 16 h under H$_2$ (760 mmHg). The mixture was filtered and concentrated in vacuo to give a residue, which was purified by Prep-HPLC (TFA conditions) to give 4-((3,4-dimethoxyphenyl)(4-fluorophenyl)methyl)piperidine (900 mg, 52%) as white solid; LC-MS: 330.3 [M+H]+.

Intermediates M-4 and M-5

(S or R)-4-((3,4-Dimethoxyphenyl)(4-fluorophenyl)methyl)piperidine and (R or <5)-4-((3,4-dimethoxyphenyl)(4-fluorophenyl)methyl)piperidine 4-((3,4-Dimethoxyphenyl)(4-fluorophenyl)methyl)piperidine (900 mg) was separated by SFC (Method: Column DAICEL CHIRALPAK AD (250 mm*50 mm, 10 μm), Condition 0.1% NH$_3$.H$_2$O MeOH, Begin B 25, End B 25 Gradient Time (min) 5.5 min:900 min, 100% B Hold Time (min) 0, FlowRate (ml/min) 50 g/min) to give (S or R)-4-((3,4-dimethoxyphenyl)(4-fluorophenyl)methyl)piperidine (278 mg, 29% yield; LC-MS: 330.3 [M+H]+) and (R or <S)-4-((3,4-dimethoxyphenyl)(4-fluorophenyl)methyl)piperidine (426 mg, 44% yield; LC-MS: 330.1 [M+H]+) as a off-white solids.

6-[4-[(S or R)-(3,4-Dimethoxyphenyl)-(4-fluorophenyl)methyl]piperidine-1-carbonyl]-4H-1,4-benzoxazin-3-one A solution of 3-oxo-4H-1,4-benzoxazine-6-carboxylic acid (35 mg, 0.18 mmol), (S or R)-4-((3,4-dimethoxyphenyl)(4-fluorophenyl)methyl)piperidine (60 mg, 0.18 mmol), O-(7-azabenzotriazol-1-yl)-N,N,N',N'-tetramethyluronium hexafluorophosphate (83 mg, 0.22 mmol) and triethylamine (0.05 mL, 0.36 mmol) in DCM (2 mL) was stirred at 25° C. for 16 h. The reaction was quenched with H$_2$O (2 mL) and extracted with DCM (5 mL). The organic layer was separated, dried over Na$_2$SO$_4$, filtered and concentrated under vacuum. The residue was purified by Prep-HPLC (TFA as additive) to afford 6-[4-[(S or R)-(3,4-Dimethoxyphenyl)-(4-fluorophenyl)methyl]piperidine-1-carbonyl]-4H-1,4-benzoxazin-3-one (41 mg, 44%) as the off-white solid; LC-MS: 505.2 [M+H]$^+$.

The other enantiomer was prepared analogously from 3-oxo-4H-1,4-benzoxazine-6-carboxylic acid (35 mg, 0.18 mmol), and (R or S)-4-((3,4-dimethoxyphenyl)(4-fluorophenyl)methyl)piperidine (60 mg, 0.18 mmol). Yield 29 mg (31%), off-white solid; LC-MS: 505.2 [M+H]$^+$.

Example 106

7-[4-[Bis(4-fluorophenyl)methyl]piperidine-1-carbonyl]-5-(2-fluoroethoxy)-3,4-dihydro-1H-quinolin-2-one

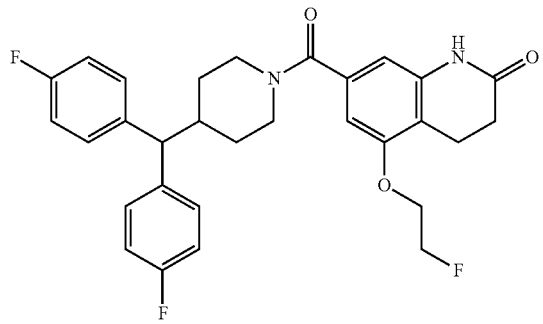 [SMILES: O=C1CCc2c(cc(C(=O)N3CCC(C(c4ccc(F)cc4)c4ccc(F)cc4)CC3)cc2OCCF)N1]

Intermediate N-1

Methyl 5-hydroxy-2-oxo-1,2,3,4-tetrahydroquinoline-7-carboxylate

BBr$_3$ (2.34 g, 9.3 mmol) was added drop-wised to a solution of methyl 5-methoxy-2-oxo-1,2,3,4-tetrahydroquinoline-7-carboxylate (intermediate K-5) (440 mg, 1.87 mmol) in DCM (15 mL) at −78° C. After stirring 16 h at rt, the reaction was quenched with MeOH (3 mL). Then the reaction solution was concentrated under vacuum, and H$_2$O (10 mL) was added. The resulting precipitate was collected and dried under vacuum to afford methyl 5-hydroxy-2-oxo-1,2,3,4-tetrahydroquinoline-7-carboxylate (340 mg, 71%) as gray solid; LCMS: 222.3 [M+H]$^+$.

Intermediate N-2

Methyl 5-(2-fluoroethoxy)-2-oxo-1,2,3,4-tetrahydroquinoline-7-carboxylate

A solution of methyl 5-hydroxy-2-oxo-1,2,3,4-tetrahydroquinoline-7-carboxylate (400 mg, 1.8 mmol), 1-bromo-2-fluoroethane (689 mg, 5.4 mmol) and potassium carbonate (750 mg, 5.4 mmol) in DMF (8 mL) was stirred at 45° C. for 16 h. The reaction was quenched with H$_2$O (3 mL), and the resulting solid was separated by filtration to afford methyl 5-(2-fluoroethoxy)-2-oxo-1,2,3,4-tetrahydroquinoline-7-carboxylate (290 mg, 57%) as yellow solid; LC-MS: 268.0 [M+H]$^+$.

Intermediate N-3

5-(2-Fluoroethoxy)-2-oxo-1,2,3,4-tetrahydroquinoline-7-carboxylic acid

A solution of methyl methyl 5-(2-fluoroethoxy)-2-oxo-1,2,3,4-tetrahydroquinoline-7-carboxylate (290 mg, 1.09 mmol) and NaOH (217 mg, 5.43 mmol) in MeOH (10 mL) and H$_2$O (5 mL) was stirred at 50° C. for 1 h. The reaction was concentrated under vacuum. The residue was dissolved in H$_2$O (15 mL), then acidified by HCl (aq., 1 M) to pH=1~2. After stirring 10 min the solid was precipitated and collected by filtration to afford 5-(2-fluoroethoxy)-2-oxo-1,2,3,4-tetrahydroquinoline-7-carboxylic acid (256 mg, 92%) as yellow solid; LC-MS: 254.0 [M+H]$^+$.

7-[4-[Bis(4-fluorophenyl)methyl]piperidine-1-carbonyl]-5-(2-fluoroethoxy)-3,4-dihydro-1H-quinolin-2-one A solution of 4-(bis(4-fluorophenyl)methyl)piperidine (intermediate B-3) (106 mg, 0.4 mmol), 5-(2-5fluoroethoxy)-2-oxo-1,2,3,4-tetrahydroquinoline-7-carboxylic acid (50 mg, 0.2 mmol), 0-(7-azabenzotriazol-1-yl)-N,N,N',N'-tetramethyluronium hexafluorophosphate (90 mg, 0.24 mmol), and triethylamine (0.03 mL, 0.2 mmol) in DCM (4 mL) was stirred at 25° C. for 16 h. The reaction was diluted with DCM (15 mL) and washed with H$_2$O (8 mL). The organic layer was separated, dried over Na$_2$SO$_4$, filtered and concentrated under vacuum. The residue was purified by Prep-HPLC (TFA as the additive) to afford 7-[4-[bis(4-fluorophenyl)methyl]piperidine-1-carbonyl]-5-(2-fluoroethoxy)-3,4-dihydro-1H-quinolin-2-one (40 mg, 38%) as white solid; LC-MS: 523.2, [M+H]$^+$.

Examples 107 and 108

6-[4-[(R or S)-[4-[2-(2-Fluoroethoxy)ethoxy]phenyl]-(4-fluorophenyl)methyl]piperidine-1-carbonyl]-4H-1,4-benzoxazin-3-one and

6-[4-[(S or R)-[4-[2-(2-Fluoroethoxy)ethoxy]phenyl]-(4-fluorophenyl)methyl]piperidine-1-carbonyl]-4H-1,4-benzoxazin-3-one

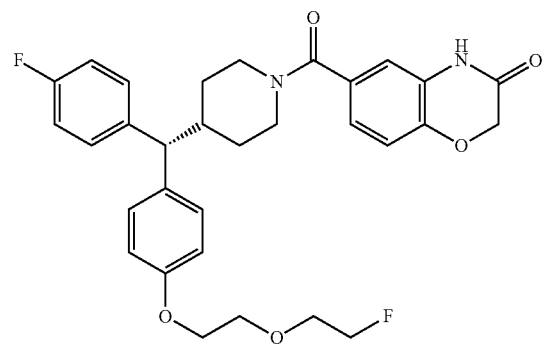

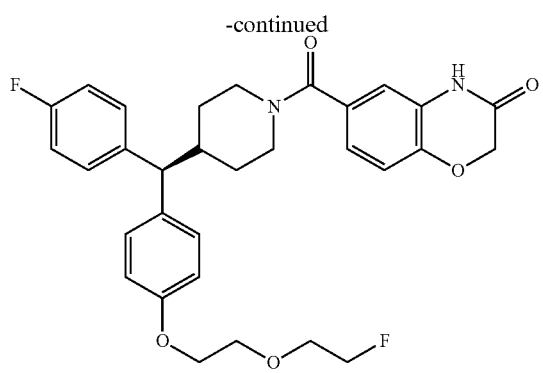

Intermediate O-1 tert-Butyl 4-((4-(2-(2-fluoroethoxy)ethoxy)phenyl)(4-fluorophenyl)(hydroxy)methyl) piperidine-1-carboxylate To a stirred mixture at −78° C. of 1-bromo-4-(2-(2-fluoroethoxy)ethoxy)benzene (intermediate 1-4) (500 mg, 1.9 mmol) in THF (10 mL) was added dropwise a butyl-lithium solution (1.06 mL, 2.66 mmol) and then stirring was continued at −78° C. for 1 h. Then tot-butyl 4-(4-fluorobenzoyl)piperidine-1-carboxylate (642.52 mg, 2.09 mmol, 1.1 eq) was added and stirring was continued at −78° C. for 4 h. The reaction mixture was poured into brine (30 mL) and extracted with ethyl acetate (2×20 mL). The combined organic layers were concentrated in vacuo to give a residue, which was purified by Prep-HPLC (TFA condition) to give tert-butyl 4-((4-(2-(2-fluoroethoxy)ethoxy)phenyl)(4-fluorophenyl)(hydroxy)methyl)piperidine-1-carboxylate (302 mg, 32%) as a light yellow oil; LC-MS: 514.4 [M+Na]+.

Intermediate O-2

4-((4-(2-(2-Fluoroethoxy)ethoxy)phenyl)(4-fluorophenyl)methylene)piperidine

A mixture of tert-butyl 4-((4-(2-(2-fluoroethoxy)ethoxy)phenyl)(4-fluorophenyl)(hydroxy)methyl)piperidine-1-carboxylate (300 mg, 0.61 mmol) and trifluoroacetic acid (0.47 mL, 6.1 mmol) in DCM (10 mL) was stirred at 25° C. for 16 h. The reaction mixture was concentrated in vacuo to give 4-((4-(2-(2-fluoroethoxy)ethoxy)phenyl)(4-fluorophenyl)methylene)piperidine (TFA salt, 210 mg, 0.560 mmol, 92%) as a brown oil; LC-MS: 374.3 [M+H]+.

Intermediate O-3

4-((4-(2-(2-Fluoroethoxy)ethoxy)phenyl)(4-fluorophenyl)methyl)piperidine

A mixture of 4-((4-(2-(2-fluoroethoxy)ethoxy)phenyl)(4-fluorophenyl)methylene)piperidine (210 mg, 0.560 mmol) and Pd/C (30 mg, 0.030 mmol) in THF (10 mL) was stirred at 25° C. for 16 h under $H_2$ (760 mmHg). The mixture was filtered and concentrated in vacuo to give 4-((4-(2-(2-fluoroethoxy)ethoxy)phenyl)(4-fluorophenyl)methyl)piperidine (160 mg, 54%) as a colorless oil; LC-MS: 376.1 [M+H]+.

Rac-6-[4-[[4-[2-(2-Fluoroethoxy)ethoxy]phenyl]-(4-fluorophenyl)methyl]piperidine-1-carbonyl]-4H-1,4-benzoxazin-3-one A mixture of 4-((4-(2-(2-fluoroethoxy)ethoxy)phenyl)(4-fluorophenyl)methyl)piperidine (160 mg, 0.430 mmol), 3-oxo-4H-1,4-benzoxazine-6-carboxylic acid (82 mg, 0.43 mmol), triethylamine (0.07 mL, 0.510 mmol) and O-(1-azabenzotriazol-1-yl)-N,N,N',N'-tetramethyluronium hexafluorophosphate (194 mg, 0.510 mmol) in DCM (5 mL) was stirred at 25° C. for 4 h. The reaction mixture was poured into brine (20 mL) and extracted with DCM (2×10 mL). The combined organic layers were concentrated in vacuo to give a residue, which was purified by Prep-HPLC (TFA conditions) to give 6-[4-[[4-[2-(2-fluoroethoxy)ethoxy]phenyl]-(4-fluorophenyl)methyl]piperidine-1-carbonyl]-4H-1,4-benzoxazin-3-one (98 mg, 41%) as a white solid; LC-MS: 551.4 [M+H]+.

6-[4-[[4-[2-(2-Fluoroethoxy)ethoxy]phenyl]-(4-fluorophenyl)methyl]piperidine-1-carbonyl]-4H-1,4-benzoxazin-3-one (98 mg, 0.18 mmol) was separated by SFC (Method: Column DAICEL CHIRALCEL OD (250 mm*30 mm, 10 µm), Condition 0.1% $NH_3*H_2O$ MeOH Begin B 45, End B 45 Gradient Time (min) 3.9 min: 90 min, 100% B Hold Time (min) 0, FlowRate (ml/min) 70 g/min) to give 6-[4-[(R or S)-[4-[2-(2-fluoroethoxy)ethoxy]phenyl]-(4-fluorophenyl)methyl]piperidine-1-carbonyl]-4H-1,4-benzoxazin-3-one (41 mg, 41% yield; LC-MS: 551.1 [M+H]+) and 6-[4-[(S or R)-[4-[2-(2-fluoroethoxy)ethoxy]phenyl]-(4-fluorophenyl)methyl]piperidine-1-carbonyl]-4H-1,4-benzoxazin-3-one (46 mg, 45% yield; LC-MS: 551.1 [M+H]+) as a white solids.

Example 109

7-(4-Benzhydrylpiperidine-1-carbonyl)-5-(2-fluoroethoxy)-3,4-dihydro-1H-quinolin-2-one

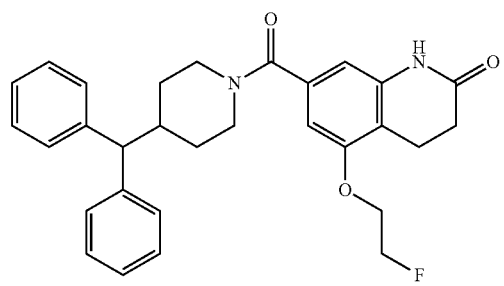 [SMILES: O=C1CCc2c(cc(C(=O)N3CCC(C(c4ccccc4)c4ccccc4)CC3)cc2OCCF)N1]

A mixture of 5-(2-fluoroethoxy)-2-oxo-1,2,3,4-tetrahydroquinoline-7-carboxylic acid (intermediate N-3) (50 mg, 0.20 mmol), 4-benzhydrylpiperidine (50 mg, 0.20 mmol), triethylamine (0.03 mL, 0.24 mmol, 1.2) and O-(1-azabenzotriazol-1-yl)-N,N,N',N'-tetramethyluronium hexafluorophosphate (113 mg, 0.300 mmol) in DCM (2 mL) was stirred at 25° C. for 4 h. The mixture was poured into brine (20 mL) and extracted with DCM (2×10 mL). The combined organic layers were concentrated in vacuo to give a residue, which was purified by Prep-HPLC (TFA condition) to give 7-(4-benzhydrylpiperidine-1-carbonyl)-5-(2-fluoroethoxy)-3,4-dihydro-1H-quinolin-2-one (28 mg, 28%) as white solid; LC-MS: 487.2 [M+H]+.

Examples 110 and 111

6-[4-[(S or R)-(4-Fluorophenyl)-(2-fluoro-4-pyridyl)methyl]piperidine-1-carbonyl]-4H-1,4-benzoxazin-3-one and 6-[4-[(R or S)-(4-Fluorophenyl)-(2-fluoro-4-pyridyl)methyl]piperidine-1-carbonyl]-4H-1,4-benzoxazin-3-one

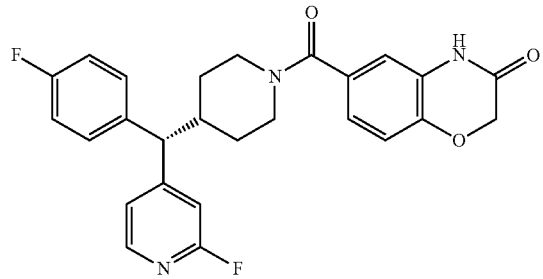

Intermediate P-1 tert-Butyl 4-((4-fluorophenyl)(2-tosylhydrazono)methyl)piperidine-1-carboxylate

A solution of 4-methylbenzenesulfonhydrazide (1.82 g, 9.76 mmol) and tert-butyl 4-(4-fluorobenzoyl)piperidine-1-carboxylate (intermediate H-2) (3.0 g, 9.8 mmol) in 1,4-dioxane (10 mL) was stirred at 80° C. for 24 h. The reaction solution was concentrated in vacuo to give a residue which was purified by flash column (petroleum ether:ethyl acetate 10:1) to give tert-butyl 4-((4-fluorophenyl)(2-tosylhydrazono)methyl)piperidine-1-carboxylate (3.1 g, 60%) as a colorless oil; LC-MS: 498.1 [M+Na]$^+$.

Intermediate P-2 tert-Butyl 4-((4-fluorophenyl)(2-fluoropyridin-4-yl)methylene)piperidine-1-carboxylate A mixture of tert-butyl 4-((4-fluorophenyl)(2-tosylhydrazono)methyl)piperidine-1-carboxylate (1.00 g, 2.1 mmol), 4-bromo-2-fluoropyridine (555 mg, 3.15 mmol, 1.5 eq), LiOtBu (252 mg, 3.15 mmol) and bis(triphenylphosphine)palladium(II) chloride (148 mg, 0.210 mmol) in 1,4-dioxane (10 mL) was stirred at 80° C. for 16 h under N$_2$. The reaction mixture was filtered and concentrated in vacuo to give a residue which was purified by flash column (petroleum ether:ethyl acetate 20:1) to give tert-butyl 4-((4-fluorophenyl)(2-fluoropyridin-4-yl)methylene)piperidine-1-carboxylate (240 mg, 21%) as a light yellow solid; LC-MS: 387.2 [M+H]$^+$.

Intermediate P-3

2-Fluoro-4-((4-fluorophenyl)(piperidin-4-ylidene)methyl)pyridine

A mixture of tert-butyl 4-((4-fluorophenyl)(2-fluoropyridin-4-yl)methylene) piperidine-1-carboxylate (240 mg, 0.620 mmol) and trifluoroacetic acid (354 mg, 3.11 mmol) in DCM (5 mL) was stirred at 25° C. for 4 h. The reaction mixture was concentrated in vacuo to give 2-fluoro-4-((4-fluorophenyl)(piperidin-4-ylidene)methyl)pyridine (TFA salt, 160 mg, 90%) as a brown oil; LC-MS: 287.2 [M+H]$^+$.

Intermediate P-4

2-Fluoro-4-((4-fluorophenyl)(piperidin-4-yl)methyl)pyridine

A mixture of 2-fluoro-4-[(4-fluorophenyl)-(4-piperidylidene)methyl]pyridine (160 mg, 0.560 mmol) and Pd/C (595 mg, 0.560 mmol) in THF (10 mL) was stirred at 25° C. for 24 h under H$_2$ (760 mmHg). The mixture was filtered and concentrated in vacuo to give 2-fluoro-4-((4-fluorophenyl)(piperidin-4-yl)methyl)pyridine (156 mg, 96%) as a white solid; LC-MS: 289.1 [M+H]$^+$.

Rac-6-[4-[(4-Fluorophenyl)-(2-fluoro-4-pyridyl)methyl]piperidine-1-carbonyl]-4H-1,4-benzoxazin-3-one A solution of 3-oxo-4H-1,4-benzoxazine-6-carboxylic acid (104 mg, 0.540 mmol), 2-fluoro-4-((4-fluorophenyl)(piperidin-4-yl)methyl)pyridine (156 mg, 0.540 mmol), triethylamine (0.09 mL, 0.650 mmol) and O-(7-azabenzotriazol-1-yl)-N,N,N',N'-tetramethyluronium hexafluorophosphate (247 mg, 0.650 mmol) in DCM (5 mL) was stirred at 25° C. for 3 h. The reaction solution was poured into brine (30 mL) and extracted with DCM (2×20 mL). The combined organic layers were concentrated in vacuo to give a residue which was purified by Prep-HPLC (TFA conditions) to give 6-[4-[(4-fluorophenyl)-(2-fluoro-4-pyridyl)methyl]piperidine-1-carbonyl]-4H-1,4-benzoxazin-3-one (50 mg, 19%) as a white solid; LC-MS: 464.3 [M+H]$^+$.

6-[4-[(4-Fluorophenyl)-(2-fluoro-4-pyridyl)methyl]piperidine-1-carbonyl]-4H-1,4-benzoxazin-3-one (50.0 mg, 0.110 mmol, 1 eq) was separated by SFC (Method: Column DAICEL CHIRALPAK AD (250 mm*50 mm, 10 μm), Condition 0.1% NH$_3$*H$_2$O MeOH, Begin B 25, End B 25 Gradient Time (min) 5.5 min:900 min, 100% B Hold Time (min) 0, FlowRate (ml/min) 50 g/min) to give 6-[4-[(S or R)-(4-fluorophenyl)-(2-fluoro-4-pyridyl)methyl]piperidine-1-carbonyl]-4H-1,4-benzoxazin-3-one (13 mg, 25%; LCMS: 464.3 [M+H]$^+$) and 6-[4-[(R or S)-(4-fluorophenyl)-(2-fluoro-4-pyridyl)methyl]piperidine-1-carbonyl]-4H-1,4-benzoxazin-3-one (18 mg, 34%; LCMS: 464.3 [M+H]$^+$) as a white solids.

Examples 112 and 113

6-[4-[(S or R)-(4-Fluorophenyl)-(p-tolyl)methyl]piperidine-1-carbonyl]-4H-1,4-benzoxazin-3-one and 6-[4-[(R or S)-(4-Fluorophenyl)-(p-tolyl)methyl]piperidine-1-carbonyl]-4H-1,4-benzoxazin-3-one

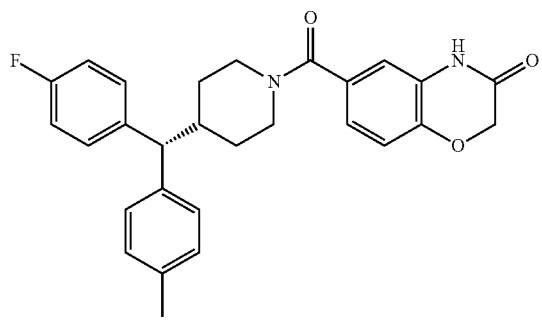

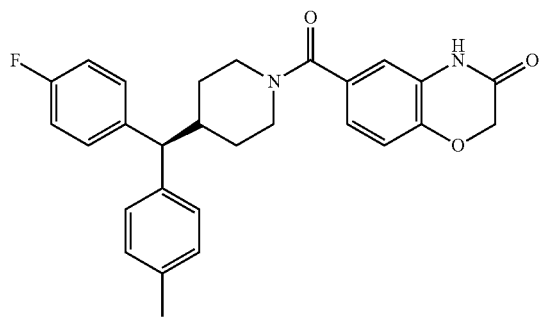

Intermediate Q-1 tert-Butyl 4-((4-fluorophenyl)(hydroxy)(p-tolyl)methyl)piperidine-1-carboxylate

To a stirred solution at −78° C. of 4-bromotoluene (1.70 g, 9.94 mmol) in THF (40 mL) was added a butyllithium solution (5.57 mL, 13.9 mmol). After stirring for 1 h, tert-butyl 4-(4-fluorobenzoyl)piperidine-1-carboxylate (intermediate H-2) (3.05 g, 9.94 mmol) was added to the mixture and stirring was continued at −78° C. for 1 h. Then the reaction was warmed to 25° C. and stirred for another 13 h. The reaction was quenched with NH$_4$Cl (sat. aq., 50 mL) and extracted with EtOAc (100 mL). The organic layer was separated, dried with over Na$_2$SO$_4$, filtered and concentrated under vacuum to afford tert-butyl 4-((4-fluorophenyl)(hydroxy)(p-tolyl)methyl)piperidine-1-carboxylate (2.85 g, 71%) as a light yellow oil; LCMS: 422.1 [M+Na]$^+$.

Intermediate Q-2

4-[(4-Fluorophenyl)-(p-tolyl)methylene]piperidine

A solution of tert-butyl 4-[(4-fluorophenyl)-hydroxy-(p-tolyl)methyl]piperidine-1-carboxylate (2.83 g, 7.08 mmol) and trifluoroacetic acid (11 mL, 142 mmol) in DCM (20 mL) was stirred at 25° C. for 3 h. The reaction was concentrated under vacuum. The residue was purification by Prep-HPLC (TFA as additive) to afford 4-[(4-fluorophenyl)-(p-tolyl)methylene]piperidine (1.36 mg, 67%) as light-yellow semi-solid; LC-MS: 282.1 [M+H]$^+$.

Intermediate Q-3

4-[(4-Fluorophenyl)-(p-tolyl)methyl]piperidine

A solution of 4-[(4-fluorophenyl)-(p-tolyl)methylene]piperidine (1.36 g, 4.83 mmol) and Pd/C (300 mg) in DMF (50 mL) was stirred at 25° C. for 16 h under H$_2$ (2280 mmHg). The reaction solution was filtered through Celite and concentrated under vacuum. The residue was purified by Prep-HPLC (TFA as additive) to afford 4-[(4-fluorophenyl)-(p-tolyl)methyl]piperidine (TFA salt, 870 mg, 45%) as white semisolid; LC-MS: 284.1 [M+H]$^+$.

Intermediate Q-4

(R or S)-4-(4-fluorophenyl)(p-tolyl)methyl piperidine and (S or R)-4-[(4-fluorophenyl)(p-tolyl)methyl]piperidine A solution of 4-[(4-fluorophenyl)-(p-tolyl)methyl]piperidine (870 mg, 3.07 mmol) was separated by SFC (Method: Column DAICEL CHIRALPAK AD 250 mm*30 mm, 5 µm, Condition 0.1% NH$_3$*H$_2$O IPA, Begin B 35, End B 35, Gradient Time (min) 4.9 min; 110 min, 100% B Hold Time (min) 0; FlowRate (mL/min) 60) to afford (R or S)-4-[(4-fluorophenyl)(p-tolyl)methyl]piperidine (253 mg, 28% yield; LCMS: 284.1 [M+H]$^+$) and (S or R)-4-[(4-fluorophenyl)(p-tolyl)methyl]piperidine (356 mg, 40% yield; LCMS: 284.1 [M+H]$^+$).

6-[4-[(S or R)-(4-Fluorophenyl)-(p-tolyl)methyl]piperidine-1-carbonyl]-4H-1,4-benzoxazin-3-one A solution of (S or R)-4-[(4-fluorophenyl)(p-tolyl)methyl]piperidine (40 mg, 0.13 mmol), 3-oxo-4H-1,4-benzoxazine-6-carboxylic acid (26 mg, 0.13 mmol), O-(7-azabenzotriazol-1-yl)-N,N,N',N'-tetramethyluronium hexafluorophosphate (56 mg, 0.15 mmol) and triethylamine (0.05 mL, 0.270 mmol) in DCM (5 mL) was stirred at 25° C. for 16 h. The reaction was quenched with H$_2$O (5 mL) and extracted with DCM (10 mL). The organic layer was separated, dried with over Na$_2$SO$_4$, filtered and concentrated under vacuum. The residue was purified by Prep-HPLC (TFA as additive) to afford 6-[4-[(S or R)-(4-fluorophenyl)-(p-tolyl)methyl]piperidine-1-carbonyl]-4H-1,4-benzoxazin-3-one (20 mg, 32%) as a white solid; LC-MS: 459.2 [M+H]$^+$.

The other enantiomer was prepared analogously from (R or S)-4-[(4-fluorophenyl)(p-tolyl)methyl]piperidine (40 mg, 0.13 mmol) and 3-oxo-4H-1,4-benzoxazine-6-carboxylic acid (26 mg, 0.13 mmol). 20 mg (32%), white solid; LC-MS: 459.2 [M+H]$^+$.

Examples 114 and 115

6-[4-[(S or R)-(4-Fluorophenyl)-(6-fluoro-3-pyridyl) methyl]piperidine-1-carbonyl]-4H-1,4-benzoxazin-3-one and 6-[4-[(R or S)-(4-Fluorophenyl)-(6-fluoro-3-pyridyl) methyl]piperidine-1-carbonyl]-4H-1,4-benzoxazin-3-one

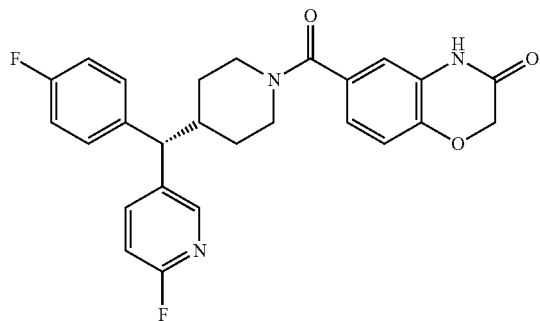

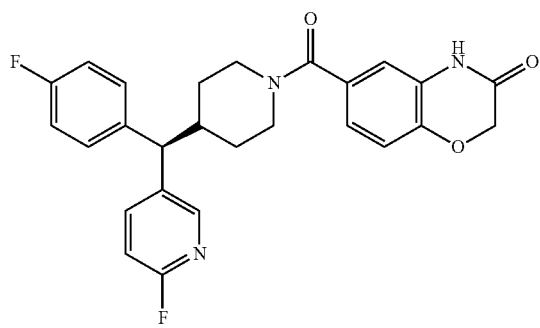

Intermediate R-1 tert-Butyl 4-((4-fluorophenyl)(6-fluoropyridin-3-yl) methylene)piperidine-1-carboxylate A mixture of 5-bromo-2-fluoropyridine (333 mg, 1.89 mmol), tert-butyl 4-((4-fluorophenyl)(2-tosylhydrazono) methyl)piperidine-1-carboxylate (P-1) (600 mg, 1.26 mmol), LiOtBu (151 mg, 1.89 mmol) and bis(triphenylphosphine)palladium(II) chloride (88 mg, 0.13 mmol) in 1,4-dioxane (10 mL) was stirred at 80° C. for 16 h under $N_2$. The reaction mixture was filtered and concentrated in vacuo to give a residue which was purified by flash column (petroleum ether:ethyl acetate 20:1) to give tert-butyl 4-((4-fluorophenyl)(6-fluoropyridin-3-yl)methylene)piperidine-1-carboxylate (180 mg, 36%) as light yellow solid; LC-MS: 331.2 [M+H-buten]+.

Intermediate R-2

2-Fluoro-5-[(4-fluorophenyl)(piperidin-4-ylidene) methyl]pyridine

A mixture of tert-butyl 4-[(4-fluorophenyl)(6-fluoropyridin-3-yl)methylene]piperidine-1-carboxylate (180 mg, 0.470 mmol) and trifluoroacetic acid (265 mg, 2.33 mmol) in DCM (5 mL) was stirred at 25° C. for 4 h. The reaction mixture was concentrated in vacuo to give 2-fluoro-5-[(4-fluorophenyl)(piperidin-4-ylidene)methy l]pyridine (TFA salt, 130 mg, 97%) as brown oil; LC-MS: 287.2 [M+H]+.

Intermediate R-3

2-Fluoro-5-[(4-fluorophenyl)(piperidin-4-yl)methyl] pyridine

A mixture of 2-fluoro-5-[(4-fluorophenyl)(piperidin-4-ylidene)methyl]pyridine (160 mg, 0.560 mmol) and Pd/C (595 mg, 0.560 mmol) in THF (10 mL) was stirred at 25° C. for 16 h under $H_2$ (760 mmHg). The mixture was filtered and concentrated in vacuo to give 2-fluoro-5-[(4-fluorophenyl) (piperidin-4-yl)methyl]pyridine (160 mg, 99%) as a colorless oil; LC-MS: 289.2 [M+H]+.

Rac-6-[4-[(4-Fluorophenyl)-(6-fluoro-3-pyridyl) methyl]piperidine-1-carbonyl]-4H-1,4-benzoxazin-3-one A solution of 3-oxo-4H-1,4-benzoxazine-6-carboxylic acid (107 mg, 0.550 mmol), 2-fluoro-5-[(4-fluorophenyl) (piperidin-4-yl)methyl]pyridine (160 mg, 0.550 mmol), triethylamine (0.09 mL, 0.670 mmol) and <9-(7-azabenzotriazol-1-yl)-N,N,N',N'-tetramethyluronium hexafluorophosphate (253 mg, 0.670 mmol) in DCM (5 mL) was stirred at 25° C. for 4 h. The reaction solution was poured into brine (30 mL) and extracted with DCM (2×20 mL). The combined organic layers were concentrated in vacuo to give a residue which was purified by Prep-HPLC (TFA conditions) to give 6-[4-[(4-fluorophenyl)-(6-fluoro-3-pyridyl)methyl]piperidine-1-carbonyl]-4H-1,4-benzoxazin-3-one (90 mg, 35%) as a white solid; LC-MS: 464.3 [M+H]+.

6-[4-[(4-Fluorophenyl)-(6-fluoro-3-pyridyl)methyl]piperidine-1-carbonyl]-4H-1,4-benzoxazin-3-one (90 mg, 0.190 mmol) was separated by SFC (Method Column DAICEL CHIRALPAK AD (250 mm*30 mm, 10 μm), Condition 0.1% $NH_3*H_2O$ MeOH, Begin B 55, End B 55 Gradient Time (min) 4.5 min; 150 min, 100% B Hold Time (min) 0, FlowRate (ml/min) 70 g/min) to give 6-[4-[(S or R)-(4-fluorophenyl)-(6-fluoro-3-pyridyl)methyl]piperidine-1-carbonyl]-4H-1,4-benzoxazin-3-one (29 mg, 32%; LC-MS: 464.3 [M+H]+) and 6-[4-[(R or S)-(4-fluorophenyl)-(6-fluoro-3-pyridyl)methyl]piperidine-1-carbonyl]-4H-1,4-benzoxazin-3-one (33 mg, 36%; LC-MS: 464.3 [M+H]+) as a white solids.

Examples 116 and 117

6-[4-[(R or S)-(3,4-Dimethoxyphenyl)-(2-pyridyl)methyl]piperidine-1-carbonyl]-4H-1,4-benzoxazin-3-one and 6-[4-[(S or R)-(3,4-Dimethoxyphenyl)-(2-pyridyl)methyl]piperidine-1-carbonyl]-4H-1,4-benzoxazin-3-one

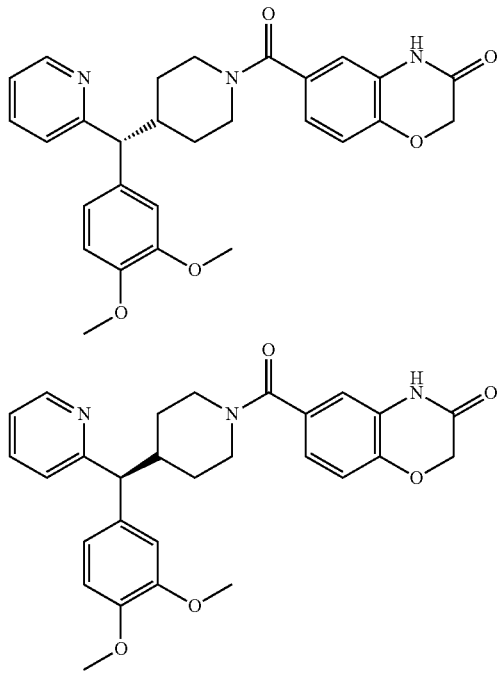

Intermediate S-1 tert-Butyl 4-(3,4-dimethoxybenzoyl)piperidine-1-carboxylate

To a stirred solution at −78° C. of 4-bromoveratrole (5.7 g, 26 mmol) in THF (20 mL) was added a solution of butyllithium (13 mL, 33 mmol). After stirring at −78° C. for 1 h a solution of tert-butyl 4-(methoxy(methyl)carbamoyl)piperidine-1-carboxylate (6.0 g, 22 mmol) was added and stirring was continued at −78° C. for 5 h. The solution was poured into brine (30 mL) and extracted with ethyl acetate (2×30 mL). The combined organic layers were concentrated in vacuo to give a residue, which was purified by flash column chromatography (petroleum ether:ethyl acetate 3:1) to give tert-butyl 4-(3,4-dimethoxybenzoyl)piperidine-1-carboxylate (3.8 g, 46%) as light yellow oil; LC-MS: 372.2 [M+Na]$^+$.

Intermediate S-2 tert-Butyl 4-[(3,4-dimethoxyphenyl)(2-tosylhydrazono)methyl]piperidine-1-carboxylate A solution of 4-methylbenzenesulfonhydrazide (2.43 g, 13.0 mmol) and tert-butyl 4-(3,4-dimethoxybenzoyl)piperidine-1-carboxylate (3.80 g, 10.9 mmol) in 1,4-dioxane (10 mL) was stirred at 80° C. for 24 h. The reaction solution was concentrated in vacuo to give a residue, which was purified by flash column chromatography (petroleum ether:ethyl acetate 10:1) to give tert-butyl 4-[(3,4-dimethoxyphenyl)(2-tosylhydrazono)methyl]piperidine-1-carboxylate (4.5 g, 70%) as colorless oil; LC-MS: 540.3 [M+Na]$^+$.

Intermediate S-3 tert-Butyl 4-[(3,4-dimethoxyphenyl)(pyridin-2-yl)methylene]piperidine-1-carboxylate A mixture of 2-bromopyridine (0.55 mL, 5.8 mmol), tert-butyl 4-[(3,4-dimethoxyphenyl)(2-tosylhydrazono)methyl]piperidine-1-carboxylate (1.50 g, 2.9 mmol), LiOtBu (348 mg, 4.35 mmol) and bis(triphenylphosphine)palladium(II) chloride (203 mg, 0.29 mmol) in 1,4-dioxane (10 mL) was stirred at 80° C. for 16 h under N$_2$. The mixture was filtered and concentrated in vacuo to give a residue, which was purified by Prep-HPLC (TFA condition) to give tert-butyl 4-[(3,4-dimethoxyphenyl)(pyridin-2-yl)methylene]piperidine-1-carboxylate (170 mg, 14% yield) as colorless oil; LC-MS: 411.2 [M+H]$^+$.

Intermediate S-4 tert-Butyl 4-((3,4-dimethoxyphenyl)(pyridin-2-yl)methyl)piperidine-1-carboxylate A mixture of tert-butyl 4-((3,4-dimethoxyphenyl)(pyridin-2-yl)methylene)piperidine-1-carboxylate (150 mg, 0.37 mmol) and Pd/C (50 mg) in THF (4 mL) was stirred at 25° C. for 16 h under H$_2$ (760 mmHg). The mixture was filtered and concentrated in vacuo to give tert-butyl 4-((3,4-dimethoxyphenyl)(pyridin-2-yl)methyl)piperidine-1-carboxylate (100 mg, 66%) as colorless oil; LC-MS: 413.1 [M+H]$^+$.

Intermediate S-5

2-[(3,4-Dimethoxyphenyl)(piperidin-4-yl)methyl]pyridine

A mixture of tert-butyl 4-((3,4-dimethoxyphenyl)(pyridin-2-yl)methyl)piperidine-1-carboxylate (100 mg, 0.240 mmol) and trifluoroacetic acid (0.19 mL, 2.42 mmol) in DCM (2 mL) was stirred at 25° C. for 4 h. The mixture was concentrated in vacuo to give 2-[(3,4-dimethoxyphenyl)(piperidin-4-yl)methyl]pyridine (70 mg, 91%) as a brown oil. LC-MS: 313.3 [M+H]$^+$.

Rac-6-[4-[(3,4-Dimethoxyphenyl)-(2-pyridyl)methyl]piperidine-1-carbonyl]-4H-1,4-benzoxazin-3-one A solution of 2-[(3,4-dimethoxyphenyl)(piperidin-4-yl)methyl]pyridine (70 mg, 0.22 mmol), 3-oxo-4H-1,4-benzoxazine-6-carboxylic acid (43 mg, 0.22 mmol), triethylamine (0.04 mL, 0.27 mmol) and O-(7-azabenzotriazol-1-yl)-N,N,N',N'-tetramethyluronium hexafluorophosphate (102 mg, 0.27 mmol) in DCM (5 mL) was stirred at 25° C. for 4 h. The reaction solution was poured into brine (30 mL) and extracted with DCM (2×20 mL). The combined organic layers were concentrated in vacuo to give a residue, which was purified by Prep-HPLC (TFA condition) to give 6-[4-[(3,4-dimethoxyphenyl)-(2-pyridyl)methyl]piperidine-1-carbonyl]-4H-1,4-benzoxazin-3-one (80 mg, 73%) as white solid; LC-MS: 488.3 [M+H]$^+$.

6-[4-[(3,4-Dimethoxyphenyl)-(2-pyridyl)methyl]piperidine-1-carbonyl]-4H-1,4-benzoxazin-3-one (80 mg, 0.16 mmol) was separated by SFC to give 6-[4-[(R or S)-(3,4-dimethoxyphenyl)-(2-pyridyl)methyl]piperidine-1-carbonyl]-4H-1,4-benzoxazin-3-one (18 mg, 22%; LC-MS: 488.3 [M+H]$^+$) and 6-[4-[(S or R)-(3,4-dimethoxyphenyl)-(2-pyridyl)methyl]piperidine-1-carbonyl]-4H-1,4-benzoxazin-3-one (9.6 mg, 11%; LC-MS: 488.1 [M+H]$^+$) as white solids.

Examples 118 and 119

6-[4-[(S or R)-(4-Fluorophenyl)-(6-fluoro-2-pyridyl)methyl]piperidine-1-carbonyl]-4H-1,4-benzoxazin-3-one and 6-[4-[(R or S)-(4-Fluorophenyl)-(6-fluoro-2-pyridyl)methyl]piperidine-1-carbonyl]-4H-1,4-benzoxazin-3-one

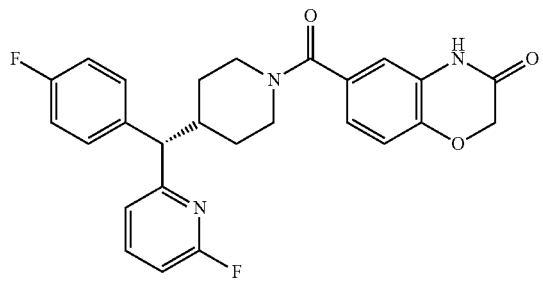

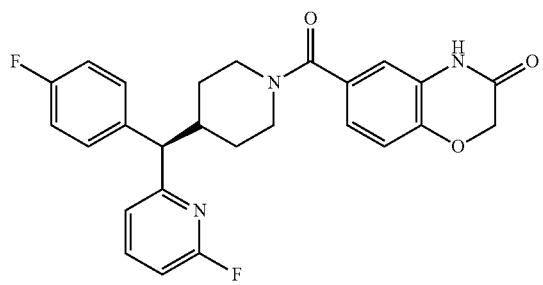

Intermediate T-1 tert-Butyl 4-[(4-Fluorophenyl)(6-fluoropyridin-2-yl)methylene]piperidine-1-carboxylate A mixture of tert-butyl 4-[(4-fluorophenyl)(2-tosylhydrazono)methyl]piperidine-1-carboxylate (intermediate P-1) (900 mg, 1.89 mmol), 2-bromo-6-fluoropyridine (400 mg, 2.27 mmol), LiOtBu (227 mg, 2.84 mmol) and bis(triphenylphosphine)palladium(II) chloride (133 mg, 0.190 mmol) in 1,4-dioxane (10 mL) was stirred at 80° C. for 16 h under N$_2$. The reaction mixture was filtered and concentrated in vacuo to give a residue which was purified by flash column (petroleum ether:ethyl acetate 20:1) to give tert-butyl 4-[(4-fluorophenyl)(6-fluoropyridin-2-yl)methylene]piperidine-1-carboxylate (231 mg, 27%) as light yellow solid; LC-MS: 409.3 [M+Na]$^+$.

Intermediate T-2

2-Fluoro-6-[(4-fluorophenyl)(piperidin-4-ylidene)methyl]pyridine

A mixture of tert-butyl 4-[(4-fluorophenyl)(6-fluoropyridin-2-yl)methylene]piperidine-1-carboxylate (231 mg, 0.600 mmol) and trifluoroacetic acid (0.46 mL, 5.97 mmol) in DCM (5 mL) was stirred at 25° C. for 1 h. The reaction mixture was concentrated in vacuo to give 2-fluoro-6-[(4-fluorophenyl)(piperidin-4-ylidene)methyl]pyridine (TFA salt, 160 mg, 93%) as a brown oil; LC-MS: 287.1 [M+H]$^+$.

Intermediate T-3

2-Fluoro-6-[(4-fluorophenyl)(piperidin-4-yl)methyl]pyridine

A mixture of 2-fluoro-6-[(4-fluorophenyl)(piperidin-4-ylidene)methyl]pyridine (0.16 g, 0.56 mmol) and Pd/C (0.09 g, 0.090 mmol) in THF (5 mL) was stirred at 25° C. for 16 h under H$_2$ (760 mmHg). The mixture was filtered and concentrated in vacuo to give 2-fluoro-6-[(4-fluorophenyl)(piperidin-4-yl)methyl]pyridine (160 mg, 99%) as colorless oil; LC-MS: 289.1 [M+H]$^+$.

Rac-6-[4-[(4-Fluorophenyl)-(6-fluoro-2-pyridyl)methyl]piperidine-1-carbonyl]-4H-1,4-benzoxazin-3-one A solution of 3-oxo-4H-1,4-benzoxazine-6-carboxylic acid (107 mg, 0.550 mmol), 2-fluoro-6-[(4-fluorophenyl)(piperidin-4-yl)methyl]pyridine (160.0 mg, 0.550 mmol), triethylamine (0.09 mL, 0.67 mmol) and <9-(7-azabenzotriazol-1-yl)-N,N,N',N'-tetramethyluronium hexafluorophosphate (253 mg, 0.670 mmol) in DCM (5 mL) was stirred at 25° C. for 4 h. The reaction solution was poured into brine (20 mL) and extracted with DCM (2×10 mL). The combined organic layers were concentrated in vacuo to give a residue, which was purified by Prep-HPLC (TFA condition) to yield 6-[4-[(4-fluorophenyl)-(6-fluoro-2-pyridyl)methyl]piperidine-1-carbonyl]-4H-1,4-benzoxazin-3-one (92 mg, 35%) as white solid; LC-MS: 464.3 [M+H]$^+$. 6-[4-[(4-Fluorophenyl)-(6-fluoro-2-pyridyl)methyl]piperidine-1-carbonyl]-4H-1,4-benzoxazin-3-one (90 mg, 0.19 mmol) was separated by SFC (Method: Column DAICEL CHIRALPAK AD (250 mm*50 mm, 10 μm), Condition 0.1% NH$_3$*H$_2$O MeOH, Begin B 25, End B 25 Gradient Time (min) 5.5 min:900 min, 100% B Hold Time (min) 0, FlowRate (ml/min) 50 g/min) to give 6-[4-[(S or R)-(4-fluorophenyl)-(6-fluoro-2-pyridyl)methyl]piperidine-1-carbonyl]-4H-1,4-benzoxazin-3-one (24 mg, 26%; LC-MS: 464.1 [M+H]$^+$) and 6-[4-[(R or S)-(4-fluorophenyl)-(6-fluoro-2-pyridyl)methyl]piperidine-1-carbonyl]-4H-1,4-benzoxazin-3-one (33 mg, 35%; LC-MS: 464.1 [M+H]$^+$) as a off-white solids.

Examples 120 and 121

6-[4-[(R or S)-(4-Fluorophenyl)-(3-methoxyphenyl)methyl]piperidine-1-carbonyl]-4H-1,4-benzoxazin-3-one and 6-[4-[(S or R)-(4-Fluorophenyl)-(3-methoxyphenyl)methyl]piperidine-1-carbonyl]-4H-1,4-benzoxazin-3-one

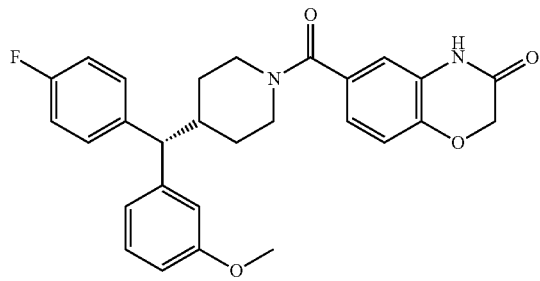

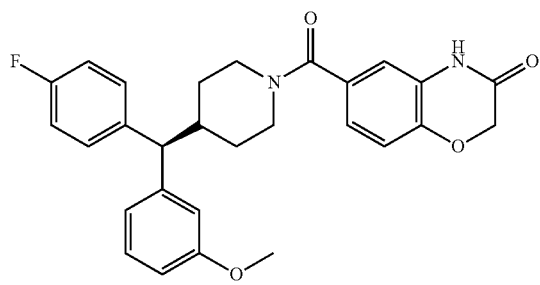

Intermediate U-1 tert-Butyl 4-[(4-fluorophenyl)(hydroxy)(3-methoxyphenyl)methyl]piperidine-1-carboxylate To a solution of 3-bromoanisole (487 mg, 2.6 mmol) in THF (40 mL) was added butyllithium (1.5 mL, 3.75 mmol, 2.5 M) at −78° C. After stirring for 1 h, tert-butyl 4-(4-fluorobenzoyl)piperidine-1-carboxylate (800 mg, 2.6 mmol) was added to the mixture and stirring was continued at −78° C. for 1 h. Then the reaction was warmed to 25° C. and stirred for another 13 h. The reaction was quenched with NH$_4$Cl (sat. aq., 50 mL) and extracted with EtOAc (100 mL). The organic layer was separated, dried over Na$_2$SO$_4$, filtered and concentrated under vacuum to afford tert-butyl 4-[(4-fluorophenyl)(hydroxy)(3-methoxyphenyl)methyl]piperidine-1-carboxylate (1100 mg, 63%) as yellow oil; LCMS: 438.1[M+Na]$^+$.

Intermediate U-2

4-[(4-Fluorophenyl)(3-methoxyphenyl)methylene]piperidine

A solution of tert-butyl 4-[(4-fluorophenyl)(hydroxy)(3-methoxyphenyl)methyl]piperidine-1-carboxylate (1.10 g, 1.64 mmol) and trifluoroacetic acid (5.0 mL, 65 mmol) in DCM (10 mL) was stirred at 25° C. for 5 h. The reaction was concentrated under vacuum. The residue was dissolved in EtOAc (50 mL) and washed with Na$_2$CO$_3$ (aq., 10%, 50 mL). The organic layer was separated, dried with over Na$_2$SO$_4$, filtered and concentrated under vacuum. The resulting oil was purified by Prep-HPLC (TFA as additive) to afford 4-[(4-fluorophenyl)(3-methoxyphenyl)methylene]piperidine (TEA salt, 430 mg, 39%) as a white solid; LCMS: 298.1 [M+H]$^+$.

Intermediate U-3

4-[(4-Fluorophenyl)(3-methoxyphenyl)methyl]piperidine

A solution of 4-[(4-fluorophenyl)(3-methoxyphenyl)methylene]piperidine (410 mg, 1.38 mmol) and Pd/C (100 mg, 1.38 mmol) in THF (10 mL) was stirred at 25° C. for 16 h under H$_2$ (760 mmHg). The reaction mixture was filtered through the Celite, then concentrated under vacuum to afford 4-[(4-fluorophenyl)(3-methoxyphenyl)methyl]piperidine (TFA salt, 260 mg, 59%) as yellow oil; LCMS: 300.1 [M+H]$^+$.

Rac-6-[4-[(4-Fluorophenyl)-(3-methoxyphenyl)methyl]piperidine-1-carbonyl]-4H-1,4-benzoxazin-3-one A solution of 3-oxo-4H-1,4-benzoxazine-6-carboxylic acid (167 mg, 0.87 mmol), 4-[(4-fluorophenyl)-(3-methoxyphenyl)methyl]piperidine (260 mg, 0.87 mmol), O-d-azabenzotriazol-1-yl)-N,N,N',N'-tetramethyluronium hexafluorophosphate (396 mg, 1.04 mmol) and triethylamine (0.36 mL, 2.61 mmol) in DCM (15 mL) was stirred at 25° C. for 16 h. The reaction was quenched with H$_2$O (5 mL) and extracted with DCM (10 mL). The organic layer was separated, dried over Na$_2$SO$_4$, filtered and concentrated under vacuum to afford 6-[4-[(4-fluorophenyl)-(3-methoxyphenyl)methyl]piperidine-1-carbonyl]-4H-1,4-benzoxazin-3-one (130 mg, 25%) as yellow solid; LCMS: 475.2 [M+H]$^+$.

6-[4-[(4-Fluorophenyl)-(3-methoxyphenyl)methyl]piperidine-1-carbonyl]-4H-1,4-benzoxazin-3-one (125 mg, 0.26 mmol) was separated by SFC (Method: Column DAICEL CHIRALPAK OD 250 mm*30 mm. 10 μm. Condition 0.1% NH$_3$*H$_2$O IPA, Begin B 50, End B 50, Gradient Time (min) 2.6 min; 183 min, 100% B Hold Time (min) 0; FlowRate (mL/min) 70) to afford 6-[4-[(R or S)-(4-fluorophenyl)-(3-methoxyphenyl)methyl]piperidine-1-carbonyl]-4H-1,4-benzoxazin-3-one (61 mg, 48%; LC-MS: 475.3 [M+H]$^+$) and 6-[4-[(S or R)-(4-fluorophenyl)-(3-methoxyphenyl)methyl]piperidine-1-carbonyl]-4H-1,4-benzoxazin-3-one (30 mg, 23%; LC-MS: 475.3 [M+H]$^+$) as off-white solids.

Examples 122 and 123

6-[4-[(R or S)-(3,4-Dimethoxyphenyl)-(3-pyridyl)methyl]piperidine-1-carbonyl]-4H-1,4-benzoxazin-3-one and 6-[4-[(S or R)-(3,4-Dimethoxyphenyl)-(3-pyridyl)methyl]piperidine-1-carbonyl]-4H-1,4-benzoxazin-3-one

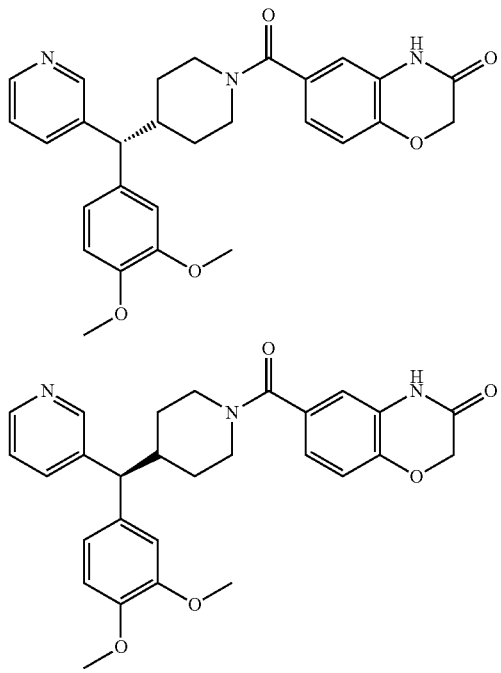

Intermediate V-1 tert-Butyl 4-[(3,4-dimethoxyphenyl)(pyridin-2-yl)methylene]piperidine-1-carboxylate A mixture of 3-bromopyridine (0.5 mL, 5.8 mmol), tert-butyl 4-[(3,4-dimethoxyphenyl)(2-tosylhydrazono)methyl]piperidine-1-carboxylate (intermediate S-2) (1.50 g, 2.9 mmol), LiOtBu (348 g, 4.35 mmol) and bis(triphenylphosphine) palladium(II) chloride (203 mg, 0.29 mmol) in 1,4-dioxane (10 mL) was stirred at 80° C. for 16 h under $N_2$. The mixture was filtered and the filtrate was poured into brine (50 mL) and then extracted with ethyl acetate (2×30 mL). The combined organic layers were concentrated in vacuo to give a residue, which was purified by flash column (petroleum ether:ethyl acetate 2:1) to give tert-butyl 4-[(3,4-dimethoxyphenyl)(pyridin-2-yl)methylene]piperidine-1-carboxylate (270 mg, 19%) as colorless oil; LC-MS: 411.1 $[M+H]^+$.

Intermediate V-2 tert-Butyl 4-[(3,4-dimethoxyphenyl)(pyridin-3-yl)methyl]piperidine-1-carboxylate A mixture of tert-butyl 4-[(3,4-dimethoxyphenyl)(pyridin-2-yl)methylene]piperidine-1-carboxylate (220 mg, 0.54 mmol), and Pd/C (57 mg) in THF (6 mL) was stirred at 25° C. for 16 h under $H_2$ (760 mmHg). The mixture was filtered and concentrated in vacuo to give tert-butyl 4-[(3,4-dimethoxyphenyl)(pyridin-3-yl)methyl]piperidine-1-carboxylate (190 mg, 69%) as colorless oil; LC-MS: 413.3 $[M+H]^+$.

Intermediate V-3

3-[(3,4-Dimethoxyphenyl)(piperidin-4-yl)methyl]pyridine

A solution of tert-butyl 4-[(3,4-dimethoxyphenyl)(pyridin-3-yl)methyl]piperidine-1-carboxylate (190 mg, 0.46 mmol) and trifluoroacetic acid (0.2 mL, 2.6 mmol) in DCM (5 mL) was stirred at 25° C. for 4 h. The solution was concentrated in vacuo to give 3-[(3,4-dimethoxyphenyl)(piperidin-4-yl)methyl]pyridine (110 mg, 76%) as colorless oil; LC-MS: 313.2 $[M+H]^+$.

Rac-6-[4-[(3,4-Dimethoxyphenyl)-(3-pyridyl)methyl]piperidine-1-carbonyl]-4H-1,4-benzoxazin-3-one A solution of 3-oxo-4H-1,4-benzoxazine-6-carboxylic acid (68 mg, 0.35 mmol), 3-[(3,4-dimethoxyphenyl)(piperidin-4-yl)methyl]pyridine (110 mg, 0.35 mmol), triethylamine (0.06 mL, 0.42 mmol) and O-(7-azabenzotriazol-1-yl)-N,N,N',N'-tetramethyluronium hexafluorophosphate (161 mg, 0.42 mmol) in DCM (5 mL) was stirred at 25° C. for 4 h. The reaction solution was poured into brine (20 mL) and extracted with DCM (2×10 mL). The combined organic layers were concentrated in vacuo to give a residue, which was purified by Prep-HPLC (TFA condition) to give 6-[4-[(3,4-dimethoxyphenyl)-(3-pyridyl)methyl]piperidine-1-carbonyl]-4H-1,4-benzoxazin-3-one (55 mg, 31%) as white solid; LC-MS: 488.1 $[M+H]^+$.

6-[4-[(3,4-Dimethoxyphenyl)-(3-pyridyl)methyl]piperidine-1-carbonyl]-4H-1,4-benzoxazin-3-one (52 mg, 0.11 mmol) was separated by SFC to give 6-[4-[(R or S)-(3,4-dimethoxyphenyl)-(3-pyridyl)methyl]piperidine-1-carbonyl]-4H-1,4-benzoxazin-3-one (11 mg, 21%; LC-MS: 488.2 $[M+H]^+$) and 6-[4-[(S or R)-(3,4-dimethoxyphenyl)-(3-pyridyl)methyl]piperidine-1-carbonyl]-4H-1,4-benzoxazin-3-one (9.2 mg, 17%; LC-MS: 488.1 $[M+H]^+$) as white solids.

Examples 124

6-(3-Benzhydrylazetidine-1-carbonyl)-4H-1,4-benzoxazin-3-one

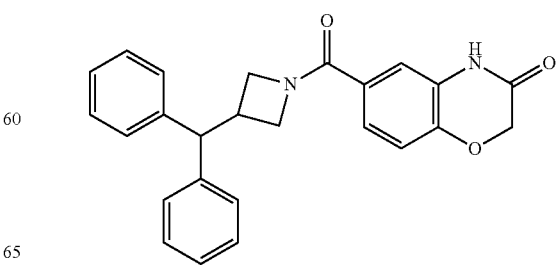

Intermediate W-1 tert-Butyl 3-[methoxy(methyl)carbamoyl]azetidine-1-carboxylate

A mixture of 1-Boc-azetidine-3-carboxylic acid (50 g, 248 mmol), triethylamine (69.3 mL, 497 mmol), 1-hydroxybenzotriazole (33.5 g, 248 mmol) and EDCl (47.6 g, 248 mmol) and O,N-dimethylhydroxylamine HCl (24.24 g, 248.5 mmol) in DMF (1000 mL) was stirred at 25° C. for 16 h. The mixture was concentrated in vacuo to give a residue, which was neutralized by HCl (1M) to pH=7 and extracted with ethyl acetate (3×200 mL). The combined organic layers were washed with NaHCO$_3$ (2×sat. aq. 200 mL), dried over Na$_2$SO$_4$ and concentrated in vacuo to give to/7-butyl 3-[methoxy(methyl)carbamoyl]azetidine-1-carboxylate (55 g, 72%) as colorless oil; LC-MS: 189.1 [M−56+H]$^+$.

Intermediate W-2 tert-Butyl 3-benzoylazetidine-1-carboxylate

To a solution of tert-butyl 3-[methoxy(methyl)carbamoyl]azetidine-1-carboxylate (55 g, 225 mmol) in THF (600 mL) was added phenylmagnesium bromide (82 mL, 248 mmol) with stirring at 0° C. and then the solution was stirred at 0° C. for 3 h. The solution was poured into NH$_4$Cl (sat. aq. 300 mL) and extracted with ethyl acetate (2×150 mL). The combined organic layers were dried over Na$_2$SO$_4$, filtered and concentrated in vacuo to give a residue, which was purified by column chromatography (petroleum ether:ethyl acetate 10:1) to give tert-butyl 3-benzoylazetidine-1-carboxylate (28 g, 46%) as light yellow solid; LC-MS: 206.1 [M−56+H]$^+$.

Intermediate W-3 tert-Butyl 3-(hydroxydiphenylmethyl)azetidine-1-carboxylate

A solution of phenylmagnesium bromide (3.06 mL, 9.18 mmol) and tert-butyl 3-benzoylazetidine-1-carboxylate (2.0 g, 7.65 mmol) in THF (20 mL) was stirred at 0° C. for 2 h. The solution was quenched by NH$_4$Cl (sat. aq. 50 mL) and extracted with ethyl acetate (2×20 mL). The combined organic layers were concentrated in vacuo to give a residue, which was purified by flash column chromatography (petroleum ether:ethyl acetate 5:1) to give tert-butyl 3-(hydroxydiphenylmethyl)azetidine-1-carboxylate (1.03 g, 39%) as white solid; LC-MS: 362.2 [M+Na]$^+$.

Intermediate W-4

3-(Diphenylmethylene)azetidine

A solution of tert-butyl 3-(hydroxydiphenylmethyl)azetidine-1-carboxylate (1.00 g, 2.95 mmol) and trifluoroacetic acid (2.27 mL, 29.5 mmol) in DCM (15 mL) was stirred at 25° C. for 4 h. The solution was concentrated in vacuo to give 3-(diphenylmethylene)azetidine (TFA salt, 650 mg, 99%) as brown oil; LC-MS: 222.1 [M+H]$^+$.

Intermediate W-5

3-Benzhydrylazetidine

A solution of 3-(diphenylmethylene)azetidine (800 mg, 3.62 mmol) and Pd/C (1923 mg) in THF (20 mL) was stirred at 25° C. for 5 h under H$_2$ (760 mmHg). The solution was filtered and concentrated in vacuo to give a residue, which was purified by Prep-HPLC (TFA condition) to give 3-benzhydrylazetidine (315 mg, 37%) as white solid; LC-MS: 224.1 [M+H]$^+$.

6-(3-Benzhydrylazetidine-1-carbonyl)-4H-1,4-benzoxazin-3-one

A solution of 3-benzhydrylazetidine (102 mg, 0.460 mmol), O-(7-azabenzotriazol-1-yl)-N,N,N',N'-tetramethyluronium hexafluorophosphate (174 mg, 0.46 mmol), 3-oxo-4H-1,4-benzoxazine-6-carboxylic acid (88 mg, 0.46 mmol) and triethylamine (0.08 mL, 0.55 mmol) in DCM (5 mL) was stirred at 25° C. for 5 h. The solution was concentrated in vacuo to give a residue, which was purified by Prep-HPLC (TFA condition) to give 6-(3-benzhydrylazetidine-1-carbonyl)-4H-1,4-benzoxazin-3-one (52 mg, 28%) as white solid; LC-MS: 399.2 [M+H]$^+$.

Examples 125 and 126

6-[4-[(S or R)-(3,4-Dimethoxyphenyl)-(4-pyridyl)methyl]piperidine-1-carbonyl]-4H-1,4-benzoxazin-3-one and

6-[4-[(R or S)-(3,4-Dimethoxyphenyl)-(4-pyridyl)methyl]piperidine-1-carbonyl]-4H-1,4-benzoxazin-3-one

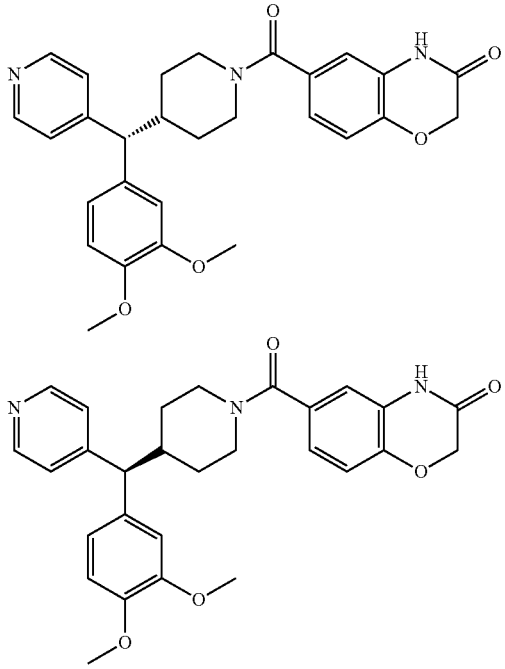

Intermediate X-1 tert-Butyl 4-[(3,4-dimethoxyphenyl)(pyridin-4-yl)methylene]piperidine-1-carboxylate A mixture of 4-bromopyridine (0.48 mL, 5.02 mmol, 1.3 eq), tert-butyl 4-((3,4-dimethoxyphenyl)(2-tosylhydrazono)

methyl)piperidine-1-carboxylate (intermediate S-2) (2.00 g, 3.86 mmol), LiOtBu (464 mg, 5.8 mmol) and bis(triphenylphosphine)palladium(II) chloride (271 mg, 0.39 mmol) in 1,4-dioxane (40 mL) was stirred at 80° C. for 16 h under $N_2$. The mixture was filtered and the filtrate was poured into brine (50 mL) and then extracted with ethyl acetate (2×30 mL). The combined organic layers were concentrated in vacuo to give a residue which was purified by flash column (petroleum ether:ethyl acetate 2:1) to give tert-butyl 4-[(3,4-dimethoxyphenyl)(pyridin-4-yl)methylene]piperidine-1-carboxylate (310 mg, 19%) as light-yellow oil; LC-MS: 411.1 $[M+H]^+$.

Intermediate X-2 tert-Butyl 4-((3,4-dimethoxyphenyl)(pyridin-4-yl)methyl)piperidine-1-carboxylate A mixture of tert-butyl 4-[(3,4-dimethoxyphenyl)(pyridin-4-yl)methylene]piperidine-1-carboxylate (300 mg, 0.73 mmol), and Pd/C (778 mg) in THF (10 mL) was stirred at 25° C. for 16 h under $H_2$ (760 mmHg). The mixture was filtered and concentrated in vacuo to give tert-butyl 4-[(3,4-dimethoxyphenyl)(pyridin-4-yl)methyl]piperidine-1-carboxylate (300 mg, 99%) as a light yellow oil; LC-MS: 413.1 $[M+H]^+$.

Intermediate X-3

4-[(3,4-Dimethoxyphenyl)(piperidin-4-yl)methyl]pyridine

A solution of tert-butyl 4-[(3,4-dimethoxyphenyl)(pyridin-4-yl)methyl]piperidine-1-carboxylate (300 mg, 0.730 mmol) and trifluoroacetic acid (0.32 mL, 4.1 mmol) in DCM (5 mL) was stirred at 25° C. for 4 h. The solution was concentrated in vacuo to give 4-[(3,4-dimethoxyphenyl)(piperidin-4-yl)methyl]pyridine (TFA salt, 200 mg, 96%) as colorless oil; LC-MS: 313.2 $[M+H]^+$.

6-[4-[(3,4-Dimethoxyphenyl)-(4-pyridyl)methyl]piperidine-1-carbonyl]-4H-1,4-benzoxazin-3-one A solution of 3-oxo-4H-1,4-benzoxazine-6-carboxylic acid (136 mg, 0.70 mmol), 4-[(3,4-dimethoxyphenyl)(piperidin-4-yl)methyl]pyridine (220 mg, 0.700 mmol), triethylamine (0.12 mL, 0.85 mmol) and O-(7-azabenzotriazol-1-yl)-N,N,N',N'-tetramethyluronium hexafluorophosphate (321 mg, 0.85 mmol) in DCM (5 mL) was stirred at 25° C. for 4 h. The reaction solution was poured into brine (20 mL) and extracted with DCM (2×10 mL). The combined organic layers were concentrated in vacuo to give a residue, which was purified by Prep-HPLC (TFA condition) to give 6-[4-[(3,4-dimethoxyphenyl)-(4-pyridyl)methyl]piperidine-1-carbonyl]-4H-1,4-benzoxazin-3-one (120 mg, 34%) as white solid; LC-MS: 488.1 $[M+H]^+$.

6-[4-[(3,4-Dimethoxyphenyl)-(4-pyridyl)methyl]piperidine-1-carbonyl]-4H-1,4-benzoxazin-3-one (120 mg, 0.250 mmol) was separated by SFC to give 6-[4-[(S or R)-(3,4-dimethoxyphenyl)-(4-pyridyl)methyl]piperidine-1-carbonyl]-4H-1,4-benzoxazin-3-one (19 mg, 15%; LCMS: 488.3 $[M+H]^+$) and 6-[4-[(R or S)-(3,4-dimethoxyphenyl)-(4-pyridyl)methyl]piperidine-1-carbonyl]-4H-1,4-benzoxazin-3-one (44 mg, 48%; LCMS: 488.3 $[M+H]^+$) as white solids.

Example 127

6-[3-[(3,4-Dimethoxyphenyl)-phenyl-methyl]azetidine-1-carbonyl]-4H-1,4-benzoxazin-3-one

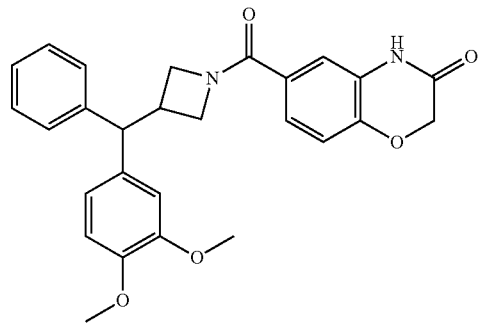 [SMILES: COc1ccc(C(c2ccccc2)C2CN(C(=O)c3ccc4c(c3)NC(=O)CO4)C2)cc1OC]

Intermediate Y-1 tert-Butyl 3-[(3,4-dimethoxyphenyl)(hydroxy)(phenyl)methyl]azetidine-1-carboxylate To a stirred solution at −78° C. of 4-bromo-1,2-dimethoxybenzene (2.00 mg, 9.21 mmol) in THF (10 mL) was added butyllithium in THF (2.5M, 4.9 mL, 12.25 mmol). The resulting mixture was stirred at −78° C. for 0.5 h, before addition of tert-butyl 3-benzoylazetidine-1-carboxylate (intermediate W-2) (2.06 g, 7.88 mmol). After stirring at −78° C. for 1.5 h the solution was quenched by $NH_4Cl$ (sat. aq. 50 mL) and extracted with ethyl acetate (2×20 mL). The combined organic layers were concentrated in vacuo to give a residue, which was purified by flash column (petroleum ether:ethyl acetate 5:1) to give tort-butyl 3-[(3,4-dimethoxyphenyl)(hydroxy)(phenyl)methyl]azetidine-1-carboxylate (1.10 g, 31%) as light yellow oil; LC-MS: 422.1 $[M+Na]^+$.

Intermediate Y-2

3-[(3,4-Dimethoxyphenyl)(phenyl)methylene]azetidine

A solution of tert-butyl 3-[(3,4-dimethoxyphenyl)(hydroxy)(phenyl)methyl]azetidine-1-carboxylate (1.18 g, 2.95 mmol) and trifluoroacetic acid (2.27 mL, 29.5 mmol) in DCM (15 mL) was stirred at 25° C. for 4 h. The solution was concentrated in vacuo to give 3-[(3,4-dimethoxyphenyl)(phenyl)methylene]azetidine (TFA salt, 800 mg, 96%) as brown oil. LC-MS: 282.2 $[M+H]^+$.

Intermediate Y-3

3-[(3,4-Dimethoxyphenyl)(phenyl)methyl]azetidine

A solution of 3-[(3,4-dimethoxyphenyl)(phenyl)methylene]azetidine (1.02 g, 3.62 mmol) and Pd/C (1.92 mg) in THF (20 mL) was stirred at 25° C. for 5 h under $H_2$ (760 mmHg). The solution was concentrated in vacuo to give a residue, which was purified by Prep-HPLC (TFA condition)

to give 3-[(3,4-dimethoxyphenyl)(phenyl)methyl]azetidine (420 mg, 36%) as colorless oil; LC-MS: 284.2 [M+H]⁺.

Rac-6-[3-[(3,4-Dimethoxyphenyl)-phenyl-methyl]azetidine-1-carbonyl]-4H-1,4-benzoxazin-3-one A solution of 3-[(3,4-dimethoxyphenyl)(phenyl)methyl]azetidine (200 mg, 0.71 mmol), 0-(7-azabenzotriazol-1-yl)-N,N,N',N'-tetramethyluronium hexafluorophosphate (268 mg, 0.71 mmol), 3-oxo-4H-1,4-benzoxazine-6-carboxylic acid (136 mg, 0.710 mmol) and triethylamine (0.12 mL, 0.85 mmol) in DCM (10 mL) was stirred at 25° C. for 5 h. The solution was concentrated in vacuo to give a residue, which was purified by Prep-HPLC (TFA condition) to give 6-[3-[(3,4-dimethoxyphenyl)-phenyl-methyl]azetidine-1-carbonyl]-4H-1,4-benzoxazin-3-one (160 mg, 32%) as white solid; LC-MS: 459.3 [M+H]⁺.

Examples 128 and 129

6-[4-[(S or R)-(3-Methylsulfonylphenyl)-phenyl-methyl]piperidine-1-carbonyl]-4H-1,4-benzoxazin-3-one and 6-[4-[(R or S)-(3-Methylsulfonylphenyl)-phenyl-methyl]piperidine-1-carbonyl]-4H-1,4-benzoxazin-3-one

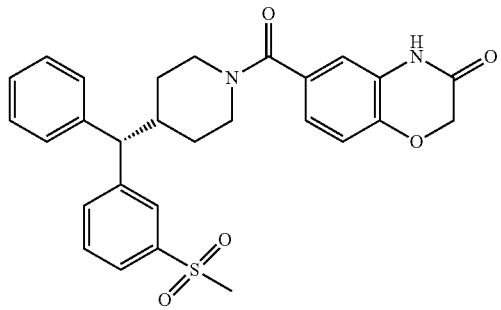

Intermediate Z-1 tert-Butyl 4-[(3-(methylsulfonyl)phenyl)(phenyl)methylene]piperidine-1-carboxylate A mixture of 3-bromophenylmethylsulfone (0.14 mL, 0.98 mmol), tert-butyl 4-(phenyl(2-tosylhydrazono)methyl)piperidine-1-carboxylate (intermediate J-1) (300 mg, 0.66 mmol), LiOtBu (79 mg, 0.98 mmol) and bis(triphenylphosphine)palladium(II) chloride (46 mg, 0.07 mmol) in DMF (10 mL) was stirred at 110° C. for 16 h under N₂. The mixture was poured into brine (30 mL) and extracted with ethyl acetate (2×20 mL). The combined organic layers were concentrated in vacuo to give a residue, which was purified by Prep-HPLC (TFA condition) to give tert-butyl 4-[(3-(methylsulfonyl)phenyl)(phenyl)methylene]piperidine-1-carboxylate (200 mg, 68%) as a light yellow oil; LC-MS: 372.1 [M−56+H]⁺.

Intermediate Z-2

4-[(3-(Methylsulfonyl)phenyl)(phenyl)methylene]piperidine

A solution of tert-butyl 4-[(3-(methylsulfonyl)phenyl)(phenyl)methylene]piperidine-1-carboxylate (200 mg, 0.47 mmol) and trifluoroacetic acid (0.2 mL, 2.64 mmol) in DCM (5 mL) was stirred at 25° C. for 4 h. The solution was concentrated in vacuo to give 4-[(3-(methylsulfonyl)phenyl)(phenyl)methylene]piperidine (TFA salt, 150 mg, 96%) as colorless oil; LC-MS: 328.1 [M+H]⁺.

Intermediate Z-3

4-[(3-(Methylsulfonyl)phenyl)(phenyl)methyl]piperidine

A mixture of 4-[(3-(methylsulfonyl)phenyl)(phenyl)methylene]piperidine (150 mg, 0.46 mmol), and Pd/C (487 mg) in DMF (5 mL) was stirred at 25° C. for 16 h under H₂ (760 mmHg). The mixture was filtered and concentrated in vacuo to give 4-[(3-(methylsulfonyl)phenyl)(phenyl)methyl]piperidine (150 mg, 96%) as colorless oil; LC-MS: 330.1 [M+H]⁺.

Rac-6-[4-(3-Methylsulfonylphenyl)-phenyl-methyl]piperidine-1-carbonyl]-4H-1,4-benzoxazin-3-one A solution of 4-[(3-(methylsulfonyl)phenyl)(phenyl)methyl]piperidine (160 mg, 0.49 mmol), 3-oxo-4H-1,4-benzoxazine-6-carboxylic acid (94 mg, 0.49 mmol), triethylamine (0.08 mL, 0.58 mmol) and <9-(7-azabenzotriazol-1-yl)-N,N,N',N'-tetramethyluronium hexafluorophosphate (221 mg, 0.58 mmol) in DMF (10 mL) was stirred at 25° C. for 4 h. The reaction solution was concentrated in vacuo to give a residue, which was purified by Prep-HPLC (TFA condition) to give 6-[4-[(R or S)-(3-methylsulfonylphenyl)-phenyl-methyl]piperidine-1-carbonyl]-4H-1,4-benzoxazin-3-one (110 mg, 44%) as white solid; LC-MS: 505.2 [M+H]⁺.

6-[4-(3-Methylsulfonylphenyl)-phenyl-methyl]piperidine-1-carbonyl]-4H-1,4-benzoxazin-3-one (105 mg, 0.210 mmol) was separated by SFC to give 6-[4-[(S or R)-(3-methylsulfonylphenyl)-phenyl-methyl]piperidine-1-carbonyl]-4H-1,4-benzoxazin-3-one (21 mg, 21%; LC-MS: 505.3 [M+H]⁺) and 6-[4-[(R or S)-(3-methylsulfonylphenyl)-phenyl-methyl]piperidine-1-carbonyl]-4H-1,4-benzoxazin-3-one (23 mg, 22%; LC-MS: 505.3 [M+H]⁺) as a white solids.

Example 130

6-[3-[Phenyl-[4-(trifluoromethyl)phenyl]methyl]azetidine-1-carbonyl]-4H-1,4-benzoxazin-3-one

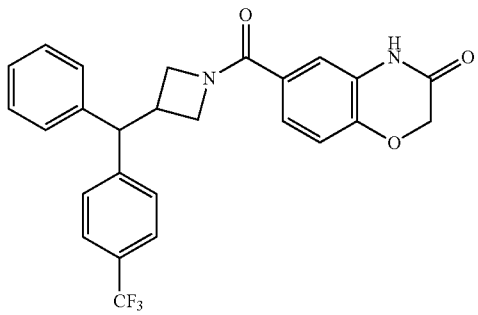 [SMILES: O=C1COc2ccc(C(=O)N3CC(C(c4ccccc4)c4ccc(C(F)(F)F)cc4)C3)cc2N1]

Intermediate AA-1 tert-Butyl 3-[hydroxy(phenyl)(4-(trifluoromethyl)phenyl)methyl]azetidine-1-carboxylate To a stirred solution at −78° C. of 4-bromobenzotrifluoride (1.21 mL, 8.67 mmol, 1 eq) in THF (10 mL) was added butyllithium in THF (2.5M, 4.85 mL, 12.1 mmol). Then tort-butyl 3-benzoylazetidine-1-carboxylate (intermediate W-2) (2.04 g, 7.8 mmol) was added to the solution and stirring was continued at −78° C. for 1.5 h. The solution was quenched by NH$_4$Cl (sat. aq. 50 mL) and extracted with ethyl acetate (2×20 mL). The combined organic layers were concentrated in vacuo to give a residue, which was purified by flash column chromatography (petroleum ether:ethyl acetate 5:1) to give tert-butyl 3-[hydroxy(phenyl)(4-(trifluoromethyl)phenyl)methyl]azetidine-1-carboxylate (960 mg, 27%) as a colorless oil; LC-MS: 308.0 [M−100+H]$^+$.

Intermediate AA-2

Azetidin-3-yl(phenyl)(4-(trifluoromethyl)phenyl)methanol

A solution of tert-butyl 3-[hydroxy(phenyl)(4-(trifluoromethyl)phenyl)methyl]azetidine-1-carboxylate (860 mg, 2.11 mmol) and trifluoroacetic acid (1.63 mL, 21.1 mmol) in DCM (15 mL) was stirred at 25° C. for 4 h. The solution was concentrated in vacuo to give a reside, which was purified by Prep-HPLC (TFA condition) to give azetidin-3-yl(phenyl)(4-(trifluoromethyl)phenyl)methanol (TFA salt, 400 mg, 61%) as colorless oil; LC-MS: 308.2 [M+H]$^+$.

Intermediate AA-3

6-[3[-Hydroxy-phenyl-[4-(trifluoromethyl)phenyl]methyl]azetidine-1-carbonyl]-4H-1,4-benzoxazin-3-one A solution of azetidin-3-yl(phenyl)(4-(trifluoromethyl)phenyl)methanol (280 mg, TFA salt, 0.66 mmol), 0-(7-azabenzotriazol-1-yl)-N,N,N',N'-tetramethyluronium hexafluorophosphate (379 mg, 1.0 mmol), 3-oxo-4H-1,4-benzoxazine-6-carboxylic acid (128 mg, 0.66 mmol) and triethylamine (0.11 mL, 0.80 mmol) in DMF (10 mL) was stirred at 25° C. for 5 h. The solution was concentrated in vacuo to give a residue, which was purified by Prep-HPLC (TFA condition) to give 6-[3-[hydroxy-phenyl-[4-(trifluoromethyl)phenyl]methyl]azetidine-1-carbonyl]-4H-1,4-benzoxazin-3-one (120 mg, 37%) as white solid; LC-MS: 483.1 [M+H]$^+$.

Intermediate AA-4

6-[3-[Phenyl-[4-(trifluoromethyl)phenyl]methylene]azetidine-1-carbonyl]-4H-1,4-benzoxazin-3-one A solution of 6-[3-[hydroxy-phenyl-[4-(trifluoromethyl)phenyl]methyl]azetidine-1-carbonyl]-4H-1,4-benzoxazin-3-one (120 mg, 0.25 mmol) and trifluoroacetic acid (0.19 mL, 2.49 mmol, 10 eq) in DCM (2 mL) was stirred at 25° C. for 16 h. The solution was concentrated in vacuo to give 6-[3-[phenyl-[4-(trifluoromethyl)phenyl]methylene]azetidine-1-carbonyl]-4H-1,4-benzoxazin-3-one (110 mg, 95%) as white solid; LC-MS: 465.0 [M+H]$^+$.

6-[3-[Phenyl-[4-(trifluoromethyl)phenyl]methyl]azetidine-1-carbonyl]-4H-1,4-benzoxazin-3-one A mixture of 6-[3-[phenyl-[4-(trifluoromethyl)phenyl]methylene]azetidine-1-carbonyl]-4H-1,4-benzoxazin-3-one (110 mg, 0.24 mmol) and Pd/C (2.5 mg) in DMF (11 mL) was stirred at 25° C. for 6 h under H$_2$ (760 mmHg). The mixture was filtered and concentrated in vacuo to give a residue, which was purified by Prep-HPLC (TFA condition) to give 6-[3-[phenyl-[4-(trifluoromethyl)phenyl]methyl]azetidine-1-carbonyl]-4H-1,4-benzoxazin-3-one (70 mg, 61% yield) as white solid; LC-MS: 467.2 [M+H]$^+$.

Example 131

6-[3-[(3-Methoxyphenyl)-phenyl-methyl]azetidine-1-carbonyl]-4H-1,4-benzoxazin-3-one

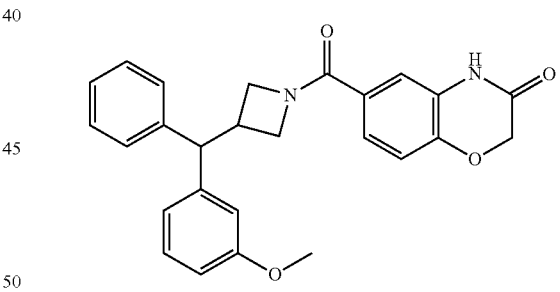

Intermediate AB-1 tert-Butyl 3-[hydroxy(3-methoxyphenyl)(phenyl)methyl]azetidine-1-carboxylate

To a stirred solution at −78° C. of 3-bromoanisole (1.01 mL, 8.67 mmol) in THF (10 mL) was added butyllithium in THF (2.5 M, 4.85 mL, 12.1 mmol) and stirring was continued for 0.5 h. Then tert-butyl 3-benzoylazetidine-1-carboxylate (intermediate W-2) (2.04 g, 7.8 mmol) was added to the solution and stirring was continued at −78° C. for 1.5 h. The solution was quenched by NH$_4$Cl (sat. aq. 50 mL) and extracted with ethyl acetate (2×20 mL). The combined organic layers were concentrated in vacuo to give a residue, which was purified by flash column chromatography (petroleum ether:ethyl acetate 5:1) to give tert-butyl 3-[hydroxy (3-methoxyphenyl)(phenyl)methyl]azetidine-1-carboxylate (1.30 g, 38%) as colorless oil; LC-MS: 392.2 [M+Na]⁺.

Intermediate AB-2

3-[(3-Methoxyphenyl)(phenyl)methylene]azetidine

A solution of tert-butyl 3-[hydroxy(3-methoxyphenyl) (phenyl)methyl]azetidine-1-carboxylate (1.30 g, 3.52 mmol) and trifluoroacetic acid (2.71 mL, 35.2 mmol) in DCM (17.9 mL) was stirred at 25° C. for 4 h. The solution was concentrated in vacuo to give 3-[(3-methoxyphenyl)(phenyl)methylene]azetidine (TFA salt, 800 mg, 90%) as light yellow oil; LC-MS: 252.2 [M+H]⁺.

Intermediate AB-3

3-[(3-Methoxyphenyl)(phenyl)methyl]azetidine

A mixture of 3-[(3-methoxyphenyl)(phenyl)methylene]azetidine (800 mg, 3.18 mmol) and Pd/C (34 mg, 0.32 mmol) in DMF (20 mL) was stirred at 25° C. for 6 h under H₂ (760 mmHg). The mixture was filtered and concentrated in vacuo to give a residue, which was purified by Prep-HPLC (HCl condition) to give 3-[(3-methoxyphenyl)(phenyl)methyl]azetidine (362 mg, HCl salt, 39%); LC-MS: 254.1 [M+H]⁺.

6-[3-[(3-Methoxyphenyl)-phenyl-methyl]azetidine-1-carbonyl]-4H-1,4-benzoxazin-3-one A solution of 3-[(3-methoxyphenyl)(phenyl)methyl]azetidine (150 mg, HCl salt, 0.52 mmol), 0-(7-azabenzotriazol-1-yl)-N,N,N',N'-tetramethyluronium hexafluorophosphate (295 mg, 0.78 mmol), 3-oxo-4H-1,4-benzoxazine-6-carboxylic acid (100 mg, 0.52 mmol) and triethylamine (0.09 mL, 0.62 mmol) in DMF (6 mL) was stirred at 25° C. for 4 h. The solution was concentrated in vacuo to give a residue, which was purified by Prep-HPLC (TFA condition) to give 6-[3-[(3-methoxyphenyl)-phenyl-methyl]azetidine-1-carbonyl]-4H-1,4-benzoxazin-3-one (141 mg, 63%) as grey solid; LC-MS: 429.2 [M+H]⁺.

Examples 132 and 133

6-[4-[(S or R)-(4-Methylsulfonylphenyl)-phenyl-methyl]piperidine-1-carbonyl]-4H-1,4-benzoxazin-3-one and 6-[4-[(R or S)-(4-Methylsulfonylphenyl)-phenyl-methyl]piperidine-1-carbonyl]-4H-1,4-benzoxazin-3-one

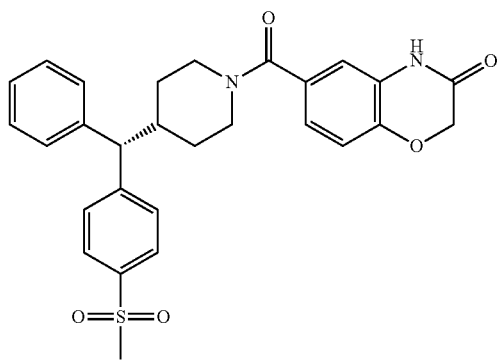

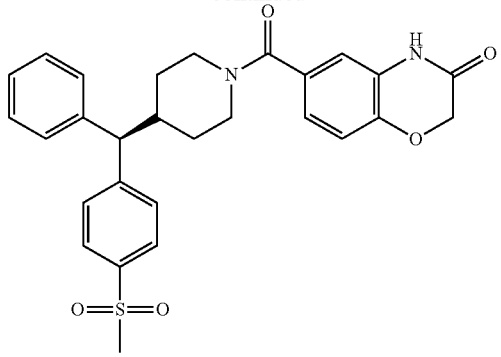

Intermediate AC-1 tert-Butyl 4-[(4-(methylsulfonyl)phenyl)(phenyl)methylene]piperidine-1-carboxylate A solution of tert-butyl 4-(phenyl(2-tosylhydrazono)methyl)piperidine-1-carboxylate (intermediate J-1) (2.00 g, 4.4 mmol), 1-bromo-4-(methylsulfonyl)benzene (1.23 g, 5.2 mmol), LiOtBu (700 mg, 8.7 mmol) and bis(triphenylphosphine)palladium(II) chloride (920 mg, 1.3 mmol) in DMF (30 mL) was stirred at 80° C. for 16 h under N₂. The reaction was cooled to room temperature and filtered through Celite. The filtrate was concentrated under vacuum, then the residue was purified by silica gel chromatography (petroleum ether: EtOAc 10:1 to 5:1) to afford tert-butyl 4-[(4-(methylsulfonyl)phenyl)(phenyl)methylene]piperidine-1-carboxylate (280 mg, 13%) as a light yellow oil; LCMS: 450.2 [M+Na]⁺, 372.1 [M-butene+H]⁺.

Intermediate A C-2 tert-Butyl 4-[(4-(methylsulfonyl)phenyl)(phenyl)methyl]piperidine-1-carboxylate

A solution of tert-butyl 4-[(4-(methylsulfonyl)phenyl)(phenyl)methylene]piperidine-1-carboxylate (280 mg, 0.65 mmol) and Pd/C (60 mg) in DMF (5 mL) was stirred at 25° C. for 16 h under H₂ (760 mmHg). The reaction was filtered through Celite. The filtrate was concentrated under vacuum to afford tert-butyl 4-[(4-(methylsulfonyl)phenyl)(phenyl)methyl]piperidine-1-carboxylate (180 mg, 55%) as yellow oil; LCMS: 452.2 [M+Na]⁺.

Intermediate AC-3

4-[(4-(Methylsulfonyl)phenyl)(phenyl)methyl]piperidine

A solution of tert-butyl 4-[(4-(methylsulfonyl)phenyl)(phenyl)methyl]piperidine-1-carboxylate (180 mg, 0.42 mmol) and trifluoroacetic acid (0.65 mL, 8.38 mmol) in DCM (4 mL) was stirred at 25° C. for 3 h. The reaction was concentrated under vacuum. The residue was purified by Prep-HPLC (TFA as additive) to afford 4-[(4-(methylsulfonyl)phenyl)(phenyl)methyl]piperidine TFA salt (120 mg, 64%) as yellow oil; LCMS: 330.1 [M+H]⁺.

Rac-6-[4-[(4-Methylsulfonylphenyl)-phenyl-methyl]piperidine-1-carbonyl]-4H-1,4-benzoxazin-3-one A solution of 4-[(4-(methylsulfonyl)phenyl)(phenyl)methyl]piperidine (TFA salt, 120 mg, 0.27 mmol), 3-oxo- 4H-1,4-benzoxazine-6-carboxylic acid (57 mg, 0.30 mmol), O-(7-azabenzotriazol-1-yl)-N,N,N',N'-tetramethyluronium hexafluorophosphate (123 mg, 0.32 mmol) and triethylamine (0.08 mL, 0.54 mmol) in DCM (3.7 mL) was stirred at 25° C. for 16 h. The reaction was diluted with DCM (50 mL) and washed with H$_2$O (30 mL). The organic layer was separated, dried over Na$_2$SO$_4$, filtered and concentrated under vacuum. The residue was purified by Prep-HPLC (TFA as additive) to afford 6-[4-[(4-methylsulfonylphenyl)-phenyl-methyl]piperidine-1-carbonyl]-4H-1,4-benzoxazin-3-one (90 mg, 48%) as white solid; LCMS: 505.2 [M+H]$^+$.

6-[4-[(4-Methylsulfonylphenyl)-phenyl-methyl]piperidine-1-carbonyl]-4H-1,4-benzoxazin-3-one (90 mg, 0.18 mmol) was separated by SFC (NH$_3$/H$_2$O as additive) to afford 6-[4-[(S or R)-(4-methylsulfonylphenyl)-phenyl-methyl]piperidine-1-carbonyl]-4H-1,4-benzoxazin-3-one (18 mg, 20%; LCMS: 505.2 [M+H]$^+$) as a white solid and 6-[4-[(R or S)-(4-methylsulfonylphenyl)-phenyl-methyl]piperidine-1-carbonyl]-4H-1,4-benzoxazin-3-one ill mg, 29%; LCMS: 505.2 [M+H]$^+$) as a light yellow solid.

Examples 134 and 135

6-[4-[(S or R)-3-(2-Fluoroethoxy)-4-methoxy-phenyl-phenyl-methyl]piperidine-1-carbonyl]-4H-1,4-benzoxazin-3-one and 6-[4-[(R or S)-[3-(2-Fluoroethoxy)-4-methoxy-phenyl]-phenyl-methyl]piperidine-1-carbonyl]-4H-1,4-benzoxazin-3-one

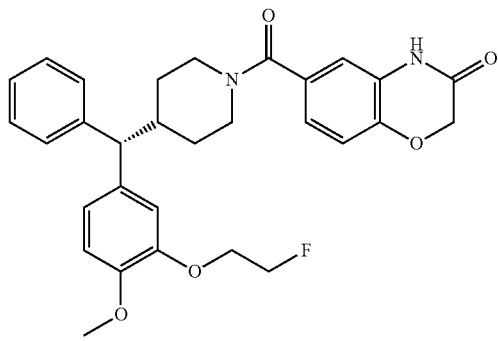

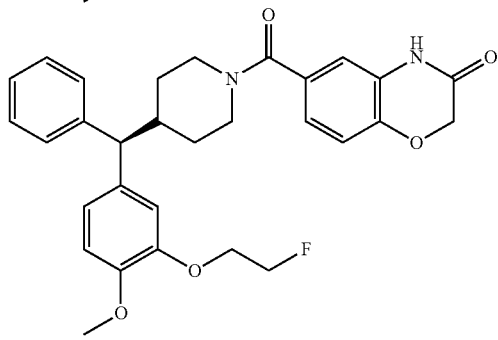

Intermediate AD-1

4-Bromo-2-(2-fluoroethoxy)-1-methoxybenzene

A solution of 5-bromo-2-methoxyphenol (5.00 g, 24.6 mmol), 1-bromo-2-fluoroethane (6.25 g, 49.2 mmol), and cesium carbonate (12.03 g, 36.94 mmol) in DMF (120 mL) was stirred at 70° C. for 16 h. The reaction was quenched with H$_2$O (200 mL) and extracted with EtOAc (300 mL). The organic layer was separated, dried over Na$_2$SO$_4$, filtered and concentrated under vacuum. The residue was purified by silica gel chromatography to afford 4-bromo-2-(2-fluoroethoxy)-1-methoxybenzene (4.86 g, 75%) as a white solid; $^1$H NMR (400 MHz, CDCl$_3$) 5=7.10 (dd, J=2.3, 8.6 Hz, 1H), 7.05 (d, J=2.2 Hz, 1H), 6.78 (d, J=8.7 Hz, 1H), 4.90-4.82 (m, 1H), 4.78-4.70 (m, 1H), 4.35-4.28 (m, 1H), 4.27-4.20 (m, 1H), 3.87 (s, 3H).

Intermediate AD-2 tert-Butyl 4-[(3-(2-fluoroethoxy)-4-methoxyphenyl)(hydroxy)(phenyl)methyl]piperidine-1-carboxylate To a stirred solution at −78° C. of 4-bromo-2-(2-fluoroethoxy)-1-methoxy-benzene (1.00 g, 4.01 mmol) in THF (35 mL) was added a solution of butyllithium (2.25 mL, 5.62 mmol). After stirring for 1 h, tert-butyl 4-benzoylpiperidine-1-carboxylate (1.16 g, 4.01 mmol) was added and stirring was continued at −78° C. for 1 h. Then the reaction mixture was warmed to 25° C. and stirred for another 13 h. The reaction was quenched with NH$_4$Cl (sat. aq., 50 mL) and extracted with EtOAc (100 mL). The organic layer was separated, dried over Na$_2$SO$_4$, filtered and concentrated under vacuum to afford tert-butyl 4-[(3-(2-fluoroethoxy)-4-methoxyphenyl)(hydroxy)(phenyl)methyl]piperidine-1-carboxylate (1.76 g, 52%) as a yellow oil that was not further purified and used as such in the next step. LCMS: 482.3 [M+Na]$^+$.

Intermediate AD-3

4-[(3-(2-Fluoroethoxy)-4-methoxyphenyl)(phenyl)methylene]piperidine

A solution of tert-butyl 4-[(3-(2-fluoroethoxy)-4-methoxyphenyl)(hydroxy)(phenyl)methyl]piperidine-1-carboxylate (1.76 g, 3.83 mmol) and trifluoroacetic acid (5.9 mL, 76.6 mmol) in DCM (12 mL) was stirred at 25° C. for 16 h. The reaction solution was concentrated. Then the residue was purified by Prep-HPLC (TFA as additive) to afford 4-[(3-(2-fluoroethoxy)-4-methoxyphenyl)(phenyl)methylene]piperidine (TFA salt, 1.03 g, 58%) as yellow oil; LCMS: 342.2 [M+H]$^+$.

Intermediate AD-4

4-[(3-(2-Fluoroethoxy)-4-methoxyphenyl)(phenyl)methyl]piperidine

A solution of 4-[(3-(2-fluoroethoxy)-4-methoxyphenyl)(phenyl)methylene]piperidine (TFA salt, 1.00 g, 2.11 mmol) and Pd/C (300 mg) in DMF (20 mL) was stirred at 25° C. for 16 h under H$_2$ (3500 mmHg). The reaction was filtered through Celite, then concentrated under vacuum. The residue was dissolved in EtOAc (50 mL) and washed with NaHCO$_3$/H$_2$O (5 g/30 mL) and H$_2$O (2×30 mL). The organic layer was separated, dried over Na$_2$SO$_4$, filtered and concentrated under vacuum to afford 4-[(3-(2-fluoroethoxy)-4-methoxyphenyl)(phenyl)methyl]piperidine (630 mg, 80%) as yellow oil; LC-MS: 344.2 [M+H]$^+$.

Rac-6-[4-[[3-(2-Fluoroethoxy)-4-methoxy-phenyl]-phenyl-methyl]piperidine-1-carbonyl]-4H-1,4-benzoxazin-3-one A solution of 4-[(3-(2-fluoroethoxy)-4-methoxyphenyl)(phenyl)methyl]piperidine (630 mg, 1.83 mmol), 3-oxo-4H-1,4-benzoxazine-6-carboxylic acid (390 mg, 2.02 mmol), 0-(7-azabenzotriazol-1-yl)-N,N,N',N'-tetramethyluronium hexafluorophosphate (837 mg, 2.2 mmol) and triethylamine (0.5 mL, 3.67 mmol) in DCM (20 mL) was stirred at 25° C. for 16 h. The reaction was quenched with H$_2$O (20 mL) and extracted with DCM (20 mL). The organic layer was separated, dried over Na$_2$SO$_4$, filtered and concentrated under vacuum. The residue was purified by Prep-HPLC (TFA as additive) to afford 6-[4-[[3-(2-fluoroethoxy)-4-methoxy-phenyl]-phenyl-methyl]piperidine-1-carbonyl]-4H-1,4-benzoxazin-3-one (580 mg, 60%) as a white solid; LCMS: 519.3 [M+H]$^+$.

6-[4-[[3-(2-Fluoroethoxy)-4-methoxy-phenyl]-phenyl-methyl]piperidine-1-carbonyl]-4H-1,4-benzoxazin-3-one (100 mg, 0.19 mmol) was separated by SFC (NH$_3$/H$_2$O as additive) to afford 6-[4-[S or R)-[3-(2-fluoroethoxy)-4-methoxy-phenyl]-phenyl-methyl]piperidine-1-carbonyl]-4H-1,4-benzoxazin-3-one (34 mg, 33%; LCMS: 519.1 [M+H]$^+$) as white solid and 6-[4-[(R or S)-[3-(2-fluoroethoxy)-4-methoxy-phenyl]-phenyl-methyl]piperidine-1-carbonyl]-4H-1,4-benzoxazin-3-one (39 mg, 38%; 519.1 [M+H]$^+$) as a white solid.

Examples 136 and 137

6-[4-[(S and R)-(2-Methoxy-4-pyridyl)-phenyl-methyl]piperidine-1-carbonyl]-4H-1,4-benzoxazin-3-one and

6-[4-[(R or S)-(2-Methoxy-4-pyridyl)-phenyl-methyl]piperidine-1-carbonyl]-4H-1,4-benzoxazin-3-one

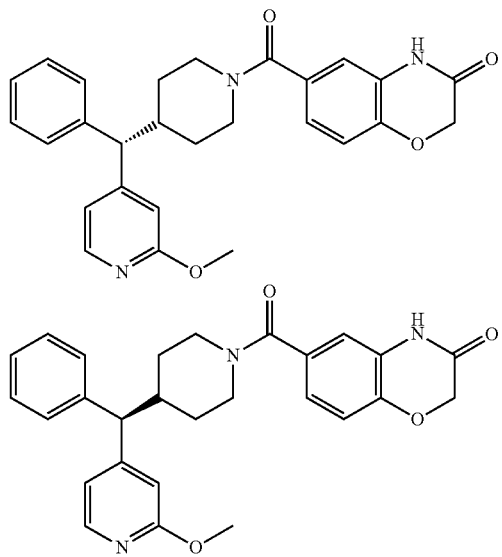

Intermediate AE-1 tert-Butyl 4-[(2-methoxypyridin-4-yl)(phenyl)methylene]piperidine-1-carboxylate A mixture of 4-bromo-2-methoxypyridine (0.75 mL, 6.56 mmol), tert-butyl 4-(phenyl(2-tosylhydrazono)methyl)piperidine-1-carboxylate (intermediate J-1) (2.00 g, 4.37 mmol), LiOtBu (525 mg, 6.56 mmol) and bis(triphenylphosphine)palladium(II) chloride (307 mg, 0.44 mmol) in DMF (30 mL) was stirred at 110° C. for 16 h under N$_2$. The mixture was poured into brine (30 mL) and extracted with ethyl acetate (2×20 mL). The combined organic layers were concentrate in vacuo to give a residue, which was purified by flash column chromatography (petroleum ether:ethyl acetate 10:1) to give tert-butyl 4-[(2-methoxypyridin-4-yl)(phenyl)methylene]piperidine-1-carboxylate (550 mg, 17%) as light yellow oil; LC-MS: 381.2 [M+H]$^+$.

Intermediate AE-2

2-Methoxy-4-[phenyl(piperidin-4-ylidene)methyl]pyridine

A solution of tert-butyl 4-[(2-methoxypyridin-4-yl)(phenyl)methylene]piperidine-1-carboxylate (550 mg, 0.77 mmol) and trifluoroacetic acid (0.3 mL, 3.83 mmol) in DCM (10 mL) was stirred at 25° C. for 4 h. The solution was concentrated in vacuo to give a residue, which was purified by Prep-HPLC (TFA condition) to give 2-methoxy-4-[phenyl(piperidin-4-ylidene)methyl]pyridine (180 mg, 81%) as colorless oil; LC-MS: 281.1 [M+H]$^+$.

Intermediate AE-3

2-Methoxy-4-[phenyl(piperidin-4-yl)methyl]pyridine

A mixture of 2-methoxy-4-[phenyl(piperidin-4-ylidene)methyl]pyridine (180 mg, 0.64 mmol) and Pd/C (34 mg) in DMF (5 mL) was stirred at 25° C. for 16 h under H$_2$ (760 mmHg). The mixture was filtered and concentrated in vacuo to give 2-methoxy-4-[phenyl(piperidin-4-yl)methyl]pyridine (180 mg, 99% yield) as colorless oil; LC-MS: 283.2 [M+H]$^+$.

Rac-6-[4-[(2-Methoxy-4-pyridyl)-phenyl-methyl]piperidine-1-carbonyl]-4H-1,4-benzoxazin-3-one A solution of 2-methoxy-4-[phenyl(piperidin-4-yl)methyl]pyridine (180 mg, 0.64 mmol), 3-oxo-4H-1,4-benzoxazine-6-carboxylic acid (123 mg, 0.64 mmol), triethylamine (0.11 mL, 0.76 mmol) and O-(7-azabenzotriazol-1-yl)-N,N,N',N'-tetramethyluronium hexafluorophosphate (291 mg, 0.76 mmol) in DMF (10 mL) was stirred at 25° C. for 4 h. The reaction solution was concentrated in vacuo to give a residue, which was purified by Prep-HPLC (TFA conditions) to give 6-[4-[(2-methoxy-4-pyridyl)-phenyl-methyl]piperidine-1-carbonyl]-4H-1,4-benzoxazin-3-one (120 mg, 41%) as white solid; LC-MS: 458.3 [M+H]$^+$.

6-[4-[(2-Methoxy-4-pyridyl)-phenyl-methyl]piperidine-1-carbonyl]-4H-1,4-benzoxazin-3-one (120 mg, 0.26 mmol) was separated by SFC to give 6-[4-[(S and R)-(2-methoxy-4-pyridyl)-phenyl-methyl]piperidine-1-carbonyl]-4H-1,4-benzoxazin-3-one (24 mg, 19%; LC-MS: 458.2 [M+H]$^+$) and 6-[4-[(R or S)-(2-methoxy-4-pyridyl)-phenyl-methyl]

piperidine-1-carbonyl]-4H-1,4-benzoxazin-3-one (24.5 mg, 20%; LC-MS: 458.2 [M+H]$^+$) as a white solids.

Examples 138 and 139

6-[4-[(S or R)-[4-(2-Fluoroethoxy)-3-methoxy-phenyl]-phenyl-methyl]piperidine-1-carbonyl]-4H-1,4-benzoxazin-3-one and 6-[4-[(R or S)-[4-(2-Fluoroethoxy)-3-methoxy-phenyl]-phenyl-methyl]piperidine-1-carbonyl]-4H-1,4-benzoxazin-3-one

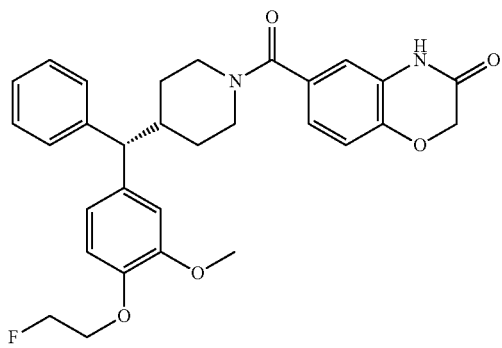

Intermediate AF-1

4-Bromo-1-(2-fluoroethoxy)-2-methoxybenzene

A mixture of 4-bromo-2-methoxyphenol (3.00 g, 14.8 mmol), 1-bromo-2-fluoroethane (2.06 g, 16.2 mmol) and cesium carbonate (7.22 g, 22.2 mmol) in DMF (100 mL) was stirred at 70° C. for 16 h. The mixture was poured into brine (50 mL) and extracted with ethyl acetate (2×30 mL). The combined organic layers were dried over Na$_2$SO$_4$, filtered and concentrated in vacuo to give a residue, which was purified by flash column chromatography (petroleum ether:ethyl acetate 10:1) to give 4-bromo-1-(2-fluoroethoxy)-2-methoxybenzene (3.40 g, 92%) as white solid; $^1$H NMR (400 MHz, DMSO-d$_6$) δ=7.14 (d, J=2.2 Hz, 1H), 7.08-7.03 (m, 1H), 6.94 (d, J=8.6 Hz, 1H), 4.79 (dd, J=3.2, 4.6 Hz, 1H), 4.67 (dd, J=3.1, 4.6 Hz, 1H), 4.28-4.21 (m, 1H), 4.19-4.13 (m, 1H), 3.79 (s, 3H).

Intermediate AF-2 tert-Butyl 4-[(4-(2-fluoroethoxy)-3-methoxyphenyl)(hydroxy)(phenyl)methyl]piperidine-1-carboxylate To a stirred solution at −78° C. of 4-bromo-1-(2-fluoroethoxy)-2-methoxybenzene (947 mg, 3.8 mmol) in THF (20 mL) was added dropwise a solution of butyllithium (1.94 mL, 4.84 mmol). After stirring at −78° C. for 1 h, tert-butyl 4-benzoylpiperidine-1-carboxylate (1.00 g, 3.46 mmol) was added and stirring was continued at −78° C. for 5 h. The reaction mixture was poured into brine (30 mL) and extracted with ethyl acetate (2×20 mL). The combined organic layers were concentrated in vacuo to give tert-butyl 4-[(4-(2-fluoroethoxy)-3-methoxyphenyl)(hydroxy)(phenyl)methyl]piperidine-1-carboxylate (1.20 g, 75%) as a light yellow oil; LC-MS: 482.1 [M+Na]$^+$.

Intermediate AF-3

4-[(4-(2-Fluoroethoxy)-3-methoxyphenyl)(phenyl)methylene]piperidine

A solution of tert-butyl 4-[(4-(2-fluoroethoxy)-3-methoxyphenyl)(hydroxy)(phenyl)methyl]piperidine-1-carboxylate (1.20 g, 2.61 mmol) and trifluoroacetic acid (1.13 mL, 14.7 mmol) in DCM (15 mL) was stirred at 25° C. for 4 h. The solution was concentrated in vacuo to give 4-[(4-(2-fluoroethoxy)-3-methoxyphenyl)(phenyl)methylene]piperidine (800 mg, TFA salt, 89%) as colorless oil. LC-MS: 342.1 [M+H]$^+$.

Intermediate AF-4

4-[(4-(2-Fluoroethoxy)-3-methoxyphenyl)(phenyl)methyl]piperidine

A mixture of 4-[(4-(2-fluoroethoxy)-3-methoxyphenyl)(phenyl)methylene]piperidine (800 mg, TFA salt, 1.76 mmol), and Pd/C (1.87 g) in DMF (7.5 mL) was stirred at 25° C. for 16 h under H$_2$ (760 mmHg). The mixture was filtered and concentrated in vacuo to give a residue, which was purified by Prep-HPLC (TFA condition) to give 4-[(4-(2-fluoroethoxy)-3-methoxyphenyl)(phenyl)methyl]piperidine (800 mg, TFA salt, 99%); LC-MS: 344.2 [M+H]$^+$.

Rac-6-[4-[4-(2-Fluoroethoxy)-3-methoxy-phenyl]-phenyl-methyl]piperidine-1-carbonyl]-4H-1,4-benzoxazin-3-one A solution of 3-oxo-4H-1,4-benzoxazine-6-carboxylic acid (105 mg, 0.55 mmol), 4-[(4-(2-fluoroethoxy)-3-methoxyphenyl)(phenyl)methyl]piperidine (250 mg, TFA salt 0.55 mmol), triethylamine (0.09 mL, 0.66 mmol) and <9-(7-azabenzotriazol-1-yl)-N,N,N',N'-tetramethyluronium hexafluorophosphate (249 mg, 0.66 mmol) in DMF (7.5 mL) was stirred at 25° C. for 4 h. The reaction mixture was concentrated in vacuo to give a residue, which was purified by Prep-HPLC (TFA condition) to give 6-[4-[4-(2-fluoroethoxy)-3-methoxy-phenyl]-phenyl-methyl]piperidine-1-carbonyl]-4H-1,4-benzoxazin-3-one (120 mg, 31%) as white solid; LC-MS: 519.2 [M+H]$^+$.

6-[4-[4-(2-Fluoroethoxy)-3-methoxy-phenyl]-phenyl-methyl]piperidine-1-carbonyl]-4H-1,4-benzoxazin-3-one (100 mg, 0.19 mmol) was separated by SFC to give 6-[4-[(S or R)-[4-(2-fluoroethoxy)-3-methoxy-phenyl]-phenyl-methyl]piperidine-1-carbonyl]-4H-1,4-benzoxazin-3-one (21 mg, 21%; LC-MS: 519.1 [M+H]$^+$) and 6-[4-[(R or S)-[4-(2-Fluoroethoxy)-3-methoxy-phenyl]-phenyl-methyl]piperidine-1-carbonyl]-4H-1,4-benzoxazin-3-one (22 mg, 21%; LC-MS: 519.1 [M+H]$^+$) as white solids.

Examples 140 and 141

6-[4-[(S or R)-(1-Methylpyrazol-4-yl)-phenyl-methyl]piperidine-1-carbonyl]-4H-1,4-benzoxazin-3-one and 6-[4-[(R or S)-(1-Methylpyrazol-4-yl)-phenyl-methyl]piperidine-1-carbonyl]-4H-1,4-benzoxazin-3-one

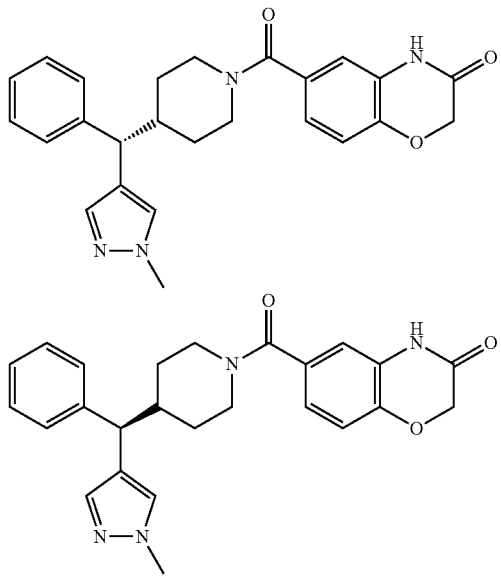

Intermediate AG-1 tert-Butyl 4-[(1-methyl-1H-pyrazol-4-yl)(phenyl) methylene]piperidine-1-carboxylate A solution of 4-bromo-1-methyl-1H-pyrazole (704 mg, 4.37 mmol), tert-butyl 4-(phenyl(2-tosylhydrazono)methyl) piperidine-1-carboxylate (intermediate J-1) (2.00 g, 4.37 mmol), LiOtBu (350 mg, 4.37 mmol) and bis(triphenylphosphine)palladium(II) chloride (3067 mg, 4.37 mmol) in DMF (25 mL) was stirred at 100° C. for 16 h under $N_2$. The reaction was diluted with EtOAC (100 mL) and filtered through Celite. The filtrate was washed with $H_2O$ (70 mL) and brine (2×70 mL). The organic layer was separated, dried over $Na_2SO_4$, filtered and concentrated under vacuum. The residue was purified by silica gel chromatography (Petroleum ether:EtOAc 10:1 to 2:1) to afford the desired product tort-butyl 4-[(1-methyl-17f-pyrazol-4-yl)(phenyl)methylene]piperidine-1-carboxylate (373 mg, 24%); LCMS: 354.3 $[M+H]^+$.

Intermediate AG-2

4-(1H-Methyl-1H-pyrazol-4-yl)(phenyl)methylene piperidine

A solution of tert-butyl 4-(1-methyl-1H-pyrazol-4-yl) (phenyl)methylene piperidine-1-carboxylate (360 mg, 1.02 mmol) and trifluoroacetic acid (4.0 mL, 51.9 mmol) in DCM (8 mL) was stirred at 25° C. for 1 h. The reaction solution was concentrated under vacuum to afford 4-[(1-methyl-1H-pyrazol-4-yl)(phenyl)methylene]piperidine (TFA salt, 380 mg, quant.) as yellow oil; LCMS: 254.2 $[M+H]^+$.

Intermediate AG-3

4-(1-Methyl-1H-pyrazol-4-yl)(phenyl)methyl piperidine

A solution of 4-[(1-methyl-1H-pyrazol-4-yl)(phenyl) methylene]piperidine (380 mg, 1.5 mmol) and Pd/C (150 mg) in DMF (10 mL) was stirred at 25° C. for 16 h under $H_2$ (760 mmHg). The reaction was filtered through Celite, and the filtrate was concentrated under vacuum. The residue was dissolved in EtOAc (20 mL) and washed with $Na_2CO_3$/$H_2O$ (200 mg/5 mL) and $H_2O$ (2×5 mL). The organic layer was separated, dried over $Na_2SO_4$, filtered and concentrated under vacuum to afford 4-[(1-methyl-1H-pyrazol-4-yl)(phenyl)methyl]piperidine (230 mg, 58%) as light yellow oil. LCMS: 256.2 $[M+H]^+$.

Rac-6-[4-[(1-Methylpyrazol-4-yl)-phenyl-methyl] piperidine-1-carbonyl]-4H-1,4-benzoxazin-3-one A solution of 3-oxo-4H-1,4-benzoxazine-6-carboxylic acid (76 mg, 0.39 mmol), 4-(1-methyl-1H-pyrazol-4-yl) (phenyl)methyl piperidine (100 mg, 0.39 mmol), O-(7-azabenzotriazol-1-yl)-N,N,N',N'-tetramethyluronium hexafluorophosphate (149 mg, 0.39 mmol) and triethylamine (0.05 mL, 0.39 mmol) in DCM (10 mL) was stirred at 25° C. for 16 h. The reaction was quenched with $H_2O$ (5 mL) and extracted with DCM (10 mL). The organic layer was separated, dried over $Na_2SO_4$, filtered and concentrated under vacuum. The residue was purified by Prep-HPLC (TFA as additive) to afford 6-[4-[(1-methylpyrazol-4-yl)-phenyl-methyl]piperidine-1-carbonyl]-4H-1,4-benzoxazin-3-one (120 mg, 70%) as white solid; LCMS: 431.2 $[M+H]^+$.

6-[4-[(1-Methylpyrazol-4-yl)-phenyl-methyl]piperidine-1-carbonyl]-4H-1,4-benzoxazin-3-one (100 mg, 0.230 mmol) was separated by SFC ($NH_3$/$H_2O$ as additive) to afford 6-[4-[(S or R)-(1-methylpyrazol-4-yl)-phenyl-methyl]piperidine-1-carbonyl]-4H-1,4-benzoxazin-3-one (38 mg, 37%; LCMS: 431.2 $[M+H]^+$) as white solid and 6-[4-[(R or S)-(1-methylpyrazol-4-yl)-phenyl-methyl]piperidine-1-carbonyl]-4H-1,4-benzoxazin-3-one (40 mg, 40%; LCMS: 431.2 $[M+H]^+$) as off-white solid.

Examples 142 and 143

6-[4-[(S or R)-(1-Methyl-2-oxo-4-pyridyl)-phenyl-methyl]piperidine-1-carbonyl]-4H-1,4-benzoxazin-3-one and 6-[4-[(R or S)-(1-Methyl-2-oxo-4-pyridyl)-phenyl-methyl]piperidine-1-carbonyl]-4H-1,4-benzoxazin-3-one

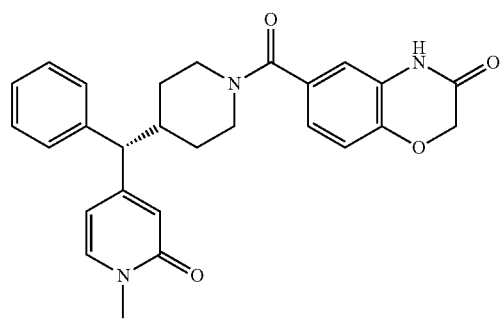

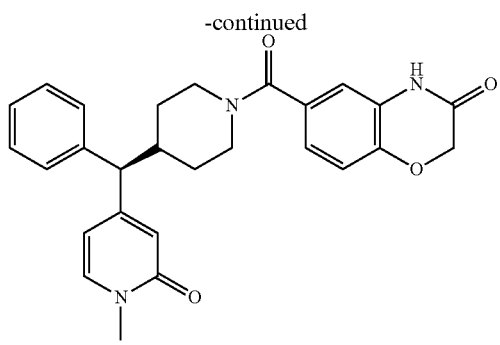

Intermediate AH-1 tert-Butyl 4-[(1-methyl-2-oxo-4-pyridyl)-phenyl-methylene]piperidine-1-carboxylate A mixture of 4-bromo-1-methyl-pyridin-2-one (0.75 mL, 6.56 mmol), tert-butyl 4-(phenyl(2-tosylhydrazono)methyl)piperidine-1-carboxylate (intermediate J-1) (2.00 g, 4.37 mmol), LiOtBu (525 mg, 6.56 mmol) and bis(triphenylphosphine)palladium(II) chloride (307 mg, 0.44 mmol) in DMF (30 mL) was stirred at 90° C. for 16 h under N$_2$. The mixture was poured into brine (30 mL) and extracted with ethyl acetate (2×20 mL). The combined organic layers were concentrated in vacuo to give a residue, which was purified by flash column chromatography (petroleum ether:ethyl acetate 3:1) to yield tert-butyl 4-[(1-methyl-2-oxo-4-pyridyl)-phenyl-methylene]piperidine-1-carboxylate (500 mg, 17%) as light yellow oil; LC-MS: 381.2 [M+H]$^+$.

Intermediate AH-2

1-Methyl-4-[phenyl(4-piperidylidene)methyl]pyridin-2-one

A solution of tert-butyl 4-[(1-methyl-2-oxo-4-pyridyl)-phenyl-methylene]piperidine-1-carboxylate (500 mg, 1.31 mmol) and trifluoroacetic acid (1.0 mL, 13.14 mmol) in DCM (10 mL) was stirred at 25° C. for 4 h. The solution was concentrated in vacuo to give a residue, which was purified by Prep-HPLC (TFA condition) to give 1-methyl-4-[phenyl(4-piperidylidene)methyl]pyridin-2-one (200 mg, 54% yield) as light yellow oil; LC-MS: 281.1 [M+H]$^+$.

Intermediate AH-3

1-Methyl-4-[phenyl(4-piperidyl)methyl]pyridin-2-one

A solution of 1-methyl-4-[phenyl(4-piperidylidene)methyl]pyridin-2-one (100 mg, 0.36 mmol) and Pd/C (379 mg) in DMF (10 mL) was stirred at 25° C. for 16 h. The solution was filtered and concentrated in vacuo to give a residue, which was purified by Prep-HPLC (TFA condition) to give 1-methyl-4-[phenyl(4-piperidyl)methyl]pyridin-2-one (80 mg, 79%) as colorless oil; LC-MS: 283.2 [M+H]$^+$.

Rac-6-[4-[(1-methyl-2-oxo-4-pyridyl)-phenyl-methyl]piperidine-1-carbonyl]-4H-1,4-benzoxazin-3-one A solution of 1-methyl-4-[phenyl(4-piperidyl)methyl]pyridin-2-one (100 mg, 0.35 mmol), 3-OXO-4H-1,4-benzoxazine-6-carboxylic acid (68 mg, 0.35 mmol), O-(1-azabenzotriazol-1-yl)-N,N,N',N'-tetramethyluronium hexafluorophosphate (202 mg, 0.53 mmol) and triethylamine (0.05 mL, 0.35 mmol) in DCM (5 mL) was stirred at 25° C. for 4 h. The reaction solution was concentrated in vacuo to give a residue, which was purified by Prep-HPLC (TFA condition) to give 6-[4-[(1-methyl-2-oxo-4-pyridyl)-phenyl-methyl]piperidine-1-carbonyl]-4H-1,4-benzoxazin-3-one (60 mg, 37%) as white solid; LC-MS: 458.2 [M+H]$^+$.

6-[4-[(1-methyl-2-oxo-4-pyridyl)-phenyl-methyl]piperidine-1-carbonyl]-4H-1,4-benzoxazin-3-one (50 mg, 0.11 mmol) was separated by SFC to give 6-[4-[(S or R)-(1-methyl-2-oxo-4-pyridyl)-phenyl-methyl]piperidine-1-carbonyl]-4H-1,4-benzoxazin-3-one (11 mg, 21%; LC-MS: 458.3 [M+H]$^+$) and 6-[4-[(R or S)-(1-methyl-2-oxo-4-pyridyl)-phenyl-methyl]piperidine-1-carbonyl]-4H-1,4-benzoxazin-3-one (5.3 mg, 10%; LC-MS: 458.3 [M+H]$^+$) as white solids.

Example 144

A compound of formula (IA) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 145

A compound of formula (IA) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

What is claimed is:

1. A compound of formula (IA):

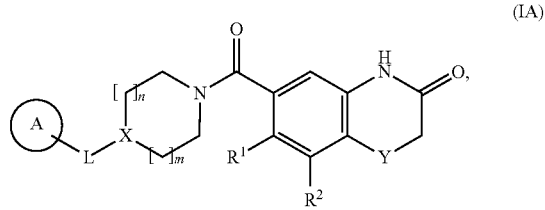

or a pharmaceutically acceptable salt thereof, wherein:
X is CH or N and L is —C($R^3R^4$)—; or
X is C($sp^2$) and together with L forms a group

 (E,Z)

wherein the asterisk indicates the point of attachment to ring A;
Y is $CH_2$ or O;
n and m are independently 0, 1, or 2;
A is selected from the group consisting of
(i) aryl substituted with $R^5$, $R^6$ and $R^7$; and
(ii) heteroaryl substituted with $R^8$, $R^9$ and $R^{10}$;
$R^1$ and $R^2$ are each independently selected from the group consisting of hydrogen, halogen, alkoxy, and haloalkoxy;
$R^3$ is selected from the group consisting of:
(iii) aryl substituted with $R^{11}$ and $R^{12}$,
(iv) heteroaryl substituted with $R^{13}$ and $R^{14}$,
(v) cycloalkyl substituted with $R^{15}$ and $R^{16}$; and
(vi) heterocyclyl substituted with $R^{17}$ and $R^{18}$;
$R^4$ is hydrogen or hydroxy; or
$R^3$ and $R^4$ together with the carbon atom to which they are attached form a heterocycle or a carbocycle; and
$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are each independently selected from the group consisting of hydrogen, halogen, alkyl, haloalkyl, hydroxyalkyl, alkoxy, haloalkoxy, haloalkoxyalkoxy, aryl, cycloalkyl, haloaryl, haloarylalkyl, alkylsulfonyl, oxo, and a fluorescent label;
wherein the compound is not 6-(4-benzhydrylpiperazine-1-carbonyl)-4H-1,4-benzoxazin-3-one.

2. The compound of claim 1, or a pharmaceutically acceptable salt thereof, wherein X is CH.

3. The compound of claim 1, or a pharmaceutically acceptable salt thereof, wherein m and n are both 0 or 1.

4. The compound of claim 1, or a pharmaceutically acceptable salt thereof, wherein m and n are both 1.

5. The compound of claim 1, or a pharmaceutically acceptable salt thereof, wherein Y is O.

6. The compound of claim 1, or a pharmaceutically acceptable salt thereof, wherein:
A is selected from the group consisting of
(i) aryl substituted with $R^5$, $R^6$ and $R^7$; and
(ii) heteroaryl substituted with $R^8$, $R^9$ and $R^{10}$;
$R^3$ is aryl substituted with $R^{11}$ and $R^{12}$;
$R^4$ is hydrogen or hydroxy;
$R^5$ is selected from the group consisting of hydrogen, alkoxy, haloalkyl and halogen;
$R^6$ is selected from the group consisting of hydrogen, alkoxy, and halogen;
$R^7$ is selected from the group consisting of hydrogen and alkoxy;
$R^8$ is selected from the group consisting of hydrogen, halogen, alkyl, hydroxyalkyl, alkoxy, aryl, cycloalkyl, haloalkyl, haloaryl, and haloarylalkyl;
$R^9$ and $R^{10}$ are each independently selected from the group consisting of hydrogen and halogen;
$R^{11}$ is selected from the group consisting of hydrogen, halogen, alkoxy, haloalkoxy, haloalkoxyalkoxy, alkylsulfonyl, and alkyl; and
$R^{12}$ is hydrogen or alkoxy.

7. The compound of claim 1, or a pharmaceutically acceptable salt thereof, wherein:
A is selected from the group consisting of
(i) aryl substituted with $R^5$, $R^6$ and $R^7$; and
(ii) heteroaryl substituted with $R^8$, $R^9$ and $R^{10}$;
$R^3$ is heteroaryl substituted with $R^{13}$ and $R^{14}$;
$R^4$ is hydrogen;
$R^5$ is selected from the group consisting of hydrogen, alkoxy, haloalkyl, and halogen;
$R^6$ is selected from the group consisting of hydrogen, alkoxy, and halogen;
$R^7$ is selected from the group consisting of hydrogen and alkoxy;
$R^8$ is selected from the group consisting of hydrogen, halogen, alkyl, hydroxyalkyl, alkoxy, aryl, cycloalkyl, haloalkyl, haloaryl, and haloarylalkyl;
$R^9$ and $R^{10}$ are each independently selected from the group consisting of hydrogen and halogen;
$R^{13}$ is hydrogen, halogen, alkoxy, or alkyl; and
$R^{14}$ is hydrogen.

8. The compound of claim 1, or a pharmaceutically acceptable salt thereof, wherein:
A is selected from the group consisting of
(i) aryl substituted with $R^5$, $R^6$ and $R^7$; and
(ii) heteroaryl substituted with $R^8$, $R^9$ and $R^{10}$;
$R^3$ is heterocyclyl substituted with $R^{17}$ and $R^{18}$;
$R^4$ is hydrogen;
$R^5$ is selected from the group consisting of hydrogen, alkoxy, haloalkyl, and halogen;
$R^6$ is selected from the group consisting of hydrogen, alkoxy, and halogen;
$R^7$ is selected from the group consisting of hydrogen and alkoxy;
$R^8$ is selected from the group consisting of hydrogen, halogen, alkyl, hydroxyalkyl, alkoxy, aryl, cycloalkyl, haloalkyl, haloaryl, and haloarylalkyl;
$R^9$ and $R^{10}$ are each independently selected from the group consisting of hydrogen and halogen;
$R^{17}$ is oxo; and
$R^{18}$ is alkyl.

9. The compound of claim 1, or a pharmaceutically acceptable salt thereof, wherein:
A is selected from the group consisting of
(i) aryl substituted with $R^5$, $R^6$ and $R^7$; and
(ii) heteroaryl substituted with $R^8$, $R^9$ and $R^{10}$;
$R^3$ and $R^4$ together with the carbon atom to which they are attached form a heterocycle or a carbocycle;
$R^5$ is selected from the group consisting of hydrogen, alkoxy, haloalkyl, and halogen;
$R^6$ is selected from the group consisting of hydrogen, alkoxy, and halogen;
$R^7$ is selected from the group consisting of hydrogen and alkoxy;
$R^8$ is selected from the group consisting of hydrogen, halogen, alkyl, hydroxyalkyl, alkoxy, aryl, cycloalkyl, haloalkyl, haloaryl, and haloarylalkyl; and
$R^9$ and $R^{10}$ are each independently selected from the group consisting of hydrogen and halogen.

10. The compound of claim 1, or a pharmaceutically acceptable salt thereof, wherein:
A is:
(i) monocyclic aryl substituted with $R^5$, $R^6$, and $R^7$; or
(ii) heteroaryl substituted with $R^8$, $R^9$, and $R^{10}$, wherein said heteroaryl comprises 1 or 2 heteroatoms selected from the group consisting of O and N;
$R^3$ is aryl substituted with $R^{11}$ and $R^{12}$, and $R^4$ is hydrogen; or R³ and R⁴ together with the carbon atom to which they are attached form a monocyclic heterocycle comprising 1 oxygen atom, or form a monocyclic carbocycle;
R⁵, R⁶, and R⁷ are hydrogen;
R⁸ is selected from the group consisting of halogen and alkyl;
R⁹ and R¹⁰ are each independently selected from the group consisting of hydrogen and halogen;
R¹¹ is halogen or alkoxy; and
R¹² is hydrogen.

11. The compound of claim 1, or a pharmaceutically acceptable salt thereof, wherein:
A is:
(i) phenyl substituted with R⁵, R⁶, and R⁷; or
(ii) heteroaryl substituted with R⁸, R⁹ and R¹⁰, wherein said heteroaryl is selected from the group consisting of indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl, and 1,2-benzoxazol-7-yl;
R³ is phenyl substituted with R¹¹ and R¹², and R⁴ is hydrogen; or
R³ and R⁴ together with the carbon atom to which they are attached form an oxolane or a cyclopropyl;
R⁵, R⁶, and R⁷ are hydrogen;
R⁸ is selected from the group consisting of F, Cl and methyl;
R⁹ and R¹⁰ are each independently selected from the group consisting of hydrogen, F, and Cl;
R¹¹ is F or methoxy; and
R¹² is hydrogen.

12. The compound of claim 1, or a pharmaceutically acceptable salt thereof, wherein:
R¹ is hydrogen, haloalkoxy, or halogen; and
R² is hydrogen or alkoxy.

13. The compound of claim 1, or a pharmaceutically acceptable salt thereof, wherein:
R¹ is hydrogen or halogen; and
R² is hydrogen.

14. The compound of claim 1, or a pharmaceutically acceptable salt thereof, wherein
R¹ is hydrogen or F; and
R² is hydrogen.

15. The compound of claim 1, selected from the group consisting of:
6-(4-Benzhydrylpiperidine-1-carbonyl)-7-fluoro-4H-1,4-benzoxazin-3-one,
6-(4-Benzhydrylpiperidine-1-carbonyl)-4H-1,4-benzoxazin-3-one,
6-[4-[Bis(4-fluorophenyl)methyl]piperidine-1-carbonyl]-4H-1,4-benzoxazin-3-one,
6-[4-[(3,4-Dichlorophenyl)-phenylmethyl]piperidine-1-carbonyl]-4H-1,4-benzoxazin-3-one,
6-[4-[Hydroxy(diphenyl)methyl]piperidine-1-carbonyl]-4H-1,4-benzoxazin-3-one,
6-[4-[(R)-(4-fluorophenyl)-phenylmethyl]piperidine-1-carbonyl]-4H-1,4-benzoxazin-3-one,
6-[4-[(S)-(4-fluorophenyl)-phenylmethyl]piperidine-1-carbonyl]-4H-1,4-benzoxazin-3-one,
6-[4-[(R)-(3,4-dimethoxyphenyl)-phenylmethyl]piperidine-1-carbonyl]-4H-1,4-benzoxazin-3-one,
6-[4-[(S)-(3,4-dimethoxyphenyl)-phenylmethyl]piperidine-1-carbonyl]-4H-1,4-benzoxazin-3-one,
6-[4-[(R)-(4-methoxyphenyl)-phenylmethyl]piperidine-1-carbonyl]-4H-1,4-benzoxazin-3-one,
6-[4-[(S)-(4-methoxyphenyl)-phenylmethyl]piperidine-1-carbonyl]-4H-1,4-benzoxazin-3-one,
6-[4-[(R)-(3-methoxyphenyl)-phenylmethyl]piperidine-1-carbonyl]-4H-1,4-benzoxazin-3-one,
6-[4-[(S)-(3-methoxyphenyl)-phenylmethyl]piperidine-1-carbonyl]-4H-1,4-benzoxazin-3-one,
6-[4-[(R)-(4-methylphenyl)-phenylmethyl]piperidine-1-carbonyl]-4H-1,4-benzoxazin-3-one,
6-[4-[(S)-(4-methylphenyl)-phenylmethyl]piperidine-1-carbonyl]-4H-1,4-benzoxazin-3-one,
6-[4-[(R)-(3-methylphenyl)-phenylmethyl]piperidine-1-carbonyl]-4H-1,4-benzoxazin-3-one,
6-[4-[(S)-(3-methylphenyl)-phenylmethyl]piperidine-1-carbonyl]-4H-1,4-benzoxazin-3-one,
6-[4-[2-(4-chlorophenyl)oxolan-2-yl]piperidine-1-carbonyl]-4H-1,4-benzoxazin-3-one,
6-[4-[2-(4-bromophenyl)-1,3-dioxolan-2-yl]piperidine-1-carbonyl]-4H-1,4-benzoxazin-3-one,
6-[4-(1-phenylcyclopropyl)piperidine-1-carbonyl]-4H-1,4-benzoxazin-3-one,
6-[4-[(4-methoxyphenyl)-phenyl-methyl]piperidine-1-carbonyl]-4H-1,4-benzoxazin-3-one,
6-[4-[m-tolyl(phenyl)methyl]piperidine-1-carbonyl]-4H-1,4-benzoxazin-3-one,
6-[4-[indol-1-yl(phenyl)methyl]piperidine-1-carbonyl]-4H-1,4-benzoxazin-3-one,
6-[4-[[4-(2-fluoroethoxy)phenyl]-(4-fluorophenyl)methyl]piperidine-1-carbonyl]-4H-1,4-benzoxazin-3-one,
6-[4-[(R)-(2-fluoro-4-pyridyl)-phenyl-methyl]piperidine-1-carbonyl]-4H-1,4-benzoxazin-3-one,
6-[4-[(S)-(2-fluoro-4-pyridyl)-phenyl-methyl]piperidine-1-carbonyl]-4H-1,4-benzoxazin-3-one,
6-[4-[(S)-[4-(2-fluoroethoxy)phenyl]-(4-fluorophenyl)methyl]piperidine-1-carbonyl]-4H-1,4-benzoxazin-3-one,
6-[4-[(R)-[4-(2-fluoroethoxy)phenyl]-(4-fluorophenyl)methyl]piperidine-1-carbonyl]-4H-1,4-benzoxazin-3-one,
6-[4-[(R)-[3-[2-(2-fluoroethoxy)ethoxy]phenyl]-phenyl-methyl]piperidine-1-carbonyl]-4H-1,4-benzoxazin-3-one,
6-[4-[(S)-[3-[2-(2-fluoroethoxy)ethoxy]phenyl]-phenyl-methyl]piperidine-1-carbonyl]-4H-1,4-benzoxazin-3-one,
6-[4-[(4-fluorophenyl)-(4-methoxyphenyl)methyl]piperidine-1-carbonyl]-4H-1,4-benzoxazin-3-one,
6-[4-[(S)-(4-fluorophenyl)-(4-methoxyphenyl)methyl]piperidine-1-carbonyl]-4H-1,4-benzoxazin-3-one,
6-[4-[(R)-(4-fluorophenyl)-(4-methoxyphenyl)methyl]piperidine-1-carbonyl]-4H-1,4-benzoxazin-3-one,
6-[4-[[3-(2-fluoroethoxy)phenyl]-phenyl-methyl]piperidine-1-carbonyl]-4H-1,4-benzoxazin-3-one,
6-[4-[[4-(2-fluoroethoxy)phenyl]-phenyl-methyl]piperidine-1-carbonyl]-4H-1,4-benzoxazin-3-one,
6-[4-[(S)-(3-fluorophenyl)-phenyl-methyl]piperidine-1-carbonyl]-4H-1,4-benzoxazin-3-one,
6-[4-[(R)-(3-fluorophenyl)-phenyl-methyl]piperidine-1-carbonyl]-4H-1,4-benzoxazin-3-one,
6-[4-[(R)-[3-(2-fluoroethoxy)phenyl]-(4-fluorophenyl)methyl]piperidine-1-carbonyl]-4H-1,4-benzoxazin-3-one,
6-[4-[(S)-[3-(2-fluoroethoxy)phenyl]-(4-fluorophenyl)methyl]piperidine-1-carbonyl]-4H-1,4-benzoxazin-3-one,
6-[4-[(2-fluoro-3-pyridyl)-phenyl-methyl]piperidine-1-carbonyl]-4H-1,4-benzoxazin-3-one, 6-[4-[(R)-[4-(2-fluoroethoxy)phenyl]-phenyl-methyl]piperidine-1-carbonyl]-4H-1,4-benzoxazin-3-one,
6-[4-[(S)-[4-(2-fluoroethoxy)phenyl]-phenyl-methyl]piperidine-1-carbonyl]-4H-1,4-benzoxazin-3-one,
6-[4-[(S)-[3-(2-fluoroethoxy)phenyl]-phenyl-methyl]piperidine-1-carbonyl]-4H-1,4-benzoxazin-3-one,
6-[4-[(3-fluorophenyl)-phenyl-methyl]piperidine-1-carbonyl]-4H-1,4-benzoxazin-3-one,
6-[4-[bis(4-fluorophenyl)methyl]piperazine-1-carbonyl]-4H-1,4-benzoxazin-3-one,
6-[4-[[4-(2-fluoroethoxy)phenyl]-(4-fluorophenyl)methylene]piperidine-1-carbonyl]-4H-1,4-benzoxazin-3-one;
6-[4-[(S)-[3-[2-(2-fluoroethoxy)ethoxy]phenyl]-(4-fluorophenyl)methyl]piperidine-1-carbonyl]-4H-1,4-benzoxazin-3-one;
6-[4-[(R)-[3-[2-(2-fluoroethoxy)ethoxy]phenyl]-(4-fluorophenyl)methyl]piperidine-1-carbonyl]-4H-1,4-benzoxazin-3-one;
6-[4-[(S)-[4-[2-(2-fluoroethoxy)ethoxy]phenyl]-phenyl-methyl]piperidine-1-carbonyl]-4H-1,4-benzoxazin-3-one;
6-[4-[(R)-[4-[2-(2-fluoroethoxy)ethoxy]phenyl]-phenyl-methyl]piperidine-1-carbonyl]-4H-1,4-benzoxazin-3-one;
6-[4-[(S)-(6-fluoro-2-pyridyl)-phenyl-methyl]piperidine-1-carbonyl]-4H-1,4-benzoxazin-3-one;
6-[4-[(R)-(6-fluoro-2-pyridyl)-phenyl-methyl]piperidine-1-carbonyl]-4H-1,4-benzoxazin-3-one;
7-[4-[bis(4-fluorophenyl)methyl]piperidine-1-carbonyl]-5-methoxy-3,4-dihydro-1H-quinolin-2-one;
7-(4-benzhydrylpiperidine-1-carbonyl)-5-methoxy-3,4-dihydro-1H-quinolin-2-one;
6-[4-[(S)-(6-fluoro-3-pyridyl)-phenyl-methyl]piperidine-1-carbonyl]-4H-1,4-benzoxazin-3-one;
6-[4-[(R)-(6-fluoro-3-pyridyl)-phenyl-methyl]piperidine-1-carbonyl]-4H-1,4-benzoxazin-3-one;
6-[4-[(S)-(3,4-dimethoxyphenyl)-(4-fluorophenyl)methyl]piperidine-1-carbonyl]-4H-1,4-benzoxazin-3-one;
6-[4-[(R)-(3,4-dimethoxyphenyl)-(4-fluorophenyl)methyl]piperidine-1-carbonyl]-4H-1,4-benzoxazin-3-one;
7-[4-[bis(4-fluorophenyl)methyl]piperidine-1-carbonyl]-5-(2-fluoroethoxy)-3,4-dihydro-1H-quinolin-2-one;
6-[4-[(R)-[4-[2-(2-fluoroethoxy)ethoxy]phenyl]-(4-fluorophenyl)methyl]piperidine-1-carbonyl]-4H-1,4-benzoxazin-3-one;
6-[4-[(S)-[4-[2-(2-fluoroethoxy)ethoxy]phenyl]-(4-fluorophenyl)methyl]piperidine-1-carbonyl]-4H-1,4-benzoxazin-3-one;
7-(4-benzhydrylpiperidine-1-carbonyl)-5-(2-fluoroethoxy)-3,4-dihydro-1H-quinolin-2-one;
6-[4-[(S)-(4-fluorophenyl)-(2-fluoro-4-pyridyl)methyl]piperidine-1-carbonyl]-4H-1,4-benzoxazin-3-one;
6-[4-[(R)-(4-fluorophenyl)-(2-fluoro-4-pyridyl)methyl]piperidine-1-carbonyl]-4H-1,4-benzoxazin-3-one;
6-[4-[(S)-(4-fluorophenyl)-(p-tolyl)methyl]piperidine-1-carbonyl]-4H-1,4-benzoxazin-3-one;
6-[4-[(R)-(4-fluorophenyl)-(p-tolyl)methyl]piperidine-1-carbonyl]-4H-1,4-benzoxazin-3-one;
6-[4-[(S)-(4-fluorophenyl)-(6-fluoro-3-pyridyl)methyl]piperidine-1-carbonyl]-4H-1,4-benzoxazin-3-one;
6-[4-[(R)-(4-fluorophenyl)-(6-fluoro-3-pyridyl)methyl]piperidine-1-carbonyl]-4H-1,4-benzoxazin-3-one;
6-[4-[(R)-(3,4-dimethoxyphenyl)-(2-pyridyl)methyl]piperidine-1-carbonyl]-4H-1,4-benzoxazin-3-one;
6-[4-[(S)-(3,4-dimethoxyphenyl)-(2-pyridyl)methyl]piperidine-1-carbonyl]-4H-1,4-benzoxazin-3-one;
6-[4-[(S)-(4-fluorophenyl)-(6-fluoro-2-pyridyl)methyl]piperidine-1-carbonyl]-4H-1,4-benzoxazin-3-one;
6-[4-[(R)-(4-fluorophenyl)-(6-fluoro-2-pyridyl)methyl]piperidine-1-carbonyl]-4H-1,4-benzoxazin-3-one;
6-[4-[(R)-(4-fluorophenyl)-(3-methoxyphenyl)methyl]piperidine-1-carbonyl]-4H-1,4-benzoxazin-3-one;
6-[4-[(S)-(4-fluorophenyl)-(3-methoxyphenyl)methyl]piperidine-1-carbonyl]-4H-1,4-benzoxazin-3-one;
6-[4-[(R)-(3,4-dimethoxyphenyl)-(3-pyridyl)methyl]piperidine-1-carbonyl]-4H-1,4-benzoxazin-3-one;
6-[4-[(S)-(3,4-dimethoxyphenyl)-(3-pyridyl)methyl]piperidine-1-carbonyl]-4H-1,4-benzoxazin-3-one;
6-(3-benzhydrylazetidine-1-carbonyl)-4H-1,4-benzoxazin-3-one;
6-[4-[(S)-(3,4-dimethoxyphenyl)-(4-pyridyl)methyl]piperidine-1-carbonyl]-4H-1,4-benzoxazin-3-one;
6-[4-[(R)-(3,4-dimethoxyphenyl)-(4-pyridyl)methyl]piperidine-1-carbonyl]-4H-1,4-benzoxazin-3-one;
6-[3-[(3,4-dimethoxyphenyl)-phenyl-methyl]azetidine-1-carbonyl]-4H-1,4-benzoxazin-3-one;
6-[4-[(S)-(3-methylsulfonylphenyl)-phenyl-methyl]piperidine-1-carbonyl]-4H-1,4-benzoxazin-3-one;
6-[4-[(R)-(3-methylsulfonylphenyl)-phenyl-methyl]piperidine-1-carbonyl]-4H-1,4-benzoxazin-3-one;
6-[3-[phenyl-[4-(trifluoromethyl)phenyl]methyl]azetidine-1-carbonyl]-4H-1,4-benzoxazin-3-one;
6-[3-[(3-methoxyphenyl)-phenyl-methyl]azetidine-1-carbonyl]-4H-1,4-benzoxazin-3-one;
6-[4-[(S)-(4-methylsulfonylphenyl)-phenyl-methyl]piperidine-1-carbonyl]-4H-1,4-benzoxazin-3-one;
6-[4-[(R)-(4-methylsulfonylphenyl)-phenyl-methyl]piperidine-1-carbonyl]-4H-1,4-benzoxazin-3-one;
6-[4-[(S)-[3-(2-fluoroethoxy)-4-methoxy-phenyl]-phenyl-methyl]piperidine-1-carbonyl]-4H-1,4-benzoxazin-3-one;
6-[4-[(R)-[3-(2-fluoroethoxy)-4-methoxy-phenyl]-phenyl-methyl]piperidine-1-carbonyl]-4H-1,4-benzoxazin-3-one;
6-[4-[(S)-(2-methoxy-4-pyridyl)-phenyl-methyl]piperidine-1-carbonyl]-4H-1,4-benzoxazin-3-one;
6-[4-[(R)-(2-methoxy-4-pyridyl)-phenyl-methyl]piperidine-1-carbonyl]-4H-1,4-benzoxazin-3-one;
6-[4-[(S)-[4-(2-fluoroethoxy)-3-methoxy-phenyl]-phenyl-methyl]piperidine-1-carbonyl]-4H-1,4-benzoxazin-3-one;
6-[4-[(R)-[4-(2-fluoroethoxy)-3-methoxy-phenyl]-phenyl-methyl]piperidine-1-carbonyl]-4H-1,4-benzoxazin-3-one;
6-[4-[(S)-(1-methylpyrazol-4-yl)-phenyl-methyl]piperidine-1-carbonyl]-4H-1,4-benzoxazin-3-one;
6-[4-[(R)-(1-methylpyrazol-4-yl)-phenyl-methyl]piperidine-1-carbonyl]-4H-1,4-benzoxazin-3-one;
6-[4-[(S)-(1-methyl-2-oxo-4-pyridyl)-phenyl-methyl]piperidine-1-carbonyl]-4H-1,4-benzoxazin-3-one; and
6-[4-[(R)-(1-methyl-2-oxo-4-pyridyl)-phenyl-methyl]piperidine-1-carbonyl]-4H-1,4-benzoxazin-3-one;
or a pharmaceutically acceptable salt thereof.

16. A pharmaceutical composition comprising a compound of claim 1, or a pharmaceutically acceptable salt thereof, and a therapeutically inert carrier.

17. A pharmaceutical composition comprising a compound of claim 15, or a pharmaceutically acceptable salt thereof, and a therapeutically inert carrier.

18. A method,
wherein the method is for the treatment or prophylaxis of neuroinflammation, or a neurodegenerative disease in a mammal,
the method comprising administering an effective amount of a compound of claim 1, or a pharmaceutically acceptable salt thereof to the mammal.

19. A method,
wherein the method is for the treatment or prophylaxis of multiple sclerosis, Alzheimer's disease, Parkinson's disease, or amyotrophic lateral sclerosis in a mammal,
the method comprising administering an effective amount of a compound of claim 1, or a pharmaceutically acceptable salt thereof, to the mammal.

* * * * *